US007507543B2

(12) United States Patent
Ekstrand

(10) Patent No.: US 7,507,543 B2
(45) Date of Patent: Mar. 24, 2009

(54) GABA$_B$ RECEPTOR POLYPEPTIDES AND SCREENING METHODS

(75) Inventor: Jonas Ekstrand, Umeå (SE)

(73) Assignee: AstraZeneca AB, Sodertalje (SE)

( * ) Notice: Subject to any disclaimer, the term of this patent is extended or adjusted under 35 U.S.C. 154(b) by 979 days.

(21) Appl. No.: 10/235,463

(22) Filed: Sep. 4, 2002

(65) Prior Publication Data

US 2004/0043448 A1  Mar. 4, 2004

Related U.S. Application Data

(60) Division of application No. 09/422,936, filed on Oct. 22, 1999, now Pat. No. 6,465,213, which is a continuation-in-part of application No. 09/242,608, filed as application No. PCT/SE98/01947 on Oct. 27, 1998, now abandoned.

(30) Foreign Application Priority Data

Oct. 27, 1997  (SE)  .................................. 9703914
Mar. 16, 1998  (SE)  .................................. 9800864
Jul. 17, 1998  (SE)  .................................. 9802575

(51) Int. Cl.
*G01N 33/53* (2006.01)
(52) U.S. Cl. ........................ 435/7.2; 530/350
(58) Field of Classification Search ................ 530/300, 530/324, 350
See application file for complete search history.

(56) References Cited

U.S. PATENT DOCUMENTS 6,689,585 B1 *  2/2004  Herzog ...................... 435/69.1
7,262,280 B1 *  8/2007  Stormann et al. ........... 530/402
2005/0130203 A1 *  6/2005  Liu et al.

FOREIGN PATENT DOCUMENTS

WO    WO 97/46675    *   3/1997
WO    WO 97/46675        12/1997
WO       99/51636    *  10/1999

OTHER PUBLICATIONS

Kerr & Ong (1995) "GABAB Receptors."Pharmacol Ther. 67(2): 187-246.*
Kaupmann et al. (Dec. 1998) "Human g-aminobutyric acid type B receptors are differentially expressed and regulate inwardly rectifying K+ channels." PNAS 95(6712): 14991-14996.*

Crunelli & Leresche (Jan. 1991) "A role for GABAB receptors in excitation and inhibition of thalamocortical cells." Trends Neurosci. 14(1): 16-21.*
Mott & Lewis (1994) "The pharmacology and function of central GABAB Receptors." International Review of Neurobiology 36: 97-223.*
Malcangio & Bowery (Aug. 1995) "Possible therapeutic application of GABAB receptor agonists and antagonists." Clin Neuropharmacol. 18(4): 285-305.*
Howard et al. (Mar. 2001) "Orphan G-protein-coupled receptors and natural ligand discovery." Trends Pharmacol Sci. 22(3): 132-40.*
Kaupmann 1998. Proc Natl Acad Sci USA 95:14991-14996.*
Alberts et al. 1994. Molecular Biology of the Cell pp. 582-585.*
Grifa 1998. Biochemical and Biophysical Research Communications 250(2):240-245.*
Kaupmann 1997. Nature 386:239-246.*
Goei et al. 1998. Biological Psychiatry 44:659-666.*
Margeta-Mitrovic 2001. Proc Natl Acad Sci USA 98:14649-14654.*
Promega Protocols and Applications 1989. pp. 116-123.*
Alberts et al. 1994. Molecular Biology of the Cell pp. 129-130.*
Honig 1999. Journal of Molecular Biology 293:283-293.*
Sigma catalog 1994 p. 623.*
Kerr; D.I.B. and Ong.; "GABAB Receptor"; J. Pharmac. & Ther., vol. 67; pp. 187-246; 1995.
Kaupmann et al.; "Expression cloning of GABAB Receptors Uncovers Similar to Metabotropic Glutamate Receptors" Nature, vol. 386; pp. 239-246; 1997.
Holloway et al.; "Pathophysiology of Gastroesophageal Reflux"; Gastroenterol. Clin. N. Amer., vol. 19; pp. 517-535; 1990.
Karlin et al.; "Methods of Assessing the Statistical Significance of Molecular Sequence Features by Using General Scoring Schemes"; Proc. Nat'l. Acad. Sci. USA, vol. 87; pp. 2264-2268; 1990.
Karlin et al.; "Applications and Statistics For Multiple High-Scoring Segments In Molecular Sequence"; Proc. Nat'l Acad. Sci. USA, vol. 90; pp. 5873-5877; 1993.
Altschul et al.; "Basic Local Alignment Search Tool"; J. Mol. Biol., vol. 215; pp. 403-410; 1990.
Altschul et al.; "Gapped BLAST and PSI-BLAST: A New Generation of Protein Database Search Programs"; Nucleic Acids Res., vol. 25, pp. 3389-3402; 1997.
Ausubel et al.; "Contents, vol. 1,2,3, and 4"; Current Protocols in Molecular Biology; John Wiley and Sons, Inc.; 1994 (manual).
Sambrook, Fritsch and Maniatis; "Contents"; Molecular Cloning: A laboratory manual 2nd Ed., Cold Spring Harbor Laboratory Press, Cold Spring Harbor, NY 1989.
Kaupmann et al.; EMBL accession Nos. Y10369; 1997.
Clontech, Lambda Library User Manual, PT 1010-1 (PR 92374) Feb. 1999.
Clontech (catalogue #6578-1); Palo Alto, CA USA, no date.

* cited by examiner

*Primary Examiner*—Daniel E. Kolker
(74) *Attorney, Agent, or Firm*—Fish & Richardson P.C.

(57) ABSTRACT

The present invention relates to a nucleic acid molecule encoding a human or canine GABA$_B$ receptor, or a conservative variant thereof.

20 Claims, 2 Drawing Sheets

GABA$_B$ RECEPTOR POLYPEPTIDES AND SCREENING METHODS

CROSS REFERENCE TO RELATED APPLICATION

This application is a continuation-in-part of U.S. Ser. No. 09/242,608, filed Feb. 19, 1999, which claims priority to PCT/SE98/01947 filed Oct. 27, 1998, and Swedish application Nos. 9703914-2, filed Oct. 27, 1997; 9800864-2, filed Mar. 16, 1998; and 9802575-2, filed Jul. 17, 1998.

FIELD OF THE INVENTION

The invention relates to nucleic acid molecules encoding GABA$_B$ receptors, and to methods for screening for compounds that are inhibitors of transient lower esophageal sphincter relaxations (TLESR).

BACKGROUND OF THE INVENTION

GABA$_B$ Receptors

GABA (4-aminobutanoic acid) is an endogenous neurotransmitter in the central and peripheral nervous systems. Receptors for GABA have traditionally been divided into GABA$_A$ and GABA$_B$ receptor subtypes. GABA$_B$ receptors (for a review see Kerr, D. I. B. and Ong, J. (1995) Pharmac. Ther. vol. 67, pp.187-246) belong to the superfamily of G-protein coupled receptors. GABA$_B$ receptor agonists are useful in the treatment of central nervous system (CNS) disorders, such as for inducing muscle relaxation in spinal spasticity, cardiovascular disorders, asthma, and gut motility disorders such as irritable bowel syndrome; and as prokinetic and anti-tussive agents. GABA$_B$ receptor agonists have also been disclosed as useful in the treatment of emesis (WO 96/11680).

The cloning of the rat GABA$_B$ receptors GABA$_B$R1a (SEQ ID NOs: 44 and 45) and GABA$_B$R1b (SEQ ID NOs: 46 and 47) was disclosed by Kaupmann et al. ((1997) Nature, vol. 386, 239-246). The mature rat GABA$_B$R1b differs from GABA$_B$R1a in that the N-terminal 147 residues are replaced by 18 different residues. It is thought that the rat GABA$_B$R1a and GABA$_B$R1b receptor variants are derived from the same gene by alternative splicing. Cloning of the human GABA$_B$R1b receptor was disclosed in WO97/46675.

Reflux

In some humans, the lower esophageal sphincter (LES) is prone to relaxing more frequently than in other humans. As a consequence, fluid from the stomach can pass into the esophagus because the mechanical barrier is temporarily lost at such times, an event hereinafter referred to as "reflux."

Gastro-esophageal reflux disease (GERD) is the most prevalent upper gastrointestinal tract disease. Conventional therapies have sought to reduce gastric acid secretion, or reduce esophageal acid exposure by enhancing esophageal clearance, lower esophageal sphincter tone, and gastric emptying. The major mechanism behind reflux has been considered to depend on a hypotonic lower esophageal sphincter. However, recent research (e.g., Holloway & Dent (1990) Gastroenterol. Clin. N. Amer. 19, 517-535) has shown that most reflux episodes occur during transient lower esophageal sphincter relaxations (TLESR), i.e., relaxations not triggered by swallowing. It has also been shown that gastric acid secretion usually is normal in patients with GERD.

SUMMARY OF THE INVENTION

The present invention provides nucleic acid molecules encoding human and canine GABA$_B$ receptors. These nucleic acid molecules make it possible to screen for compounds that are agonists or antagonists of GABA$_B$ receptors, e.g., to identify compounds which are inhibitors of TLESR.

Consequently, the invention provides an isolated nucleic acid molecule encoding a human or canine GABA$_B$ receptor, or a conservative variant thereof. An "isolated nucleic acid" is a nucleic acid the structure of which is not identical to that of any naturally occurring nucleic acid or to that of any fragment of a naturally occurring genomic nucleic acid spanning more than three separate genes. The term therefor covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transfected cells, and (iii) cell clones: e.g., as these occur in a DNA library such as a cDNA or genomic DNA library.

In various embodiments, the nucleic acid molecule encodes a human GABA$_B$ receptor 1a (SEQ ID NOs: 48 and 49), 1b (SEQ ID NOs: 50 and 51), 1c (SEQ ID NOs: 54 and 55) or 1d (SEQ ID NOs: 56 and 57); or a canine GABA$_B$ receptor 1a (SEQ ID NOs: 52 and 53) or 1c (SEQ ID NOs: 58 and 59). Accordingly, the invention includes the following nucleic acid molecules:

(1) a nucleic acid molecule that includes a nucleotide sequence set forth as SEQ ID NO: 48, 50, 52, 54, 56, or 58, or a degenerate variant thereof;

(2) an RNA molecule that includes a nucleotide sequence set forth as SEQ ID NO: 48, 50, 52, 54, 56, or 58, or a degenerate variant thereof, wherein T is replaced by U;

(3) a nucleic acid molecule that includes a nucleotide sequence that is capable of hybridizing under stringent conditions (e.g., is complementary) to a nucleotide sequence of (1) or (2), or to the complement of (1) or (2); and (4) nucleic acid fragments that are at least 15 base pairs in length and which hybridize under stringent conditions to genomic DNA encoding the human or canine GABA$_B$ polypeptides described herein, or to the complement of such genomic DNA.

The invention also includes isolated nucleic acid molecules corresponding to genomic sequences encoding human GABA$_B$ receptors (SEQ ID NOs: 60 and 61), as well as nucleic acid molecules (set forth as SEQ ID NO: 70, 72, 74, 76, 78, 80, 82, and 84) encoding additional isoforms of the human GABA$_B$ receptor, which isoforms are generated by alternative splicing.

The nucleic acid molecules of the invention are not limited strictly to molecules including the sequences set forth as SEQ ID NOs: 48, 50, 52, 54, 56 or 58. Rather, the invention encompasses nucleic acid molecules carrying modifications such as substitutions, small deletions, insertions, or inversions, which nevertheless encode proteins having substantially the biochemical activity of the $GABA_B$ receptors according to the invention, and/or which can serve as hybridization probes for identifying a nucleic acid with one of the disclosed sequences. Included in the invention are nucleic acid molecules, the nucleotide sequence of which is at least 95% identical (e.g., at least 96%, 97%, 98%, or 99% identical) to the nucleotide sequence shown as SEQ ID NO: 48, 50, 52, 54, 56, or 58 in the Sequence Listing.

The determination of percent identity or homology between two sequences is accomplished using the algorithm of Karlin and Altschul (1990) *Proc. Nat'l Acad. Sci. USA* 87: 2264-2268, modified as in Karlin and Altschul (1993) *Proc. Nat'l Acad. Sci. USA* 90:5873-5877. Such an algorithm is incorporated into the NBLAST and XBLAST programs of Altschul et al. (1990) *J. Mol. Biol.* 215:403-410. BLAST nucleotide searches are performed with the NBLAST program, score=100, wordlength=12 to obtain nucleotide sequences homologous to the nucleic acid molecules of the invention. BLAST protein searches are performed with the XBLAST program, score=50, wordlength=3 to obtain amino acid sequences homologous to the protein molecules of the invention. To obtain gapped alignments for comparison purposes, Gapped BLAST is utilized as described in Altschul et al. (1997) *Nucleic Acids Res*. 25: 3389- 3402. When utilizing BLAST and Gapped BLAST programs, the default parameters of the respective programs (e.g., XBLAST and NBLAST) are used. See the internet at ncbi.nlm.nih.gov.

The term "stringent hybridization conditions" is known in the art from standard protocols (e.g., Current Protocols in Molecular Biology, editors F. Ausubel et al., John Wiley and Sons, Inc. 1994) and is to be understood as conditions as stringent as those defined by the following: hybridization to filter-bound DNA in 0.5 M $NaHPO_4$ (pH 7.2), 7% sodium dodecyl sulfate (SDS), 1 mM EDTA at +65° C., and washing in 0.1×SSC/0.1% SDS at +68° C.

Also included in the invention is a nucleic acid molecule that has a nucleotide sequence which is a degenerate variant of a nucleic acid disclosed herein, e.g., SEQ ID NOs: 48, 50, 52, 54, 56, and 58. A sequential grouping of three nucleotides, a "codon," encodes one amino acid. Since there are 64 possible codons, but only 20 natural amino acids, most amino acids are encoded by more than one codon. This natural "degeneracy" or "redundancy" of the genetic code is well known in the art. It will thus be appreciated that the nucleic acid sequences shown in the Sequence Listing provide only an example within a large but definite group of nucleic acid sequences that will encode the polypeptides as described above.

The invention also includes an isolated polypeptide encoded by a nucleic acid of the invention. An "isolated" polypeptide is a polypeptide that is substantially free from the proteins and other naturally occurring organic molecules with which it is naturally associated. Purity can be measured by any art-known method, e.g., column chromatography, polyacrylamide gel electrophoresis, or HPLC. An isolated polypeptide may be obtained, for example, by extraction from a natural source (e.g., a human cell); by expression of a recombinant nucleic acid encoding the polypeptide; or by chemical synthesis of the polypeptide. In the context of a polypeptide obtained by extraction from a natural source, "substantially free" means that the polypeptide constitutes at least 60% (e.g., at least 75%, 90%, or 99%) of the dry weight of the preparation. A protein that is chemically synthesized, or produced from a source different from the source from which the protein naturally originates, is by definition substantially free from its naturally associated components.

Thus, an isolated polypeptide includes recombinant polypeptides synthesized, for example, in vivo, e.g., in the milk of transgenic animals, or in vitro, e.g., in a mammalian cell line, in *E. coli* or another single-celled microorganism, or in insect cells.

In various embodiments, the polypeptide of the invention has an amino acid sequence as set forth in SEQ ID NO: 49, 51, 53, 55, 57, 59, 71, 73, 75, 77, 79, 81, 83, and 85. However, polypeptides of the present invention are not to limited to those having an amino acid sequence identical to one of SEQ ID NOs: 49, 51, 53, 55, 59, 71, 73, 75, 77, 79, 81, 83, or 85 in the Sequence Listing. Rather, the invention also encompasses conservative variants of the disclosed sequences. "Conservative variants" include substitutions within the following groups: glycine and alanine; valine, alanine, isoleucine, and leucine; aspartic acid and glutamic acid; asparagine, glutamine, serine, and threonine; lysine, arginine, and histidine; and phenylalanine and tyrosine.

Also included in the invention are polypeptides carrying modifications such as substitutions, small deletions, insertions, or inversions, which polypeptides nevertheless have substantially the biological activities of the $GABA_B$ receptor. Consequently, included in the invention is a polypeptide, the amino acid sequence of which is at least 95% identical (e.g., at least 96%, 97%, 98%, or 99% identical) to an amino acid sequence set forth as SEQ ID NO: 49, 51, 53, 55, 57 59, 71, 73, 75, 77, 79, 81, 83, or 85 in the Sequence Listing. "Percent identity" is defined in accordance with the algorithm described above.

Also included in the invention are polypeptides of the invention that have been post-translationally modified, e.g., by cleavage of an N-terminal signal sequence, which can be, e.g., 1 to 25 amino acids long.

The invention also includes a vector that contains a nucleic acid molecule of the present invention. The vector can, e.g., be a replicable expression vector that is capable of mediating the expression of a nucleic acid molecule of the invention. A "replicable" vector is able to replicate in a given type of host cell into which it has been introduced. Examples of suitable vectors include virus-based vectors (e.g., bacteriophages, retroviruses, adenoviruses, herpes viruses, polio viruses, and vaccinia viruses), cosmids, plasmids, and other recombination vectors. Nucleic acid molecules can be inserted into vectors by methods well known in the art.

Also included in the invention is a host cell harboring a nucleic acid (e.g., on a vector) of the invention. Without limitation, such a host cell can be a prokaryotic cell, a unicellular eukaryotic cell, or a cell derived from a multicellular organism. For example, the host cell can be a bacterial cell, such as an *E. coli* cell; a yeast cell, such as *Saccharomyces cerevisiae* or *Pichia pastoris*; an insect cell, an amphibian cell (e.g., a frog oocyte), or a mammalian cell. It is preferably not a neuron, e.g., a human, dog, rat or other mammalian neuron. Conventional methods can be employed to introduce the vector into the host cell.

Host cells containing nucleic acids of the invention can be used to produce a $GABA_B$ receptor polypeptide of the invention or a conservative variant thereof. Generally, the process includes culturing a host cell as defined above under conditions such that the polypeptide is produced, and recovering the polypeptide.

A further aspect of the invention is a method for determining whether a test compound is an inhibitor of TLESR. The method entails (a) expressing in a cell (preferably a cell that does not naturally express the $GABA_B$ receptor, such as a fibroblast or other non-neural cell) a nucleic acid molecule that includes a nucleotide sequence of the invention, thereby producing a cell having on its surface a $GABA_B$ receptor or a conservative variant thereof; (b) contacting the $GABA_B$ receptor or conservative variant with a test compound; and (c) detecting binding of the test compound to the $GABA_B$ receptor or conservative variant, wherein binding of the test compound to the $GABA_B$ receptor or conservative variant indicates that the test compound is an inhibitor of TLESR. This activity can be further validated by other in vitro or in vivo tests: e.g., by administration of the test compound to an animal model for this condition. It should be understood that this aspect of the invention is not limited to use of human and canine $GABA_B$ receptors, but rather encompasses the use of any $GABA_B$ receptor for screening for compounds which are inhibitors of TLESRs.

Nucleic acid molecules encoding human or canine $GABA_B$ receptors also can be used in a related method for screening for compounds that are agonists or antagonists. Generally, in this method, binding is detected by detecting activation, or inhibition of activation, of the $GABA_B$ receptor or a conservative variant thereof, wherein activation indicates that the test compound is an agonist of the $GABA_B$ receptor, and inhibition of activation indicates that the test compound is an antagonist of the $GABA_B$ receptor.

The screening methods according to the invention can e.g., comprise the steps (a) transforming a cultured cell with a nucleic acid molecule encoding a $GABA_B$ receptor, so that a $GABA_B$ receptor is expressed on the surface of the cell; (b) contacting a test compound with the cell; and (c) determining whether the test compound binds to, and/or activates, the $GABA_B$ receptor.

$GABA_B$ receptor-expressing cells, transgenic animals, or cells and tissues derived therefrom can be used to screen substance libraries (i.e., libraries of test compounds) for antagonist or agonist activity. For this purpose, $GABA_B$ receptor expression may be directed to cells and tissues containing, either naturally or artificially, the necessary components allowing correct receptor transport and processing as well as coupling to second messenger pathways. Screening may be performed as ligand binding assays or functional assays. For screening, cells and tissues can be prepared in various ways, each uniquely suited to its purpose. Ligand binding assays can be performed in vivo or in vitro using, e.g., radiolabelled GABA. Functional assays (e.g., $Ca^{++}$-responses, cAMP-responses, and effects on $K^+$ channels) can be performed in living cells, broken cells, isolated cell membranes, tissues, or living animals. To facilitate measurement of physiological $GABA_B$ receptor mediated responses, $GABA_B$ receptors may be co-expressed with promiscuous G-proteins, e.g., $G\alpha16$ or $Gqi5$, increasing G-protein coupling. Another way to increase G-protein coupling is to fuse the $GABA_B$ receptor to appropriate G-proteins using standard molecular techniques. To further improve readouts in $Ca^{++}$-response assays, $GABA_B$ receptors can be co-expressed with aequorin, a photoprotein cloned from the luminescent jellyfish *Aequorea victoria*.

The invention also provides a pharmaceutical composition that includes a $GABA_B$ receptor (e.g., a soluble receptor), or a conservative variant thereof, and at least one of (a) a pharmaceutically acceptable carrier and (b) a pharmaceutically acceptable diluent.

The pharmaceutical composition can be used in methods of treating conditions involving GABA-dysfunction, e.g., epilepsy, psychiatric disorders such as depression and anxiety, cognitive dysfunction, gastroesophageal reflux disease, emesis, irritable bowel syndrome, dyspepsia, spasticity, arthritis, allergies, autoimmune diseases, neoplastic diseases, pain, and infectious diseases. Typically, the $GABA_B$ receptor is a soluble form of the $GABA_B$ receptor, such as the human $GABA_B$ receptor 1c or 1d or a conservative variant thereof.

A soluble form of the receptor can be a form that lacks some or all of the membrane-spanning domains of the wild-type receptor protein, but retains the ligand-binding portion or portions of the receptor. The membrane-spanning domains are readily identified by their predominance of non-polar amino acid residues, and/or by comparison with related receptors (e.g., other G-protein receptors).

Soluble forms of the $GABA_B$ receptor can be produced by culturing a host cell containing a vector that includes a nucleic acid encoding the soluble $GABA_B$ receptor under conditions such that the $GABA_B$ receptor polypeptide is produced. The polypeptide then is recovered, and a pharmaceutical composition containing the polypeptide is administered to a mammal (e.g., a human or dog) in need thereof.

In a related aspect, the invention provides a method for diagnosing a mammal as having a condition involving altered levels of $GABA_B$ receptors in body fluid (e.g., serum or cerebrospinal fluid). Such conditions include epilepsy, psychiatric disorders, cognitive dysfunction, gastroesophageal reflux disease, emesis, irritable bowel syndrome, dyspepsia, spasticity, arthritis, allergies, auto immune diseases, neoplastic diseases, pain, and infectious diseases. Diagnosis involves measuring the level of $GABA_B$ receptor in a body fluid of a mammal (e.g., a human), wherein an increase or decrease in the level of $GABA_B$ receptor, relative to the level found in a normal mammal, indicates that the mammal has a condition involving altered levels of $GABA_B$ receptors in body fluid.

Throughout this description, the terms "standard protocols" and "standard procedures," when used in the context of molecular cloning techniques, are to be understood as protocols and procedures found in an ordinary laboratory manual such as *Current Protocols in Molecular Biology*, editors F. Ausubel et al., John Wiley and Sons, Inc. 1994, or Sambrook, J., Fritsch, E. F. and Maniatis, T., Molecular Cloning: A laboratory manual, 2nd Ed., Cold Spring Harbor Laboratory Press, Cold Spring Harbor, N.Y. 1989.

Figure 1:
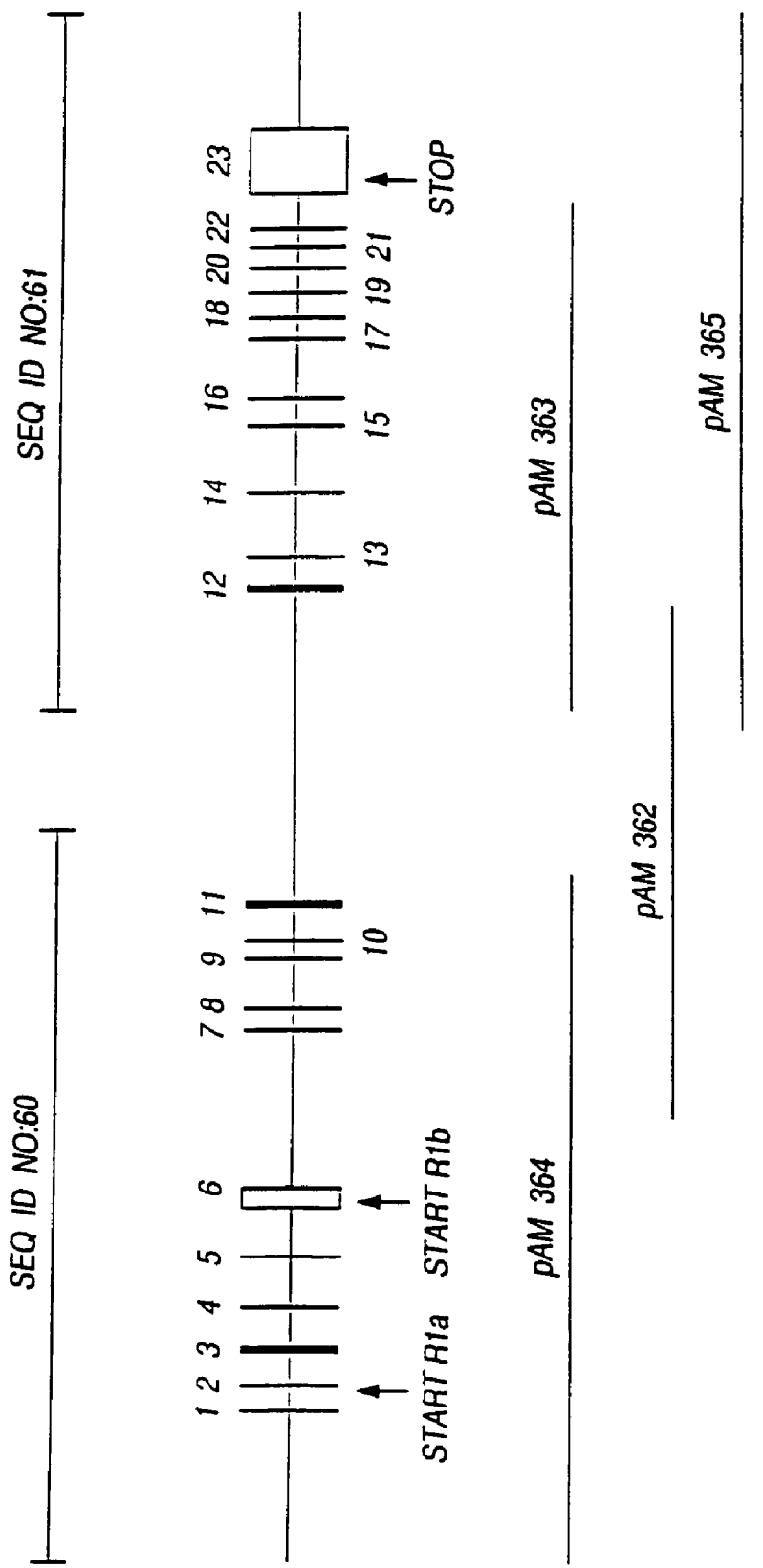
FIG. 1 is a map of the human $GABA_B$ receptor gene. The exon/intron organization is shown. Exons are indicated as solid boxes numbered 1-23. The part of intron 5 that is retained together with exon 6 giving rise to $GABA_B$ receptor 1b is indicated as an open box.

Lysate from an uninduced *E. coli* culture transformed with an pET-based expression construct encoding the human GABA$_B$ receptor 1d cDNA. Lane 2: Lysate from an IPTG-induced *E. coli* culture transformed with an expression construct encoding the human GABA$_B$ receptor 1d cDNA. Lane 3: Lysate from an IPTG-induced *E. coli* culture transformed with an expression construct encoding an unrelated protein. Lane 4: An aliquot of the BSA-conjugated peptide used for immunization was loaded on the gel as a positive antibody control.

and 795, 797 and 865, 864 and 865, and 864 and 863, which correspond to the 5'-end of the GABA$_B$ receptor 1a cDNA. The combinations of 932 and 831, 932 and 796, and 794 and 831 produced PCR products that correspond to the 3'-ends of both GABA$_B$ receptor 1a and 1b cDNA. The primer combination 839 and 918 produced a PCR product corresponding to the 5'-end of the GABA$_B$ receptor 1b cDNA.

TABLE 1

Primers used for RT-PCR on rnRNA from human hippocampus

| Nr. | Species | Seqences 5'-3' | SEQ ID NO |
|---|---|---|---|
| 794 | Rat | GTTTCTTCTCGGATCCAGCTGTGCCTG | 1 |
| 795 | Rat | CAGGCACAGCTGGATCCGAGAAGAAACT | 2 |
| 796 | Rat | CGGTCGACTCACTTGTAAAGCAAATGTACTCGACTCCC | 3 |
| 797 | Rat | ATGCGCGCCGGCAGCCAACATGCTGCTGCTGCTGGTGC | 4 |
| 831 | Rat | CGGTCGACTCACTTGTAAAGCAAATGTACTCGACTCCCATCACAGC | 5 |
| 838 | Rat | ATGCGCGCCGGCAGCCAACATGCTGCTGCTGCTGGTGCCTCTCTTCC | 6 |
| 842 | Rat | CAGGCACAGCTGGATCCGAGAAGAAACTCTGTCGGAAAGT | 7 |
| 863 | Rat | GGTCATCCAGCGTTGAGGTGAAGAC | 8 |
| 864 | Rat | GAAGGTTGCCAGATTATACATCCGC | 9 |
| 865 | Rat | CCACGATGATTCGAGCATCTTGACG | 10 |
| 866 | Rat | GCCTCTCACTCCCCTCATCTCC | 11 |
| 932 | Human | GAGTGAAGGAGGCTGGAATTG | 12 |

DETAILED DESCRIPTION

EXAMPLE 1A

Cloning and Sequencing of cDNA Encoding Human GABA$_B$ Receptor 1a and 1b

Messenger RNA from human hippocampus was obtained from Clontech (Palo Alto, Calif., USA) (catalog #6578-1). First-strand cDNA synthesis reactions were performed using the First-strand™ cDNA Synthesis kit from Amersham Pharmacia Biotech (Uppsala, Sweden). The pd(N)$_6$ primer was used to prime the first-strand synthesis. The generated cDNA molecules were used as templates in the PCR reactions described below.

Specific PCR primers were designed (as shown in Table 1) based on the sequences of the rat GABA$_B$ receptor 1a and 1b cDNA (Kaupmann et al., 1997, EMBL accession numbers Y10369 (SEQ ID NO: 44) and Y10370 (SEQ ID NO: 46)). Various cDNA fragments encoding parts of the human GABA$_B$ receptors were amplified directly by PCR using the designed primers with the generated cDNA molecules as templates. All PCR experiments were carried out using Perkin Elmer Taq DNA polymerase with Gene Amp™ (Roche Molecular Systems Inc., NJ, USA) with the following PCR program: +95° C. for 1 minute, +50° C. for 30 seconds, +72° C. for 3 minutes, repeated 44 times, and then +72° C. for 7 minutes. The following combinations of primers gave PCR products with the expected sizes: primers 838 and 842, 838

The PCR products were subcloned into the pGEM-T vector from Promega (Madison, USA). The inserts were subjected to nucleotide sequence analysis, and the complete nucleotide sequences for all subclones were determined using a Thermo Sequences™ dye terminator cycle sequencing pre-mix kit (Amersham Pharmacia Biotech, Uppsala, Sweden). Specific oligonucleotides complementary to the vector pGEM-T, or primers complementary to the cDNA encoding the GABA$_B$ receptor, were used as primers for the sequencing reactions.

Additional PCR primers were designed based on the obtained sequences encoding fragments of the human GABA$_B$ receptor, additional DNA fragments encoding parts of the human GABA$_B$ receptors were amplified by PCR, and the PCR products were subcloned and sequenced as described above.

EXAMPLE 1B

Cloning and Sequencing of the 3'-ends of the cDNA Encoding Human GABA$_B$ Receptors 1a and 1b Messenger RNA from human hippocampus was obtained from Clontech (Palo Alto, Calif., USA) (catalogue #6578-1). First strand cDNA synthesis reactions were performed using the First-strand™ cDNA Synthesis kit from Amersham Pharmacia Biotech (Uppsala, Sweden). The Not-I-d(T)$_{18}$ primer was used to prime the first-strand synthesis. The generated cDNA molecules were used as templates in the PCR reactions described below.

Specific PCR primers were designed (as shown in Table 2) based on the sequences of the human GABA$_B$ receptor 1a and 1b cDNA obtained in Example 1A and the EST sequence set forth in EMBL accession number Y11044.

By homology searches in the EMBL database using the GABA$_B$ receptor cDNA sequences obtained in Example 1A as the query sequences, the EST sequence set forth in EMBL accession number Y11044 has been found to be homologous to the 3'-end of the GABA$_B$ receptor cDNA.

TABLE 2

Primers used in PCR to amplify 3' ends of human GABA$_B$ receptor cDNA

| Nr. | Species | Sequence 5'-3' | SEQ ID NO |
|---|---|---|---|
| 938 | Human | GACGCTTATCGAGCAGCTTC | 13 |
| 972 | Human | AGCCCAGAACTCACAGGGGACAT | 14 |
| 973 | Human | GCTTCAAGCCAGGTACGAACTAA | 15 |

Various cDNA fragments encoding parts of the human GABA$_B$ receptors were amplified directly by PCR using the designed primers with the generated cDNA molecules as templates. All PCR experiments were carried out using Perkin Elmer Taq DNA polymerase with Gene Amp™ (Roche Molecular Systems Inc., NJ, USA) with the following PCR program: +95° C. for 1 minute, +50° C. for 30 seconds, +72° C. for 3 minutes, repeated 44 times, and then +72° C. for 7 minutes. The following combinations of primers gave PCR products with the expected sizes: 938 and 972, and 938 and 973, corresponding to the 3'-end of both GABA$_B$ receptor 1a and 1b cDNA.

The PCR products were subcloned into the pGEM-T™ vector from Promega (Madison, USA). The inserts were subjected to nucleotide sequence analysis, and the complete nucleotide sequences for all subclones were determined using a Thermo Sequenase™ dye terminator cycle sequencing pre-mix kit (Amersham Pharmacia Biotech, Uppsala, Sweden). Specific oligonucleotides complementary to the vector pGEM-T™, or primers complementary to the cDNA encoding the GABA$_B$ receptor, were used as primers for the sequencing reactions.

EXAMPLE 1C

Cloning and Sequencing of the 5'-end of the cDNA Encoding Human GABA$_B$ Receptor 1b Messenger RNA from human hippocampus was obtained from Clontech (Palo Alto, Calif., USA) (catalogue #6578-1). A Marathon™ cDNA amplification kit (Clontech) was used for performing 5'/3'-RACE (Rapid Amplification of cDNA Ends). Adaptor-ligated double stranded cDNA molecules were amplified according to standard methods, as described by the manufacturer. A pd(N)$_6$ primer from the First-strand™ cDNA Synthesis kit from Amersham Pharmacia Biotech (Uppsala, Sweden) was used to produce the adaptor-ligated cDNA.

A specific PCR primer was designed (Table 3) based on the sequences of the human GABA$_B$ receptor 1b cDNA obtained in Example 1A.

TABLE 3

Primers used in PCR to amplify the 5'-ends of human GABA$_B$ receptor cDNA

| Nr. | Source | Sequence 5'-3' | SEQ ID NO |
|---|---|---|---|
| 958 | Human | TGGCCCTCCACCGCCTCAGTCATCTCA | 16 |
| AP1 | Marathon kit | CCATCCTAATACGACTCACTATAGGGC | 17 | cDNA fragments encoding part of the human GABA$_B$ receptors were amplified directly by PCR using the designed primers with the generated adaptor-ligated cDNA molecules as templates. PCR was carried out using the Expand Long Template™ PCR System (Boehringer Mannheim GmbH, Germany) with the following PCR program: +94° C. for 1 minute, +94° C. for 30 seconds, +60° C. for 30 seconds, and +68° C. for 4 minutes, repeated 24 times. The primer combination AP1 and 958 produced a PCR product that corresponded to the 5'-end of the GABA$_B$ receptor 1b cDNA, including 190 base pairs upstream of the initiation codon.

The PCR products were subcloned into the pGEM-T™ vector from Promega (Madison, USA). The inserts were subjected to nucleotide sequence analysis, and the complete nucleotide sequences for all subclones were determined using a Thermo Sequenase™ dye terminator cycle sequencing pre-mix kit (Amersham Pharmacia Biotech, Uppsala, Sweden). Specific oligonucleotides complementary to the vector pGEM-T™, or primers complementary to the cDNA encoding the GABA$_B$ receptor, were used as primers for the sequencing reactions.

EXAMPLE 1D

Cloning and Sequencing of the 51'-end of the cDNA Encoding Human GABA$_B$ Receptor 1a Messenger RNA from human hippocampus was obtained from Clontech (Palo Alto, USA) (catalogue #6578-1). A Marathon™ cDNA amplification Kit (Clontech) was used to obtain adaptor-ligated double stranded cDNA molecules according to conventional methods as described by the manufacturer. The pd(N)$_6$ primer from the First-strand™ cDNA Synthesis kit from Amersham Pharmacia Biotech (Uppsala, Sweden) was used to obtain the adaptor-ligated cDNA.

Specific PCR primers were designed (as shown in Table 4) based on the sequences of the human GABA$_B$ receptor 1a cDNA obtained in Example 1 and the rat GABA$_B$ receptor 1a cDNA disclosed in WO 97/46675.

TABLE 4

Primers used to amplify the 5'-ends of the human GABA$_B$ receptor 1a cDNA

| Nr. | Species | Sequence 5'-3' | SEQ ID NO |
|---|---|---|---|
| 1033 | Human | CTCAATCTCATAGTCCACTGG | 18 |
| 1087 | Rat | CCTTGAGGCCCGGGGAGAG | 19 |

A cDNA fragment encoding part of the human GABA$_B$ 1a receptor was amplified directly by PCR using the designed primers with the generated adaptor-ligated cDNA molecules as templates. PCR was performed using Perkin Elmer Taq DNA polymerase with Gene Amp™ (Roche Molecular Systems Inc., NJ, USA) with the following PCR program: +94° C. for 1 minute, +50° C. for 30 seconds, +72° C. for 3 minutes, +94° C. for 1 minute, +60° C. for 30 seconds, and +72° C. for 4 minutes, repeated 34 times, and then +72° C. for 7 minutes.

The primer combination 1087 and 1033 produced a PCR product corresponding to the 5'-end of the GABA$_B$ receptor 1a cDNA, including 26 base pairs upstream of the initiation codon.

The PCR products were subcloned into the pGEM-T™ vector from Promega (Madison, USA). The inserts were subjected to nucleotide sequence analysis, and the complete nucleotide sequences for all subclones were determined using a Thermo Sequenase™ dye terminator cycle sequencing premix kit (Amersham Pharmacia Biotech, Uppsala, Sweden). Specific oligonucleotides complementary to the vector pGEM-T™ were used as primers for the sequencing reactions.

Complete cDNA sequences encoding the human GABA$_B$ receptor 1a (SEQ ID NO: 48) and the human GABA$_B$ receptor 1b (SEQ ID NO: 50) were obtained by aligning the sequences of the different fragments cloned and sequenced in Examples 1A, 1B, 1C, and 1D.

EXAMPLE 2A

Cloning and Sequencing of cDNA Encoding Canine GABA$_B$ Receptor 1a

A QuickPrep Micro mRNA Purification™ kit (Amersham Pharmacia Biotech, Uppsala, Sweden) was used to isolate mRNA from canine neural tissue according to conventional methods, as described by the manufacturer. First-strand cDNA synthesis reactions were performed using the First-strand™ cDNA Synthesis kit from Amersham Pharmacia Biotech (Uppsala, Sweden). The Not-I-d(T)$_{18}$ bifunctional or pd(N)$_6$ primer was used to prime the first-strand synthesis. The generated cDNA molecules were used as templates in the PCR reactions described below.

Specific PCR primers (as shown in Table 5) were designed based on the sequences of the rat GABA$_B$ receptor 1a and 1b cDNA (Kaupmann et al., 1997, EMBL accession numbers Y10369 (SEQ ID NO: 44) and Y10370 (SEQ ID NO: 46)). Various cDNA fragments encoding parts of the canine GABA$_B$ receptor were amplified directly by PCR using the designed primers with the generated cDNA molecules as templates. All PCR experiments were carried out using the Perkin Elmer Taq DNA polymerase with Gene Amp™ (Roche Molecular Systems Inc., NJ, USA) with the following PCR program: +95° C. for 1 minute, +50° C. for 30 seconds, and +72° C. for 3 minutes, repeated 44 times, and then +72° C. for 7 minutes. The following primer combinations produced PCR products with the expected sizes: 842 and 838, 838 and 795, and 838 and 865, which correspond to the 5'-part of the canine GABA$_B$ receptor cDNA. Primer pairs 848 and 844, 848 and 831, 848 and 841, and 840 and 841 produced PCR products which correspond to the 3'-part of the canine GABA$_B$ receptor cDNA.

TABLE 5

Primers used for RT-PCR on mRNA from canine cortex

| Nr. | Species | Sequence 5'-3' | SEQ ID NO |
|-----|---------|----------------|-----------|
| 795 | Rat | CAGGCACAGCTGGATCCGAGAAGAAACT | 20 |
| 831 | Rat | CGGTCGACTCACTTGTAAAGCAAATGTACTCGACTCCCATCACAGC | 21 |
| 838 | Rat | ATGCGCGCCGGCAGCCAACATGCTGCTGCTGCTGCTGGTGCCTCTCTTCC | 22 |
| 840 | Rat | CGTCAAGATGCTCGAATCATCG | 23 |
| 841 | Rat | CAGGGGGCTCAGAGGGTCCC | 24 |
| 842 | Rat | CAGGCACAGCTGGATCCGAGAAGAAACTCTGTCGGAAAGT | 25 |
| 844 | Rat | CGGTCGACTCACTTGTAAAGCAAATGTACTCGACTCCCATCACAGCTAAG | 26 |
| 848 | Rat | ACTTTCCGACAGAGTTTCTTCTCGGATCCAGCTGTGCCTG | 27 |
| 865 | Rat | CCACGATGATTCGAGCATCTTGACG | 28 |

The PCR products were subcloned into the pGEM-T™ vector from Promega (Madison, USA). The inserts were subjected to nucleotide sequence analysis, and the complete nucleotide sequences for all subclones were determined using a Thermo Sequenase™ dye terminator cycle sequencing premix kit (Amersham Pharmacia Biotech, Uppsala, Sweden). Specific oligonucleotides complementary to the vector pGEM-T™, or primers complementary to the cDNA encoding the GABA$_B$ receptor, were used as primers for the sequencing reactions.

EXAMPLE 2B

Cloning and Sequencing of the 3'- and 5'-ends of the cDNA Encoding Canine GABA$_B$ Receptor 1a A QuickPrep™ Micro mRNA Purification kit (Amersham Pharmacia Biotech, Uppsala, Sweden) was used to isolate mRNA from canine nerve tissue according to conventional methods, as described by the manufacturer. A Marathon™ cDNA amplification Kit (Clontech, Palo Alto, Calif., USA) was used for performing both 5'- and 3'-RACE. Two adaptor-ligated double stranded cDNA libraries were amplified according to conventional methods, as described by the manufacturer. A random primer (pd(N)$_6$) was used when amplifying the adaptor-ligated cDNA for the 5'-RACE, and the Marathon™ cDNA Synthesis primer (52-mer) was used when amplifying the adaptor ligated cDNA for the 3'-RACE.

Specific PCR primers were designed (as shown in Table 6) based on the sequence of canine GABA$_B$ receptor 1a cDNA obtained in Example 2A.

TABLE 6

Primers used in PCR to amplify the 5'- and 3'-ends of canine GABA$_B$ receptor 1a cDNA

| Nr. | Species | Sequence 5'-3' | SEQ ID NO |
|---|---|---|---|
| 936 | canine | CTACCGCGCAATGAACTCCTCGTC | 29 |
| 1076 | canine | CGAGGTGGCGTTGGGGGTCTGTGC | 30 |
| AP1 | Marathon kit | CCATCCTAATACGACTCACTATAGGGC | 31 |
| AP2 | Marathon kit | ACTCACTATAGGGCTCGAGCGGC | 32 |

Various cDNA fragments encoding parts of the canine GABA$_B$ receptor were amplified by PCR from the adaptor-ligated cDNA using the designed primers. A number of different PCR programs were tested to find conditions under which PCR products corresponding to GABA$_B$ receptor DNA were obtained. The 5'-PCR experiments were carried out using the Expand Long Template™ PCR System (Boehringer Mannheim GmbH, Germany) with the following PCR program: +94° C. for 30 seconds, +72° C. for 3 minutes, repeated 4 times; +94° C. for 30 seconds, +70° C. for 3 minutes, repeated 4 times; and +94° C. for 30 seconds, +68° C. for 3 minutes, repeated 24 times. The primer combination AP2 and 1076 produced a PCR product that corresponded to the 5'-end of the GABA$_B$ receptor cDNA, including 114 base pairs upstream the initiation codon.

The 3'-PCR experiments were carried out using the Expand Long Template™ PCR System (Boehringer Mannheim GmbH, Germany) with the following PCR program: +94° C. for 1 minute; +94° C. for 30 seconds, +60° C. for 30 seconds, and +68° C. for 4 minutes, repeated 29 times. The primer combination AP1 and 936 produced a PCR fragment that corresponded to the 3'-end of the GABA$_B$ receptor cDNA, including the poly(A) tail.

The PCR products were subcloned into the pGEM-T vector from Promega (Madison, USA). The inserts were subjected to nucleotide sequence analysis, and the complete nucleotide sequences for all subclones were determined using a Thermo Sequenase™ dye terminator cycle sequencing premix kit (Amersham Pharmacia Biotech, Uppsala, Sweden). Specific oligonucleotides complementary to the vector pGEM-T or primers complementary to GABA$_B$ receptor DNA were used as primers for sequencing reactions.

A complete cDNA sequence encoding the canine GABA$_B$ receptor 1a (SEQ ID NO: 52) was obtained by aligning the sequences of the various fragments obtained in Example 2A and Example 2B.

EXAMPLE 3A

Cloning of cDNA Encoding Human GABA$_B$ Receptor 1c and 1d from Jurkat Cells

A guanidine isothiocyanate/CsCl purification method was used to isolate total RNA from Jurkat cells. The first-strand cDNA synthesis was performed using a First-strand™ cDNA Synthesis kit from Amersham Pharmacia Biotech (Uppsala, Sweden). The pd(N)$_6$ primer was used to prime the first strand synthesis. The generated cDNA molecules were used as templates in the PCR reaction described below.

Specific PCR primers (as shown in Table 7) were designed based on the sequences of human GABA$_B$ receptor 1a and 1b cDNAs (Example 1), rat GABA$_B$ receptor (Kaupmann et al. 1997) and the EST sequence set forth in EMBL accession number Y11044.

TABLE 7

Primers used in RT-PCR on mRNA from Jurkat cells

| Nr. | Species | Sequence 5'-3' | SEQ ID NO |
|---|---|---|---|
| 938 | human | GACGCTTATCGAGCAGCTTC | 33 |
| 972 | human | AGCCCAGAACTCACAGGGGGACAT | 34 |
| 973 | human | GCTTCAAGCCAGGTACGAACTAA | 35 |
| 893 | rat | GGAGCACCCCCAAGCCCCACTG | 36 |
| 937 | human | CTGGTTCCTCCCAATGTG | 37 |
| 1005 | rat | CCTCTCACTCCCCTCATCTC | 38 |
| 1030 | human | AAGCCAACCTTCCCTGCTTCTC | 39 |

Various cDNA fragments encoding parts of the GABA$_B$ receptor were amplified directly by PCR using human- and rat-specific primers. All PCR experiments were carried out using Perkin Elmer Taq DNA polymerase with Gene Amp™ (Roche Molecular Systems Inc., NJ, USA) with the following PCR program: +95° C. for 1 minute; +54° C. for 1 minute, and +72° C. for 3 minutes, repeated 44 times; and then +72° C. for 7 minutes.

The PCR products were subcloned into the pGEM-T™ vector from Promega (Madison, USA). The inserts were subjected to nucleotide sequence analysis, and the complete nucleotide sequences for all subclones were determined using a Thermo Sequenase™ dye terminator cycle sequencing premix kit (Amersham Pharmacia Biotech, Uppsala, Sweden). Specific oligonucleotides complementary to the vector pGEM-T™ or primers complementary to GABA$_B$ receptor DNA were used as primers for the sequencing reactions.

The following primer combination produced PCR products corresponding to the 3'-end of the GABA$_B$ receptor cDNA: primer pairs 938 and 972; and 938 and 973. Unexpectedly, both of these fragments lacked 149 base pairs, resulting in a frame shift and the insertion of a new termination codon. The following primer combination produced a PCR product corresponding to the 5'-part of the GABA$_B$ receptor 1a cDNA: 893 and 937. The primer pairs 1005 and 937, and 1030 and 937 produced PCR products corresponding to the 5'-part of the GABA$_B$ receptor 1b cDNA. These PCR fragments lacked the same 149 base pairs that resulted in a frame shift and the insertion of a new termination codon.

These results show that Jurkat cells contain mRNA encoding two new forms of the human GABA$_B$ receptor. These new forms are designated GABA$_B$ receptor 1c (SEQ ID NO: 54 and 55) (with the mRNA including the same 5'-part as the GABA$_B$ receptor 1a) and GABA$_B$ receptor 1d (SEQ ID NO: 56 and 57) (with the mRNA including the same 5'-part as the GABA$_B$ receptor 1b). These two forms of the GABA$_B$ receptor do not contain any of the transmembrane region of the receptor and are therefore expected to be soluble forms of the receptor.

EXAMPLE 3B

Analysis of cDNA Encoding Human GABA$_B$ Receptors from Hippocampus

Messenger RNA from human hippocampus was obtained from Clontech (Palo Alto, USA) (catalogue #6578-1). First strand cDNA synthesis reactions were performed using the First-strand™ cDNA Synthesis kit from Amersham Pharmacia Biotech (Uppsala, Sweden). The pd(N)$_6$ primer was used to prime the first-strand synthesis. The generated cDNA molecules were used as templates in the PCR reactions described below.

Specific PCR primers were designed (as shown in Table 8) based on the sequences of the cDNAs encoding human GABA$_B$ receptors 1a and 1b.

TABLE 8

Primers used for RT-PCR on mRNA from human hippocampus

| Nr. | Species | Sequence 5'-3' | SEQ ID NO |
| --- | --- | --- | --- |
| 937 | Human | CTGGTTCCTCCCAATGTG | 40 |
| 938 | Human | GACGCTTATCGAGCAGCTTC | 41 | cDNA fragments encoding parts of the human GABA$_B$ receptors were amplified directly by PCR using the designed primers with the generated cDNA molecules as templates. All PCR experiments were carried out using Perkin Elmer Taq DNA polymerase with Gene Amp™ (Roche Molecular Systems Inc., NJ, USA) with the following PCR program: +94° C. for 1 minute, +50° C. for 30 seconds, +72° C. for 3 minutes; +94° C. for 1 minute, +54° C. for 30 seconds, and +72° C. for 3 minutes, repeated 44 times; and then +72° C. for 7 minutes. The primer combination of 938 and 937 produced PCR products that corresponded to the expected size of the GABA$_B$ receptor 1a and 1b cDNAs, and to a fragment of a smaller size.

The PCR products were subcloned into the pGEM-T vector from Promega (Madison, USA). The inserts were subjected to nucleotide sequence analysis, and the complete nucleotide sequences for all subclones were determined using a Thermo Sequenase™ dye terminator cycle sequencing premix kit (Amersham Pharmacia Biotech, Uppsala, Sweden). Specific oligonucleotides complementary to the vector pGEM-T™ or primers complementary to the cDNA encoding the GABA$_B$ receptor were used as primers for the sequencing reactions.

The larger PCR fragment was found to correspond to the 3'-part of the GABA$_B$ receptor 1a and 1b cDNA, and the smaller fragment which lacked 149 base pairs was found to correspond to the 3'-part of the GABA$_B$ receptors 1c and 1d cDNA identified in Example 3A.

EXAMPLE 4

Cloning and Sequencing of cDNA Encoding Canine GABA$_B$ Receptor 1b

A cDNA encoding the canine GABA$_B$ receptor 1b can be isolated in a manner similar to that described in Example 2 for receptor 1a. PCR primers specifically designed to be complementary to the 5'-end of the cDNA encoding the rat and human GABA$_B$ receptor 1b, together with PCR primers complementary to the 3'-end of the cDNA encoding the canine GABA$_B$ receptor 1a, and mRNA prepared from a suitable canine tissue, can be used.

EXAMPLE 5

Cloning of cDNA Encoding Canine GABA$_B$ Receptor 1c

Total RNA from canine liver was prepared using RNeasy™ Total RNA Purification Protocols (Qiagen GmbH, Germany). The first-strand cDNA synthesis was performed using a First-strand™ cDNA Synthesis kit from (Amersham Pharmacia Biotech, Uppsala, Sweden). The pd(N)$_6$ primer was used to prime the first-strand synthesis. The generated cDNA molecules were used as templates in the PCR reaction described below.

Specific PCR primers (as shown in Table 9) were designed based on the sequence of canine GABA$_B$ receptor 1a cDNA.

TABLE 9

Primers used in RT-PCR

| Nr. | Species | Sequence 5'-3' | SEQ ID NO |
| --- | --- | --- | --- |
| 936 | canine | CTACCGCGCAATGAACTCCTCGTC | 42 |
| 954 | canine | CCTTCTTCTCCTCCTTCTTAGTGA | 43 | cDNA fragments encoding part of the canine GABA$_B$ receptor were amplified directly by PCR using canine specific primers. All PCR reactions were carried out using Perkin Elmer Taq DNA polymerase with Gene Amp™ (Roche Molecular Systems Inc., NJ, USA) with the following PCR program: +95° C. for 1 minute, +54° C. for 30 seconds, and +72° C. for 3 minutes, repeated 44 times, and then +72° C. for 7 minutes. The primer combination produced PCR products having a size corresponding to the GABA$_B$ receptor 1a cDNA and a fragment of a smaller size, indicating the presence of GABA$_B$ receptor 1c cDNA.

The PCR products were subcloned into the pGEM-T™ vector from Promega (Madison, Wis.; USA). The inserts were subjected to nucleotide sequence analysis, and the complete nucleotide sequences for all subclones were determined using a Thermo Sequenase™ dye terminator cycle sequencing premix kit (Amersham Pharmacia Biotech, Uppsala, Sweden). Specific oligonucleotides complementary to the vector pGEM-T™ were used as primers for the sequencing reactions.

The smaller fragment was shown to have a deletion of 149 base pairs. This deletion caused a frame shift and insertion of a new termination codon, verifying the existence of a canine GABA$_B$ receptor 1c.

A complete cDNA sequence encoding the canine GABA$_B$ receptor 1c (SEQ ID NO: 58) was obtained by aligning the sequences of the fragments obtained in Example 2A, Example 2B and Example 5.

EXAMPLE 6

Cloning, Sequencing, and Organization of Human GABA$_B$ Receptor Genomic Fragments To determine the structural organization and sequence of the human GABA$_B$ receptor gene, human genomic DNA libraries and human genomic DNA were screened and analyzed. Human genomic libraries were obtained from Clontech (Palo Alto, Calif., USA). The libraries were constructed from female leukocyte DNA (catalog # HL1111J) cloned into a λEMBL-3 vector. The average size of the inserts was 16 kb, and the number of independent clones was $1.7 \times 10^6$. Human genomic DNA was obtained from Clontech (catalog #6550-1). In order to isolate recombinant phage containing exon and intron sequences of the human $GABA_B$ receptor gene, 48 individual bacterial plates, each having a diameter of 150 mm and approximately $4 \times 10^4$ individual plaques, were screened. Conventional methods and solutions were used, as described in The *Library Protocol Handbook: General Procedures for the Hybridization of Lambda Phage Libraries w/DNA Probes* (Clontech) with modifications as described below.

The experiment was carried out essentially as follows, and the following numbers are given on a per plate basis. A sample of the phage library, diluted in 0.1 ml sterile lambda diluent, was prepared to obtain an estimated titer of 40,000 pfu (plaque forming units). A 0.6 ml culture of the *E. coli* host strain K802 (obtained from Clontech) in LB-medium was infected with 40,000 pfu recombinant phage for 15 minutes at +37° C. The culture then was mixed with 7 ml top agarose (6.5 g of agarose added per liter of LB) and poured onto LB plates. The plates were incubated at +37° C. for approximately 7 hours. The plates were then chilled at +4° C.

Plaque hybridization experiments were carried out as follows. Membrane filters (Colony/Plaque Screen (DuPont, Wilmington, Del., USA)) were placed on top of the plates for 3 minutes. For denaturation of DNA, the filters were removed and floated in 0.5 M NaOH on plastic wrap for 2 minutes, with the plaque side up. This step was repeated to ensure efficient denaturation. Following neutralization, the membrane filters were placed in 1M Tris-HCl, pH 7.5, twice for 2 minutes, and allowed to dry.

Probes for screening of the membrane filters by DNA hybridization were obtained as follows. A $GABA_B$ receptor cDNA clone was digested with SacII to release a 479 bp fragment (base pairs 573-1051 of the cDNA encoding human $GABA_B$ receptor 1a, SEQ ID NO: 48). This 479 bp fragment was separated from the remaining $GABA_B$ receptor cDNA by electrophoresis on an agarose gel. A segment of the gel containing the 479 bp fragment was excised and transferred to a polypropylene microcentrifuge tube. Water was then added to the microcentrifuge tube at a ratio of 3 ml per gram of gel. The microcentrifuge tube then was placed in a boiling water bath for 7 minutes to melt the agarose gel and denature the DNA.

DNA (25 ng) contained within the melted agarose was labeled with $^{32}P$ using a Megaprime™ DNA labeling system (Amersham Pharmacia Biotech, Uppsala, Sweden) according to the supplier's instructions. Unincorporated $^{32}P$-labeled nucleotides were removed from the DNA sample with a MicroSpin™ G-50 Column (Amersham Pharmacia Biotech, Uppsala, Sweden). Additional probes were prepared by PCR amplification of various regions of the $GABA_B$ receptor cDNA (base pairs 68-486 and 2368-2863 of the cDNA encoding human $GABA_B$ receptor 1a, SEQ ID NO: 48). These probes also were labeled with $^{32}P$ and purified as described above.

The DNA hybridization reaction was performed under stringent conditions according to the method described below. The filter membranes were prehybridized at +65° C. for at least 1 hour in a solution of 1% SDS, 1M NaCl, and 10% dextran sulfate using a hybridization oven (Hybaid Ltd, Ashford, UK). Following prehybridization, a solution containing denatured herring sperm DNA at a final concentration of 100 µg/ml and the $^{32}P$-labeled DNA probe at a concentration <10 ng/ml (for optimal signal to background ratio) was added to the prehybridization solution, and the membrane filters were incubated at +65° C. for 10-20 hours. Following the removal of the hybridization solution, the membrane filters were washed in a solution of 2×SSC (0.3 M NaCl, 0.03 M Na-citrate), 1% SDS twice for 5 minutes at room temperature. The membrane filters then were washed twice more in the same solution, incubating at +60° C. for 30 minutes each wash. The filters then were washed twice at room temperature in 0.1×SSC. Finally, the membrane filters were placed on a sheet of filter paper with the DNA face up, and allowed to dry. The dried membrane filters were then exposed to X-ray films and autoradiographed.

Of the approximately $2 \times 10^6$ individual plaques analyzed, four hybridizing plaques were detected and isolated. These four isolates were designated #GR1, #GR12, #GR13 and #GR41, respectively. After several rescreening experiments, the recombinant phage DNA was purified using a Qiagen Lambda Midi™ Kit (Qiagen GmbH, Germany). The purified DNA was digested with SalI, and the fragments representing the inserts were isolated by agarose electrophoresis.

The approximate sizes of the inserts were: for isolate #GR1, 12 kb; for isolate #GR12, 12 kb; for isolate #GR13, 16 kb; and for isolate #GR41, 19 kb. These fragments were cloned into SalI digested linearized pUC19, resulting in the plasmids pAM362 (isolate #GR1), pAM363 (isolate #GR12), pAM364 (isolate #GR13), and pAM365 (isolate #GR41). The inserts from the four plaques that hybridized to $GABA_B$ receptor cDNA probes were analyzed by PCR, restriction mapping, and hybridization to $^{32}P$-labeled DNA fragments representing various regions of the $GABA_B$ receptor gene.

The cloned fragments in the plasmids pAM362, pAM363, pAM364, and pAM365 were characterized by restriction enzyme mapping, using EcoRI, HindIII, PstI, and BamHI. The approximate positions of the exons, and the approximate sizes of the introns, were analyzed and determined by PCR-based exon-exon linking and agarose gel electrophoresis.

To facilitate nucleotide sequence analysis, seven restriction sub-fragments derived from pAM364, two restriction fragments derived from pAM362, and one restriction sub-fragment derived from pAM365 were isolated and cloned into pUC19, resulting in the plasmids pAM366-pAM375. To this end, PCR primers located within the pUC19 sequence either upstream or downstream of the cloning site were combined with a PCR primer having a defined orientation and specific for the $GABA_B$ receptors derived subcloned fragment.

The inserts in the 10 plasmids pAM366-pAM375 were subjected to nucleotide sequence analysis. The nucleotide sequences for all subclones were determined using a Thermo Sequenase™ dye terminator cycle sequencing pre-mix kit (Amersham Pharmacia Biotech, Uppsala, Sweden). Specific oligonucleotides complementary to pUC19 or primers complementary to the $GABA_B$ receptor cDNA were used as primers for the sequencing reactions.

The genomic fragments cloned in the plasmids pAM362-pAM365 contain the complete transcribed part of the human $GABA_B$ receptor gene and extend more than 3 kb upstream of the first exon and more than 2 kb downstream of the last exon. The fragment cloned in the plasmid pAM362 contains exons 7-11; pAM363 contains exons 12-22; pAM364 contains exons 1-11; and pAM365 contains exons 12-23 of the $GABA_B$ receptor gene (FIG. 1). The sequences of exons 1-11 and introns 1-10 are set forth in SEQ ID NO: 60, and the sequences of exons 12-23 and introns 12-22 are set forth in SEQ ID NO: 61.

The human GABA$_B$ receptor gene consists of 23 exons and 22 introns (FIG. 1). The exons range in size from 21 bp to 1486 bp. As indicated in Table 10, the exon/intron boundaries are in accordance with the AG/GT rule and conform well to the consensus sequence suggested by Mount et al. 1982.

TABLE 10

Exon-Intron boundaries of the GABA$_B$ receptor gene, sequences at exon-intron junctions.

5' splice donor . . . 3' splice acceptor

```
Exon 1-Exon 2    CGAG    GTAAGAG (nt 3441-3451 of SEQ ID NO:60) . . . CCGCCTCTCACTTAG
                         ATGT    (nt 3894-3912 of SEQ ID NO:60)

Exon 2-Exon 3    GAAG    GTGCATC (nt 3990-4000 of SEQ ID NO:60) . . . CGACTCACCCCTTAG
                         GTTG    (nt 4680-4698 of SEQ ID NO:60)

Exon 3-Exon 4    TGTG    GTGAGTA (nt 4895-4905 of SEQ ID NO:60) . . . CCWATCTCTCCACAG
                         TCCG    (nt 5638-5656 of SEQ ID NO:60)

Exon 4-Exon 5    CAGG    GTGAGGG (nt 5835-5845 of SEQ ID NO:60) . . . CTTTCCTGCTGCCAG
                         TGAA    (nt 7170-7188 of SEQ ID NO:60)

Exon 5-Exon 6    TCAG    GTGAGAT (nt 7202-7212 of SEQ ID NO:60) . . . CGCACCCCTCCTCAG
                         AACG    (nt 8631-8649 of SEQ ID NO:60)

Exon 6-Exon 7    CAAG    GTAGCCC (nt 8803-8813 of SEQ ID NO:60) . . . CCTCTTGTCTTTCAG
                         TGTG    (nt 12257-12275 of SEQ ID NO:60)

Exon 7-Exon 8    TGTG    GTAAGCA (nt 12403-12413 of SEQ ID NO:60) . . . CTCCCTGCCCCACAG
                         CTTT    (nt 12806-12824 of SEQ ID NO:60)

Exon 8-Exon 9    TTCG    GTGAGCA (nt 12988-12998 of SEQ ID NO:60) . . . TTATTCCCACCCAAG
                         ACTC    (nt 14075-14093 of SEQ ID NO:60)

Exon 9-Exon 10   GAAG    GTCAGAT (nt 14188-14198 of SEQ ID NO:60) . . . CTTTCTCTGTKGTAG
                         CGCC    (nt 14463-14481 of SEQ ID NO:60)

Exon 10-Exon 11  TGAG    GTGGART (nt 14540-14550 of SEQ ID NO:60) . . . CTCCTCTGTATTCAG
                         GTGT    (nt 14988-15006 of SEQ ID NO:60)

Exon 11-Exon 12  CATG    GTGAGAG (nt 15191-15201 of SEQ ID NO:60) . . . TTTTTTCCTCCCAAG
                         ACAT    (nt 1910-1928 of SEQ ID NO:61)

Exon 12-Exon 13  CTCT    GTGAGTT (nt 2164-2174 of SEQ ID NO:61) . . . TGTTCCTTCCCTCAG
                         GGCC    (nt 2781-2799 of SEQ ID NO:61)

Exon 13-Exon 14  CAGG    CTTAGTA (nt 2856-2866 of SEQ ID NO:61) . . . TTGTCGTCTGCCCAG
                         GTGG    (nt 4394-4412 of SEQ ID NO:61)

Exon 14-Exon 15  ATTG    GTGAGTG (nt 4483-4493 of SEQ ID NO:61) . . . CCCTGTGCCATGCAG
                         GAGG    (nt 6016-6034 of SEQ ID NO:61)

Exon 15-Exon 16  TCCG    GTXAGTT (nt 6178-6188 of SEQ ID NO:61) . . . CCACCTCTGCCCTAG
                         TTAT    (nt 6664-6682 of SEQ ID NO:61)

Exon 16-Exon 17  CCAG    GTCAGGA (nt 6808-6818 of SEQ ID NO:61) . . . TCTCTTCCTTTCTAG
                         GCCC    (nt 8180-8198 of SEQ ID NO:61)

Exon 17-Exon 18  GAAG    GTGAGCT (nt 8308-8318 of SEQ ID NO:61) . . . CACATATTTATCCAG
                         ACTC    (nt 8394-8412 of SEQ ID NO:61)

Exon 18-Exon 19  TGAG    GTACCAC (nt 8513-8523 of SEQ ID NO:61) . . . TYGTTTCTGCCCTAG
                         ACAT    (nt 8914-8932 of SEQ ID NO:61)

Exon 19-Exon 20  CTTG    GTGTGTG (nt 9019-9029 of SEQ ID NO:61) . . . CTCCTGCCATCCTAG
                         GCAT    (nt 9702-9720 of SEQ ID NO:61)

Exon 20-Exon 21  GGCA    GTGAGCA (nt 9841-9851 of SEQ ID NO:61) . . . TGTCTTTCCCTCTAG
                         GTCC    (nt 10410-10428 of SEQ ID NO:61)

Exon 21-Exon 22  CAAG    GTAAGGA (nt 10550-10560 of SEQ ID NO:61) . . . AACATTTGCCCCAG
                         ATGC    (nt 10761-10779 of SEQ ID NO:61)

Exon 22-Exon 23  TGAG    GTGCGGG (nt 10916-10926 of SEQ ID NO:61) . . . TGCTTCTTCCTCCAG
                         AAAG    (nt 11686-11704 of SEQ ID NO:61)
```

A comparison of the sequences of the different forms of the human GABA$_B$ receptor cDNA (SEQ ID NO: 48, 50, 54, and 56) with the sequence of the human GABA$_B$ gene (SEQ ID NO: 60 and 61) reveals that various mRNAs encoding human GABA$_B$ receptors are formed by alternative splicing. The translational start site of the GABA$_B$ receptor 1a is in exon 2 and the translational stop signal is in exon 23. The mRNA encoding GABA$_B$ receptor 1b is formed by alternative splicing such that part of intron 5 is retained together with exon 6, and the translational start of the GABA$_B$ receptor 1b is derived from the intron sequence. The mRNA encoding GABA$_B$ receptor 1c is formed by alternative splicing such that exon 15 is removed along with introns 14 and 15, and a frame shift and a translational stop signal are generated in the sequence corresponding to exon 16. The mRNA encoding GABA$_B$ receptor 1d is formed when the translational start of the GABA$_B$ receptor 1b is generated together with the translational stop of the GABA$_B$ receptor 1c.

The GABA$_B$ receptor 1a isoform is formed by splicing exon 5 to a cryptic splice site in the middle of exon 6. Transcription of the GABA$_B$ receptor 1b isoform mRNA is most likely initiated from regulatory elements in intron 5. The ATG that initiates translation of GABA$_B$ receptor 1b mRNA is located in the 5'-end of exon 6.

Additional mRNA variants encoding variants of the human GABA$_B$ receptor can be derived by alternative splicing such that one or more of the exons, or parts of exons, are excised in the processing of the pre-mRNA. Subsequent translation of these mRNAs gives rise to variants of the human GABA$_B$ receptor having potentially different biological and/or pharmacological activities.

EXAMPLE 7

Analysis of cDNA Encoding Human GABA$_B$ Receptors from Human Brain

Messenger RNA from human fetal brain (catalog #6525-1) and adult human brain (catalog #6516-1) were obtained from Clontech (Palo Alto, Calif., USA). First strand cDNA synthesis reactions were performed using a First Strand™ cDNA Synthesis kit from Amersham Pharmacia Biotech (Uppsala, Sweden). The pd(N)$_6$ primer was used to prime the first-strand synthesis. The generated cDNA molecules were used as templates in the PCR reactions described below.

Specific PCR primers were designed (as shown in Table 11) based on the sequences of the rat GABA$_B$ receptor 1a and 1b cDNA and human GABA$_B$ receptor 1a and 1b cDNA. Various cDNA fragments encoding parts of the human GABA$_B$ receptors were amplified directly by PCR using the designed primers with the generated cDNA molecules as templates. PCR experiments with primers 838, 863, 864, and 865 were carried out using Perkin Elmer Taq DNA polymerase with GeneAmp™ (Roche Molecular System Inc., NJ, USA) with the following PCR program: +95° C. for 1 minute, +50° C. for 30 seconds, and +72° C. for 3 minutes, repeated 44 times, and then +72° C. for 7 minutes. PCR experiments with primers 937 and 1015 were carried out using the Expand Long Template™ PCR System (Boehringer Mannheim GmbH, Germany) with the following PCR program: +94° C. for 2 minutes, +94° C. for 10 seconds, +55° C. for 30 seconds, and +68° C. for 3 minutes, repeated 35 times, and then +68° C. for 7 minutes. The primer combinations 838 and 863, 864 and 863, 864 and 865, and 937 and 1015 produced the expected PCR products.

TABLE 11

Primers used for RT-PCR on mRNA from human fetal brain

| Nr. | Species | Sequence 5'-3' | SEQ ID NO |
|---|---|---|---|
| 838 | Rat | ATGCGCGCCGGCAGCCAACATGCTGCTGCTGCTGCTGGTGCCTCTCTTCC | 62 |
| 863 | Rat | GGTCATCCAGCGTTGAGGTGAAGAC | 63 |
| 864 | Rat | GAAGGTTGCCAGATTATACATCCGC | 64 |
| 865 | Rat | CCACGATGATTCGAGCATCTTGACG | 65 |
| 937 | Human | CTGGTTCCTCCCAATGTG | 66 |
| 1015 | Human | CCAGTGGACTATGAGATTGAG | 67 |

The PCR products were subcloned into the pGEM-T™ vector from Promega (Madison, Wis., USA), and the inserts were subjected to nucleotide sequence analysis. The complete nucleotide sequences for all subclones were determined using a Thermo Sequenase™ dye terminator cycle sequencing pre-mix kit (Amersham Pharmacia Biotech, Uppsala, Sweden). Specific oligonucleotides complementary to the vector pGEM-T™ or primers complementary to the cDNA encoding the GABA$_B$ receptor were used as primers for the sequencing reactions.

A number of analyzed clones isolated from fetal brain lacked 186 base pairs corresponding to exon 4. Such alternative splicing resulted in a cDNA (SEQ ID NO: 70) encoding a protein (SEQ ID NO: 71) containing 899 amino acids, and designated GABA$_B$ receptor 1e.

Other clones from fetal brain lacked 368 base pairs, corresponding to exons 4, 5, and 6, and resulting in a cDNA (SEQ ID NO: 72) having a frame shift and a translational stop codon generated in the sequence corresponding to exon 7. This cDNA encoded a protein (SEQ ID NO: 73) that included only 97 amino acids, which was designated GABA$_B$ receptor 1f.

One clone lacked 207 base pairs, corresponding to exons 4 and 5, and resulting in a cDNA (SEQ ID NO: 74) encoding a protein (SEQ ID NO: 75) containing 892 amino acids and designated GABA$_B$ receptor 1g.

Another clone had two deletions: the first deleted 186 base pairs corresponding to exon 4, and the second deleted 39 base pairs corresponding to part of exon 6. The resulting cDNA (SEQ ID NO: 76) encoded a protein (SEQ ID NO: 77) containing 886 amino acids, designated GABA$_B$ receptor 1h.

Another clone from adult human brain had a deletion of 1194 base pairs corresponding to base pairs 319-1512 of the cDNA encoding human $GABA_B$ receptor 1a. This deletion corresponds to part of exon 4, exons 5-11, and part of exon 12. This cDNA (SEQ ID NO: 78) encodes a protein (SEQ ID NO: 79) containing 563 amino acids, designated $GABA_B$ receptor 1i.

One clone isolated from fetal brain lacked 284 base pairs corresponding to part of exon 3 and all of exon 4, generating a frame shift and a translational stop codon in the sequence corresponding to exon 5. This cDNA (SEQ ID NO: 80) encodes a protein (SEQ ID NO: 81) containing only 105 amino acids, designated $GABA_B$ receptor 1j.

EXAMPLE 8

Analysis of cDNA Encoding Human $GABA_B$ Receptors from Jurkat Cells

A guanidine isothiocyanate/CsCl method was used to isolate total RNA from Jurkat cells. First strand cDNA synthesis reactions were performed using the First Strand™ cDNA Synthesis kit from Amersham Pharmacia Biotech (Uppsala, Sweden). The $pd(N)_6$ primer was used to prime the first-strand synthesis. The generated cDNA molecules were used as templates in the PCR reactions described below.

Specific PCR primers were designed (as shown in Table 12) based on the sequences of the human $GABA_B$ receptor 1a and 1b cDNA.

TABLE 12

Primers used for RT-PCR on mRNA from Jurkat cells

| Nr. | Species | Sequence 5'-3' | SEQ ID NO |
|---|---|---|---|
| 937 | Human | CTGGTTCCTCCCAATGTG | 68 |
| 1015 | Human | CCAGTGGACTATGAGATTGAG | 69 | cDNA fragments encoding parts of the human $GABA_B$ receptors were amplified directly by PCR using the designed primers with the generated cDNA molecules as templates. PCR was carried out using the Expand Long Template™ PCR System (Boehringer Mannheim GmbH, Germany) with the following PCR program: +94° C. for 2 minutes; +94° C. for 10 seconds, +55° C. for 30 seconds, and +68° C. for 3 minutes, repeated 35 times; and then +68° C. for 7 minutes. The primer combination 937 and 1015 produced a PCR product.

The PCR products were subcloned into the pGEM-T vector from Promega (Madison, Wis., USA), and the inserts were subjected to nucleotide sequence analysis. The complete nucleotide sequences for all subclones were determined using a Thermo Sequenase™ dye terminator cycle sequencing premix kit (Amersham Pharmacia Biotech, Uppsala, Sweden). Specific oligonucleotides complementary to the vector pGEM-T or primers complementary to the cDNA encoding the $GABA_B$ receptor were used as primers for the sequencing reactions.

Two clones had two deletions: the first deleted 368 base pairs corresponding to exons 4, 5, and 6; the second deleted 151 base pairs corresponding to exon 15, with a frame shift and a translational stop codon generated in the sequence corresponding to exon 7. This cDNA (SEQ ID NO: 82) encodes a protein (SEQ ID NO: 83) containing only 98 amino acids, which is designated $GABA_B$ receptor 1k, and which is identical to the $GABA_B$ receptor 1f described above.

Two other clones also had two deletions: the first a deletion of 246 base pairs corresponding to part of exon 4, exon 5, and exon 6; the second deletion lacked 149 base pairs corresponding to exon 15, generating a frame shift and a translational stop codon in the sequence corresponding to exon 16. This cDNA (SEQ ID NO: 84) encodes a protein (SEQ ID NO: 5) containing 496 amino acids, which is designated $GABA_B$ receptor 1l.

Additional variants of cDNAs encoding the human $GABA_B$ receptors can be identified in a similar manner using PCR primers based on the sequences of the cDNAs and genomic fragments encoding the human $GABA_B$ receptors disclosed herein.

The biological activity of these variants of the human $GABA_B$ receptor can be evaluated by transfection of suitable host cells with expression vectors containing the corresponding cDNA sequences, and measuring binding of labeled ligands activation of the receptor, or modulation of receptor function.

EXAMPLE 9

Generation of Antibodies

Antibodies were raised in rabbits against four different BSA-conjugated 20 amino acid-long synthetic peptides corresponding to selected regions of the human and canine $GABA_B$ receptor extracellular domains. Two polyclonal antibodies were directed against a sequence common to $GABA_B$ receptors 1a and b (ab1 and ab2), one against a $GABA_B$ receptor 1a-specific region (a1), and one against a $GABA_B$ receptor 1b-specific sequence (b1). To allow BSA-conjugation, a cysteine residue was added to the amino terminus in all peptides except a1, which contains an endogenous cysteine. The peptide sequences are as follows:

Peptide a1: (amino acids 18-37 of SEQ ID NO: 49) $NH_2$-Gly Gly Ala Gln Thr Pro Asn Ala Thr Ser Glu Gly Cys Gln Ile Ile His Pro Pro Trp-COOH Peptide ab1: (amino acids 197-216 of SEQ ID NO: 49, with N-terminally added Cys) $NH_2$-Cys Glu Asp Val Asn Ser Arg Arg Asp Ile Leu Pro Asp Tyr Glu Leu Lys Leu Ile His His-COOH Peptide ab2: (amino acids 271-290 of SEQ ID NO: 49, with N-terminally added Cys) $NH_2$-Cys Ser Pro Ala Leu Ser Asn Arg Gln Arg Phe Pro Thr Phe Phe Arg Thr His Pro Ser Ala-COOH Peptide b1: (amino acids 30-47 of SEQ ID NO: 57, with N-terminally added Cys) $NH_2$-Cys Ser His Ser Pro His Leu Pro Arg Pro His Ser Arg Val Pro Pro His Pro Ser-COOH The antibodies were purified from rabbit serum by affinity chromatography using the corresponding immobilized peptide. The antibodies subsequently were used to detect expression of recombinant $GABA_B$ receptor isoforms on Western blots.

EXAMPLE 10

Heterologous Expression of $GABA_B$ Receptor Isoforms in Mammalian Cells

Figure 2:
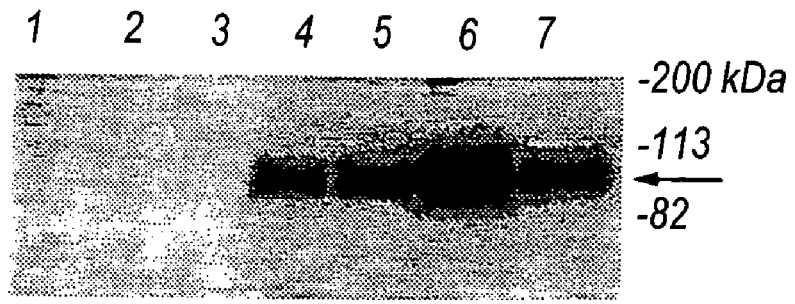
FIG. 2 is a Western blot illustrating expression of the human $GABA_B$ receptor 1b isoform in transfected C127 cells. A polyclonal anti-human $GABA_B$ receptor antibody was used. Lane 1: Untransfected C127 whole cell lysate. Lanes 2-7: Whole cell lysates of six independent clones transfected with cDNA encoding the human $GABA_B$ receptor 1b isoform. The clones analyzed in lanes 4 to 7 express a $GABA_B$ receptor of the expected molecular weight (arrow)

A HindIII/SalI cDNA fragment encoding the human $GABA_B$ receptor 1b isoform was cloned into a BPV (bovine papilloma virus)-based expression vector containing the mMT-1 (murine metallothionein) promoter. Using a calcium phosphate transfection method, murine C127 cells were co-transfected with the $GABA_B$ receptor expression construct and an expression plasmid containing a G418 resistance marker gene. G418 resistant clones were evaluated by Western blot analysis for expression of the approximately 100 kDa $GABA_B$ receptor 1b isoform (FIG. 2). The human $GABA_B$ receptor 1b isoform also was expressed in human HEK-293 cells using a pCI-neo expression vector and Lipofectamine™ (Life Technologies, Inc., Rockville, Md., USA) for transfection. The identity of the heterologously expressed receptor was verified in HEK-293 cells by Western blot analysis and radioligand binding experiments.

Figure 3:
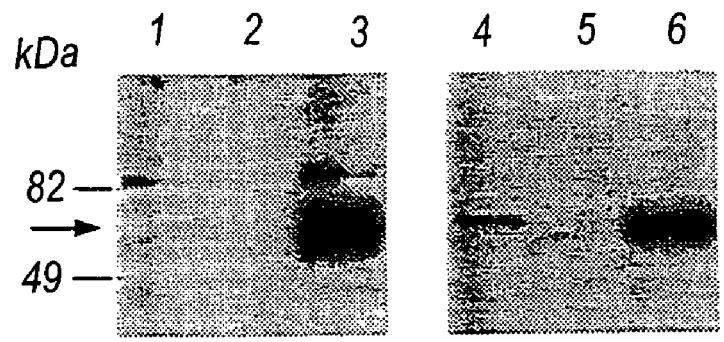
FIG. 3 is a Western blot illustrating expression of the human $GABA_B$ receptor 1d isoform in transfected C127 cells. A polyclonal anti-human $GABA_B$ receptor antibody was used. Lanes 1-3: Concentrated culture media from three independent C127 clones transfected with a cDNA expression construct encoding the human $GABA_B$ receptor 1d isoform. Lanes 4-6: Whole cell lysates corresponding to the clones analyzed in lanes 1-3. The figure shows that the human $GABA_B$ receptor 1d cDNA encodes a secreted isoform. The arrow indicates the bands corresponding to the 1d isoform.

A cDNA fragment encoding the human $GABA_B$ receptor 1d isoform was cloned into a BPV-based expression vector containing the mMT-1 promoter. Using a calcium phosphate transfection method, murine C127 cells were co-transfected with the $GABA_B$ receptor expression construct and an expression plasmid containing a G418 resistance marker gene. G418 resistant clones, and concentrated medium from such clones, were evaluated for $GABA_B$ receptor 1d isoform expression by Western blot analysis (FIG. 3). This experiment revealed that the human $GABA_B$ receptor 1d is a secreted isoform.

EXAMPLE 11

Heterologous Expression of $GABA_B$ Receptor Isoforms in E. Coli

Figure 4:
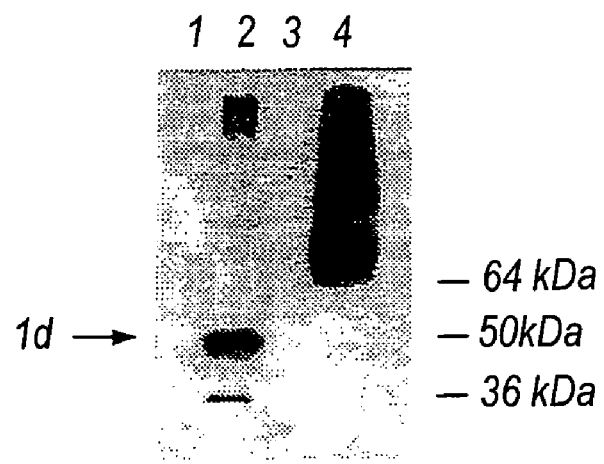
FIG. 4 is a Western blot illustrating expression of the human $GABA_B$ receptor 1d isoform in *E. coli*. A polyclonal anti-human $GABA_B$ receptor antibody was used. Lane 1.

A cDNA fragment encoding the human $GABA_B$ receptor 1d isoform was cloned into a modified pET (Pharmacia Amersham, Uppsala, Sweden) vector downstream of a STII (heat stable enterotoxin II of E. coli) signal peptide. The cDNA insert was followed by a thrombin cleavage site and a hexahistidine tag. The expression construct was subsequently used to transform the BL21 (DE3) E. coli strain BL21 (DE3). Western blot analysis of IPTG-induced bacteria revealed expression of a human $GABA_B$ receptor 1d isoform of the expected size (FIG. 4).

In addition, the human $GABA_B$ receptor 1d isoform was successfully expressed in E. coli strain AD494 (DE3) without fusion to a bacterial signal peptide.

EXAMPLE 12

Method for the Screening of Substances which are $GABA_B$ Receptor Antagonists or Agonists $GABA_B$ receptor expressing cells, and transgenic animals or cells and tissues derived therefrom, are used to screen substance libraries for antagonist or agonist activities. Screening can be performed as ligand binding assays or functional assays. For screening, cells and tissues are prepared in various ways, each uniquely suited to its purpose. Ligand binding assays are performed in vivo or in vitro. Functional assays exemplified by, but not limited to, $Ca^{++}$-responses, cAMP-responses and effects on $Cl^-$ and $K^+$ channels, are performed in living cells, broken cells, or isolated cell membranes, as well as in tissues and in living animals.

What is claimed is:

1. An isolated GABA$_B$ receptor polypeptide comprising a sequence at least 99% identical to SEQ ID NO:49.

2. An isolated polypeptide comprising the sequence of SEQ ID NO:49.

3. An isolated polypeptide comprising the sequence of SEQ ID NO:49 minus an N-terminal sequence of SEQ ID NO:49, wherein the N-terminal sequence is 1-25 amino acids long.

4. An isolated polypeptide the amino acid sequence of which consists of SEQ ID NO:49.

5. An isolated polypeptide consisting of the sequence of SEQ ID NO:49 minus an N-terminal sequence of SEQ ID NO:49, wherein the N-terminal sequence is 1-25 amino acids long.

6. A screening method comprising
   (a) contacting the polypeptide of claim 1 with a test compound; and
   (b) detecting binding of the test compound to the polypeptide.

7. The method of claim 6, further comprising
   (c) selecting a test compound that binds to the polypeptide; and
   (d) testing the compound for its ability to inhibit transient lower esophageal sphincter relaxations (TLESR).

8. The method of claim 6, wherein the polypeptide is expressed on a cell that contains a recombinant DNA encoding the polypeptide.

9. A screening method comprising
(a) contacting the polypeptide of claim 2 with a test compound; and
(b) detecting binding of the test compound to the polypeptide.

10. The method of claim 9, further comprising
(c) selecting a test compound that binds to the polypeptide; and
(d) testing the compound for its ability to inhibit transient lower esophageal sphincter relaxations (TLESR).

11. The method of claim 9, wherein the polypeptide is expressed on a cell that contains a recombinant DNA encoding the polypeptide.

12. A screening method comprising
(a) contacting the polypeptide of claim 3 with a test compound; and
(b) detecting binding of the test compound to the polypeptide.

13. The method of claim 12, further comprising
(c) selecting a test compound that binds to the polypeptide; and
(d) testing the compound for its ability to inhibit transient lower esophageal sphincter relaxations (TLESR).

14. The method of claim 12, wherein the polypeptide is expressed on a cell that contains a recombinant DNA encoding the polypeptide.

15. A screening method comprising
(a) contacting the polypeptide of claim 4 with a test compound; and
(b) detecting binding of the test compound to the polypeptide.

16. The method of claim 15, further comprising
(c) selecting a test compound that binds to the polypeptide; and
(d) testing the compound for its ability to inhibit transient lower esophageal sphincter relaxations (TLESR).

17. The method of claim 15, wherein the polypeptide is expressed on a cell that contains a recombinant DNA encoding the polypeptide.

18. A screening method comprising
(a) contacting the polypeptide of claim 5 with a test compound; and
(b) detecting binding of the test compound to the polypeptide.

19. The method of claim 18, further comprising
(c) selecting a test compound that binds to the polypeptide; and
(d) testing the compound for its ability to inhibit transient lower esophageal sphincter relaxations (TLESR).

20. The method of claim 18, wherein the polypeptide is expressed on a cell that contains a recombinant DNA encoding the polypeptide.

\* \* \* \* \*

SEQUENCE LISTING

<160> NUMBER OF SEQ ID NOS: 85

<210> SEQ ID NO 1
<211> LENGTH: 27
<212> TYPE: DNA
<213> ORGANISM: Rattus norvegicus

<400> SEQUENCE: 1
gtttcttctc ggatccagct gtgcctg                                    27

<210> SEQ ID NO 2
<211> LENGTH: 28
<212> TYPE: DNA
<213> ORGANISM: Rattus norvegicus

<400> SEQUENCE: 2
caggcacagc tggatccgag aagaaact                                   28

<210> SEQ ID NO 3
<211> LENGTH: 38
<212> TYPE: DNA
<213> ORGANISM: Rattus norvegicus

<400> SEQUENCE: 3
cggtcgactc acttgtaaag caaatgtact cgactccc                        38

<210> SEQ ID NO 4
<211> LENGTH: 41
<212> TYPE: DNA
<213> ORGANISM: Rattus norvegicus

<400> SEQUENCE: 4
atgcgcgccg gcagccaaca tgctgctgct gctgctggtg c                    41

<210> SEQ ID NO 5
<211> LENGTH: 46
<212> TYPE: DNA
<213> ORGANISM: Rattus norvegicus

<400> SEQUENCE: 5
cggtcgactc acttgtaaag caaatgtact cgactcccat cacagc        46

<210> SEQ ID NO 6
<211> LENGTH: 50
<212> TYPE: DNA
<213> ORGANISM: Rattus norvegicus

<400> SEQUENCE: 6
atgcgcgccg gcagccaaca tgctgctgct gctgctggtg cctctcttcc        50

<210> SEQ ID NO 7
<211> LENGTH: 40
<212> TYPE: DNA
<213> ORGANISM: Rattus norvegicus

<400> SEQUENCE: 7
caggcacagc tggatccgag aagaaactct gtcggaaagt        40

<210> SEQ ID NO 8
<211> LENGTH: 25
<212> TYPE: DNA
<213> ORGANISM: Rattus norvegicus

<400> SEQUENCE: 8
ggtcatccag cgttgaggtg aagac        25

<210> SEQ ID NO 9
<211> LENGTH: 25
<212> TYPE: DNA
<213> ORGANISM: Rattus norvegicus

<400> SEQUENCE: 9
gaaggttgcc agattataca tccgc        25

<210> SEQ ID NO 10
<211> LENGTH: 25
<212> TYPE: DNA
<213> ORGANISM: Rattus norvegicus

<400> SEQUENCE: 10
ccacgatgat tcgagcatct tgacg        25

<210> SEQ ID NO 11
<211> LENGTH: 22
<212> TYPE: DNA
<213> ORGANISM: Rattus norvegicus

<400> SEQUENCE: 11
gcctctcact cccctcatct cc        22

<210> SEQ ID NO 12
<211> LENGTH: 21
<212> TYPE: DNA
<213> ORGANISM: Homo sapiens

<400> SEQUENCE: 12

```
gagtgaagga ggctggaatt g                                             21

<210> SEQ ID NO 13
<211> LENGTH: 20
<212> TYPE: DNA
<213> ORGANISM: Homo sapiens

<400> SEQUENCE: 13
gacgcttatc gagcagcttc                                               20

<210> SEQ ID NO 14
<211> LENGTH: 24
<212> TYPE: DNA
<213> ORGANISM: Homo sapiens

<400> SEQUENCE: 14
agcccagaac tcacaggggg acat                                          24

<210> SEQ ID NO 15
<211> LENGTH: 23
<212> TYPE: DNA
<213> ORGANISM: Homo sapiens

<400> SEQUENCE: 15
gcttcaagcc aggtacgaac taa                                           23

<210> SEQ ID NO 16
<211> LENGTH: 27
<212> TYPE: DNA
<213> ORGANISM: Homo sapiens

<400> SEQUENCE: 16
tggccctcca ccgcctcagt catctca                                       27

<210> SEQ ID NO 17
<211> LENGTH: 27
<212> TYPE: DNA
<213> ORGANISM: Artificial Sequence
<220> FEATURE:
<223> OTHER INFORMATION: primer for PCR

<400> SEQUENCE: 17
ccatcctaat acgactcact atagggc                                       27

<210> SEQ ID NO 18
<211> LENGTH: 21
<212> TYPE: DNA
<213> ORGANISM: Homo sapiens

<400> SEQUENCE: 18
ctcaatctca tagtccactg g                                             21

<210> SEQ ID NO 19
<211> LENGTH: 19
<212> TYPE: DNA
<213> ORGANISM: Rattus norvegicus

<400> SEQUENCE: 19
ccttgaggcc cggggagag                                                19

<210> SEQ ID NO 20
<211> LENGTH: 28
<212> TYPE: DNA
<213> ORGANISM: Rattus norvegicus
```

<400> SEQUENCE: 20
caggcacagc tggatccgag aagaaact                                  28

<210> SEQ ID NO 21
<211> LENGTH: 46
<212> TYPE: DNA
<213> ORGANISM: Rattus norvegicus

<400> SEQUENCE: 21
cggtcgactc acttgtaaag caaatgtact cgactcccat cacagc              46

<210> SEQ ID NO 22
<211> LENGTH: 50
<212> TYPE: DNA
<213> ORGANISM: Rattus norvegicus

<400> SEQUENCE: 22
atgcgcgccg gcagccaaca tgctgctgct gctgctggtg cctctcttcc          50

<210> SEQ ID NO 23
<211> LENGTH: 22
<212> TYPE: DNA
<213> ORGANISM: Rattus norvegicus

<400> SEQUENCE: 23
cgtcaagatg ctcgaatcat cg                                        22

<210> SEQ ID NO 24
<211> LENGTH: 20
<212> TYPE: DNA
<213> ORGANISM: Rattus norvegicus

<400> SEQUENCE: 24 caggggctc agagggtccc                                            20

<210> SEQ ID NO 25
<211> LENGTH: 40
<212> TYPE: DNA
<213> ORGANISM: Rattus norvegicus

<400> SEQUENCE: 25
caggcacagc tggatccgag aagaaactct gtcggaaagt                     40

<210> SEQ ID NO 26
<211> LENGTH: 50
<212> TYPE: DNA
<213> ORGANISM: Rattus norvegicus

<400> SEQUENCE: 26
cggtcgactc acttgtaaag caaatgtact cgactcccat cacagctaag          50

<210> SEQ ID NO 27
<211> LENGTH: 40
<212> TYPE: DNA
<213> ORGANISM: Rattus norvegicus

<400> SEQUENCE: 27
actttccgac agagtttctt ctcggatcca gctgtgcctg                     40

<210> SEQ ID NO 28
<211> LENGTH: 25
<212> TYPE: DNA

```
<213> ORGANISM: Rattus norvegicus

<400> SEQUENCE: 28
ccacgatgat tcgagcatct tgacg                                    25

<210> SEQ ID NO 29
<211> LENGTH: 24
<212> TYPE: DNA
<213> ORGANISM: Canis familiaris

<400> SEQUENCE: 29
ctaccgcgca atgaactcct cgtc                                     24

<210> SEQ ID NO 30
<211> LENGTH: 24
<212> TYPE: DNA
<213> ORGANISM: Canis familiaris

<400> SEQUENCE: 30
cgaggtggcg ttgggggtct gtgc                                     24

<210> SEQ ID NO 31
<211> LENGTH: 27
<212> TYPE: DNA
<213> ORGANISM: Artificial Sequence
<220> FEATURE:
<223> OTHER INFORMATION: primer for PCR

<400> SEQUENCE: 31
ccatcctaat acgactcact atagggc                                  27

<210> SEQ ID NO 32
<211> LENGTH: 23
<212> TYPE: DNA
<213> ORGANISM: Artificial Sequence
<220> FEATURE:
<223> OTHER INFORMATION: primer for PCR

<400> SEQUENCE: 32
actcactata gggctcgagc ggc                                      23

<210> SEQ ID NO 33
<211> LENGTH: 20
<212> TYPE: DNA
<213> ORGANISM: Homo sapiens

<400> SEQUENCE: 33
gacgcttatc gagcagcttc                                          20

<210> SEQ ID NO 34
<211> LENGTH: 24
<212> TYPE: DNA
<213> ORGANISM: Homo sapiens

<400> SEQUENCE: 34
agcccagaac tcacaggggg acat                                     24

<210> SEQ ID NO 35
<211> LENGTH: 23
<212> TYPE: DNA
<213> ORGANISM: Homo sapiens

<400> SEQUENCE: 35
gcttcaagcc aggtacgaac taa                                      23
```

```
<210> SEQ ID NO 36
<211> LENGTH: 22
<212> TYPE: DNA
<213> ORGANISM: Rattus norvegicus

<400> SEQUENCE: 36
ggagcacccc caagccccac tg                                              22

<210> SEQ ID NO 37
<211> LENGTH: 18
<212> TYPE: DNA
<213> ORGANISM: Homo sapiens

<400> SEQUENCE: 37
ctggttcctc ccaatgtg                                                   18

<210> SEQ ID NO 38
<211> LENGTH: 20
<212> TYPE: DNA
<213> ORGANISM: Rattus norvegicus

<400> SEQUENCE: 38
cctctcactc ccctcatctc                                                 20

<210> SEQ ID NO 39
<211> LENGTH: 22
<212> TYPE: DNA
<213> ORGANISM: Homo sapiens

<400> SEQUENCE: 39
aagccaacct tccctgcttc tc                                              22

<210> SEQ ID NO 40
<211> LENGTH: 18
<212> TYPE: DNA
<213> ORGANISM: Homo sapiens

<400> SEQUENCE: 40
ctggttcctc ccaatgtg                                                   18

<210> SEQ ID NO 41
<211> LENGTH: 20
<212> TYPE: DNA
<213> ORGANISM: Homo sapiens

<400> SEQUENCE: 41
gacgcttatc gagcagcttc                                                 20

<210> SEQ ID NO 42
<211> LENGTH: 24
<212> TYPE: DNA
<213> ORGANISM: Canis familiaris

<400> SEQUENCE: 42
ctaccgcgca atgaactcct cgtc                                            24

<210> SEQ ID NO 43
<211> LENGTH: 24
<212> TYPE: DNA
<213> ORGANISM: Canis familiaris

<400> SEQUENCE: 43
```

-continued

```
ccttcttctc ctccttctta gtga                                              24
```

<210> SEQ ID NO 44
<211> LENGTH: 2883
<212> TYPE: DNA
<213> ORGANISM: Rattus norvegicus
<220> FEATURE:
<221> NAME/KEY: CDS
<222> LOCATION: (1)...(2880)

<400> SEQUENCE: 44

| | | | | | | | | | | | | | | | | |
|---|---|---|---|---|---|---|---|---|---|---|---|---|---|---|---|---|
| atg | ctg | ctg | ctg | ctg | ctg | gtg | cct | ctc | ttc | ctc | cgc | ccc | ctg | ggc | gct | 48 |
| Met | Leu | Leu | Leu | Leu | Leu | Val | Pro | Leu | Phe | Leu | Arg | Pro | Leu | Gly | Ala | |
| 1 | | | | 5 | | | | | 10 | | | | | 15 | | |

| ggg | gcg | cag | acc | ccc | aac | gcc | acc | tcg | gaa | ggt | tgc | cag | att | ata | 96 |
|---|---|---|---|---|---|---|---|---|---|---|---|---|---|---|---|
| Gly | Gly | Ala | Gln | Thr | Pro | Asn | Ala | Thr | Ser | Glu | Gly | Cys | Gln | Ile | Ile |
| | | 20 | | | | | 25 | | | | | 30 | | | |

| cat | ccg | ccc | tgg | gaa | ggt | ggc | atc | agg | tac | cgt | ggc | ttg | act | cgc | gac | 144 |
|---|---|---|---|---|---|---|---|---|---|---|---|---|---|---|---|---|
| His | Pro | Pro | Trp | Glu | Gly | Gly | Ile | Arg | Tyr | Arg | Gly | Leu | Thr | Arg | Asp | |
| | | 35 | | | | | 40 | | | | | 45 | | | | |

| cag | gtg | aag | gcc | atc | aac | ttc | ctg | cct | gtg | gac | tat | gag | atc | gaa | tat | 192 |
|---|---|---|---|---|---|---|---|---|---|---|---|---|---|---|---|---|
| Gln | Val | Lys | Ala | Ile | Asn | Phe | Leu | Pro | Val | Asp | Tyr | Glu | Ile | Glu | Tyr | |
| 50 | | | | | 55 | | | | | 60 | | | | | | |

| gtg | tgc | cga | ggg | gag | cgc | gag | gtg | gtg | ggg | ccc | aag | gtg | cgc | aaa | tgc | 240 |
|---|---|---|---|---|---|---|---|---|---|---|---|---|---|---|---|---|
| Val | Cys | Arg | Gly | Glu | Arg | Glu | Val | Val | Gly | Pro | Lys | Val | Arg | Lys | Cys | |
| 65 | | | | | 70 | | | | | 75 | | | | | 80 | |

| ctg | gcc | aac | ggc | tcc | tgg | acg | gat | atg | gac | aca | ccc | agc | cgc | tgt | gtc | 288 |
|---|---|---|---|---|---|---|---|---|---|---|---|---|---|---|---|---|
| Leu | Ala | Asn | Gly | Ser | Trp | Thr | Asp | Met | Asp | Thr | Pro | Ser | Arg | Cys | Val | |
| | | | | 85 | | | | | 90 | | | | | 95 | | |

| cga | atc | tgc | tcc | aag | tct | tat | ttg | acc | ctg | gaa | aat | ggg | aag | gtt | ttc | 336 |
|---|---|---|---|---|---|---|---|---|---|---|---|---|---|---|---|---|
| Arg | Ile | Cys | Ser | Lys | Ser | Tyr | Leu | Thr | Leu | Glu | Asn | Gly | Lys | Val | Phe | |
| | | | 100 | | | | | 105 | | | | | 110 | | | |

| ctg | acg | ggt | ggg | gac | ctc | cca | gct | ctg | gat | gga | gcc | cgg | gtg | gag | ttc | 384 |
|---|---|---|---|---|---|---|---|---|---|---|---|---|---|---|---|---|
| Leu | Thr | Gly | Gly | Asp | Leu | Pro | Ala | Leu | Asp | Gly | Ala | Arg | Val | Glu | Phe | |
| | | 115 | | | | | 120 | | | | | 125 | | | | |

| cga | tgt | gac | ccc | gac | ttc | cat | ctg | gtg | ggc | agc | tcc | cgg | agc | gtc | tgt | 432 |
|---|---|---|---|---|---|---|---|---|---|---|---|---|---|---|---|---|
| Arg | Cys | Asp | Pro | Asp | Phe | His | Leu | Val | Gly | Ser | Ser | Arg | Ser | Val | Cys | |
| | 130 | | | | | 135 | | | | | 140 | | | | | |

| agt | cag | ggc | cag | tgg | agc | acc | ccc | aag | ccc | cac | tgc | cag | gtg | aat | cga | 480 |
|---|---|---|---|---|---|---|---|---|---|---|---|---|---|---|---|---|
| Ser | Gln | Gly | Gln | Trp | Ser | Thr | Pro | Lys | Pro | His | Cys | Gln | Val | Asn | Arg | |
| 145 | | | | | 150 | | | | | 155 | | | | | 160 | |

| acg | cca | cac | tca | gaa | cgg | cgt | gca | gta | tac | atc | ggg | gcg | ctg | ttt | ccc | 528 |
|---|---|---|---|---|---|---|---|---|---|---|---|---|---|---|---|---|
| Thr | Pro | His | Ser | Glu | Arg | Arg | Ala | Val | Tyr | Ile | Gly | Ala | Leu | Phe | Pro | |
| | | | | 165 | | | | | 170 | | | | | 175 | | |

| atg | agc | ggg | ggc | tgg | ccg | ggg | ggc | cag | gcc | tgc | cag | ccc | gcg | gtg | gag | 576 |
|---|---|---|---|---|---|---|---|---|---|---|---|---|---|---|---|---|
| Met | Ser | Gly | Gly | Trp | Pro | Gly | Gly | Gln | Ala | Cys | Gln | Pro | Ala | Val | Glu | |
| | | | 180 | | | | | 185 | | | | | 190 | | | |

| atg | gcg | ctg | gag | gac | gtt | aac | agc | cgc | aga | gac | atc | ctg | ccg | gac | tac | 624 |
|---|---|---|---|---|---|---|---|---|---|---|---|---|---|---|---|---|
| Met | Ala | Leu | Glu | Asp | Val | Asn | Ser | Arg | Arg | Asp | Ile | Leu | Pro | Asp | Tyr | |
| | | 195 | | | | | 200 | | | | | 205 | | | | |

| gag | ctc | aag | ctt | atc | cac | cac | gac | agc | aag | tgt | gac | cca | ggg | caa | gcc | 672 |
|---|---|---|---|---|---|---|---|---|---|---|---|---|---|---|---|---|
| Glu | Leu | Lys | Leu | Ile | His | His | Asp | Ser | Lys | Cys | Asp | Pro | Gly | Gln | Ala | |
| | 210 | | | | | 215 | | | | | 220 | | | | | |

| acc | aag | tac | ttg | tac | gaa | cta | ctc | tac | aat | gac | ccc | atc | aag | atc | att | 720 |
|---|---|---|---|---|---|---|---|---|---|---|---|---|---|---|---|---|
| Thr | Lys | Tyr | Leu | Tyr | Glu | Leu | Leu | Tyr | Asn | Asp | Pro | Ile | Lys | Ile | Ile | |
| 225 | | | | | 230 | | | | | 235 | | | | | 240 | |

| ctc | atg | cct | ggc | tgt | agt | tct | gtc | tcc | aca | ctt | gta | gct | gag | gct | gcc | 768 |
|---|---|---|---|---|---|---|---|---|---|---|---|---|---|---|---|---|
| Leu | Met | Pro | Gly | Cys | Ser | Ser | Val | Ser | Thr | Leu | Val | Ala | Glu | Ala | Ala | |
| | | | | 245 | | | | | 250 | | | | | 255 | | |

| cgg | atg | tgg | aac | ctt | att | gtg | ctc | tca | tat | ggc | tcc | agt | tca | cca | gcc | 816 |
|---|---|---|---|---|---|---|---|---|---|---|---|---|---|---|---|---|
| Arg | Met | Trp | Asn | Leu | Ile | Val | Leu | Ser | Tyr | Gly | Ser | Ser | Ser | Pro | Ala | |

-continued

```
                260                 265                 270
ttg tca aac cga cag cgg ttt ccc acg ttc ttc cgg acg cat cca tcc      864
Leu Ser Asn Arg Gln Arg Phe Pro Thr Phe Phe Arg Thr His Pro Ser
        275                 280                 285 gcc aca ctc cac aat ccc acc cgg gtg aaa ctc ttc gaa aag tgg ggc      912
Ala Thr Leu His Asn Pro Thr Arg Val Lys Leu Phe Glu Lys Trp Gly
    290                 295                 300 tgg aag aag atc gct acc atc caa cag acc acc gag gtc ttc acc tca      960
Trp Lys Lys Ile Ala Thr Ile Gln Gln Thr Thr Glu Val Phe Thr Ser
305                 310                 315                 320 acg ctg gat gac ctg gag gag cga gtg aaa gag gct ggg atc gag atc     1008
Thr Leu Asp Asp Leu Glu Glu Arg Val Lys Glu Ala Gly Ile Glu Ile
                325                 330                 335 act ttc cga cag agt ttc ttc tcg gat cca gct gtg cct gtt aaa aac     1056
Thr Phe Arg Gln Ser Phe Phe Ser Asp Pro Ala Val Pro Val Lys Asn
            340                 345                 350 ctg aag cgt caa gat gct cga atc atc gtg gga ctt ttc tat gag acg     1104
Leu Lys Arg Gln Asp Ala Arg Ile Ile Val Gly Leu Phe Tyr Glu Thr
        355                 360                 365 gaa gcc cgg aaa gtt ttt tgt gag gtc tat aag gaa agg ctc ttt ggg     1152
Glu Ala Arg Lys Val Phe Cys Glu Val Tyr Lys Glu Arg Leu Phe Gly
    370                 375                 380 aag aag tac gtc tgg ttc ctc atc ggg tgg tat gct gac aac tgg ttc     1200
Lys Lys Tyr Val Trp Phe Leu Ile Gly Trp Tyr Ala Asp Asn Trp Phe
385                 390                 395                 400 aag acc tat gac ccg tca atc aat tgt aca gtg gaa gaa atg acc gag     1248
Lys Thr Tyr Asp Pro Ser Ile Asn Cys Thr Val Glu Glu Met Thr Glu
                405                 410                 415 gcg gtg gag ggc cac atc acc acg gag att gtc atg ctg aac cct gcc     1296
Ala Val Glu Gly His Ile Thr Thr Glu Ile Val Met Leu Asn Pro Ala
            420                 425                 430 aac acc cga agc att tcc aac atg acg tca cag gaa ttt gtg gag aaa     1344
Asn Thr Arg Ser Ile Ser Asn Met Thr Ser Gln Glu Phe Val Glu Lys
        435                 440                 445 cta acc aag cgg ctg aaa aga cac ccc gag gag act gga ggc ttc cag     1392
Leu Thr Lys Arg Leu Lys Arg His Pro Glu Glu Thr Gly Gly Phe Gln
    450                 455                 460 gag gca cca ctg gcc tat gat gct atc tgg gcc ttg gct ttg gcc ttg     1440
Glu Ala Pro Leu Ala Tyr Asp Ala Ile Trp Ala Leu Ala Leu Ala Leu
465                 470                 475                 480 aac aag acg tct gga gga ggt ggt cgt tcc ggc gtg cgc ctg gag gac     1488
Asn Lys Thr Ser Gly Gly Gly Gly Arg Ser Gly Val Arg Leu Glu Asp
                485                 490                 495 ttt aac tac aac aac cag acc att aca gac cag atc tac cgg gcc atg     1536
Phe Asn Tyr Asn Asn Gln Thr Ile Thr Asp Gln Ile Tyr Arg Ala Met
            500                 505                 510 aac tcc tcc tcc ttt gag ggc gtt tct ggc cat gtg gtc ttt gat gcc     1584
Asn Ser Ser Ser Phe Glu Gly Val Ser Gly His Val Val Phe Asp Ala
        515                 520                 525 agc ggc tcc cgg atg gca tgg aca ctt atc gag cag cta cag ggc ggc     1632
Ser Gly Ser Arg Met Ala Trp Thr Leu Ile Glu Gln Leu Gln Gly Gly
    530                 535                 540 agc tac aag aag atc ggc tac tac gac agc acc aag gat gat ctt tcc     1680
Ser Tyr Lys Lys Ile Gly Tyr Tyr Asp Ser Thr Lys Asp Asp Leu Ser
545                 550                 555                 560 tgg tcc aaa acg gac aag tgg att gga ggg tct ccc cca gct gac cag     1728
Trp Ser Lys Thr Asp Lys Trp Ile Gly Gly Ser Pro Pro Ala Asp Gln
                565                 570                 575 acc ttg gtc atc aag aca ttc cgt ttc ctg tct cag aaa ctc ttt atc     1776
```

```
                Thr Leu Val Ile Lys Thr Phe Arg Phe Leu Ser Gln Lys Leu Phe Ile
                                580                 585                 590 tcc gtc tca gtt ctc tcc agc ctg ggc att gtt ctt gct gtt gtc tgt         1824
Ser Val Ser Val Leu Ser Ser Leu Gly Ile Val Leu Ala Val Val Cys
            595                 600                 605 ctg tcc ttt aac atc tac aac tcc cac gtt cgt tat atc cag aac tcc         1872
Leu Ser Phe Asn Ile Tyr Asn Ser His Val Arg Tyr Ile Gln Asn Ser
        610                 615                 620 cag ccc aac ctg aac aat ctg act gct gtg ggc tgc tca ctg gca ctg         1920
Gln Pro Asn Leu Asn Asn Leu Thr Ala Val Gly Cys Ser Leu Ala Leu
625                 630                 635                 640 gct gct gtc ttc cct ctc ggg ctg gat ggt tac cac ata ggg aga agc         1968
Ala Ala Val Phe Pro Leu Gly Leu Asp Gly Tyr His Ile Gly Arg Ser
                645                 650                 655 cag ttc ccg ttt gtc tgc cag gcc cgc ctt tgg ctc ttg ggc ttg ggc         2016
Gln Phe Pro Phe Val Cys Gln Ala Arg Leu Trp Leu Leu Gly Leu Gly
            660                 665                 670 ttt agt ctg ggc tat ggc tct atg ttc acc aag atc tgg tgg gtc cac         2064
Phe Ser Leu Gly Tyr Gly Ser Met Phe Thr Lys Ile Trp Trp Val His
        675                 680                 685 aca gtc ttc acg aag aag gag gag aag aag gag tgg agg aag acc cta         2112
Thr Val Phe Thr Lys Lys Glu Glu Lys Lys Glu Trp Arg Lys Thr Leu
    690                 695                 700 gag ccc tgg aaa ctc tat gcc act gtg ggc ctg ctg gtg ggc atg gat         2160
Glu Pro Trp Lys Leu Tyr Ala Thr Val Gly Leu Leu Val Gly Met Asp
705                 710                 715                 720 gtc ctg act ctt gcc atc tgg cag att gtg gac ccc ttg cac cga acc         2208
Val Leu Thr Leu Ala Ile Trp Gln Ile Val Asp Pro Leu His Arg Thr
                725                 730                 735 att gag act ttt gcc aag gag gaa cca aag gaa gac atc gat gtc tcc         2256
Ile Glu Thr Phe Ala Lys Glu Glu Pro Lys Glu Asp Ile Asp Val Ser
            740                 745                 750 att ctg ccc cag ttg gag cac tgc agc tcc aag aag atg aat acg tgg         2304
Ile Leu Pro Gln Leu Glu His Cys Ser Ser Lys Lys Met Asn Thr Trp
        755                 760                 765 ctt ggc att ttc tat ggt tac aag ggg ctg ctg ctg ctg gga atc              2352
Leu Gly Ile Phe Tyr Gly Tyr Lys Gly Leu Leu Leu Leu Gly Ile
    770                 775                 780 ttt ctt gct tac gaa acc aag agc gtg tcc act gaa aag atc aat gac         2400
Phe Leu Ala Tyr Glu Thr Lys Ser Val Ser Thr Glu Lys Ile Asn Asp
785                 790                 795                 800 cac agg gcc gtg ggc atg gct atc tac aat gtc gcg gtc ctg tgt ctc         2448
His Arg Ala Val Gly Met Ala Ile Tyr Asn Val Ala Val Leu Cys Leu
                805                 810                 815 atc act gct cct gtg acc atg atc ctt tcc agt cag cag gac gca gcc         2496
Ile Thr Ala Pro Val Thr Met Ile Leu Ser Ser Gln Gln Asp Ala Ala
            820                 825                 830 ttt gcc ttt gcc tct ctg gcc atc gtg ttc tct tcc tac atc act ctg         2544
Phe Ala Phe Ala Ser Leu Ala Ile Val Phe Ser Ser Tyr Ile Thr Leu
        835                 840                 845 gtt gtg ctc ttt gtg ccc aag atg cgc agg ctg atc acc cga ggg gaa         2592
Val Val Leu Phe Val Pro Lys Met Arg Arg Leu Ile Thr Arg Gly Glu
    850                 855                 860 tgg cag tct gaa acg cag gac acc atg aaa aca gga tca tcc acc aac         2640
Trp Gln Ser Glu Thr Gln Asp Thr Met Lys Thr Gly Ser Ser Thr Asn
865                 870                 875                 880 aac aac gag gaa gag aag tcc cga ctg ttg gag aag gaa aac cga gaa         2688
Asn Asn Glu Glu Glu Lys Ser Arg Leu Leu Glu Lys Glu Asn Arg Glu
                885                 890                 895
```

```
ctg gaa aag atc atc gct gag aaa gag gag cgc gtc tct gaa ctg cgc    2736
Leu Glu Lys Ile Ile Ala Glu Lys Glu Glu Arg Val Ser Glu Leu Arg
        900                 905                 910 cat cag ctc cag tct cgg cag caa ctc cgc tca cgg cgc cac ccc cca    2784
His Gln Leu Gln Ser Arg Gln Gln Leu Arg Ser Arg Arg His Pro Pro
        915                 920                 925 aca ccc cca gat ccc tct ggg ggc ctt ccc agg gga ccc tct gag ccc    2832
Thr Pro Pro Asp Pro Ser Gly Gly Leu Pro Arg Gly Pro Ser Glu Pro
        930                 935                 940 cct gac cgg ctt agc tgt gat ggg agt cga gta cat ttg ctt tac aag    2880
Pro Asp Arg Leu Ser Cys Asp Gly Ser Arg Val His Leu Leu Tyr Lys
945                 950                 955                 960 tga                                                                2883
```

```
<210> SEQ ID NO 45
<211> LENGTH: 960
<212> TYPE: PRT
<213> ORGANISM: Rattus norvegicus

<400> SEQUENCE: 45

Met Leu Leu Leu Leu Val Pro Leu Phe Leu Arg Pro Leu Gly Ala
 1               5                  10                  15

Gly Gly Ala Gln Thr Pro Asn Ala Thr Ser Glu Gly Cys Gln Ile Ile
                20                  25                  30

His Pro Pro Trp Glu Gly Gly Ile Arg Tyr Arg Gly Leu Thr Arg Asp
            35                  40                  45

Gln Val Lys Ala Ile Asn Phe Leu Pro Val Asp Tyr Glu Ile Glu Tyr
        50                  55                  60

Val Cys Arg Gly Glu Arg Glu Val Val Gly Pro Lys Val Arg Lys Cys
65                  70                  75                  80

Leu Ala Asn Gly Ser Trp Thr Asp Met Asp Thr Pro Ser Arg Cys Val
                85                  90                  95

Arg Ile Cys Ser Lys Ser Tyr Leu Thr Leu Glu Asn Gly Lys Val Phe
            100                 105                 110

Leu Thr Gly Gly Asp Leu Pro Ala Leu Asp Gly Ala Arg Val Glu Phe
        115                 120                 125

Arg Cys Asp Pro Asp Phe His Leu Val Gly Ser Ser Arg Ser Val Cys
    130                 135                 140

Ser Gln Gly Gln Trp Ser Thr Pro Lys Pro His Cys Gln Val Asn Arg
145                 150                 155                 160

Thr Pro His Ser Glu Arg Arg Ala Val Tyr Ile Gly Ala Leu Phe Pro
                165                 170                 175

Met Ser Gly Gly Trp Pro Gly Gly Gln Ala Cys Gln Pro Ala Val Glu
            180                 185                 190

Met Ala Leu Glu Asp Val Asn Ser Arg Arg Asp Ile Leu Pro Asp Tyr
        195                 200                 205

Glu Leu Lys Leu Ile His His Asp Ser Lys Cys Asp Pro Gly Gln Ala
    210                 215                 220

Thr Lys Tyr Leu Tyr Glu Leu Leu Tyr Asn Asp Pro Ile Lys Ile Ile
225                 230                 235                 240

Leu Met Pro Gly Cys Ser Ser Val Ser Thr Leu Val Ala Glu Ala Ala
                245                 250                 255

Arg Met Trp Asn Leu Ile Val Leu Ser Tyr Gly Ser Ser Ser Pro Ala
            260                 265                 270

Leu Ser Asn Arg Gln Arg Phe Pro Thr Phe Phe Arg Thr His Pro Ser
        275                 280                 285
```

-continued

```
Ala Thr Leu His Asn Pro Thr Arg Val Lys Leu Phe Glu Lys Trp Gly
    290                 295                 300
Trp Lys Lys Ile Ala Thr Ile Gln Gln Thr Thr Glu Val Phe Thr Ser
305                 310                 315                 320
Thr Leu Asp Asp Leu Glu Arg Val Lys Glu Ala Gly Ile Glu Ile
                325                 330                 335
Thr Phe Arg Gln Ser Phe Phe Ser Asp Pro Ala Val Pro Val Lys Asn
                340                 345                 350
Leu Lys Arg Gln Asp Ala Arg Ile Ile Val Gly Leu Phe Tyr Glu Thr
            355                 360                 365
Glu Ala Arg Lys Val Phe Cys Glu Val Tyr Lys Glu Arg Leu Phe Gly
370                 375                 380
Lys Lys Tyr Val Trp Phe Leu Ile Gly Trp Tyr Ala Asp Asn Trp Phe
385                 390                 395                 400
Lys Thr Tyr Asp Pro Ser Ile Asn Cys Thr Val Glu Glu Met Thr Glu
                405                 410                 415
Ala Val Glu Gly His Ile Thr Thr Glu Ile Val Met Leu Asn Pro Ala
            420                 425                 430
Asn Thr Arg Ser Ile Ser Asn Met Thr Ser Gln Glu Phe Val Glu Lys
        435                 440                 445
Leu Thr Lys Arg Leu Lys Arg His Pro Glu Glu Thr Gly Gly Phe Gln
    450                 455                 460
Glu Ala Pro Leu Ala Tyr Asp Ala Ile Trp Ala Leu Ala Leu Ala Leu
465                 470                 475                 480
Asn Lys Thr Ser Gly Gly Gly Arg Ser Gly Val Arg Leu Glu Asp
                485                 490                 495
Phe Asn Tyr Asn Asn Gln Thr Ile Thr Asp Gln Ile Tyr Arg Ala Met
                500                 505                 510
Asn Ser Ser Ser Phe Glu Gly Val Ser Gly His Val Val Phe Asp Ala
            515                 520                 525
Ser Gly Ser Arg Met Ala Trp Thr Leu Ile Glu Gln Leu Gln Gly Gly
    530                 535                 540
Ser Tyr Lys Lys Ile Gly Tyr Tyr Asp Ser Thr Lys Asp Asp Leu Ser
545                 550                 555                 560
Trp Ser Lys Thr Asp Lys Trp Ile Gly Gly Ser Pro Pro Ala Asp Gln
                565                 570                 575
Thr Leu Val Ile Lys Thr Phe Arg Phe Leu Ser Gln Lys Leu Phe Ile
                580                 585                 590
Ser Val Ser Val Leu Ser Ser Leu Gly Ile Val Leu Ala Val Val Cys
            595                 600                 605
Leu Ser Phe Asn Ile Tyr Asn Ser His Val Arg Tyr Ile Gln Asn Ser
        610                 615                 620
Gln Pro Asn Leu Asn Asn Leu Thr Ala Val Gly Cys Ser Leu Ala Leu
625                 630                 635                 640
Ala Ala Val Phe Pro Leu Gly Leu Asp Gly Tyr His Ile Gly Arg Ser
                645                 650                 655
Gln Phe Pro Phe Val Cys Gln Ala Arg Leu Trp Leu Leu Gly Leu Gly
                660                 665                 670
Phe Ser Leu Gly Tyr Gly Ser Met Phe Thr Lys Ile Trp Trp Val His
            675                 680                 685
Thr Val Phe Thr Lys Lys Glu Glu Lys Glu Trp Arg Lys Thr Leu
        690                 695                 700
```

```
Glu Pro Trp Lys Leu Tyr Ala Thr Val Gly Leu Leu Val Gly Met Asp
705                 710                 715                 720

Val Leu Thr Leu Ala Ile Trp Gln Ile Val Asp Pro Leu His Arg Thr
            725                 730                 735

Ile Glu Thr Phe Ala Lys Glu Glu Pro Lys Glu Asp Ile Asp Val Ser
        740                 745                 750

Ile Leu Pro Gln Leu Glu His Cys Ser Ser Lys Lys Met Asn Thr Trp
    755                 760                 765

Leu Gly Ile Phe Tyr Gly Tyr Lys Gly Leu Leu Leu Leu Gly Ile
770                 775                 780

Phe Leu Ala Tyr Glu Thr Lys Ser Val Ser Thr Glu Lys Ile Asn Asp
785                 790                 795                 800

His Arg Ala Val Gly Met Ala Ile Tyr Asn Val Ala Val Leu Cys Leu
                805                 810                 815

Ile Thr Ala Pro Val Thr Met Ile Leu Ser Ser Gln Gln Asp Ala Ala
            820                 825                 830

Phe Ala Phe Ala Ser Leu Ala Ile Val Phe Ser Ser Tyr Ile Thr Leu
        835                 840                 845

Val Val Leu Phe Val Pro Lys Met Arg Arg Leu Ile Thr Arg Gly Glu
    850                 855                 860

Trp Gln Ser Glu Thr Gln Asp Thr Met Lys Thr Gly Ser Ser Thr Asn
865                 870                 875                 880

Asn Asn Glu Glu Glu Lys Ser Arg Leu Leu Glu Lys Glu Asn Arg Glu
                885                 890                 895

Leu Glu Lys Ile Ile Ala Glu Lys Glu Glu Arg Val Ser Glu Leu Arg
            900                 905                 910

His Gln Leu Gln Ser Arg Gln Gln Leu Arg Ser Arg His Pro Pro
        915                 920                 925

Thr Pro Pro Asp Pro Ser Gly Gly Leu Pro Arg Gly Pro Ser Glu Pro
    930                 935                 940

Pro Asp Arg Leu Ser Cys Asp Gly Ser Arg Val His Leu Leu Tyr Lys
945                 950                 955                 960

<210> SEQ ID NO 46
<211> LENGTH: 2535
<212> TYPE: DNA
<213> ORGANISM: Rattus norvegicus
<220> FEATURE:
<221> NAME/KEY: CDS
<222> LOCATION: (1)...(2532)

<400> SEQUENCE: 46 atg ggc ccg ggg gga ccc tgt acc cca gtg ggg tgg ccg ctg cct ctt    48
Met Gly Pro Gly Gly Pro Cys Thr Pro Val Gly Trp Pro Leu Pro Leu
1               5                   10                  15 ctg ctg gtg atg gcg gct ggg gtg gct ccg gtg tgg gcc tct cac tcc    96
Leu Leu Val Met Ala Ala Gly Val Ala Pro Val Trp Ala Ser His Ser
                20                  25                  30 cct cat ctc ccg cgg cct cac ccg agg gtc ccc cgg cac ccc tcc tca   144
Pro His Leu Pro Arg Pro His Pro Arg Val Pro Arg His Pro Ser Ser
            35                  40                  45 gaa cgg cgt gca gta tac atc ggg gcg ctg ttt ccc atg agc ggg ggc   192
Glu Arg Arg Ala Val Tyr Ile Gly Ala Leu Phe Pro Met Ser Gly Gly
        50                  55                  60 tgg ccg ggg ggc cag gcc tgc cag ccc gcg gtg gag atg gcg ctg gag   240
Trp Pro Gly Gly Gln Ala Cys Gln Pro Ala Val Glu Met Ala Leu Glu
65                  70                  75                  80
```

```
gac gtt aac agc cgc aga gac atc ctg ccg gac tac gag ctc aag ctt    288
Asp Val Asn Ser Arg Arg Asp Ile Leu Pro Asp Tyr Glu Leu Lys Leu
             85                  90                  95 atc cac cac gac agc aag tgt gac cca ggg caa gcc acc aag tac ttg    336
Ile His His Asp Ser Lys Cys Asp Pro Gly Gln Ala Thr Lys Tyr Leu
            100                 105                 110 tac gaa cta ctc tac aat gac ccc atc aag atc att ctc atg cct ggc    384
Tyr Glu Leu Leu Tyr Asn Asp Pro Ile Lys Ile Ile Leu Met Pro Gly
        115                 120                 125 tgt agt tct gtc tcc aca ctt gta gct gag gct gcc cgg atg tgg aac    432
Cys Ser Ser Val Ser Thr Leu Val Ala Glu Ala Ala Arg Met Trp Asn
130                 135                 140 ctt att gtg ctc tca tat ggc tcc agt tca cca gcc ttg tca aac cga    480
Leu Ile Val Leu Ser Tyr Gly Ser Ser Ser Pro Ala Leu Ser Asn Arg
145                 150                 155                 160 cag cgg ttt ccc acg ttc ttc cgg acg cat cca tcc gcc aca ctc cac    528
Gln Arg Phe Pro Thr Phe Phe Arg Thr His Pro Ser Ala Thr Leu His
                165                 170                 175 aat ccc acc cgg gtg aaa ctc ttc gaa aag tgg ggc tgg aag aag atc    576
Asn Pro Thr Arg Val Lys Leu Phe Glu Lys Trp Gly Trp Lys Lys Ile
            180                 185                 190 gct acc atc caa cag acc acc gag gtc ttc acc tca acg ctg gat gac    624
Ala Thr Ile Gln Gln Thr Thr Glu Val Phe Thr Ser Thr Leu Asp Asp
        195                 200                 205 ctg gag gag cga gtg aaa gag gct ggg atc gag atc act ttc cga cag    672
Leu Glu Glu Arg Val Lys Glu Ala Gly Ile Glu Ile Thr Phe Arg Gln
210                 215                 220 agt ttc ttc tcg gat cca gct gtg cct gtt aaa aac ctg aag cgt caa    720
Ser Phe Phe Ser Asp Pro Ala Val Pro Val Lys Asn Leu Lys Arg Gln
225                 230                 235                 240 gat gct cga atc atc gtg gga ctt ttc tat gag acg gaa gcc cgg aaa    768
Asp Ala Arg Ile Ile Val Gly Leu Phe Tyr Glu Thr Glu Ala Arg Lys
                245                 250                 255 gtt ttt tgt gag gtc tat aag gaa agg ctc ttt ggg aag aag tac gtc    816
Val Phe Cys Glu Val Tyr Lys Glu Arg Leu Phe Gly Lys Lys Tyr Val
            260                 265                 270 tgg ttc ctc atc ggg tgg tat gct gac aac tgg ttc aag acc tat gac    864
Trp Phe Leu Ile Gly Trp Tyr Ala Asp Asn Trp Phe Lys Thr Tyr Asp
        275                 280                 285 ccg tca atc aat tgt aca gtg gaa gaa atg acc gag gcg gtg gag ggc    912
Pro Ser Ile Asn Cys Thr Val Glu Glu Met Thr Glu Ala Val Glu Gly
290                 295                 300 cac atc acc acg gag att gtc atg ctg aac cct gcc aac acc cga agc    960
His Ile Thr Thr Glu Ile Val Met Leu Asn Pro Ala Asn Thr Arg Ser
305                 310                 315                 320 att tcc aac atg acg tca cag gaa ttt gtg gag aaa cta acc aag cgg   1008
Ile Ser Asn Met Thr Ser Gln Glu Phe Val Glu Lys Leu Thr Lys Arg
                325                 330                 335 ctg aaa aga cac ccc gag gag act gga ggc ttc cag gag gca cca ctg   1056
Leu Lys Arg His Pro Glu Glu Thr Gly Gly Phe Gln Glu Ala Pro Leu
            340                 345                 350 gcc tat gat gct atc tgg gcc ttg gct ttg gcc ttg aac aag acg tct   1104
Ala Tyr Asp Ala Ile Trp Ala Leu Ala Leu Ala Leu Asn Lys Thr Ser
        355                 360                 365 gga gga ggt ggt cgt tcc ggc gtg cgc ctg gag gac ttt aac tac aac   1152
Gly Gly Gly Gly Arg Ser Gly Val Arg Leu Glu Asp Phe Asn Tyr Asn
370                 375                 380 aac cag acc att aca gac cag atc tac cgg gcc atg aac tcc tcc tcc   1200
Asn Gln Thr Ile Thr Asp Gln Ile Tyr Arg Ala Met Asn Ser Ser Ser
385                 390                 395                 400
```

-continued

| | |
|---|---|
| ttt gag ggc gtt tct ggc cat gtg gtc ttt gat gcc agc ggc tcc cgg<br>Phe Glu Gly Val Ser Gly His Val Val Phe Asp Ala Ser Gly Ser Arg<br>405                        410                    415 | 1248 |
| atg gca tgg aca ctt atc gag cag cta cag ggc ggc agc tac aag aag<br>Met Ala Trp Thr Leu Ile Glu Gln Leu Gln Gly Gly Ser Tyr Lys Lys<br>420                        425                    430 | 1296 |
| atc ggc tac tac gac agc acc aag gat gat ctt tcc tgg tcc aaa acg<br>Ile Gly Tyr Tyr Asp Ser Thr Lys Asp Asp Leu Ser Trp Ser Lys Thr<br>435                        440                    445 | 1344 |
| gac aag tgg att gga ggg tct ccc cca gct gac cag acc ttg gtc atc<br>Asp Lys Trp Ile Gly Gly Ser Pro Pro Ala Asp Gln Thr Leu Val Ile<br>450                        455                    460 | 1392 |
| aag aca ttc cgt ttc ctg tct cag aaa ctc ttt atc tcc gtc tca gtt<br>Lys Thr Phe Arg Phe Leu Ser Gln Lys Leu Phe Ile Ser Val Ser Val<br>465                        470                    475                    480 | 1440 |
| ctc tcc agc ctg ggc att gtt ctt gct gtt gtc tgt ctg tcc ttt aac<br>Leu Ser Ser Leu Gly Ile Val Leu Ala Val Val Cys Leu Ser Phe Asn<br>                    485                    490                    495 | 1488 |
| atc tac aac tcc cac gtt cgt tat atc cag aac tcc cag ccc aac ctg<br>Ile Tyr Asn Ser His Val Arg Tyr Ile Gln Asn Ser Gln Pro Asn Leu<br>                500                    505                    510 | 1536 |
| aac aat ctg act gct gtg ggc tgc tca ctg gca ctg gct gct gtc ttc<br>Asn Asn Leu Thr Ala Val Gly Cys Ser Leu Ala Leu Ala Ala Val Phe<br>                515                    520                    525 | 1584 |
| cct ctc ggg ctg gat ggt tac cac ata ggg aga agc cag ttc ccg ttt<br>Pro Leu Gly Leu Asp Gly Tyr His Ile Gly Arg Ser Gln Phe Pro Phe<br>530                        535                    540 | 1632 |
| gtc tgc cag gcc cgc ctt tgg ctc ttg ggc ttg ggc ttt agt ctg ggc<br>Val Cys Gln Ala Arg Leu Trp Leu Leu Gly Leu Gly Phe Ser Leu Gly<br>545                        550                    555                    560 | 1680 |
| tat ggc tct atg ttc acc aag atc tgg tgg gtc cac aca gtc ttc acg<br>Tyr Gly Ser Met Phe Thr Lys Ile Trp Trp Val His Thr Val Phe Thr<br>                565                    570                    575 | 1728 |
| aag aag gag gag aag aag gag tgg agg aag acc cta gag ccc tgg aaa<br>Lys Lys Glu Glu Lys Lys Glu Trp Arg Lys Thr Leu Glu Pro Trp Lys<br>580                        585                    590 | 1776 |
| ctc tat gcc act gtg ggc ctg ctg gtg ggc atg gat gtc ctg act ctt<br>Leu Tyr Ala Thr Val Gly Leu Leu Val Gly Met Asp Val Leu Thr Leu<br>                595                    600                    605 | 1824 |
| gcc atc tgg cag att gtg gac ccc ttg cac cga acc att gag act ttt<br>Ala Ile Trp Gln Ile Val Asp Pro Leu His Arg Thr Ile Glu Thr Phe<br>610                        615                    620 | 1872 |
| gcc aag gag gaa cca aag gaa gac atc gat gtc tcc att ctg ccc cag<br>Ala Lys Glu Glu Pro Lys Glu Asp Ile Asp Val Ser Ile Leu Pro Gln<br>625                        630                    635                    640 | 1920 |
| ttg gag cac tgc agc tcc aag aag atg aat acg tgg ctt ggc att ttc<br>Leu Glu His Cys Ser Ser Lys Lys Met Asn Thr Trp Leu Gly Ile Phe<br>                645                    650                    655 | 1968 |
| tat ggt tac aag ggg ctg ctg ctg ctg gga atc ttt ctt gct tac<br>Tyr Gly Tyr Lys Gly Leu Leu Leu Leu Gly Ile Phe Leu Ala Tyr<br>660                        665                    670 | 2016 |
| gaa acc aag agc gtg tcc act gaa aag atc aat gac cac agg gcc gtg<br>Glu Thr Lys Ser Val Ser Thr Glu Lys Ile Asn Asp His Arg Ala Val<br>675                        680                    685 | 2064 |
| ggc atg gct atc tac aat gtc gcg gtc ctg tgt ctc atc act gct cct<br>Gly Met Ala Ile Tyr Asn Val Ala Val Leu Cys Leu Ile Thr Ala Pro<br>690                        695                    700 | 2112 |
| gtg acc atg atc ctt tcc agt cag cag gac gca gcc ttt gcc ttt gcc<br>Val Thr Met Ile Leu Ser Ser Gln Gln Asp Ala Ala Phe Ala Phe Ala | 2160 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 705 |     |     |     | 710 |     |     |     | 715 |     |     |     | 720 |     |     |      |
| tct | ctg | gcc | atc | gtg | ttc | tct | tcc | tac | atc | act | ctg | gtt | gtg | ctc | ttt | 2208 |
| Ser | Leu | Ala | Ile | Val | Phe | Ser | Ser | Tyr | Ile | Thr | Leu | Val | Val | Leu | Phe |      |
|     |     |     |     | 725 |     |     |     |     | 730 |     |     |     | 735 |     |     |      |
| gtg | ccc | aag | atg | cgc | agg | ctg | atc | acc | cga | ggg | gaa | tgg | cag | tct | gaa | 2256 |
| Val | Pro | Lys | Met | Arg | Arg | Leu | Ile | Thr | Arg | Gly | Glu | Trp | Gln | Ser | Glu |      |
|     |     |     | 740 |     |     |     |     | 745 |     |     |     |     | 750 |     |     |      |
| acg | cag | gac | acc | atg | aaa | aca | gga | tca | tcc | acc | aac | aac | aac | gag | gaa | 2304 |
| Thr | Gln | Asp | Thr | Met | Lys | Thr | Gly | Ser | Ser | Thr | Asn | Asn | Asn | Glu | Glu |      |
|     |     | 755 |     |     |     |     | 760 |     |     |     |     | 765 |     |     |     |      |
| gag | aag | tcc | cga | ctg | ttg | gag | aag | gaa | aac | cga | gaa | ctg | gaa | aag | atc | 2352 |
| Glu | Lys | Ser | Arg | Leu | Leu | Glu | Lys | Glu | Asn | Arg | Glu | Leu | Glu | Lys | Ile |      |
|     | 770 |     |     |     |     | 775 |     |     |     |     | 780 |     |     |     |     |      |
| atc | gct | gag | aaa | gag | gag | cgc | gtc | tct | gaa | ctg | cgc | cat | cag | ctc | cag | 2400 |
| Ile | Ala | Glu | Lys | Glu | Glu | Arg | Val | Ser | Glu | Leu | Arg | His | Gln | Leu | Gln |      |
| 785 |     |     |     |     | 790 |     |     |     |     | 795 |     |     |     |     | 800 |      |
| tct | cgg | cag | caa | ctc | cgc | tca | cgg | cgc | cac | ccc | cca | aca | ccc | cca | gat | 2448 |
| Ser | Arg | Gln | Gln | Leu | Arg | Ser | Arg | Arg | His | Pro | Pro | Thr | Pro | Pro | Asp |      |
|     |     |     |     | 805 |     |     |     |     | 810 |     |     |     |     | 815 |     |      |
| ccc | tct | ggg | ggc | ctt | ccc | agg | gga | ccc | tct | gag | ccc | cct | gac | cgg | ctt | 2496 |
| Pro | Ser | Gly | Gly | Leu | Pro | Arg | Gly | Pro | Ser | Glu | Pro | Pro | Asp | Arg | Leu |      |
|     |     |     | 820 |     |     |     |     | 825 |     |     |     |     | 830 |     |     |      |
| agc | tgt | gat | ggg | agt | cga | gta | cat | ttg | ctt | tac | aag | tga |     |     |     | 2535 |
| Ser | Cys | Asp | Gly | Ser | Arg | Val | His | Leu | Leu | Tyr | Lys |     |     |     |     |      |
|     |     | 835 |     |     |     |     | 840 |     |     |     |     |     |     |     |     |      |

<210> SEQ ID NO 47
<211> LENGTH: 844
<212> TYPE: PRT
<213> ORGANISM: Rattus norvegicus

<400> SEQUENCE: 47

Met Gly Pro Gly Gly Pro Cys Thr Pro Val Gly Trp Pro Leu Pro Leu
1               5                   10                  15

Leu Leu Val Met Ala Ala Gly Val Ala Pro Val Trp Ala Ser His Ser
            20                  25                  30

Pro His Leu Pro Arg Pro His Pro Arg Val Pro Pro His Pro Ser Ser
        35                  40                  45

Glu Arg Arg Ala Val Tyr Ile Gly Ala Leu Phe Pro Met Ser Gly Gly
    50                  55                  60

Trp Pro Gly Gly Gln Ala Cys Gln Pro Ala Val Glu Met Ala Leu Glu
65                  70                  75                  80

Asp Val Asn Ser Arg Arg Asp Ile Leu Pro Asp Tyr Glu Leu Lys Leu
                85                  90                  95

Ile His His Asp Ser Lys Cys Asp Pro Gly Gln Ala Thr Lys Tyr Leu
            100                 105                 110

Tyr Glu Leu Leu Tyr Asn Asp Pro Ile Lys Ile Ile Leu Met Pro Gly
        115                 120                 125

Cys Ser Ser Val Ser Thr Leu Val Ala Glu Ala Ala Arg Met Trp Asn
    130                 135                 140

Leu Ile Val Leu Ser Tyr Gly Ser Ser Ser Pro Ala Leu Ser Asn Arg
145                 150                 155                 160

Gln Arg Phe Pro Thr Phe Phe Arg Thr His Pro Ser Ala Thr Leu His
                165                 170                 175

Asn Pro Thr Arg Val Lys Leu Phe Glu Lys Trp Gly Trp Lys Lys Ile
            180                 185                 190

Ala Thr Ile Gln Gln Thr Thr Glu Val Phe Thr Ser Thr Leu Asp Asp

-continued

```
            195                 200                 205
Leu Glu Glu Arg Val Lys Glu Ala Gly Ile Glu Ile Thr Phe Arg Gln
210                 215                 220

Ser Phe Phe Ser Asp Pro Ala Val Pro Val Lys Asn Leu Lys Arg Gln
225                 230                 235                 240

Asp Ala Arg Ile Ile Val Gly Leu Phe Tyr Glu Thr Glu Ala Arg Lys
                245                 250                 255

Val Phe Cys Glu Val Tyr Lys Glu Arg Leu Phe Gly Lys Lys Tyr Val
                260                 265                 270

Trp Phe Leu Ile Gly Trp Tyr Ala Asp Asn Trp Phe Lys Thr Tyr Asp
                275                 280                 285

Pro Ser Ile Asn Cys Thr Val Glu Glu Met Thr Glu Ala Val Glu Gly
290                 295                 300

His Ile Thr Thr Glu Ile Val Met Leu Asn Pro Ala Asn Thr Arg Ser
305                 310                 315                 320

Ile Ser Asn Met Thr Ser Gln Glu Phe Val Lys Leu Thr Lys Arg
                325                 330                 335

Leu Lys Arg His Pro Glu Glu Thr Gly Gly Phe Gln Glu Ala Pro Leu
                340                 345                 350

Ala Tyr Asp Ala Ile Trp Ala Leu Ala Leu Ala Leu Asn Lys Thr Ser
                355                 360                 365

Gly Gly Gly Gly Arg Ser Gly Val Arg Leu Glu Asp Phe Asn Tyr Asn
370                 375                 380

Asn Gln Thr Ile Thr Asp Gln Ile Tyr Arg Ala Met Asn Ser Ser Ser
385                 390                 395                 400

Phe Glu Gly Val Ser Gly His Val Val Phe Asp Ala Ser Gly Ser Arg
                405                 410                 415

Met Ala Trp Thr Leu Ile Glu Gln Leu Gln Gly Gly Ser Tyr Lys Lys
                420                 425                 430

Ile Gly Tyr Tyr Asp Ser Thr Lys Asp Asp Leu Ser Trp Ser Lys Thr
                435                 440                 445

Asp Lys Trp Ile Gly Gly Ser Pro Pro Ala Asp Gln Thr Leu Val Ile
450                 455                 460

Lys Thr Phe Arg Phe Leu Ser Gln Lys Leu Phe Ile Ser Val Ser Val
465                 470                 475                 480

Leu Ser Ser Leu Gly Ile Val Leu Ala Val Val Cys Leu Ser Phe Asn
                485                 490                 495

Ile Tyr Asn Ser His Val Arg Tyr Ile Gln Asn Ser Gln Pro Asn Leu
                500                 505                 510

Asn Asn Leu Thr Ala Val Gly Cys Ser Leu Ala Leu Ala Ala Val Phe
                515                 520                 525

Pro Leu Gly Leu Asp Gly Tyr His Ile Gly Arg Ser Gln Phe Pro Phe
530                 535                 540

Val Cys Gln Ala Arg Leu Trp Leu Leu Gly Leu Gly Phe Ser Leu Gly
545                 550                 555                 560

Tyr Gly Ser Met Phe Thr Lys Ile Trp Trp Val His Thr Val Phe Thr
                565                 570                 575

Lys Lys Glu Glu Lys Lys Glu Trp Arg Lys Thr Leu Glu Pro Trp Lys
                580                 585                 590

Leu Tyr Ala Thr Val Gly Leu Leu Val Gly Met Asp Val Leu Thr Leu
                595                 600                 605

Ala Ile Trp Gln Ile Val Asp Pro Leu His Arg Thr Ile Glu Thr Phe
610                 615                 620
```

```
Ala Lys Glu Glu Pro Lys Glu Asp Ile Asp Val Ser Ile Leu Pro Gln
625                 630                 635                 640

Leu Glu His Cys Ser Ser Lys Lys Met Asn Thr Trp Leu Gly Ile Phe
            645                 650                 655

Tyr Gly Tyr Lys Gly Leu Leu Leu Leu Gly Ile Phe Leu Ala Tyr
        660                 665                 670

Glu Thr Lys Ser Val Ser Thr Glu Lys Ile Asn Asp His Arg Ala Val
    675                 680                 685

Gly Met Ala Ile Tyr Asn Val Ala Val Leu Cys Leu Ile Thr Ala Pro
690                 695                 700

Val Thr Met Ile Leu Ser Ser Gln Gln Asp Ala Ala Phe Ala Phe Ala
705                 710                 715                 720

Ser Leu Ala Ile Val Phe Ser Ser Tyr Ile Thr Leu Val Val Leu Phe
                725                 730                 735

Val Pro Lys Met Arg Arg Leu Ile Thr Arg Gly Glu Trp Gln Ser Glu
            740                 745                 750

Thr Gln Asp Thr Met Lys Thr Gly Ser Ser Thr Asn Asn Asn Glu Glu
        755                 760                 765

Glu Lys Ser Arg Leu Leu Glu Lys Glu Asn Arg Glu Leu Glu Lys Ile
770                 775                 780

Ile Ala Glu Lys Glu Glu Arg Val Ser Glu Leu Arg His Gln Leu Gln
785                 790                 795                 800

Ser Arg Gln Gln Leu Arg Ser Arg Arg His Pro Pro Thr Pro Pro Asp
                805                 810                 815

Pro Ser Gly Gly Leu Pro Arg Gly Pro Ser Glu Pro Pro Asp Arg Leu
            820                 825                 830

Ser Cys Asp Gly Ser Arg Val His Leu Leu Tyr Lys
            835                 840

<210> SEQ ID NO 48
<211> LENGTH: 2886
<212> TYPE: DNA
<213> ORGANISM: Homo sapiens
<220> FEATURE:
<221> NAME/KEY: CDS
<222> LOCATION: (1)...(2883)

<400> SEQUENCE: 48 atg ttg ctg ctg ctg cta ctg gcg cca ctc ttc ctc cgc ccc ccg ggc      48
Met Leu Leu Leu Leu Leu Leu Ala Pro Leu Phe Leu Arg Pro Pro Gly
 1               5                  10                  15 gcg ggc ggg gcg cag acc ccc aac gcc acc tca gaa ggt tgc cag atc      96
Ala Gly Gly Ala Gln Thr Pro Asn Ala Thr Ser Glu Gly Cys Gln Ile
            20                  25                  30 ata cac ccg ccc tgg gaa ggg ggc atc agg tac cgg ggc ctg act cgg     144
Ile His Pro Pro Trp Glu Gly Gly Ile Arg Tyr Arg Gly Leu Thr Arg
        35                  40                  45 gac cag gtg aag gct atc aac ttc ctg cca gtg gac tat gag att gag     192
Asp Gln Val Lys Ala Ile Asn Phe Leu Pro Val Asp Tyr Glu Ile Glu
    50                  55                  60 tat gtg tgc cgg ggg gag cgc gag gtg gtg ggg ccc aag gtc cgc aag     240
Tyr Val Cys Arg Gly Glu Arg Glu Val Val Gly Pro Lys Val Arg Lys
65                  70                  75                  80 tgc ctg gcc aac ggc tcc tgg aca gat atg gac aca ccc agc cgc tgt     288
Cys Leu Ala Asn Gly Ser Trp Thr Asp Met Asp Thr Pro Ser Arg Cys
                85                  90                  95 gtc cga atc tgc tcc aag tct tat ttg acc ctg gaa aat ggg aag gtt     336
```

|     |     |     |     |     |     |     |     |     |     |     |     |     |     |     |     |
|---|---|---|---|---|---|---|---|---|---|---|---|---|---|---|---|
| Val | Arg | Ile | Cys | Ser | Lys | Ser | Tyr | Leu | Thr | Leu | Glu | Asn | Gly | Lys | Val |
|  |  |  | 100 |  |  |  | 105 |  |  |  | 110 |  |  |  |  |

```
ttc ctg acg ggt ggg gac ctc cca gct ctg gac gga gcc cgg gtg gat      384
Phe Leu Thr Gly Gly Asp Leu Pro Ala Leu Asp Gly Ala Arg Val Asp
            115                 120                 125 ttc cgg tgt gac ccc gac ttc cat ctg gtg ggc agc tcc cgg agc atc      432
Phe Arg Cys Asp Pro Asp Phe His Leu Val Gly Ser Ser Arg Ser Ile
        130                 135                 140 tgt agt cag ggc cag tgg agc acc ccc aag ccc cac tgc cag gtg aat      480
Cys Ser Gln Gly Gln Trp Ser Thr Pro Lys Pro His Cys Gln Val Asn
145                 150                 155                 160 cga acg cca cac tca gaa cgg cgc gca gtg tac atc ggg gca ctg ttt      528
Arg Thr Pro His Ser Glu Arg Arg Ala Val Tyr Ile Gly Ala Leu Phe
                165                 170                 175 ccc atg agc ggg ggc tgg cca ggg ggc cag gcc tgc cag ccc gcg gtg      576
Pro Met Ser Gly Gly Trp Pro Gly Gly Gln Ala Cys Gln Pro Ala Val
            180                 185                 190 gag atg gcg ctg gag gac gtg aat agc cgc agg gac atc ctg ccg gac      624
Glu Met Ala Leu Glu Asp Val Asn Ser Arg Arg Asp Ile Leu Pro Asp
        195                 200                 205 tat gag ctc aag ctc atc cac cac gac agc aag tgt gat cca ggc caa      672
Tyr Glu Leu Lys Leu Ile His His Asp Ser Lys Cys Asp Pro Gly Gln
210                 215                 220 gcc acc aag tac cta tat gag ctc ctc tac aac gac cct atc aag atc      720
Ala Thr Lys Tyr Leu Tyr Glu Leu Leu Tyr Asn Asp Pro Ile Lys Ile
225                 230                 235                 240 atc ctt atg cct ggc tgc agc tct gtc tcc acg ctg gtg gct gag gct      768
Ile Leu Met Pro Gly Cys Ser Ser Val Ser Thr Leu Val Ala Glu Ala
                245                 250                 255 gct agg atg tgg aac ctc att gtg ctt tcc tat ggc tcc agc tca cca      816
Ala Arg Met Trp Asn Leu Ile Val Leu Ser Tyr Gly Ser Ser Ser Pro
            260                 265                 270 gcc ctg tca aac cgg cag cgt ttc ccc act ttc ttc cga acg cac cca      864
Ala Leu Ser Asn Arg Gln Arg Phe Pro Thr Phe Phe Arg Thr His Pro
        275                 280                 285 tca gcc aca ctc cac aac cct acc cgc gtg aaa ctc ttt gaa aag tgg      912
Ser Ala Thr Leu His Asn Pro Thr Arg Val Lys Leu Phe Glu Lys Trp
290                 295                 300 ggc tgg aag aag att gct acc atc cag cag acc act gag gtc ttc act      960
Gly Trp Lys Lys Ile Ala Thr Ile Gln Gln Thr Thr Glu Val Phe Thr
305                 310                 315                 320 tcg act ctg gac gac ctg gag gaa cga gtg aag gag gct gga att gag     1008
Ser Thr Leu Asp Asp Leu Glu Glu Arg Val Lys Glu Ala Gly Ile Glu
                325                 330                 335 att act ttc cgc cag agt ttc ttc tca gat cca gct gtg ccc gtc aaa     1056
Ile Thr Phe Arg Gln Ser Phe Phe Ser Asp Pro Ala Val Pro Val Lys
            340                 345                 350 aac ctg aag cgc cag gat gcc cga atc atc gtg gga ctt ttc tat gag     1104
Asn Leu Lys Arg Gln Asp Ala Arg Ile Ile Val Gly Leu Phe Tyr Glu
        355                 360                 365 act gaa gcc cgg aaa gtt ttt tgt gag gtg tac aag gag cgt ctc ttt     1152
Thr Glu Ala Arg Lys Val Phe Cys Glu Val Tyr Lys Glu Arg Leu Phe
370                 375                 380 ggg aag aag tac gtc tgg ttc ctc att ggg tgg tat gct gac aat tgg     1200
Gly Lys Lys Tyr Val Trp Phe Leu Ile Gly Trp Tyr Ala Asp Asn Trp
385                 390                 395                 400 ttc aag atc tac gac cct tct atc aac tgc aca gtg gat gag atg act     1248
Phe Lys Ile Tyr Asp Pro Ser Ile Asn Cys Thr Val Asp Glu Met Thr
                405                 410                 415
```

-continued

| | | |
|---|---|---|
| gag gcg gtg gag ggc cac atc aca act gag att gtc atg ctg aat cct<br>Glu Ala Val Glu Gly His Ile Thr Thr Glu Ile Val Met Leu Asn Pro<br>420 425 430 | 1296 |
| gcc aat acc cgc agc att tcc aac atg aca tcc cag gaa ttt gtg gag<br>Ala Asn Thr Arg Ser Ile Ser Asn Met Thr Ser Gln Glu Phe Val Glu<br>435 440 445 | 1344 |
| aaa cta acc aag cga ctg aaa aga cac cct gag gag aca gga ggc ttc<br>Lys Leu Thr Lys Arg Leu Lys Arg His Pro Glu Glu Thr Gly Gly Phe<br>450 455 460 | 1392 |
| cag gag gca ccg ctg gcc tat gat gcc atc tgg gcc ttg gca ctg gcc<br>Gln Glu Ala Pro Leu Ala Tyr Asp Ala Ile Trp Ala Leu Ala Leu Ala<br>465 470 475 480 | 1440 |
| ctg aac aag aca tct gga gga ggc ggt cgt tct ggt gtg cgc ctg gag<br>Leu Asn Lys Thr Ser Gly Gly Gly Arg Ser Gly Val Arg Leu Glu<br>485 490 495 | 1488 |
| gac ttc aac tac aac aac cag acc att acc gac caa atc tac cgg gca<br>Asp Phe Asn Tyr Asn Asn Gln Thr Ile Thr Asp Gln Ile Tyr Arg Ala<br>500 505 510 | 1536 |
| atg aac tct tcg tcc ttt gag ggt gtc tct ggc cat gtg gtg ttt gat<br>Met Asn Ser Ser Ser Phe Glu Gly Val Ser Gly His Val Val Phe Asp<br>515 520 525 | 1584 |
| gcc agc ggc tct cgg atg gca tgg acg ctt atc gag cag ctt cag ggt<br>Ala Ser Gly Ser Arg Met Ala Trp Thr Leu Ile Glu Gln Leu Gln Gly<br>530 535 540 | 1632 |
| ggc agc tac aag aag att ggc tac tat gac agc acc aag gat gat ctt<br>Gly Ser Tyr Lys Lys Ile Gly Tyr Tyr Asp Ser Thr Lys Asp Asp Leu<br>545 550 555 560 | 1680 |
| tcc tgg tcc aaa aca gat aaa tgg att gga ggg tcc ccc cca gct gac<br>Ser Trp Ser Lys Thr Asp Lys Trp Ile Gly Gly Ser Pro Pro Ala Asp<br>565 570 575 | 1728 |
| cag acc ctg gtc atc aag aca ttc cgc ttc ctg tca cag aaa ctc ttt<br>Gln Thr Leu Val Ile Lys Thr Phe Arg Phe Leu Ser Gln Lys Leu Phe<br>580 585 590 | 1776 |
| atc tcc gtc tca gtt ctc tcc agc ctg ggc att gtc cta gct gtt gtc<br>Ile Ser Val Ser Val Leu Ser Ser Leu Gly Ile Val Leu Ala Val Val<br>595 600 605 | 1824 |
| tgt ctg tcc ttt aac atc tac aac tca cat gtc cgt tat atc cag aac<br>Cys Leu Ser Phe Asn Ile Tyr Asn Ser His Val Arg Tyr Ile Gln Asn<br>610 615 620 | 1872 |
| tca cag ccc aac ctg aac aac ctg act gct gtg ggc tgc tca ctg gct<br>Ser Gln Pro Asn Leu Asn Asn Leu Thr Ala Val Gly Cys Ser Leu Ala<br>625 630 635 640 | 1920 |
| tta gct gct gtc ttc ccc ctg ggg ctc gat ggt tac cac att ggg agg<br>Leu Ala Ala Val Phe Pro Leu Gly Leu Asp Gly Tyr His Ile Gly Arg<br>645 650 655 | 1968 |
| aac cag ttt cct ttc gtc tgc cag gcc cgc ctc tgg ctc ctg ggc ctg<br>Asn Gln Phe Pro Phe Val Cys Gln Ala Arg Leu Trp Leu Leu Gly Leu<br>660 665 670 | 2016 |
| ggc ttt agt ctg ggc tac ggt tcc atg ttc acc aag att tgg tgg gtc<br>Gly Phe Ser Leu Gly Tyr Gly Ser Met Phe Thr Lys Ile Trp Trp Val<br>675 680 685 | 2064 |
| cac acg gtc ttc aca aag aag gaa gaa aag aag gag tgg agg aag act<br>His Thr Val Phe Thr Lys Lys Glu Glu Lys Lys Glu Trp Arg Lys Thr<br>690 695 700 | 2112 |
| ctg gaa ccc tgg aag ctg tat gcc aca gtg ggc ctg ctg gtg ggc atg<br>Leu Glu Pro Trp Lys Leu Tyr Ala Thr Val Gly Leu Leu Val Gly Met<br>705 710 715 720 | 2160 |
| gat gtc ctc act ctc gcc atc tgg cag atc gtg gac cct ctg cac cgg<br>Asp Val Leu Thr Leu Ala Ile Trp Gln Ile Val Asp Pro Leu His Arg<br>725 730 735 | 2208 |

```
acc att gag aca ttt gcc aag gag gaa cct aag gaa gat att gac gtc    2256
Thr Ile Glu Thr Phe Ala Lys Glu Glu Pro Lys Glu Asp Ile Asp Val
        740                 745                 750 tct att ctg ccc cag ctg gag cat tgc agc tcc agg aag atg aat aca    2304
Ser Ile Leu Pro Gln Leu Glu His Cys Ser Ser Arg Lys Met Asn Thr
755                 760                 765 tgg ctt ggc att ttc tat ggt tac aag ggg ctg ctg ctg ctg gga        2352
Trp Leu Gly Ile Phe Tyr Gly Tyr Lys Gly Leu Leu Leu Leu Gly
    770                 775                 780 atc ttc ctt gct tat gag acc aag agt gtg tcc act gag aag atc aat    2400
Ile Phe Leu Ala Tyr Glu Thr Lys Ser Val Ser Thr Glu Lys Ile Asn
785                 790                 795                 800 gat cac cgg gct gtg ggc atg gct atc tac aat gtg gca gtc ctg tgc    2448
Asp His Arg Ala Val Gly Met Ala Ile Tyr Asn Val Ala Val Leu Cys
                805                 810                 815 ctc atc act gct cct gtc acc atg att ctg tcc agc cag cag gat gca    2496
Leu Ile Thr Ala Pro Val Thr Met Ile Leu Ser Ser Gln Gln Asp Ala
            820                 825                 830 gcc ttt gcc ttt gcc tct ctt gcc ata gtt ttc tcc tcc tat atc act    2544
Ala Phe Ala Phe Ala Ser Leu Ala Ile Val Phe Ser Ser Tyr Ile Thr
        835                 840                 845 ctt gtt gtg ctc ttt gtg ccc aag atg cgc agg ctg atc acc cga ggg    2592
Leu Val Val Leu Phe Val Pro Lys Met Arg Arg Leu Ile Thr Arg Gly
    850                 855                 860 gaa tgg cag tcg gag gcg cag gac acc atg aag aca ggg tca tcg acc    2640
Glu Trp Gln Ser Glu Ala Gln Asp Thr Met Lys Thr Gly Ser Ser Thr
865                 870                 875                 880 aac aac aac gag gag gag aag tcc cgg ctg ttg gag aag gag aac cgt    2688
Asn Asn Asn Glu Glu Glu Lys Ser Arg Leu Leu Glu Lys Glu Asn Arg
                885                 890                 895 gaa ctg gaa aag atc att gct gag aaa gag gag cgt gtc tct gaa ctg    2736
Glu Leu Glu Lys Ile Ile Ala Glu Lys Glu Glu Arg Val Ser Glu Leu
            900                 905                 910 cgc cat caa ctc cag tct cgg cag cag ctc cgc tcc cgg cgc cac cca    2784
Arg His Gln Leu Gln Ser Arg Gln Gln Leu Arg Ser Arg Arg His Pro
        915                 920                 925 ccg aca ccc cca gaa ccc tct ggg ggc ctg ccc agg gga ccc cct gag    2832
Pro Thr Pro Pro Glu Pro Ser Gly Gly Leu Pro Arg Gly Pro Pro Glu
    930                 935                 940 ccc ccc gac cgg ctt agc tgt gat ggg agt cga gtg cat ttg ctt tat    2880
Pro Pro Asp Arg Leu Ser Cys Asp Gly Ser Arg Val His Leu Leu Tyr
945                 950                 955                 960 aag tga                                                             2886
Lys

<210> SEQ ID NO 49
<211> LENGTH: 961
<212> TYPE: PRT
<213> ORGANISM: Homo sapiens

<400> SEQUENCE: 49

Met Leu Leu Leu Leu Leu Ala Pro Leu Phe Leu Arg Pro Pro Gly
  1               5                  10                  15

Ala Gly Gly Ala Gln Thr Pro Asn Ala Thr Ser Glu Gly Cys Gln Ile
                 20                  25                  30

Ile His Pro Pro Trp Glu Gly Gly Ile Arg Tyr Arg Gly Leu Thr Arg
             35                  40                  45

Asp Gln Val Lys Ala Ile Asn Phe Leu Pro Val Asp Tyr Glu Ile Glu
         50                  55                  60
```

```
Tyr Val Cys Arg Gly Glu Arg Glu Val Val Gly Pro Lys Val Arg Lys
 65                  70                  75                  80

Cys Leu Ala Asn Gly Ser Trp Thr Asp Met Asp Thr Pro Ser Arg Cys
                 85                  90                  95

Val Arg Ile Cys Ser Lys Ser Tyr Leu Thr Leu Glu Asn Gly Lys Val
            100                 105                 110

Phe Leu Thr Gly Gly Asp Leu Pro Ala Leu Asp Gly Ala Arg Val Asp
        115                 120                 125

Phe Arg Cys Asp Pro Asp Phe His Leu Val Gly Ser Ser Arg Ser Ile
    130                 135                 140

Cys Ser Gln Gly Gln Trp Ser Thr Pro Lys Pro His Cys Gln Val Asn
145                 150                 155                 160

Arg Thr Pro His Ser Glu Arg Arg Ala Val Tyr Ile Gly Ala Leu Phe
                165                 170                 175

Pro Met Ser Gly Gly Trp Pro Gly Gly Gln Ala Cys Gln Pro Ala Val
            180                 185                 190

Glu Met Ala Leu Glu Asp Val Asn Ser Arg Arg Asp Ile Leu Pro Asp
        195                 200                 205

Tyr Glu Leu Lys Leu Ile His His Asp Ser Lys Cys Asp Pro Gly Gln
    210                 215                 220

Ala Thr Lys Tyr Leu Tyr Glu Leu Leu Tyr Asn Asp Pro Ile Lys Ile
225                 230                 235                 240

Ile Leu Met Pro Gly Cys Ser Ser Val Ser Thr Leu Val Ala Glu Ala
                245                 250                 255

Ala Arg Met Trp Asn Leu Ile Val Leu Ser Tyr Gly Ser Ser Ser Pro
            260                 265                 270

Ala Leu Ser Asn Arg Gln Arg Phe Pro Thr Phe Phe Arg Thr His Pro
        275                 280                 285

Ser Ala Thr Leu His Asn Pro Thr Arg Val Lys Leu Phe Glu Lys Trp
    290                 295                 300

Gly Trp Lys Lys Ile Ala Thr Ile Gln Gln Thr Thr Glu Val Phe Thr
305                 310                 315                 320

Ser Thr Leu Asp Asp Leu Glu Glu Arg Val Lys Glu Ala Gly Ile Glu
                325                 330                 335

Ile Thr Phe Arg Gln Ser Phe Phe Ser Asp Pro Ala Val Pro Val Lys
            340                 345                 350

Asn Leu Lys Arg Gln Asp Ala Arg Ile Ile Val Gly Leu Phe Tyr Glu
        355                 360                 365

Thr Glu Ala Arg Lys Val Phe Cys Glu Val Tyr Lys Glu Arg Leu Phe
    370                 375                 380

Gly Lys Lys Tyr Val Trp Phe Leu Ile Gly Trp Tyr Ala Asp Asn Trp
385                 390                 395                 400

Phe Lys Ile Tyr Asp Pro Ser Ile Asn Cys Thr Val Asp Glu Met Thr
                405                 410                 415

Glu Ala Val Glu Gly His Ile Thr Thr Glu Ile Val Met Leu Asn Pro
            420                 425                 430

Ala Asn Thr Arg Ser Ile Ser Asn Met Thr Ser Gln Glu Phe Val Glu
        435                 440                 445

Lys Leu Thr Lys Arg Leu Lys Arg His Pro Glu Glu Thr Gly Gly Phe
    450                 455                 460

Gln Glu Ala Pro Leu Ala Tyr Asp Ala Ile Trp Ala Leu Ala Leu Ala
465                 470                 475                 480
```

-continued

```
Leu Asn Lys Thr Ser Gly Gly Gly Arg Ser Gly Val Arg Leu Glu
            485                 490                 495

Asp Phe Asn Tyr Asn Asn Gln Thr Ile Thr Asp Gln Ile Tyr Arg Ala
                500                 505                 510

Met Asn Ser Ser Ser Phe Glu Gly Val Ser Gly His Val Val Phe Asp
                515                 520                 525

Ala Ser Gly Ser Arg Met Ala Trp Thr Leu Ile Glu Gln Leu Gln Gly
            530                 535                 540

Gly Ser Tyr Lys Lys Ile Gly Tyr Tyr Asp Ser Thr Lys Asp Asp Leu
545                 550                 555                 560

Ser Trp Ser Lys Thr Asp Lys Trp Ile Gly Ser Pro Pro Ala Asp
                565                 570                 575

Gln Thr Leu Val Ile Lys Thr Phe Arg Phe Leu Ser Gln Lys Leu Phe
            580                 585                 590

Ile Ser Val Ser Val Leu Ser Ser Leu Gly Ile Val Leu Ala Val Val
        595                 600                 605

Cys Leu Ser Phe Asn Ile Tyr Asn Ser His Val Arg Tyr Ile Gln Asn
610                 615                 620

Ser Gln Pro Asn Leu Asn Asn Leu Thr Ala Val Gly Cys Ser Leu Ala
625                 630                 635                 640

Leu Ala Ala Val Phe Pro Leu Gly Leu Asp Gly Tyr His Ile Gly Arg
                645                 650                 655

Asn Gln Phe Pro Phe Val Cys Gln Ala Arg Leu Trp Leu Leu Gly Leu
                660                 665                 670

Gly Phe Ser Leu Gly Tyr Gly Ser Met Phe Thr Lys Ile Trp Trp Val
            675                 680                 685

His Thr Val Phe Thr Lys Lys Glu Glu Lys Glu Trp Arg Lys Thr
            690                 695                 700

Leu Glu Pro Trp Lys Leu Tyr Ala Thr Val Gly Leu Leu Val Gly Met
705                 710                 715                 720

Asp Val Leu Thr Leu Ala Ile Trp Gln Ile Val Asp Pro Leu His Arg
            725                 730                 735

Thr Ile Glu Thr Phe Ala Lys Glu Pro Lys Glu Asp Ile Asp Val
            740                 745                 750

Ser Ile Leu Pro Gln Leu Glu His Cys Ser Ser Arg Lys Met Asn Thr
            755                 760                 765

Trp Leu Gly Ile Phe Tyr Gly Tyr Lys Gly Leu Leu Leu Leu Gly
        770                 775                 780

Ile Phe Leu Ala Tyr Glu Thr Lys Ser Val Ser Thr Glu Lys Ile Asn
785                 790                 795                 800

Asp His Arg Ala Val Gly Met Ala Ile Tyr Asn Val Ala Val Leu Cys
                805                 810                 815

Leu Ile Thr Ala Pro Val Thr Met Ile Leu Ser Ser Gln Gln Asp Ala
            820                 825                 830

Ala Phe Ala Phe Ala Ser Leu Ala Ile Val Phe Ser Ser Tyr Ile Thr
        835                 840                 845

Leu Val Val Leu Phe Val Pro Lys Met Arg Arg Leu Ile Thr Arg Gly
        850                 855                 860

Glu Trp Gln Ser Glu Ala Gln Asp Thr Met Lys Thr Gly Ser Ser Thr
865                 870                 875                 880

Asn Asn Asn Glu Glu Glu Lys Ser Arg Leu Leu Glu Lys Glu Asn Arg
                885                 890                 895

Glu Leu Glu Lys Ile Ile Ala Glu Lys Glu Glu Arg Val Ser Glu Leu
```

```
                    900             905             910
Arg His Gln Leu Gln Ser Arg Gln Gln Leu Arg Ser Arg Arg His Pro
        915                 920                 925
Pro Thr Pro Pro Glu Pro Ser Gly Gly Leu Pro Arg Gly Pro Pro Glu
        930                 935                 940
Pro Pro Asp Arg Leu Ser Cys Asp Gly Ser Arg Val His Leu Leu Tyr
945                 950                 955                 960
Lys

<210> SEQ ID NO 50
<211> LENGTH: 2535
<212> TYPE: DNA
<213> ORGANISM: Homo sapiens
<220> FEATURE:
<221> NAME/KEY: CDS
<222> LOCATION: (1)...(2532)

<400> SEQUENCE: 50 atg ggg ccc ggg gcc cct ttt gcc cgg gtg ggg tgg cca ctg ccg ctt       48
Met Gly Pro Gly Ala Pro Phe Ala Arg Val Gly Trp Pro Leu Pro Leu
1               5                   10                  15 ctg gtt gtg atg gcg gca ggg gtg gct ccg gtg tgg gcc tcc cac tcc       96
Leu Val Val Met Ala Ala Gly Val Ala Pro Val Trp Ala Ser His Ser
                20                  25                  30 ccc cat ctc ccg cgg cct cac tcg cgg gtc ccc ccg cac ccc tcc tca      144
Pro His Leu Pro Arg Pro His Ser Arg Val Pro Pro His Pro Ser Ser
            35                  40                  45 gaa cgg cgc gca gtg tac atc ggg gca ctg ttt ccc atg agc ggg ggc      192
Glu Arg Arg Ala Val Tyr Ile Gly Ala Leu Phe Pro Met Ser Gly Gly
        50                  55                  60 tgg cca ggg ggc cag gcc tgc cag ccc gcg gtg gag atg gcg ctg gag      240
Trp Pro Gly Gly Gln Ala Cys Gln Pro Ala Val Glu Met Ala Leu Glu
65                  70                  75                  80 gac gtg aat agc cgc agg gac atc ctg ccg gac tat gag ctc aag ctc      288
Asp Val Asn Ser Arg Arg Asp Ile Leu Pro Asp Tyr Glu Leu Lys Leu
                85                  90                  95 atc cac cac gac agc aag tgt gat cca ggc caa gcc acc aag tac cta      336
Ile His His Asp Ser Lys Cys Asp Pro Gly Gln Ala Thr Lys Tyr Leu
            100                 105                 110 tat gag ctg ctc tac aac gac cct atc aag atc atc ctt atg cct ggc      384
Tyr Glu Leu Leu Tyr Asn Asp Pro Ile Lys Ile Ile Leu Met Pro Gly
        115                 120                 125 tgc agc tct gtc tcc acg ctg gtg gct gag gct gct agg atg tgg aac      432
Cys Ser Ser Val Ser Thr Leu Val Ala Glu Ala Ala Arg Met Trp Asn
130                 135                 140 ctc att gtg ctt tcc tat ggc tcc agc tca cca gcc ctg tca aac cgg      480
Leu Ile Val Leu Ser Tyr Gly Ser Ser Ser Pro Ala Leu Ser Asn Arg
145                 150                 155                 160 cag cgt ttc ccc act ttc ttc cga acg cac cca tca gcc aca ctc cac      528
Gln Arg Phe Pro Thr Phe Phe Arg Thr His Pro Ser Ala Thr Leu His
                165                 170                 175 aac cct acc cgc gtg aaa ctc ttt gaa aag tgg ggc tgg aag aag att      576
Asn Pro Thr Arg Val Lys Leu Phe Glu Lys Trp Gly Trp Lys Lys Ile
            180                 185                 190 gct acc atc cag cag acc act gag gtc ttc act tcg act ctg gac gac      624
Ala Thr Ile Gln Gln Thr Thr Glu Val Phe Thr Ser Thr Leu Asp Asp
        195                 200                 205 ctg gag gaa cga gtg aag gag gct gga att gag att act ttc cgc cag      672
Leu Glu Glu Arg Val Lys Glu Ala Gly Ile Glu Ile Thr Phe Arg Gln
210                 215                 220
```

```
agt ttc ttc tca gat cca gct gtg ccc gtc aaa aac ctg aag cgc cag        720
Ser Phe Phe Ser Asp Pro Ala Val Pro Val Lys Asn Leu Lys Arg Gln
225                 230                 235                 240 gat gcc cga atc atc gtg gga ctt ttc tat gag act gaa gcc cgg aaa        768
Asp Ala Arg Ile Ile Val Gly Leu Phe Tyr Glu Thr Glu Ala Arg Lys
            245                 250                 255 gtt ttt tgt gag gtg tac aag gag cgt ctc ttt ggg aag aag tac gtc        816
Val Phe Cys Glu Val Tyr Lys Glu Arg Leu Phe Gly Lys Lys Tyr Val
        260                 265                 270 tgg ttc ctc att ggg tgg tat gct gac aat tgg ttc aag atc tac gac        864
Trp Phe Leu Ile Gly Trp Tyr Ala Asp Asn Trp Phe Lys Ile Tyr Asp
    275                 280                 285 cct tct atc aac tgc aca gtg gat gag atg act gag gcg gtg gag ggc        912
Pro Ser Ile Asn Cys Thr Val Asp Glu Met Thr Glu Ala Val Glu Gly
290                 295                 300 cac atc aca act gag att gtc atg ctg aat cct gcc aat acc cgc agc        960
His Ile Thr Thr Glu Ile Val Met Leu Asn Pro Ala Asn Thr Arg Ser
305                 310                 315                 320 att tcc aac atg aca tcc cag gaa ttt gtg gag aaa cta acc aag cga       1008
Ile Ser Asn Met Thr Ser Gln Glu Phe Val Glu Lys Leu Thr Lys Arg
            325                 330                 335 ctg aaa aga cac cct gag gag aca gga ggc ttc cag gag gca ccg ctg       1056
Leu Lys Arg His Pro Glu Glu Thr Gly Gly Phe Gln Glu Ala Pro Leu
        340                 345                 350 gcc tat gat gcc atc tgg gcc ttg gca ctg gcc ctg aac aag aca tct       1104
Ala Tyr Asp Ala Ile Trp Ala Leu Ala Leu Ala Leu Asn Lys Thr Ser
    355                 360                 365 gga gga ggc ggc cgt tct ggt gtg cgc ctg gag gac ttc aac tac aac       1152
Gly Gly Gly Gly Arg Ser Gly Val Arg Leu Glu Asp Phe Asn Tyr Asn
370                 375                 380 aac cag acc att acc gac caa atc tac cgg gca atg aac tct tcg tcc       1200
Asn Gln Thr Ile Thr Asp Gln Ile Tyr Arg Ala Met Asn Ser Ser Ser
385                 390                 395                 400 ttt gag ggt gtc tct ggc cat gtg gtg ttt gat gcc agc ggc tct cgg       1248
Phe Glu Gly Val Ser Gly His Val Val Phe Asp Ala Ser Gly Ser Arg
            405                 410                 415 atg gca tgg acg ctt atc gag cag ctt cag ggt ggc agc tac aag aag       1296
Met Ala Trp Thr Leu Ile Glu Gln Leu Gln Gly Gly Ser Tyr Lys Lys
        420                 425                 430 att ggc tac tat gac agc acc aag gat gat ctt tcc tgg tcc aaa aca       1344
Ile Gly Tyr Tyr Asp Ser Thr Lys Asp Asp Leu Ser Trp Ser Lys Thr
    435                 440                 445 gat aaa tgg att gga ggg tcc ccc cca gct gac cag acc ctg gtc atc       1392
Asp Lys Trp Ile Gly Gly Ser Pro Pro Ala Asp Gln Thr Leu Val Ile
450                 455                 460 aag aca ttc cgc ttc ctg tca cag aaa ctc ttt atc tcc gtc tca gtt       1440
Lys Thr Phe Arg Phe Leu Ser Gln Lys Leu Phe Ile Ser Val Ser Val
465                 470                 475                 480 ctc tcc agc ctg ggc att gtc cta gct gtt gtc tgt ctg tcc ttt aac       1488
Leu Ser Ser Leu Gly Ile Val Leu Ala Val Val Cys Leu Ser Phe Asn
            485                 490                 495 atc tac aac tca cat gtc cgt tat atc cag aac tca cag ccc aac ctg       1536
Ile Tyr Asn Ser His Val Arg Tyr Ile Gln Asn Ser Gln Pro Asn Leu
        500                 505                 510 aac aac ctg act gct gtg ggc tgc tca ctg gct tta gct gct gtc ttc       1584
Asn Asn Leu Thr Ala Val Gly Cys Ser Leu Ala Leu Ala Ala Val Phe
    515                 520                 525 ccc ctg ggg ctc gat ggt tac cac att ggg agg aac cag ttt cct ttc       1632
Pro Leu Gly Leu Asp Gly Tyr His Ile Gly Arg Asn Gln Phe Pro Phe
```

-continued

|     |     | 530 |     |     |     | 535 |     |     |     | 540 |     |     |     |      |
|---|---|---|---|---|---|---|---|---|---|---|---|---|---|---|
| gtc | tgc | cag | gcc | cgc | ctc | tgg | ctc | ctg | ggc | ctg | ggc | ttt | agt | ctg | ggc | 1680 |
| Val | Cys | Gln | Ala | Arg | Leu | Trp | Leu | Leu | Gly | Leu | Gly | Phe | Ser | Leu | Gly |
| 545 |     |     |     |     | 550 |     |     |     |     | 555 |     |     |     |     | 560 |

| tac | ggt | tcc | atg | ttc | acc | aag | att | tgg | tgg | gtc | cac | acg | gtc | ttc | aca | 1728 |
| Tyr | Gly | Ser | Met | Phe | Thr | Lys | Ile | Trp | Trp | Val | His | Thr | Val | Phe | Thr |
|     |     |     |     |     | 565 |     |     |     |     | 570 |     |     |     |     | 575 |

| aag | aag | gaa | gaa | aag | aag | gag | tgg | agg | aag | act | ctg | gaa | ccc | tgg | aag | 1776 |
| Lys | Lys | Glu | Glu | Lys | Lys | Glu | Trp | Arg | Lys | Thr | Leu | Glu | Pro | Trp | Lys |
|     |     |     |     | 580 |     |     |     |     | 585 |     |     |     |     | 590 |     |

| ctg | tat | gcc | aca | gtg | ggc | ctg | ctg | gtg | ggc | atg | gat | gtc | ctc | act | ctc | 1824 |
| Leu | Tyr | Ala | Thr | Val | Gly | Leu | Leu | Val | Gly | Met | Asp | Val | Leu | Thr | Leu |
|     |     |     | 595 |     |     |     |     | 600 |     |     |     |     | 605 |     |     |

| gcc | atc | tgg | cag | atc | gtg | gac | cct | ctg | cac | cgg | acc | att | gag | aca | ttt | 1872 |
| Ala | Ile | Trp | Gln | Ile | Val | Asp | Pro | Leu | His | Arg | Thr | Ile | Glu | Thr | Phe |
|     |     | 610 |     |     |     |     | 615 |     |     |     |     | 620 |     |     |     |

| gcc | aag | gag | gaa | cct | aag | gaa | gat | att | gac | gtc | tct | att | ctg | ccc | cag | 1920 |
| Ala | Lys | Glu | Glu | Pro | Lys | Glu | Asp | Ile | Asp | Val | Ser | Ile | Leu | Pro | Gln |
| 625 |     |     |     |     | 630 |     |     |     |     | 635 |     |     |     |     | 640 |

| ctg | gag | cat | tgc | agc | tcc | agg | aag | atg | aat | aca | tgg | ctt | ggc | att | ttc | 1968 |
| Leu | Glu | His | Cys | Ser | Ser | Arg | Lys | Met | Asn | Thr | Trp | Leu | Gly | Ile | Phe |
|     |     |     |     |     | 645 |     |     |     |     | 650 |     |     |     |     | 655 |

| tat | ggt | tac | aag | ggg | ctg | ctg | ctg | ctg | gga | atc | ttc | ctt | gct | tat |     | 2016 |
| Tyr | Gly | Tyr | Lys | Gly | Leu | Leu | Leu | Leu | Gly | Ile | Phe | Leu | Ala | Tyr |     |
|     |     |     | 660 |     |     |     |     | 665 |     |     |     |     | 670 |     |     |

| gag | acc | aag | agt | gtg | tcc | act | gag | aag | atc | aat | gat | cac | cgg | gct | gtg | 2064 |
| Glu | Thr | Lys | Ser | Val | Ser | Thr | Glu | Lys | Ile | Asn | Asp | His | Arg | Ala | Val |
|     |     | 675 |     |     |     |     | 680 |     |     |     |     | 685 |     |     |     |

| ggc | atg | gct | atc | tac | aat | gtg | gca | gtc | ctg | tgc | ctc | atc | act | gct | cct | 2112 |
| Gly | Met | Ala | Ile | Tyr | Asn | Val | Ala | Val | Leu | Cys | Leu | Ile | Thr | Ala | Pro |
| 690 |     |     |     |     | 695 |     |     |     |     | 700 |     |     |     |     |     |

| gtc | acc | atg | att | ctg | tcc | agc | cag | cag | gat | gca | gcc | ttt | gcc | ttt | gcc | 2160 |
| Val | Thr | Met | Ile | Leu | Ser | Ser | Gln | Gln | Asp | Ala | Ala | Phe | Ala | Phe | Ala |
| 705 |     |     |     |     | 710 |     |     |     |     | 715 |     |     |     |     | 720 |

| tct | ctt | gcc | ata | gtt | ttc | tcc | tcc | tat | atc | act | ctt | gtt | gtg | ctc | ttt | 2208 |
| Ser | Leu | Ala | Ile | Val | Phe | Ser | Ser | Tyr | Ile | Thr | Leu | Val | Val | Leu | Phe |
|     |     |     |     | 725 |     |     |     |     | 730 |     |     |     |     | 735 |     |

| gtg | ccc | aag | atg | cgc | agg | ctg | atc | acc | cga | ggg | gaa | tgg | cag | tcg | gag | 2256 |
| Val | Pro | Lys | Met | Arg | Arg | Leu | Ile | Thr | Arg | Gly | Glu | Trp | Gln | Ser | Glu |
|     |     |     | 740 |     |     |     |     | 745 |     |     |     |     | 750 |     |     |

| gcg | cag | gac | acc | atg | aag | aca | ggg | tca | tcg | acc | aac | aac | aac | gag | gag | 2304 |
| Ala | Gln | Asp | Thr | Met | Lys | Thr | Gly | Ser | Ser | Thr | Asn | Asn | Asn | Glu | Glu |
|     |     | 755 |     |     |     |     | 760 |     |     |     |     | 765 |     |     |     |

| gag | aag | tcc | cgg | ctg | ttg | gag | aag | gag | aac | cgt | gaa | ctg | gaa | aag | atc | 2352 |
| Glu | Lys | Ser | Arg | Leu | Leu | Glu | Lys | Glu | Asn | Arg | Glu | Leu | Glu | Lys | Ile |
| 770 |     |     |     |     | 775 |     |     |     |     | 780 |     |     |     |     |     |

| att | gct | gag | aaa | gag | gag | cgt | gtc | tct | gaa | ctg | cgc | cat | caa | ctc | cag | 2400 |
| Ile | Ala | Glu | Lys | Glu | Glu | Arg | Val | Ser | Glu | Leu | Arg | His | Gln | Leu | Gln |
| 785 |     |     |     |     | 790 |     |     |     |     | 795 |     |     |     |     | 800 |

| tct | cgg | cag | cag | ctc | cgc | tcc | cgg | cgc | cac | cca | ccg | aca | ccc | cca | gaa | 2448 |
| Ser | Arg | Gln | Gln | Leu | Arg | Ser | Arg | Arg | His | Pro | Pro | Thr | Pro | Pro | Glu |
|     |     |     |     | 805 |     |     |     |     | 810 |     |     |     |     | 815 |     |

| ccc | tct | ggg | ggc | ctg | ccc | agg | gga | ccc | cct | gag | ccc | ccc | gac | cgg | ctt | 2496 |
| Pro | Ser | Gly | Gly | Leu | Pro | Arg | Gly | Pro | Pro | Glu | Pro | Pro | Asp | Arg | Leu |
|     |     |     | 820 |     |     |     |     | 825 |     |     |     |     | 830 |     |     |

| agc | tgt | gat | ggg | agt | cga | gtg | cat | ttg | ctt | tat | aag | tga |     |     |     | 2535 |
| Ser | Cys | Asp | Gly | Ser | Arg | Val | His | Leu | Leu | Tyr | Lys |     |     |     |     |
|     |     | 835 |     |     |     |     | 840 |     |     |     |     |     |     |     |     |

<210> SEQ ID NO 51
<211> LENGTH: 844
<212> TYPE: PRT
<213> ORGANISM: Homo sapiens

<400> SEQUENCE: 51

Met Gly Pro Gly Ala Pro Phe Ala Arg Val Gly Trp Pro Leu Pro Leu
1               5                   10                  15

Leu Val Val Met Ala Ala Gly Val Ala Pro Val Trp Ala Ser His Ser
            20                  25                  30

Pro His Leu Pro Arg Pro His Ser Arg Val Pro Pro His Pro Ser Ser
        35                  40                  45

Glu Arg Arg Ala Val Tyr Ile Gly Ala Leu Phe Pro Met Ser Gly Gly
    50                  55                  60

Trp Pro Gly Gly Gln Ala Cys Gln Pro Ala Val Glu Met Ala Leu Glu
65                  70                  75                  80

Asp Val Asn Ser Arg Arg Asp Ile Leu Pro Asp Tyr Glu Leu Lys Leu
                85                  90                  95

Ile His His Asp Ser Lys Cys Asp Pro Gly Gln Ala Thr Lys Tyr Leu
            100                 105                 110

Tyr Glu Leu Leu Tyr Asn Asp Pro Ile Lys Ile Ile Leu Met Pro Gly
        115                 120                 125

Cys Ser Ser Val Ser Thr Leu Val Ala Glu Ala Ala Arg Met Trp Asn
130                 135                 140

Leu Ile Val Leu Ser Tyr Gly Ser Ser Ser Pro Ala Leu Ser Asn Arg
145                 150                 155                 160

Gln Arg Phe Pro Thr Phe Phe Arg Thr His Pro Ser Ala Thr Leu His
                165                 170                 175

Asn Pro Thr Arg Val Lys Leu Phe Glu Lys Trp Gly Trp Lys Lys Ile
            180                 185                 190

Ala Thr Ile Gln Gln Thr Thr Glu Val Phe Thr Ser Thr Leu Asp Asp
        195                 200                 205

Leu Glu Glu Arg Val Lys Glu Ala Gly Ile Glu Ile Thr Phe Arg Gln
    210                 215                 220

Ser Phe Phe Ser Asp Pro Ala Val Pro Val Lys Asn Leu Lys Arg Gln
225                 230                 235                 240

Asp Ala Arg Ile Ile Val Gly Leu Phe Tyr Glu Thr Glu Ala Arg Lys
                245                 250                 255

Val Phe Cys Glu Val Tyr Lys Glu Arg Leu Phe Gly Lys Lys Tyr Val
            260                 265                 270

Trp Phe Leu Ile Gly Trp Tyr Ala Asp Asn Trp Phe Lys Ile Tyr Asp
        275                 280                 285

Pro Ser Ile Asn Cys Thr Val Asp Glu Met Thr Glu Ala Val Glu Gly
    290                 295                 300

His Ile Thr Thr Glu Ile Val Met Leu Asn Pro Ala Asn Thr Arg Ser
305                 310                 315                 320

Ile Ser Asn Met Thr Ser Gln Glu Phe Val Glu Lys Leu Thr Lys Arg
                325                 330                 335

Leu Lys Arg His Pro Glu Glu Thr Gly Gly Phe Gln Glu Ala Pro Leu
            340                 345                 350

Ala Tyr Asp Ala Ile Trp Ala Leu Ala Leu Ala Leu Asn Lys Thr Ser
        355                 360                 365

Gly Gly Gly Gly Arg Ser Gly Val Arg Leu Glu Asp Phe Asn Tyr Asn
    370                 375                 380

```
Asn Gln Thr Ile Thr Asp Gln Ile Tyr Arg Ala Met Asn Ser Ser Ser
385                 390                 395                 400

Phe Glu Gly Val Ser Gly His Val Val Phe Asp Ala Ser Gly Ser Arg
            405                 410                 415

Met Ala Trp Thr Leu Ile Glu Gln Leu Gln Gly Gly Ser Tyr Lys Lys
                420                 425                 430

Ile Gly Tyr Tyr Asp Ser Thr Lys Asp Asp Leu Ser Trp Ser Lys Thr
            435                 440                 445

Asp Lys Trp Ile Gly Gly Ser Pro Pro Ala Asp Gln Thr Leu Val Ile
        450                 455                 460

Lys Thr Phe Arg Phe Leu Ser Gln Lys Leu Phe Ile Ser Val Ser Val
465                 470                 475                 480

Leu Ser Ser Leu Gly Ile Val Leu Ala Val Val Cys Leu Ser Phe Asn
                485                 490                 495

Ile Tyr Asn Ser His Val Arg Tyr Ile Gln Asn Ser Gln Pro Asn Leu
            500                 505                 510

Asn Asn Leu Thr Ala Val Gly Cys Ser Leu Ala Leu Ala Ala Val Phe
        515                 520                 525

Pro Leu Gly Leu Asp Gly Tyr His Ile Gly Arg Asn Gln Phe Pro Phe
    530                 535                 540

Val Cys Gln Ala Arg Leu Trp Leu Leu Gly Leu Gly Phe Ser Leu Gly
545                 550                 555                 560

Tyr Gly Ser Met Phe Thr Lys Ile Trp Trp Val His Thr Val Phe Thr
                565                 570                 575

Lys Lys Glu Glu Lys Lys Glu Trp Arg Lys Thr Leu Glu Pro Trp Lys
            580                 585                 590

Leu Tyr Ala Thr Val Gly Leu Leu Val Gly Met Asp Val Leu Thr Leu
        595                 600                 605

Ala Ile Trp Gln Ile Val Asp Pro Leu His Arg Thr Ile Glu Thr Phe
610                 615                 620

Ala Lys Glu Glu Pro Lys Glu Asp Ile Asp Val Ser Ile Leu Pro Gln
625                 630                 635                 640

Leu Glu His Cys Ser Ser Arg Lys Met Asn Thr Trp Leu Gly Ile Phe
                645                 650                 655

Tyr Gly Tyr Lys Gly Leu Leu Leu Leu Gly Ile Phe Leu Ala Tyr
            660                 665                 670

Glu Thr Lys Ser Val Ser Thr Glu Lys Ile Asn Asp His Arg Ala Val
        675                 680                 685

Gly Met Ala Ile Tyr Asn Val Ala Val Leu Cys Leu Ile Thr Ala Pro
    690                 695                 700

Val Thr Met Ile Leu Ser Ser Gln Gln Asp Ala Ala Phe Ala Phe Ala
705                 710                 715                 720

Ser Leu Ala Ile Val Phe Ser Ser Tyr Ile Thr Leu Val Val Leu Phe
                725                 730                 735

Val Pro Lys Met Arg Arg Leu Ile Thr Arg Gly Glu Trp Gln Ser Glu
            740                 745                 750

Ala Gln Asp Thr Met Lys Thr Gly Ser Ser Thr Asn Asn Asn Glu Glu
        755                 760                 765

Glu Lys Ser Arg Leu Leu Glu Lys Glu Asn Arg Glu Leu Glu Lys Ile
    770                 775                 780

Ile Ala Glu Lys Glu Glu Arg Val Ser Glu Leu Arg His Gln Leu Gln
785                 790                 795                 800

Ser Arg Gln Gln Leu Arg Ser Arg Arg His Pro Pro Thr Pro Pro Glu
```

```
                  805                 810                 815
Pro Ser Gly Gly Leu Pro Arg Gly Pro Pro Glu Pro Pro Asp Arg Leu
        820                 825                 830

Ser Cys Asp Gly Ser Arg Val His Leu Leu Tyr Lys
        835                 840

<210> SEQ ID NO 52
<211> LENGTH: 2895
<212> TYPE: DNA
<213> ORGANISM: Canis familiaris
<220> FEATURE:
<221> NAME/KEY: CDS
<222> LOCATION: (1)...(2892)

<400> SEQUENCE: 52 atg ctg ctg ctg ctc ctg ccg ctg gcg ctg gcg ccg ctc ttc ctc cgc     48
Met Leu Leu Leu Leu Leu Pro Leu Ala Leu Ala Pro Leu Phe Leu Arg
 1               5                  10                  15 ccc ccg ggc gcg ggc ggg gca cag acc ccc aac gcc acc tcg gaa ggt     96
Pro Pro Gly Ala Gly Gly Ala Gln Thr Pro Asn Ala Thr Ser Glu Gly
            20                  25                  30 tgc cag atc ata cac ccg cct tgg gaa ggg ggt atc agg tac agg ggc    144
Cys Gln Ile Ile His Pro Pro Trp Glu Gly Gly Ile Arg Tyr Arg Gly
        35                  40                  45 ctg act cgt gac cag gtg aag gct atc aac ttc ctg ccg gtg gac tat    192
Leu Thr Arg Asp Gln Val Lys Ala Ile Asn Phe Leu Pro Val Asp Tyr
    50                  55                  60 gag att gag tat gtg tgc cgg gga gag cga gag gtg gtg ggg ccc aag    240
Glu Ile Glu Tyr Val Cys Arg Gly Glu Arg Glu Val Val Gly Pro Lys
65                  70                  75                  80 gtc cga aag tgc ctg gcc aat ggc tcc tgg aca gat atg gac aca ccc    288
Val Arg Lys Cys Leu Ala Asn Gly Ser Trp Thr Asp Met Asp Thr Pro
                85                  90                  95 agc cgc tgt gtc cga atc tgt tcc aag tca tat ttg gcc ctg gaa aat    336
Ser Arg Cys Val Arg Ile Cys Ser Lys Ser Tyr Leu Ala Leu Glu Asn
            100                 105                 110 ggg aag gtc ttc ctg acg ggt ggg gac ctc ccc gct ctg gat gga gcc    384
Gly Lys Val Phe Leu Thr Gly Gly Asp Leu Pro Ala Leu Asp Gly Ala
        115                 120                 125 cgg gtg gat ttc cgg tgt gac cct gac ttc cat ctt gtg ggc agc tcc    432
Arg Val Asp Phe Arg Cys Asp Pro Asp Phe His Leu Val Gly Ser Ser
    130                 135                 140 cgg agt atc tgt agt cag ggc cag tgg agc act ccc aag ccc cac tgc    480
Arg Ser Ile Cys Ser Gln Gly Gln Trp Ser Thr Pro Lys Pro His Cys
145                 150                 155                 160 cag gtg agc cga acg ccg cac tca gag cgg cga gcg gtg tac atc ggg    528
Gln Val Ser Arg Thr Pro His Ser Glu Arg Arg Ala Val Tyr Ile Gly
                165                 170                 175 gcg ctg ttt ccc atg agc ggg ggc tgg ccg ggg ggc cag gcc tgc cag    576
Ala Leu Phe Pro Met Ser Gly Gly Trp Pro Gly Gly Gln Ala Cys Gln
            180                 185                 190 ccc gcg gtg gag atg gcg ctg gag gac gtg aat agc cgc agg gac atc    624
Pro Ala Val Glu Met Ala Leu Glu Asp Val Asn Ser Arg Arg Asp Ile
        195                 200                 205 ctg ccg gac tac gag ctc aag ctc atc cac cac gac agc aag tgt gac    672
Leu Pro Asp Tyr Glu Leu Lys Leu Ile His His Asp Ser Lys Cys Asp
    210                 215                 220 cca ggc caa gct acc aag tac ctg tat gaa ctg ctc tac aac gac ccc    720
Pro Gly Gln Ala Thr Lys Tyr Leu Tyr Glu Leu Leu Tyr Asn Asp Pro
225                 230                 235                 240
```

-continued

| | |
|---|---|
| atc aag atc atc ctc atg cct ggc tgc agc tct gtc tcc acg ctt gtg<br>Ile Lys Ile Ile Leu Met Pro Gly Cys Ser Ser Val Ser Thr Leu Val<br>               245                   250                255 | 768 |
| gct gag gct gcc agg atg tgg aac ctc att gtg ctc tcc tat ggt tcc<br>Ala Glu Ala Ala Arg Met Trp Asn Leu Ile Val Leu Ser Tyr Gly Ser<br>           260                   265                270 | 816 |
| agc tca cca gct ctg tcc aac cgg cag cgc ttt cct acc ttc ttc cga<br>Ser Ser Pro Ala Leu Ser Asn Arg Gln Arg Phe Pro Thr Phe Phe Arg<br>                275                  280             285 | 864 |
| act cat ccc tcg gcc acg ctc cac aac cct acg cga gtg aag ctc ttt<br>Thr His Pro Ser Ala Thr Leu His Asn Pro Thr Arg Val Lys Leu Phe<br>290                     295                   300 | 912 |
| gag aag tgg ggc tgg agg aag att gcc acc atc cag cag acc acc gag<br>Glu Lys Trp Gly Trp Arg Lys Ile Ala Thr Ile Gln Gln Thr Thr Glu<br>305                310                315            320 | 960 |
| gtg ttc aca tcg act ctg gac gac cta gag gaa cga gtg aag gag gct<br>Val Phe Thr Ser Thr Leu Asp Asp Leu Glu Glu Arg Val Lys Glu Ala<br>                  325                330            335 | 1008 |
| ggg att gag att act ttc cgc cag agc ttc ttc tca gat cct gcc gtg<br>Gly Ile Glu Ile Thr Phe Arg Gln Ser Phe Phe Ser Asp Pro Ala Val<br>                    340                345            350 | 1056 |
| cct gtc aag aac ctc aag cgc cag gat gcc cga atc atc gtg gga ctt<br>Pro Val Lys Asn Leu Lys Arg Gln Asp Ala Arg Ile Ile Val Gly Leu<br>           355                   360                365 | 1104 |
| ttc tat gag act gaa gcc cgg aaa gtg ttc tgt gag gta tac aag gag<br>Phe Tyr Glu Thr Glu Ala Arg Lys Val Phe Cys Glu Val Tyr Lys Glu<br>370                    375                  380 | 1152 |
| cgg ctc ttt ggg aag aag tat gtg tgg ttc ctc att ggg tgg tat gct<br>Arg Leu Phe Gly Lys Lys Tyr Val Trp Phe Leu Ile Gly Trp Tyr Ala<br>385                390                395            400 | 1200 |
| gac aat tgg ttc aag acc tac gac ccc tcc atc aac tgc aca gtg gat<br>Asp Asn Trp Phe Lys Thr Tyr Asp Pro Ser Ile Asn Cys Thr Val Asp<br>                  405                410            415 | 1248 |
| gag atg acc gag gct gtg gaa ggc cac atc acc act gag att gtc atg<br>Glu Met Thr Glu Ala Val Glu Gly His Ile Thr Thr Glu Ile Val Met<br>                    420                425            430 | 1296 |
| ctg aac cca gcc aac acc cgc agc atc tcc aac atg aca tcc cag gag<br>Leu Asn Pro Ala Asn Thr Arg Ser Ile Ser Asn Met Thr Ser Gln Glu<br>           435                   440                445 | 1344 |
| ttt gtg gag aaa ctg acc aag aga ctc aag aga cac cct gag gag aca<br>Phe Val Glu Lys Leu Thr Lys Arg Leu Lys Arg His Pro Glu Glu Thr<br>450                    455                  460 | 1392 |
| ggc ggc ttc cag gag gca ccg ctg gcc tat gat gcc atc tgg gcc ttg<br>Gly Gly Phe Gln Glu Ala Pro Leu Ala Tyr Asp Ala Ile Trp Ala Leu<br>465                470                475            480 | 1440 |
| gca ttg gcc ctg aac aag aca tct gga ggg agc ggc cgt tcg ggg gtg<br>Ala Leu Ala Leu Asn Lys Thr Ser Gly Gly Ser Gly Arg Ser Gly Val<br>                    485                490            495 | 1488 |
| cgc ctg gaa gac ttc aac tac aac aac cag acg atc aca gac caa atc<br>Arg Leu Glu Asp Phe Asn Tyr Asn Asn Gln Thr Ile Thr Asp Gln Ile<br>           500                   505                510 | 1536 |
| tac cgc gca atg aac tcc tcg tcc ttt gag ggt gtc tct ggc cac gtg<br>Tyr Arg Ala Met Asn Ser Ser Ser Phe Glu Gly Val Ser Gly His Val<br>                515                 520             525 | 1584 |
| gtg ttt gat gcc agc ggc tca cgg atg gcc tgg act ctg att gag cag<br>Val Phe Asp Ala Ser Gly Ser Arg Met Ala Trp Thr Leu Ile Glu Gln<br>           530                   535               540 | 1632 |
| ctg cag ggt ggc agc tac aag aag atc ggc tac tat gac agc acc aag<br>Leu Gln Gly Gly Ser Tyr Lys Lys Ile Gly Tyr Tyr Asp Ser Thr Lys<br>545                    550                  555            560 | 1680 |

```
gat gac ctt tcc tgg tct aaa acg gac aaa tgg att gga ggg gcc ccc      1728
Asp Asp Leu Ser Trp Ser Lys Thr Asp Lys Trp Ile Gly Gly Ala Pro
            565                 570                 575 ccg gcc gac cag acc ctg gtc atc aag aca ttt cgc ttc atg tca cag      1776
Pro Ala Asp Gln Thr Leu Val Ile Lys Thr Phe Arg Phe Met Ser Gln
        580                 585                 590 aag ctc ttc att tca gtc tct gtc ctc tcc agc ctg ggc att gtc ctg      1824
Lys Leu Phe Ile Ser Val Ser Val Leu Ser Ser Leu Gly Ile Val Leu
            595                 600                 605 gct gtg gtc tgt ctg tcc ttt aac atc tac aac tct cat gtc cgt tac      1872
Ala Val Val Cys Leu Ser Phe Asn Ile Tyr Asn Ser His Val Arg Tyr
        610                 615                 620 atc cag aac tcc cag ccc aac ttg aac aat ctg act gct gtg ggc tgc      1920
Ile Gln Asn Ser Gln Pro Asn Leu Asn Asn Leu Thr Ala Val Gly Cys
625                 630                 635                 640 tcc ctg gca ttg gct gcc gtc ttc ccc ctg ggg cta gat ggg tac cac      1968
Ser Leu Ala Leu Ala Ala Val Phe Pro Leu Gly Leu Asp Gly Tyr His
        645                 650                 655 atc ggg aga agc cag ttt cct ttt gtg tgt cag gca cgc ctc tgg ctc      2016
Ile Gly Arg Ser Gln Phe Pro Phe Val Cys Gln Ala Arg Leu Trp Leu
            660                 665                 670 ctg ggt ctg ggc ttc agt ctg ggc tat ggc tcc atg ttc acg aag atc      2064
Leu Gly Leu Gly Phe Ser Leu Gly Tyr Gly Ser Met Phe Thr Lys Ile
        675                 680                 685 tgg tgg gtc cac acg gtc ttc act aag aag gag gag aag aag gag tgg      2112
Trp Trp Val His Thr Val Phe Thr Lys Lys Glu Glu Lys Lys Glu Trp
            690                 695                 700 agg aag acc ctg gag ccc tgg aag ctg tac acc aca gtg ggc ttg cta      2160
Arg Lys Thr Leu Glu Pro Trp Lys Leu Tyr Thr Thr Val Gly Leu Leu
705                 710                 715                 720 gtg ggc atg gat gtc ctc act ctt gcc att tgg cag atg gta gac ccc      2208
Val Gly Met Asp Val Leu Thr Leu Ala Ile Trp Gln Met Val Asp Pro
            725                 730                 735 ttg cac cgg acc att gag act ttt gcc aag gag gaa cca aag gaa gat      2256
Leu His Arg Thr Ile Glu Thr Phe Ala Lys Glu Glu Pro Lys Glu Asp
        740                 745                 750 att gat gtg tcc atc ctg ccc cag ctg gag cac tgc agc tcc aag aaa      2304
Ile Asp Val Ser Ile Leu Pro Gln Leu Glu His Cys Ser Ser Lys Lys
            755                 760                 765 atg aac acc tgg ctt ggc att ttc tat ggt tac aag ggg ctg ctg ctg      2352
Met Asn Thr Trp Leu Gly Ile Phe Tyr Gly Tyr Lys Gly Leu Leu Leu
        770                 775                 780 ctg cta ggc atc ttt ctt gct tat gag acc aag agc gtg tct act gag      2400
Leu Leu Gly Ile Phe Leu Ala Tyr Glu Thr Lys Ser Val Ser Thr Glu
785                 790                 795                 800 aag atc aat gac cac cgg gct gtg ggc atg gcc atg tac aac gtg gcg      2448
Lys Ile Asn Asp His Arg Ala Val Gly Met Ala Met Tyr Asn Val Ala
            805                 810                 815 gtc ctg tgc ctc atc act gcc ccg gtc acc atg atc ctg tcc agc cag      2496
Val Leu Cys Leu Ile Thr Ala Pro Val Thr Met Ile Leu Ser Ser Gln
        820                 825                 830 cag gat gca gct ttc gcc ttt gca gct ctt gcc ata gtg ttc tcc tcc      2544
Gln Asp Ala Ala Phe Ala Phe Ala Ala Leu Ala Ile Val Phe Ser Ser
            835                 840                 845 tac atc act ctg gtc gtt ctg ttc gtg ccg aag atg cgc agg ttg atc      2592
Tyr Ile Thr Leu Val Val Leu Phe Val Pro Lys Met Arg Arg Leu Ile
850                 855                 860 acc cgg ggt gag tgg cag tcg gag gcg cag gat acc atg aaa acg ggg      2640
Thr Arg Gly Glu Trp Gln Ser Glu Ala Gln Asp Thr Met Lys Thr Gly
```

-continued

```
                865                 870                 875                 880
tcg tcg acc aac aac aat gag gaa gag aag tcc cga ctg ttg gag aag          2688
Ser Ser Thr Asn Asn Asn Glu Glu Glu Lys Ser Arg Leu Leu Glu Lys
                    885                 890                 895 gag aac cgg gag ctg gag aag atc att gct gag aaa gag gag cga gtg          2736
Glu Asn Arg Glu Leu Glu Lys Ile Ile Ala Glu Lys Glu Glu Arg Val
            900                 905                 910 tcc gag ctg cgc cat cag ctt cgt tct cgg cag cag ctg cgc cct cgg          2784
Ser Glu Leu Arg His Gln Leu Arg Ser Arg Gln Gln Leu Arg Pro Arg
        915                 920                 925 cgt cac ccc ccg acg ccc cca gac ccc tca ggg ggc ctg ccc agg gga          2832
Arg His Pro Pro Thr Pro Pro Asp Pro Ser Gly Gly Leu Pro Arg Gly
    930                 935                 940 ccc cat gag ccc cct gac cgg ctc agc tgt gac ggg agc cgg gtt cac          2880
Pro His Glu Pro Pro Asp Arg Leu Ser Cys Asp Gly Ser Arg Val His
945                 950                 955                 960 ttg ctg tac aag tga                                                       2895
Leu Leu Tyr Lys <210> SEQ ID NO 53
<211> LENGTH: 964
<212> TYPE: PRT
<213> ORGANISM: Canis familiaris

<400> SEQUENCE: 53

Met Leu Leu Leu Leu Pro Leu Ala Leu Ala Pro Leu Phe Leu Arg
 1               5                  10                  15

Pro Pro Gly Ala Gly Ala Gln Thr Pro Asn Ala Thr Ser Glu Gly
            20                  25                  30

Cys Gln Ile Ile His Pro Pro Trp Glu Gly Ile Arg Tyr Arg Gly
        35                  40                  45

Leu Thr Arg Asp Gln Val Lys Ala Ile Asn Phe Leu Pro Val Asp Tyr
    50                  55                  60

Glu Ile Glu Tyr Val Cys Arg Gly Glu Arg Glu Val Val Gly Pro Lys
65                  70                  75                  80

Val Arg Lys Cys Leu Ala Asn Gly Ser Trp Thr Asp Met Asp Thr Pro
                85                  90                  95

Ser Arg Cys Val Arg Ile Cys Ser Lys Ser Tyr Leu Ala Leu Glu Asn
            100                 105                 110

Gly Lys Val Phe Leu Thr Gly Gly Asp Leu Pro Ala Leu Asp Gly Ala
        115                 120                 125

Arg Val Asp Phe Arg Cys Asp Pro Asp Phe His Leu Val Gly Ser Ser
    130                 135                 140

Arg Ser Ile Cys Ser Gln Gly Gln Trp Ser Thr Pro Lys Pro His Cys
145                 150                 155                 160

Gln Val Ser Arg Thr Pro His Ser Glu Arg Arg Ala Val Tyr Ile Gly
                165                 170                 175

Ala Leu Phe Pro Met Ser Gly Gly Trp Pro Gly Gly Gln Ala Cys Gln
            180                 185                 190

Pro Ala Val Glu Met Ala Leu Glu Asp Val Asn Ser Arg Arg Asp Ile
        195                 200                 205

Leu Pro Asp Tyr Glu Leu Lys Leu Ile His His Asp Ser Lys Cys Asp
    210                 215                 220

Pro Gly Gln Ala Thr Lys Tyr Leu Tyr Glu Leu Leu Tyr Asn Asp Pro
225                 230                 235                 240

Ile Lys Ile Ile Leu Met Pro Gly Cys Ser Ser Val Ser Thr Leu Val
```

-continued

```
                245                 250                 255
Ala Glu Ala Ala Arg Met Trp Asn Leu Ile Val Leu Ser Tyr Gly Ser
            260                 265                 270

Ser Ser Pro Ala Leu Ser Asn Arg Gln Arg Phe Pro Thr Phe Phe Arg
        275                 280                 285

Thr His Pro Ser Ala Thr Leu His Asn Pro Thr Arg Val Lys Leu Phe
    290                 295                 300

Glu Lys Trp Gly Trp Arg Lys Ile Ala Thr Ile Gln Gln Thr Thr Glu
305                 310                 315                 320

Val Phe Thr Ser Thr Leu Asp Asp Leu Glu Glu Arg Val Lys Glu Ala
                325                 330                 335

Gly Ile Glu Ile Thr Phe Arg Gln Ser Phe Phe Ser Asp Pro Ala Val
            340                 345                 350

Pro Val Lys Asn Leu Lys Arg Gln Asp Ala Arg Ile Ile Val Gly Leu
        355                 360                 365

Phe Tyr Glu Thr Glu Ala Arg Lys Val Phe Cys Glu Val Tyr Lys Glu
    370                 375                 380

Arg Leu Phe Gly Lys Lys Tyr Val Trp Phe Leu Ile Gly Trp Tyr Ala
385                 390                 395                 400

Asp Asn Trp Phe Lys Thr Tyr Asp Pro Ser Ile Asn Cys Thr Val Asp
                405                 410                 415

Glu Met Thr Glu Ala Val Glu Gly His Ile Thr Thr Glu Ile Val Met
            420                 425                 430

Leu Asn Pro Ala Asn Thr Arg Ser Ile Ser Asn Met Thr Ser Gln Glu
        435                 440                 445

Phe Val Glu Lys Leu Thr Lys Arg Leu Lys Arg His Pro Glu Glu Thr
    450                 455                 460

Gly Gly Phe Gln Glu Ala Pro Leu Ala Tyr Asp Ala Ile Trp Ala Leu
465                 470                 475                 480

Ala Leu Ala Leu Asn Lys Thr Ser Gly Gly Ser Gly Arg Ser Gly Val
                485                 490                 495

Arg Leu Glu Asp Phe Asn Tyr Asn Asn Gln Thr Ile Thr Asp Gln Ile
            500                 505                 510

Tyr Arg Ala Met Asn Ser Ser Ser Phe Glu Gly Val Ser Gly His Val
        515                 520                 525

Val Phe Asp Ala Ser Gly Ser Arg Met Ala Trp Thr Leu Ile Glu Gln
    530                 535                 540

Leu Gln Gly Gly Ser Tyr Lys Lys Ile Gly Tyr Tyr Asp Ser Thr Lys
545                 550                 555                 560

Asp Asp Leu Ser Trp Ser Lys Thr Asp Lys Trp Ile Gly Gly Ala Pro
                565                 570                 575

Pro Ala Asp Gln Thr Leu Val Ile Lys Thr Phe Arg Phe Met Ser Gln
            580                 585                 590

Lys Leu Phe Ile Ser Val Ser Val Leu Ser Ser Leu Gly Ile Val Leu
        595                 600                 605

Ala Val Val Cys Leu Ser Phe Asn Ile Tyr Asn Ser His Val Arg Tyr
    610                 615                 620

Ile Gln Asn Ser Gln Pro Asn Leu Asn Asn Leu Thr Ala Val Gly Cys
625                 630                 635                 640

Ser Leu Ala Leu Ala Ala Val Phe Pro Leu Gly Leu Asp Gly Tyr His
                645                 650                 655

Ile Gly Arg Ser Gln Phe Pro Phe Val Cys Gln Ala Arg Leu Trp Leu
            660                 665                 670
```

-continued

```
Leu Gly Leu Gly Phe Ser Leu Gly Tyr Gly Ser Met Phe Thr Lys Ile
            675                 680                 685

Trp Trp Val His Thr Val Phe Thr Lys Lys Glu Glu Lys Lys Glu Trp
        690                 695                 700

Arg Lys Thr Leu Glu Pro Trp Lys Leu Tyr Thr Thr Val Gly Leu Leu
705                 710                 715                 720

Val Gly Met Asp Val Leu Thr Leu Ala Ile Trp Gln Met Val Asp Pro
                725                 730                 735

Leu His Arg Thr Ile Glu Thr Phe Ala Lys Glu Glu Pro Lys Glu Asp
            740                 745                 750

Ile Asp Val Ser Ile Leu Pro Gln Leu Glu His Cys Ser Ser Lys Lys
        755                 760                 765

Met Asn Thr Trp Leu Gly Ile Phe Tyr Gly Tyr Lys Gly Leu Leu Leu
    770                 775                 780

Leu Leu Gly Ile Phe Leu Ala Tyr Glu Thr Lys Ser Val Ser Thr Glu
785                 790                 795                 800

Lys Ile Asn Asp His Arg Ala Val Gly Met Ala Met Tyr Asn Val Ala
                805                 810                 815

Val Leu Cys Leu Ile Thr Ala Pro Val Thr Met Ile Leu Ser Ser Gln
            820                 825                 830

Gln Asp Ala Ala Phe Ala Phe Ala Ala Leu Ala Ile Val Phe Ser Ser
        835                 840                 845

Tyr Ile Thr Leu Val Val Leu Phe Val Pro Lys Met Arg Arg Leu Ile
    850                 855                 860

Thr Arg Gly Glu Trp Gln Ser Glu Ala Gln Asp Thr Met Lys Thr Gly
865                 870                 875                 880

Ser Ser Thr Asn Asn Asn Glu Glu Glu Lys Ser Arg Leu Leu Glu Lys
                885                 890                 895

Glu Asn Arg Glu Leu Glu Lys Ile Ile Ala Glu Lys Glu Glu Arg Val
                900                 905                 910

Ser Glu Leu Arg His Gln Leu Arg Ser Arg Gln Gln Leu Arg Pro Arg
            915                 920                 925

Arg His Pro Pro Thr Pro Pro Asp Pro Ser Gly Gly Leu Pro Arg Gly
        930                 935                 940

Pro His Glu Pro Pro Asp Arg Leu Ser Cys Asp Gly Ser Arg Val His
945                 950                 955                 960

Leu Leu Tyr Lys

<210> SEQ ID NO 54
<211> LENGTH: 1737
<212> TYPE: DNA
<213> ORGANISM: Homo sapiens
<220> FEATURE:
<221> NAME/KEY: CDS
<222> LOCATION: (1)...(1734)

<400> SEQUENCE: 54 atg ttg ctg ctg ctg cta ctg gcg cca ctc ttc ctc cgc ccc ccg ggc      48
Met Leu Leu Leu Leu Leu Leu Ala Pro Leu Phe Leu Arg Pro Pro Gly
  1               5                  10                  15 gcg ggc ggg gcg cag acc ccc aac gcc acc tca gaa ggt tgc cag atc      96
Ala Gly Gly Ala Gln Thr Pro Asn Ala Thr Ser Glu Gly Cys Gln Ile
             20                  25                  30 ata cac ccg ccc tgg gaa ggg ggc atc agg tac cgg ggc ctg act cgg     144
Ile His Pro Pro Trp Glu Gly Gly Ile Arg Tyr Arg Gly Leu Thr Arg
         35                  40                  45
```

-continued

```
gac cag gtg aag gct atc aac ttc ctg cca gtg gac tat gag att gag      192
Asp Gln Val Lys Ala Ile Asn Phe Leu Pro Val Asp Tyr Glu Ile Glu
         50                  55                  60 tat gtg tgc cgg ggg gag cgc gag gtg gtg ggg ccc aag gtc cgc aag      240
Tyr Val Cys Arg Gly Glu Arg Glu Val Val Gly Pro Lys Val Arg Lys
 65                  70                  75                  80 tgc ctg gcc aac ggc tcc tgg aca gat atg gac aca ccc agc cgc tgt      288
Cys Leu Ala Asn Gly Ser Trp Thr Asp Met Asp Thr Pro Ser Arg Cys
                     85                  90                  95 gtc cga atc tgc tcc aag tct tat ttg acc ctg gaa aat ggg aag gtt      336
Val Arg Ile Cys Ser Lys Ser Tyr Leu Thr Leu Glu Asn Gly Lys Val
            100                 105                 110 ttc ctg acg ggt ggg gac ctc cca gct ctg gac gga gcc cgg gtg gat      384
Phe Leu Thr Gly Gly Asp Leu Pro Ala Leu Asp Gly Ala Arg Val Asp
        115                 120                 125 ttc cgg tgt gac ccc gac ttc cat ctg gtg ggc agc tcc cgg agc atc      432
Phe Arg Cys Asp Pro Asp Phe His Leu Val Gly Ser Ser Arg Ser Ile
    130                 135                 140 tgt agt cag ggc cag tgg agc acc ccc aag ccc cac tgc cag gtg aat      480
Cys Ser Gln Gly Gln Trp Ser Thr Pro Lys Pro His Cys Gln Val Asn
145                 150                 155                 160 cga acg cca cac tca gaa cgg cgc gca gtg tac atc ggg gca ctg ttt      528
Arg Thr Pro His Ser Glu Arg Arg Ala Val Tyr Ile Gly Ala Leu Phe
                165                 170                 175 ccc atg agc ggg ggc tgg cca ggg ggc cag gcc tgc cag ccc gcg gtg      576
Pro Met Ser Gly Gly Trp Pro Gly Gly Gln Ala Cys Gln Pro Ala Val
            180                 185                 190 gag atg gcg ctg gag gac gtg aat agc cgc agg gac atc ctg ccg gac      624
Glu Met Ala Leu Glu Asp Val Asn Ser Arg Arg Asp Ile Leu Pro Asp
        195                 200                 205 tat gag ctc aag ctc atc cac cac gac agc aag tgt gat cca ggc caa      672
Tyr Glu Leu Lys Leu Ile His His Asp Ser Lys Cys Asp Pro Gly Gln
    210                 215                 220 gcc acc aag tac cta tat gag ctg ctc tac aac gac cct atc aag atc      720
Ala Thr Lys Tyr Leu Tyr Glu Leu Leu Tyr Asn Asp Pro Ile Lys Ile
225                 230                 235                 240 atc ctt atg cct ggc tgc agc tct gtc tcc acg ctg gtg gct gag gct      768
Ile Leu Met Pro Gly Cys Ser Ser Val Ser Thr Leu Val Ala Glu Ala
                245                 250                 255 gct agg atg tgg aac ctc att gtg ctt tcc tat ggc tcc agc tca cca      816
Ala Arg Met Trp Asn Leu Ile Val Leu Ser Tyr Gly Ser Ser Ser Pro
            260                 265                 270 gcc ctg tca aac cgg cag cgt ttc ccc act ttc ttc cga acg cac cca      864
Ala Leu Ser Asn Arg Gln Arg Phe Pro Thr Phe Phe Arg Thr His Pro
        275                 280                 285 tca gcc aca ctc cac aac cct acc cgc gtg aaa ctc ttt gaa aag tgg      912
Ser Ala Thr Leu His Asn Pro Thr Arg Val Lys Leu Phe Glu Lys Trp
    290                 295                 300 ggc tgg aag aag att gct acc atc cag cag acc act gag gtc ttc act      960
Gly Trp Lys Lys Ile Ala Thr Ile Gln Gln Thr Thr Glu Val Phe Thr
305                 310                 315                 320 tcg act ctg gac gac ctg gag gaa cga gtg aag gag gct gga att gag     1008
Ser Thr Leu Asp Asp Leu Glu Glu Arg Val Lys Glu Ala Gly Ile Glu
                325                 330                 335 att act ttc cgc cag agt ttc ttc tca gat cca gct gtg ccc gtc aaa     1056
Ile Thr Phe Arg Gln Ser Phe Phe Ser Asp Pro Ala Val Pro Val Lys
            340                 345                 350 aac ctg aag cgc cag gat gcc cga atc atc gtg gga ctt ttc tat gag     1104
Asn Leu Lys Arg Gln Asp Ala Arg Ile Ile Val Gly Leu Phe Tyr Glu
```

-continued

```
                 355                 360                 365
act gaa gcc cgg aaa gtt ttt tgt gag gtg tac aag gag cgt ctc ttt      1152
Thr Glu Ala Arg Lys Val Phe Cys Glu Val Tyr Lys Glu Arg Leu Phe
    370                 375                 380 ggg aag aag tac gtc tgg ttc ctc att ggg tgg tat gct gac aat tgg      1200
Gly Lys Lys Tyr Val Trp Phe Leu Ile Gly Trp Tyr Ala Asp Asn Trp
385                 390                 395                 400 ttc aag atc tac gac cct tct atc aac tgc aca gtg gat gag atg act      1248
Phe Lys Ile Tyr Asp Pro Ser Ile Asn Cys Thr Val Asp Glu Met Thr
                405                 410                 415 gag gcg gtg gag ggc cac atc aca act gag att gtc atg ctg aat cct      1296
Glu Ala Val Glu Gly His Ile Thr Thr Glu Ile Val Met Leu Asn Pro
            420                 425                 430 gcc aat acc cgc agc att tcc aac atg aca tcc cag gaa ttt gtg gag      1344
Ala Asn Thr Arg Ser Ile Ser Asn Met Thr Ser Gln Glu Phe Val Glu
        435                 440                 445 aaa cta acc aag cga ctg aaa aga cac cct gag gag aca gga ggc ttc      1392
Lys Leu Thr Lys Arg Leu Lys Arg His Pro Glu Glu Thr Gly Gly Phe
    450                 455                 460 cag gag gca ccg ctg gcc tat gat gcc atc tgg gcc ttg gca ctg gcc      1440
Gln Glu Ala Pro Leu Ala Tyr Asp Ala Ile Trp Ala Leu Ala Leu Ala
465                 470                 475                 480 ctg aac aag aca tct gga gga ggc ggt cgt tct ggt gtg cgc ctg gag      1488
Leu Asn Lys Thr Ser Gly Gly Gly Gly Arg Ser Gly Val Arg Leu Glu
                485                 490                 495 gac ttc aac tac aac aac cag acc att acc gac caa atc tac cgg gca      1536
Asp Phe Asn Tyr Asn Asn Gln Thr Ile Thr Asp Gln Ile Tyr Arg Ala
            500                 505                 510 atg aac tct tcg tcc ttt gag ggt gtc tct ggc cat gtg gtg ttt gat      1584
Met Asn Ser Ser Ser Phe Glu Gly Val Ser Gly His Val Val Phe Asp
        515                 520                 525 gcc agc ggc tct cgg atg gca tgg acg ctt atc gag cag ctt cag ggt      1632
Ala Ser Gly Ser Arg Met Ala Trp Thr Leu Ile Glu Gln Leu Gln Gly
    530                 535                 540 ggc agc tac aag aag att ggc tac tat gac agc acc aag gat gat ctt      1680
Gly Ser Tyr Lys Lys Ile Gly Tyr Tyr Asp Ser Thr Lys Asp Asp Leu
545                 550                 555                 560 tcc tgg tcc aaa aca gat aaa tgg att gtt ata tcc aga act cac agc      1728
Ser Trp Ser Lys Thr Asp Lys Trp Ile Val Ile Ser Arg Thr His Ser
                565                 570                 575 cca acc tga                                                           1737
Pro Thr
```

<210> SEQ ID NO 55
<211> LENGTH: 578
<212> TYPE: PRT
<213> ORGANISM: Homo sapiens

<400> SEQUENCE: 55

```
Met Leu Leu Leu Leu Leu Ala Pro Leu Phe Leu Arg Pro Pro Gly
1               5                   10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
        35                  40                  45

Asp Gln Val Lys Ala Ile Asn Phe Leu Pro Val Asp Tyr Glu Ile Glu
    50                  55                  60

Tyr Val Cys Arg Gly Glu Arg Glu Val Val Gly Pro Lys Val Arg Lys
65                  70                  75                  80
```

-continued

```
Cys Leu Ala Asn Gly Ser Trp Thr Asp Met Asp Thr Pro Ser Arg Cys
                85                  90                  95
Val Arg Ile Cys Ser Lys Ser Tyr Leu Thr Leu Glu Asn Gly Lys Val
            100                 105                 110
Phe Leu Thr Gly Gly Asp Leu Pro Ala Leu Asp Gly Ala Arg Val Asp
        115                 120                 125
Phe Arg Cys Asp Pro Asp Phe His Leu Val Gly Ser Ser Arg Ser Ile
    130                 135                 140
Cys Ser Gln Gly Gln Trp Ser Thr Pro Lys Pro His Cys Gln Val Asn
145                 150                 155                 160
Arg Thr Pro His Ser Glu Arg Arg Ala Val Tyr Ile Gly Ala Leu Phe
                165                 170                 175
Pro Met Ser Gly Gly Trp Pro Gly Gly Gln Ala Cys Gln Pro Ala Val
            180                 185                 190
Glu Met Ala Leu Glu Asp Val Asn Ser Arg Arg Asp Ile Leu Pro Asp
        195                 200                 205
Tyr Glu Leu Lys Leu Ile His His Asp Ser Lys Cys Asp Pro Gly Gln
    210                 215                 220
Ala Thr Lys Tyr Leu Tyr Glu Leu Leu Tyr Asn Asp Pro Ile Lys Ile
225                 230                 235                 240
Ile Leu Met Pro Gly Cys Ser Ser Val Ser Thr Leu Val Ala Glu Ala
                245                 250                 255
Ala Arg Met Trp Asn Leu Ile Val Leu Ser Tyr Gly Ser Ser Ser Pro
            260                 265                 270
Ala Leu Ser Asn Arg Gln Arg Phe Pro Thr Phe Phe Arg Thr His Pro
        275                 280                 285
Ser Ala Thr Leu His Asn Pro Thr Arg Val Lys Leu Phe Glu Lys Trp
    290                 295                 300
Gly Trp Lys Lys Ile Ala Thr Ile Gln Gln Thr Thr Glu Val Phe Thr
305                 310                 315                 320
Ser Thr Leu Asp Asp Leu Glu Glu Arg Val Lys Glu Ala Gly Ile Glu
                325                 330                 335
Ile Thr Phe Arg Gln Ser Phe Phe Ser Asp Pro Ala Val Pro Val Lys
            340                 345                 350
Asn Leu Lys Arg Gln Asp Ala Arg Ile Ile Val Gly Leu Phe Tyr Glu
        355                 360                 365
Thr Glu Ala Arg Lys Val Phe Cys Glu Val Tyr Lys Glu Arg Leu Phe
    370                 375                 380
Gly Lys Lys Tyr Val Trp Phe Leu Ile Gly Trp Tyr Ala Asp Asn Trp
385                 390                 395                 400
Phe Lys Ile Tyr Asp Pro Ser Ile Asn Cys Thr Val Asp Glu Met Thr
                405                 410                 415
Glu Ala Val Glu Gly His Ile Thr Thr Glu Ile Val Met Leu Asn Pro
            420                 425                 430
Ala Asn Thr Arg Ser Ile Ser Asn Met Thr Ser Gln Glu Phe Val Glu
        435                 440                 445
Lys Leu Thr Lys Arg Leu Lys Arg His Pro Glu Glu Thr Gly Gly Phe
    450                 455                 460
Gln Glu Ala Pro Leu Ala Tyr Asp Ala Ile Trp Ala Leu Ala Leu Ala
465                 470                 475                 480
Leu Asn Lys Thr Ser Gly Gly Gly Gly Arg Ser Gly Val Arg Leu Glu
                485                 490                 495
```

```
Asp Phe Asn Tyr Asn Asn Gln Thr Ile Thr Asp Gln Ile Tyr Arg Ala
            500                 505                 510

Met Asn Ser Ser Ser Phe Glu Gly Val Ser Gly His Val Val Phe Asp
            515                 520                 525

Ala Ser Gly Ser Arg Met Ala Trp Thr Leu Ile Glu Gln Leu Gln Gly
        530                 535                 540

Gly Ser Tyr Lys Lys Ile Gly Tyr Tyr Asp Ser Thr Lys Asp Asp Leu
545                 550                 555                 560

Ser Trp Ser Lys Thr Asp Lys Trp Ile Val Ile Ser Arg Thr His Ser
                565                 570                 575

Pro Thr

<210> SEQ ID NO 56
<211> LENGTH: 1386
<212> TYPE: DNA
<213> ORGANISM: Homo sapiens
<220> FEATURE:
<221> NAME/KEY: CDS
<222> LOCATION: (1)...(1383)

<400> SEQUENCE: 56 atg ggg ccc ggg gcc cct ttt gcc cgg gtg ggg tgg cca ctg ccg ctt      48
Met Gly Pro Gly Ala Pro Phe Ala Arg Val Gly Trp Pro Leu Pro Leu
 1               5                  10                  15 ctg gtt gtg atg gcg gca ggg gtg gct ccg gtg tgg gcc tcc cac tcc      96
Leu Val Val Met Ala Ala Gly Val Ala Pro Val Trp Ala Ser His Ser
            20                  25                  30 ccc cat ctc ccg cgg cct cac tcg cgg gtc ccc ccg cac ccc tcc tca     144
Pro His Leu Pro Arg Pro His Ser Arg Val Pro Pro His Pro Ser Ser
        35                  40                  45 gaa cgg cgc gca gtg tac atc ggg gca ctg ttt ccc atg agc ggg ggc     192
Glu Arg Arg Ala Val Tyr Ile Gly Ala Leu Phe Pro Met Ser Gly Gly
    50                  55                  60 tgg cca ggg ggc cag gcc tgc cag ccc gcg gtg gag atg gcg ctg gag     240
Trp Pro Gly Gly Gln Ala Cys Gln Pro Ala Val Glu Met Ala Leu Glu
65                  70                  75                  80 gac gtg aat agc cgc agg gac atc ctg ccg gac tat gag ctc aag ctc     288
Asp Val Asn Ser Arg Arg Asp Ile Leu Pro Asp Tyr Glu Leu Lys Leu
                85                  90                  95 atc cac cac gac agc aag tgt gat cca ggc caa gcc acc aag tac cta     336
Ile His His Asp Ser Lys Cys Asp Pro Gly Gln Ala Thr Lys Tyr Leu
            100                 105                 110 tat gag ctg ctc tac aac gac cct atc aag atc atc ctt atg cct ggc     384
Tyr Glu Leu Leu Tyr Asn Asp Pro Ile Lys Ile Ile Leu Met Pro Gly
        115                 120                 125 tgc agc tct gtc tcc acg ctg gtg gct gag gct gct agg atg tgg aac     432
Cys Ser Ser Val Ser Thr Leu Val Ala Glu Ala Ala Arg Met Trp Asn
    130                 135                 140 ctc att gtg ctt tcc tat ggc tcc agc tca cca gcc ctg tca aac cgg     480
Leu Ile Val Leu Ser Tyr Gly Ser Ser Ser Pro Ala Leu Ser Asn Arg
145                 150                 155                 160 cag cgt ttc ccc act ttc ttc cga acg cac cca tca gcc aca ctc cac     528
Gln Arg Phe Pro Thr Phe Phe Arg Thr His Pro Ser Ala Thr Leu His
                165                 170                 175 aac cct acc cgc gtg aaa ctc ttt gaa aag tgg ggc tgg aag aag att     576
Asn Pro Thr Arg Val Lys Leu Phe Glu Lys Trp Gly Trp Lys Lys Ile
            180                 185                 190 gct acc atc cag cag acc act gag gtc ttc act tcg act ctg gac gac     624
Ala Thr Ile Gln Gln Thr Thr Glu Val Phe Thr Ser Thr Leu Asp Asp
        195                 200                 205
```

```
ctg gag gaa cga gtg aag gag gct gga att gag att act ttc cgc cag      672
Leu Glu Glu Arg Val Lys Glu Ala Gly Ile Glu Ile Thr Phe Arg Gln
210                 215                 220 agt ttc ttc tca gat cca gct gtg ccc gtc aaa aac ctg aag cgc cag      720
Ser Phe Phe Ser Asp Pro Ala Val Pro Val Lys Asn Leu Lys Arg Gln
225                 230                 235                 240 gat gcc cga atc atc gtg gga ctt ttc tat gag act gaa gcc cgg aaa      768
Asp Ala Arg Ile Ile Val Gly Leu Phe Tyr Glu Thr Glu Ala Arg Lys
                245                 250                 255 gtt ttt tgt gag gtg tac aag gag cgt ctc ttt ggg aag aag tac gtc      816
Val Phe Cys Glu Val Tyr Lys Glu Arg Leu Phe Gly Lys Lys Tyr Val
        260                 265                 270 tgg ttc ctc att ggg tgg tat gct gac aat tgg ttc aag atc tac gac      864
Trp Phe Leu Ile Gly Trp Tyr Ala Asp Asn Trp Phe Lys Ile Tyr Asp
    275                 280                 285 cct tct atc aac tgc aca gtg gat gag atg act gag gcg gtg gag ggc      912
Pro Ser Ile Asn Cys Thr Val Asp Glu Met Thr Glu Ala Val Glu Gly
290                 295                 300 cac atc aca act gag att gtc atg ctg aat cct gcc aat acc cgc agc      960
His Ile Thr Thr Glu Ile Val Met Leu Asn Pro Ala Asn Thr Arg Ser
305                 310                 315                 320 att tcc aac atg aca tcc cag gaa ttt gtg gag aaa cta acc aag cga     1008
Ile Ser Asn Met Thr Ser Gln Glu Phe Val Glu Lys Leu Thr Lys Arg
                325                 330                 335 ctg aaa aga cac cct gag gag aca gga ggc ttc cag gag gca ccg ctg     1056
Leu Lys Arg His Pro Glu Glu Thr Gly Gly Phe Gln Glu Ala Pro Leu
                340                 345                 350 gcc tat gat gcc atc tgg gcc ttg gca ctg gcc ctg aac aag aca tct     1104
Ala Tyr Asp Ala Ile Trp Ala Leu Ala Leu Ala Leu Asn Lys Thr Ser
        355                 360                 365 gga gga ggc ggc cgt tct ggt gtg cgc ctg gag gac ttc aac tac aac     1152
Gly Gly Gly Gly Arg Ser Gly Val Arg Leu Glu Asp Phe Asn Tyr Asn
    370                 375                 380 aac cag acc att acc gac caa atc tac cgg gca atg aac tct tcg tcc     1200
Asn Gln Thr Ile Thr Asp Gln Ile Tyr Arg Ala Met Asn Ser Ser Ser
385                 390                 395                 400 ttt gag ggt gtc tct ggc cat gtg gtg ttt gat gcc agc ggc tct cgg     1248
Phe Glu Gly Val Ser Gly His Val Val Phe Asp Ala Ser Gly Ser Arg
                405                 410                 415 atg gca tgg acg ctt atc gag cag ctt cag ggt ggc agc tac aag aag     1296
Met Ala Trp Thr Leu Ile Glu Gln Leu Gln Gly Gly Ser Tyr Lys Lys
                420                 425                 430 att ggc tac tat gac agc acc aag gat gat ctt tcc tgg tcc aaa aca     1344
Ile Gly Tyr Tyr Asp Ser Thr Lys Asp Asp Leu Ser Trp Ser Lys Thr
        435                 440                 445 gat aaa tgg att gtt ata tcc aga act cac agc cca acc tga             1386
Asp Lys Trp Ile Val Ile Ser Arg Thr His Ser Pro Thr
450                 455                 460

<210> SEQ ID NO 57
<211> LENGTH: 461
<212> TYPE: PRT
<213> ORGANISM: Homo sapiens

<400> SEQUENCE: 57

Met Gly Pro Gly Ala Pro Phe Ala Arg Val Gly Trp Pro Leu Pro Leu
 1               5                  10                  15

Leu Val Val Met Ala Ala Gly Val Ala Pro Val Trp Ala Ser His Ser
                20                  25                  30
```

-continued

```
Pro His Leu Pro Arg Pro His Ser Arg Val Pro Pro His Pro Ser Ser
         35                  40                  45

Glu Arg Arg Ala Val Tyr Ile Gly Ala Leu Phe Pro Met Ser Gly Gly
     50                  55                  60

Trp Pro Gly Gly Gln Ala Cys Gln Pro Ala Val Glu Met Ala Leu Glu
 65                  70                  75                  80

Asp Val Asn Ser Arg Arg Asp Ile Leu Pro Asp Tyr Glu Leu Lys Leu
                 85                  90                  95

Ile His His Asp Ser Lys Cys Asp Pro Gly Gln Ala Thr Lys Tyr Leu
                100                 105                 110

Tyr Glu Leu Leu Tyr Asn Asp Pro Ile Lys Ile Leu Met Pro Gly
            115                 120                 125

Cys Ser Ser Val Ser Thr Leu Val Ala Glu Ala Arg Met Trp Asn
130                 135                 140

Leu Ile Val Leu Ser Tyr Gly Ser Ser Pro Ala Leu Ser Asn Arg
145                 150                 155                 160

Gln Arg Phe Pro Thr Phe Phe Arg Thr His Pro Ser Ala Thr Leu His
                165                 170                 175

Asn Pro Thr Arg Val Lys Leu Phe Glu Lys Trp Gly Trp Lys Lys Ile
                180                 185                 190

Ala Thr Ile Gln Gln Thr Thr Glu Val Phe Thr Ser Thr Leu Asp Asp
            195                 200                 205

Leu Glu Glu Arg Val Lys Glu Ala Gly Ile Glu Ile Thr Phe Arg Gln
210                 215                 220

Ser Phe Phe Ser Asp Pro Ala Val Pro Val Lys Asn Leu Lys Arg Gln
225                 230                 235                 240

Asp Ala Arg Ile Ile Val Gly Leu Phe Tyr Glu Thr Glu Ala Arg Lys
                245                 250                 255

Val Phe Cys Glu Val Tyr Lys Glu Arg Leu Phe Gly Lys Lys Tyr Val
                260                 265                 270

Trp Phe Leu Ile Gly Trp Tyr Ala Asp Asn Trp Phe Lys Ile Tyr Asp
            275                 280                 285

Pro Ser Ile Asn Cys Thr Val Asp Glu Met Thr Glu Ala Val Glu Gly
            290                 295                 300

His Ile Thr Thr Glu Ile Val Met Leu Asn Pro Ala Asn Thr Arg Ser
305                 310                 315                 320

Ile Ser Asn Met Thr Ser Gln Glu Phe Val Glu Lys Leu Thr Lys Arg
                325                 330                 335

Leu Lys Arg His Pro Glu Glu Thr Gly Gly Phe Gln Glu Ala Pro Leu
                340                 345                 350

Ala Tyr Asp Ala Ile Trp Ala Leu Ala Leu Ala Leu Asn Lys Thr Ser
            355                 360                 365

Gly Gly Gly Gly Arg Ser Gly Val Arg Leu Glu Asp Phe Asn Tyr Asn
370                 375                 380

Asn Gln Thr Ile Thr Asp Gln Ile Tyr Arg Ala Met Asn Ser Ser Ser
385                 390                 395                 400

Phe Glu Gly Val Ser Gly His Val Val Phe Asp Ala Ser Gly Ser Arg
                405                 410                 415

Met Ala Trp Thr Leu Ile Glu Gln Leu Gln Gly Gly Ser Tyr Lys Lys
                420                 425                 430

Ile Gly Tyr Tyr Asp Ser Thr Lys Asp Asp Leu Ser Trp Ser Lys Thr
            435                 440                 445

Asp Lys Trp Ile Val Ile Ser Arg Thr His Ser Pro Thr
```

<210> SEQ ID NO 58
<211> LENGTH: 1746
<212> TYPE: DNA
<213> ORGANISM: Canis familiaris
<220> FEATURE:
<221> NAME/KEY: CDS
<222> LOCATION: (1)...(1743)

<400> SEQUENCE: 58

| | | |
|---|---|---|
| atg ctg ctg ctg ctc ctg ccg ctg gcg ctg gcg ccg ctc ttc ctc cgc<br>Met Leu Leu Leu Leu Leu Pro Leu Ala Leu Ala Pro Leu Phe Leu Arg<br>1                    5                      10                   15 | | 48 |
| ccc ccg ggc gcg ggc ggg gca cag acc ccc aac gcc acc tcg gaa ggt<br>Pro Pro Gly Ala Gly Gly Ala Gln Thr Pro Asn Ala Thr Ser Glu Gly<br>                    20                     25                     30 | | 96 |
| tgc cag atc ata cac ccg cct tgg gaa ggg ggt atc agg tac agg ggc<br>Cys Gln Ile Ile His Pro Pro Trp Glu Gly Gly Ile Arg Tyr Arg Gly<br>        35                     40                     45 | | 144 |
| ctg act cgt gac cag gtg aag gct atc aac ttc ctg ccg gtg gac tat<br>Leu Thr Arg Asp Gln Val Lys Ala Ile Asn Phe Leu Pro Val Asp Tyr<br> 50                     55                     60 | | 192 |
| gag att gag tat gtg tgc cgg gga gag cga gag gtg gtg ggg ccc aag<br>Glu Ile Glu Tyr Val Cys Arg Gly Glu Arg Glu Val Val Gly Pro Lys<br>65                    70                     75                   80 | | 240 |
| gtc cga aag tgc ctg gcc aat ggc tcc tgg aca gat atg gac aca ccc<br>Val Arg Lys Cys Leu Ala Asn Gly Ser Trp Thr Asp Met Asp Thr Pro<br>                  85                     90                     95 | | 288 |
| agc cgc tgt gtc cga atc tgt tcc aag tca tat ttg gcc ctg gaa aat<br>Ser Arg Cys Val Arg Ile Cys Ser Lys Ser Tyr Leu Ala Leu Glu Asn<br>                 100                    105                   110 | | 336 |
| ggg aag gtc ttc ctg acg ggt ggg gac ctc ccc gct ctg gat gga gcc<br>Gly Lys Val Phe Leu Thr Gly Gly Asp Leu Pro Ala Leu Asp Gly Ala<br>       115                    120                    125 | | 384 |
| cgg gtg gat ttc cgg tgt gac cct gac ttc cat ctt gtg ggc agc tcc<br>Arg Val Asp Phe Arg Cys Asp Pro Asp Phe His Leu Val Gly Ser Ser<br>130                     135                    140 | | 432 |
| cgg agt atc tgt agt cag ggc cag tgg agc act ccc aag ccc cac tgc<br>Arg Ser Ile Cys Ser Gln Gly Gln Trp Ser Thr Pro Lys Pro His Cys<br>145                     150                    155                   160 | | 480 |
| cag gtg agc cga acg ccg cac tca gag cgg cga gcg gtg tac atc ggg<br>Gln Val Ser Arg Thr Pro His Ser Glu Arg Arg Ala Val Tyr Ile Gly<br>                 165                    170                   175 | | 528 |
| gcg ctg ttt ccc atg agc ggg ggc tgg ccg ggg ggc cag gcc tgc cag<br>Ala Leu Phe Pro Met Ser Gly Gly Trp Pro Gly Gly Gln Ala Cys Gln<br>       180                    185                    190 | | 576 |
| ccc gcg gtg gag atg gcg ctg gag gac gtg aat agc cgc agg gac atc<br>Pro Ala Val Glu Met Ala Leu Glu Asp Val Asn Ser Arg Arg Asp Ile<br>           195                    200                    205 | | 624 |
| ctg ccg gac tac gag ctc aag ctc atc cac cac gac agc aag tgt gac<br>Leu Pro Asp Tyr Glu Leu Lys Leu Ile His His Asp Ser Lys Cys Asp<br>210                     215                    220 | | 672 |
| cca ggc caa gct acc aag tac ctg tat gaa ctg ctc tac aac gac ccc<br>Pro Gly Gln Ala Thr Lys Tyr Leu Tyr Glu Leu Leu Tyr Asn Asp Pro<br>225                     230                    235                   240 | | 720 |
| atc aag atc atc ctc atg cct ggc tgc agc tct gtc tcc acg ctt gtg<br>Ile Lys Ile Ile Leu Met Pro Gly Cys Ser Ser Val Ser Thr Leu Val<br>                 245                    250                   255 | | 768 |
| gct gag gct gcc agg atg tgg aac ctc att gtg ctc tcc tat ggt tcc<br>Ala Glu Ala Ala Arg Met Trp Asn Leu Ile Val Leu Ser Tyr Gly Ser | | 816 |

-continued

```
                   260                 265                 270
agc tca cca gct ctg tcc aac cgg cag cgc ttt cct acc ttc ttc cga         864
Ser Ser Pro Ala Leu Ser Asn Arg Gln Arg Phe Pro Thr Phe Phe Arg
        275                 280                 285 act cat ccc tcg gcc acg ctc cac aac cct acg cga gtg aag ctc ttt         912
Thr His Pro Ser Ala Thr Leu His Asn Pro Thr Arg Val Lys Leu Phe
    290                 295                 300 gag aag tgg ggc tgg agg aag att gcc acc atc cag cag acc acc gag         960
Glu Lys Trp Gly Trp Arg Lys Ile Ala Thr Ile Gln Gln Thr Thr Glu
305                 310                 315                 320 gtg ttc aca tcg act ctg gac gac cta gag gaa cga gtg aag gag gct        1008
Val Phe Thr Ser Thr Leu Asp Asp Leu Glu Glu Arg Val Lys Glu Ala
                325                 330                 335 ggg att gag att act ttc cgc cag agc ttc ttc tca gat cct gcc gtg        1056
Gly Ile Glu Ile Thr Phe Arg Gln Ser Phe Phe Ser Asp Pro Ala Val
            340                 345                 350 cct gtc aag aac ctc aag cgc cag gat gcc cga atc atc gtg gga ctt        1104
Pro Val Lys Asn Leu Lys Arg Gln Asp Ala Arg Ile Ile Val Gly Leu
        355                 360                 365 ttc tat gag act gaa gcc cgg aaa gtg ttc tgt gag gta tac aag gag        1152
Phe Tyr Glu Thr Glu Ala Arg Lys Val Phe Cys Glu Val Tyr Lys Glu
    370                 375                 380 cgg ctc ttt ggg aag aag tat gtg tgg ttc ctc att ggg tgg tat gct        1200
Arg Leu Phe Gly Lys Lys Tyr Val Trp Phe Leu Ile Gly Trp Tyr Ala
385                 390                 395                 400 gac aat tgg ttc aag acc tac gac ccc tcc atc aac tgc aca gtg gat        1248
Asp Asn Trp Phe Lys Thr Tyr Asp Pro Ser Ile Asn Cys Thr Val Asp
                405                 410                 415 gag atg acc gag gct gtg gaa ggc cac atc acc act gag att gtc atg        1296
Glu Met Thr Glu Ala Val Glu Gly His Ile Thr Thr Glu Ile Val Met
            420                 425                 430 ctg aac cca gcc aac acc cgc agc atc tcc aac atg aca tcc cag gag        1344
Leu Asn Pro Ala Asn Thr Arg Ser Ile Ser Asn Met Thr Ser Gln Glu
        435                 440                 445 ttt gtg gag aaa ctg acc aag aga ctc aag aga cac cct gag gag aca        1392
Phe Val Glu Lys Leu Thr Lys Arg Leu Lys Arg His Pro Glu Glu Thr
    450                 455                 460 ggc ggc ttc cag gag gca ccg ctg gcc tat gat gcc atc tgg gcc ttg        1440
Gly Gly Phe Gln Glu Ala Pro Leu Ala Tyr Asp Ala Ile Trp Ala Leu
465                 470                 475                 480 gca ttg gcc ctg aac aag aca tct gga ggg agc ggc cgt tcg ggg gtg        1488
Ala Leu Ala Leu Asn Lys Thr Ser Gly Gly Ser Gly Arg Ser Gly Val
                485                 490                 495 cgc ctg gaa gac ttc aac tac aac aac cag acg atc aca gac caa atc        1536
Arg Leu Glu Asp Phe Asn Tyr Asn Asn Gln Thr Ile Thr Asp Gln Ile
            500                 505                 510 tac cgc gca atg aac tcc tcg tcc ttt gag ggt gtc tct ggc cac gtg        1584
Tyr Arg Ala Met Asn Ser Ser Ser Phe Glu Gly Val Ser Gly His Val
        515                 520                 525 gtg ttt gat gcc agc ggc tca cgg atg gcc tgg act ctg att gag cag        1632
Val Phe Asp Ala Ser Gly Ser Arg Met Ala Trp Thr Leu Ile Glu Gln
    530                 535                 540 ctg cag ggt ggc agc tac aag aag atc ggc tac tat gac agc acc aag        1680
Leu Gln Gly Gly Ser Tyr Lys Lys Ile Gly Tyr Tyr Asp Ser Thr Lys
545                 550                 555                 560 gat gac ctt tcc tgg tct aaa acg gac aaa tgg att gtt aca tcc aga        1728
Asp Asp Leu Ser Trp Ser Lys Thr Asp Lys Trp Ile Val Thr Ser Arg
                565                 570                 575 act ccc agc cca act tga                                                1746
```

```
Thr Pro Ser Pro Thr
            580
```

<210> SEQ ID NO 59
<211> LENGTH: 581
<212> TYPE: PRT
<213> ORGANISM: Canis familiaris

<400> SEQUENCE: 59

```
Met Leu Leu Leu Leu Pro Leu Ala Leu Ala Pro Leu Phe Leu Arg
 1               5                  10                  15

Pro Pro Gly Ala Gly Ala Gln Thr Pro Asn Ala Thr Ser Glu Gly
                20                  25                  30

Cys Gln Ile Ile His Pro Pro Trp Glu Gly Ile Arg Tyr Arg Gly
                35                  40                  45

Leu Thr Arg Asp Gln Val Lys Ala Ile Asn Phe Leu Pro Val Asp Tyr
    50                  55                  60

Glu Ile Glu Tyr Val Cys Arg Gly Glu Arg Val Val Gly Pro Lys
 65                  70                  75                  80

Val Arg Lys Cys Leu Ala Asn Gly Ser Trp Thr Asp Met Asp Thr Pro
                85                  90                  95

Ser Arg Cys Val Arg Ile Cys Ser Lys Ser Tyr Leu Ala Leu Glu Asn
                100                 105                 110

Gly Lys Val Phe Leu Thr Gly Gly Asp Leu Pro Ala Leu Asp Gly Ala
                115                 120                 125

Arg Val Asp Phe Arg Cys Asp Pro Asp Phe His Leu Val Gly Ser Ser
    130                 135                 140

Arg Ser Ile Cys Ser Gln Gly Gln Trp Ser Thr Pro Lys Pro His Cys
145                 150                 155                 160

Gln Val Ser Arg Thr Pro His Ser Glu Arg Arg Ala Val Tyr Ile Gly
                165                 170                 175

Ala Leu Phe Pro Met Ser Gly Gly Trp Pro Gly Gly Gln Ala Cys Gln
                180                 185                 190

Pro Ala Val Glu Met Ala Leu Glu Asp Val Asn Ser Arg Arg Asp Ile
                195                 200                 205

Leu Pro Asp Tyr Glu Leu Lys Leu Ile His His Asp Ser Lys Cys Asp
    210                 215                 220

Pro Gly Gln Ala Thr Lys Tyr Leu Tyr Glu Leu Leu Tyr Asn Asp Pro
225                 230                 235                 240

Ile Lys Ile Ile Leu Met Pro Gly Cys Ser Ser Val Ser Thr Leu Val
                245                 250                 255

Ala Glu Ala Ala Arg Met Trp Asn Leu Ile Val Leu Ser Tyr Gly Ser
                260                 265                 270

Ser Ser Pro Ala Leu Ser Asn Arg Gln Arg Phe Pro Thr Phe Phe Arg
    275                 280                 285

Thr His Pro Ser Ala Thr Leu His Asn Pro Thr Arg Val Lys Leu Phe
    290                 295                 300

Glu Lys Trp Gly Trp Arg Lys Ile Ala Thr Ile Gln Gln Thr Thr Glu
305                 310                 315                 320

Val Phe Thr Ser Thr Leu Asp Asp Leu Glu Glu Arg Val Lys Glu Ala
                325                 330                 335

Gly Ile Glu Ile Thr Phe Arg Gln Ser Phe Phe Ser Asp Pro Ala Val
                340                 345                 350

Pro Val Lys Asn Leu Lys Arg Gln Asp Ala Arg Ile Ile Val Gly Leu
    355                 360                 365
```

```
Phe Tyr Glu Thr Glu Ala Arg Lys Val Phe Cys Glu Val Tyr Lys Glu
        370                 375                 380

Arg Leu Phe Gly Lys Lys Tyr Val Trp Phe Leu Ile Gly Trp Tyr Ala
385                 390                 395                 400

Asp Asn Trp Phe Lys Thr Tyr Asp Pro Ser Ile Asn Cys Thr Val Asp
                405                 410                 415

Glu Met Thr Glu Ala Val Glu Gly His Ile Thr Thr Glu Ile Val Met
                420                 425                 430

Leu Asn Pro Ala Asn Thr Arg Ser Ile Ser Asn Met Thr Ser Gln Glu
            435                 440                 445

Phe Val Glu Lys Leu Thr Lys Arg Leu Lys Arg His Pro Glu Glu Thr
    450                 455                 460

Gly Gly Phe Gln Glu Ala Pro Leu Ala Tyr Asp Ala Ile Trp Ala Leu
465                 470                 475                 480

Ala Leu Ala Leu Asn Lys Thr Ser Gly Gly Ser Gly Arg Ser Gly Val
                485                 490                 495

Arg Leu Glu Asp Phe Asn Tyr Asn Asn Gln Thr Ile Thr Asp Gln Ile
            500                 505                 510

Tyr Arg Ala Met Asn Ser Ser Ser Phe Glu Gly Val Ser Gly His Val
        515                 520                 525

Val Phe Asp Ala Ser Gly Ser Arg Met Ala Trp Thr Leu Ile Glu Gln
    530                 535                 540

Leu Gln Gly Gly Ser Tyr Lys Lys Ile Gly Tyr Tyr Asp Ser Thr Lys
545                 550                 555                 560

Asp Asp Leu Ser Trp Ser Lys Thr Asp Lys Trp Ile Val Thr Ser Arg
                565                 570                 575

Thr Pro Ser Pro Thr
            580

<210> SEQ ID NO 60
<211> LENGTH: 15652
<212> TYPE: DNA
<213> ORGANISM: Homo sapiens
<220> FEATURE:
<221> NAME/KEY: misc_feature
<222> LOCATION: (1)...(15652)
<223> OTHER INFORMATION: n = A, T, G, or C
<220> FEATURE:
<221> NAME/KEY: misc_feature
<222> LOCATION: (1)...(15652)
<223> OTHER INFORMATION: r = G or A; y = T/U or C; m = A or C;
      k = G or T/U; s = G or C; w = A or T/U;
      b = G, C, or T/U; d = A, G, or T/U;
      h = A, C, or T/U; v = A, G, or C
<220> FEATURE:
<221> NAME/KEY: exon
<222> LOCATION: (3419)...(3444)
<220> FEATURE:
<221> NAME/KEY: intron
<222> LOCATION: (3445)...(3908)
<220> FEATURE:
<221> NAME/KEY: exon
<222> LOCATION: (3909)...(3993)
<220> FEATURE:
<221> NAME/KEY: intron
<222> LOCATION: (3994)...(4694)
<220> FEATURE:
<221> NAME/KEY: exon
<222> LOCATION: (4695)...(4898)
<220> FEATURE:
<221> NAME/KEY: intron
<222> LOCATION: (4899)...(5652)
<220> FEATURE:
<221> NAME/KEY: exon
```

```
<222> LOCATION: (5653)...(5838)
<220> FEATURE:
<221> NAME/KEY: intron
<222> LOCATION: (5839)...(7184)
<220> FEATURE:
<221> NAME/KEY: exon
<222> LOCATION: (7185)...(7205)
<220> FEATURE:
<221> NAME/KEY: intron
<222> LOCATION: (7206)...(8310)
<220> FEATURE:
<221> NAME/KEY: exon
<222> LOCATION: (8311)...(8806)
<220> FEATURE:
<221> NAME/KEY: intron
<222> LOCATION: (8807)...(12271)
<220> FEATURE:
<221> NAME/KEY: exon
<222> LOCATION: (12272)...(12406)
<220> FEATURE:
<221> NAME/KEY: intron
<222> LOCATION: (12407)...(12820)
<220> FEATURE:
<221> NAME/KEY: exon
<222> LOCATION: (12821)...(12991)
<220> FEATURE:
<221> NAME/KEY: intron
<222> LOCATION: (12992)...(14089)
<220> FEATURE:
<221> NAME/KEY: exon
<222> LOCATION: (14090)...(14191)
<220> FEATURE:
<221> NAME/KEY: intron
<222> LOCATION: (14192)...(14477)
<220> FEATURE:
<221> NAME/KEY: exon
<222> LOCATION: (14478)...(14543)
<220> FEATURE:
<221> NAME/KEY: intron
<222> LOCATION: (14544)...(15002)
<220> FEATURE:
<221> NAME/KEY: exon
<222> LOCATION: (15003)...(15194)
<220> FEATURE:
<221> NAME/KEY: intron
<222> LOCATION: (15195)...(15652)

<400> SEQUENCE: 60
gatcatatta atttgaaggt ggcggggcag gatggttctg tggtgcagtt taagattaag      60
aggcatacac cacttagtaa actaatgaaa gcctattgtg aacgacaggg attgtcaatg     120
aggcagatca gattccgatt cgacgggcaa ccaatgaaac agacacacct gcacagttgg     180
aaatggagga tgaagataca attgatgtgt ccaacagca gacgggaggt gtctactgaa      240
aagggaacct gcttctttac tccagaactc tgttctttaa agaccaagat tacattctca     300
attagaaaac tgcaatttgc ttccaccaca tcctgactac taccgtatag ttttctctat     360
tctttcattt ccccccttccc cattcctttta ctgtacataa agtaactggt atatgtgcac    420
aagcatatta cttttttttt ttaaaactaa acagccaatg gtatgttttg attgacatca     480
agttggagac ggggggggaaa atactgattc tgtgaaaata ccccctttct ccattagtgg    540
catgctcatt cagctcttat ctttatattc cagtaagtta ttttgctctc actgttttaa     600
caacaacaac aaaaaaacaa caacataaaa atccttgcat accttgttca attggagaat     660
tttaatgttt ttcatttatc attgtaaaac caaggacaca tttataactt ttttgtactt    720
agctgttaca tgcagagcaa tctgtcttta agtagggata aattactcta aaacaaaaaa    780
gaatcctaga tagttttccc ttcaagtcaa gcgtcttgtt gtttaaataa acttcttgtt    840
taaaaaaaaa aaagtaaaaa aagaaaagtt atgcaacaat taatgcccca gaggcaatcc    900
```

```
ttgttaacat tttgatgcat cttttagctg tttttttttt tttttttttt tttgactgag    960
tttgactctt gtcacccagg ctgaagtgca atggcatggc atgatcttgg ctcactgcaa   1020
cctccgcctc ccgggttcaa gtgattctcc tgcctcagcc tcctgagtag ctaggattac   1080
gggcatgcac caccatgcct ggctaatttt gtattttag tagagttggg gcttctccac    1140
actggtcagg ctggtctcga actcccaacc tcaggtgata agggaagggg cactattgac   1200
atttatggtt ggggcagaag tgtaagatat tcttcaaagc actacctaca tgttgaagaa   1260
ttgttcctca cccagattct caaaagtccc ccaggacatt cacgtagtga aaacctgtgt   1320
ttaattatct gagcctataa cttaatacag ttttaaaatt tttttttaaa tatacagtga   1380
actttctagg aatgcaatta tagttgtgtg ttaaattagg gaaaattaac tttgctacca   1440
agagttgttc aacattttgt taaatcactt cattgatggc aacatgctgg aggtagttga   1500
gtcaccaact cagcacctgg atcagcctgt gttggtagca gtttcatccc cgtggttctg   1560
tgaataggtg gaagcatctg cttactccat caggacttct agggtagtcg ggccttggca   1620
ctcacacatt aaaatactgt ttatgttatt ttattgcaag ttacttttct ttcatttccc   1680
ctntacgtta cagaaaggga agcatttgc tttctgttta aagttgtgta tgtaggtagg    1740
ttatatcatc taagactttc tctccctcct tcccttct tttgtttgag atggagtctt     1800
gctctgtcac ccaggctgga gtgcagtggt gcgatcttgg ctcactgcaa cctctgcctc   1860
ccgggttcaa gcgattctgg tgtctcagct gggattacag gcgcacacca tcacaccacg   1920
ctaattttc tattttagt agagatgggg tttcgccatg ctggccaggc caggctggtc     1980
tcaaactcct gagctcaagt gatcagtccg cctcggcctc ccaaagttct gggatttcag   2040
gcgtgagcyt catctatgaa tctcaattta ggacagtaaa agtgtcatwa caaaaatatt   2100
tattgtaaaa aagggttgga ggttgagaat ctcaattcta gtcagtctct cagtgtttgg   2160
tttcttccta ccatttttcc ccctaggacc agccagaaag cagcttttt tttgtccccc    2220
ccaacaagga gcccactgtt tcctctccca gcccaaactc aggcctacga acaacaacag   2280
cactacacac acacacacac acacacacac acacacacac acacccttcc atttcaaggt   2340
atagccaaga gcttctggag ccgtcaaaaa ggtctgtacc tgctgtcttt agagcttcca   2400
gtttgccctt ggtcaagaaa tactgtttgc taggctctgc tggagtacat caggtaatac   2460
tggcttctaa accaccctga ggttcttttc tcttgtcctt ttactccctt cgtacttcaa   2520
tttctctcct tgatgtcccc ctccctgttt tgttttttgc ctccaatccg ttctgcgcgt   2580
tccctgcaga gcaggcgagt agcaatgctg ctggaccatg gagctgctct agtctcccag   2640
aaatctcttc tacacccaac ccttcttgcg cttaggtggt cytcagtccc cctccccac    2700
ttccttctga cccaggcttc tttctcgccc tccggtcgca gttctcctgg gcatctgcct   2760
ctgcctctct cctctcaccc ggatctaggg ctgcttctc tttgtgcagc cgtctttctc    2820
caccttcatc ccagactccc tgtctcagcg ccagctcctc tgcctttggc tcgggttccc   2880
tctcccccac cccagcttcc agttgtttgg cccgcaggtc cctcggcagt gaccggcgcc   2940
ccccgacgag tgcgtgtgca ccagggcacc tccctctccc ccacctctca gccccgcgcc   3000
tctccaccgc ccgccccacc gcgctgtggg cggtccaggg cggggctggg atccggggcg   3060
gctcccgggg ctcgggttgt gggaggcgcc ctctccccgg tcttcccctc ttcttccccc   3120
cgccctgcct tcccttgcac cctccttctt ccctccgccc gggagctctc cctggtcccc   3180
cggcgccgcc tccttccctc ccggctcccc gctcccgct cccgtggctg ccgccgcccc    3240
ggggaagaag agacaggggt ggggtttggg ggaagcgaga gaggagggga gagaccctgg   3300
```

```
ccaggctgga gcctggattc gaggggagga gggacgggag gaggagaaag gtggaaggag   3360
aagggagggg ggagcgggga ggagcggccg ggcctggggc cttgaggccc ggggagagcc   3420
ggggagccgg gcccgcgcgc cgaggtaaga gccaagggcc ccgggttagc agggctcgga   3480
gaggggcgc scgcgtggt gggggagggg gcagtgggcg cagggcccag ctgggggaag    3540
cggggctggg ggagaggagg aaccgcgggg atggaatcgg ggagcgctga ggcggccgat   3600
gccgggagcg tgggtaagcc aggcttctgc gagccgcggg ggccggggga gaggaggtgg   3660
tgagaggtgg agtccgggag ggttgggggc cgagggaggc aggaggaggg tggggacagg   3720
cttctctcc tcctctcccc ccaccccgcg cggggctccg ccccgcctc ctccgcgggg    3780
cgctctcttg gtccccaggc tgagcccggt cggagcctgc gaggcaaccg gcaagaggtc   3840
gagtagtctc cgggtgcggg ccgcgccggc ggggctcggt ccagtcctca tggccgcctc   3900
tcacttagat gttgctgctg ctgctactgg cgccactctt cctccgcccc ccgggcgcgg   3960
gcggggcgca gacccccaac gccacctcag aaggtgcatc cttcttcgac gacctccggc   4020
cctccttcgc tccacttccc tttccctgca tctcctcatt tctggtcctc atcactatcc   4080
catcagtccc acatatcatc ccggnctggc aaccccttct gctcggnccg actttactac   4140
tgctgacctc cttctgtcac cccacgttac tatccagcac ctcttttctc tgcccacatt   4200
gctacactat accaccttcc tgtgcatttt ctccgcctca atcccctttc ccagcccac    4260
attamtacyt caattactcc cttttcttgg tcccactttg ctgtccarat gatcttatwa   4320
gcctccctt atcytcctat cctaattcaa ytsgaatatc ctcatttagc ctttttttt    4380
aaagaaaagc tccacccaca tatcatacc ttcatgattt cttaattact tttcttctt   4440
acytccaccc agcaccctcc cytccccact ngtgggttct ctcatcagct ttaaccctgg   4500
cccttactc tytgtcctt agccagggga tntgtacctg tccccactcc caccctctag    4560
tgccccatcc ctcttcctct gtcccagcc tgcccacaga ccacgcccta ctctcccctt   4620
cctcccaskg gggagcskgc cttttcytct ttcccaccat tcctctctgt atgcctcccc   4680
gactcacccc ttaggttgcc agatcataca cccgccctgg gaaggggca tcaggtaccg   4740
gggcctgact cgggaccagg tgaaggctat caacttcctg ccagtggact atgagatkga   4800
gtatgtgtgc cgggggagc gcgaggtggt ggggcccaag gtccgcaagt gcctggccaa    4860
cggctcctgg acagatatgg acacacccag ccgctgtggt gagtagcctc ggaagcccct   4920
cccctcttca agactattcc ttttcctgcc gcaaacttag cattactgct tgcaagtcag   4980
cactttaaat ccagtatacc aaaattcaca aatacattta ttgaatgact actacataag   5040
agcaattttg ctctgtgcgg ttggaggtag tagagctagc agcctgcaca gttcatttca   5100
tcctcccttc attaggccac tgatcattgg cctataacat tgataattca tcttgtcagt   5160
tattctcttk gaggatcatt agtggcagat gatgacaaaa aaaattctaa atgatttca    5220
tcacatttt gaataccttc tgtcaccaac ccagagacca tatgcccaag aaacaaaagc   5280
cagtttaata ttaatagaag ccaactataa taagaaaagc aaatctgatt gtgcatccaa   5340
agttatatac atctacatat ttcaaagcca gagaaccgcc cactgtagct gactttgaag   5400
agatcccatt ttgtgtgctt atagcccat cttgggttcc taaaatggta attttttttt    5460
tcttttggga atgtgtggat gcttgcacag gtaagggagg attggaagat aggtaggcaa   5520
atccttttca catgtgattt tctttagagc aggatgcttg tggacccaaa cctgcamctg   5580
agtcccctgy tctttaaagg gaaagagcct tcttcaaytc gcctytcttc ttattttccw   5640
```

```
atctctccac agtccgaatc tgctccaagt cttatttgac cctggaaaat gggaaggttt    5700
tcctgacggg tggggacctc ccasctctgg acggagcccg ggtggatttc cggtgtgacc    5760
ccracttcca tctggtgggc asctcccgga gcatctgtag tcrgggccag tggagcaccc    5820
ccaagcccca ctgccagggt gaggggaaca gctgcctgca tgcagctgat gaggacsctt    5880
gtgtgaggat gggagtgggg tgggaatgga taatgggaaa raatggarag ctataaaawt    5940 gtggggagg acactggaaa ggggagatra aagtccctttt ttcctccatc acctgcctca    6000
aacttcctct tgcagtcccc ggtatcctct gtwggtkggg ggcttccttc ctttacctttt   6060 taaaaaaatc ttcctgctcc cgattcttag accycacgtt ttctcttttc ctttatgaat    6120
ctcacctctc tcaccttctt caggtttaaa tactccaatt ttccctttct ctaaacttag    6180
aaatttccat gcatcaccct cttctagaat ycctcaccat tccttatata attgatttat    6240
tgtaaagact cagaaataaa tcaaacattc tactaagaaa aattgagaag gggagctctg    6300
ggggtggaaa catattaggg taaaagactt aaaattggag gcagcattat cagaagatga    6360
agaacaactc agggatgggg tgggaagaag acaggtcctt ttctgtactt cctagacaac    6420
ctccattatt ccctaaggga atcagtgttg tgtctgtcta cttttttttt ttttttttg     6480 ccacgtnatt ttacaaactc tcccttttct aggcacccga actctctgcc atcttctctc    6540
ctgggakgca gtcatcccat ttgtatgcyt cawacttcyt ctaccctggt agattctttc    6600
aagatccttg ggcttwactt tcctcacata actcagttat tctgcttcta gtttaccatt    6660
ttattctgga aattgagagt cccatccagg ggtggactta tgacactact gaaacttaga    6720
cttcaaggtt cctcacctac agggccytct tcctgtgctc taataatata garggctcga    6780
tggatatgtg ttcatatggt aacaggcttt tgtwaaaatt gcagaaataa gattttaaca    6840
gcmattgctt aaagccmawt gtatgtgtwa ttttttttct taaagactcc cmattttgtw   6900
atattcaggc mccmcagaac caagatctgc cccaaactta gctattggca ttcccgtctc    6960
aaattctgtt gtcctatgaa aaatcgaaga agaaaataag tcctgaccccc ttaccccca    7020 gacccacctt gttcttatcc ccaggcaccc tccctcaga aacgcaggct tctgctctcc     7080
ccggtcttca gcatggacag gtgtgggagg gggctgggga tcaggccagg gaagctgggc    7140
gccagtggta actcttctct gatccccgtc tttcctgctg ccagtgaatc gaacgccaca    7200
ctcaggtgag atgagaaacc cttaccgcgc gcactgcaat gccctcccct tcactctgca    7260
ccctccaccc cctgaaatt ctgccctag gctacgggc gtcgtccttt cgcaccttcc       7320
ccaacccacc ccaktttgcg gccaccccct tcctccccta cctgtttcct gcctccagtc    7380
ccggttttcc acraggctgc ggtctctcct tgtccctgct tggctacact tccctgggct    7440
ccacctcctc ccagactgag cctcgccggt gtcaggcaga gcccancara aggcggcagg    7500
gtgctgggag accctgagct cccaccacgt tttcccctgt ggggttcctt gcgaccttcg    7560
ctggaacctt ttcagcctg ctgcctccta ggatttcacc taatggactt tctcagcctg     7620
tyccacccat yccaaccctg gscaggcctc tcgcgctctt ccccacatct tttccttccg    7680
tgtacccttc cctcgtcttt tctcaattcc atgtcctgtc tccctttctt aaggyttctg    7740
tctacccagc cccaggytcc yttccacrac cccaccaytc cytcaaaccaa gcytcccttc   7800 cgtacccaac tcgttccctc caaaaccgtt tcctctcccc cacatcctca gtgcttcact    7860
gtatcgactc atactcccac ttcagacctc aggcgccagc ccgtttctc tcccgtccca    7920 ctcgcatcct tcccttccta ccctggttcc tccgtgcttc agcctcccgc ggctccctcc    7980 gcccacccg ccytcytggc acgccccgtc cccatttctc ctcccctcgg gtccccttaa    8040
```

```
gtgagatccc tcccttcctc tttcgttcct ttcctcctcg aggttgcatc cccctcccc     8100 tccccgcccc tccgactgtc gctcccacct cggcgctcgc ttccctcccc gccccttcc     8160 tgcctcccca gctcccgccc gcccccccac ccccgctgc cgcgcgccgc ccgtgacgtc     8220
agagccccct cccagcccca catctccctc ctgctcctcc tcctcccctc cgtcggtcag    8280
tcagtccgcg aggagagtcc gcggtggcgg cgacggtggc gagagccgcg ggggccgtag    8340
gaagccaacc ttccctgctt ctccggggcc ctcgcccyt cctccccaca aaatcaggga     8400
tggaggcgcc tccccggcac chtcttagca gccctcccg ggaaaagtgt cccccctgag     8460
ctcctaacgc tccccaacag ctaccctgc ccccacgcc atggggcccg ggcccctt      8520 tgcccgggtg gggtggccac tgccgcttct ggttgtgatg gcggcagggg tggctccggt    8580
gtgggcctcc cactcccccc atctcccgcg gcctcactcg cgggtccccc cgcacccctc    8640
ctcagaacgg cgcgcagtgt acatcggggc actgtttccc atgagcgggg gctggccagg    8700
gggccaggcc tgccagcccg cggtggagat ggcgctggag gacgtraata gccgcaggga    8760
catcctgccg gactatgagc tcaagctcat ccaccacrac agcaaggtas ccctrgacat    8820
gggggtgggt gggakgtggg gscttgcggg gcaggggggcc aagcaagctt gcacgcgccc   8880
ccatctgtct gagtcgtctc tgggattgcg aggcagaccc ctcccttgtg tgactggcag    8940
gagatgggct gggggtgcag gagcttggga agagtcgcag gggctggagg tccaagatga    9000
gggtctaggg gctcaagatg gttaagcatg ctgcaaggca gacccttctg ccccgctgcg    9060
ggagtctcgc agaagtgtcg gggtttggag aaactggtgg tggatttaag gtattaggag    9120
acactgatcc tctgagggag taaactaacc ctggaatggg ttggggtgg agggaatgtc     9180 agaggtgggg agctggattg gggggttaca tttaccatgg taacaaggta aaatcttggc    9240
gtaggttgga gctggaagga atagggacag aatgaggaaa attttgagag acttgagagc    9300
tctagtttat ttatcttaac aaaacagcaa ggtagtggtg agccctacct gactccttct    9360
catccttcta ttcccaaccc tgttgagcat tcccagactg tgggatagat ggcatatggt    9420
gattggggaa ggctaatgat caagaggtgg gcagaggcac tggaaaatg aattggattg     9480 gggatccaca tgggaacccc cacaatagca tggggatgaa gaagagtcaa catcaagga    9540 gaagagaaca gaaagaatg gcagtggggg agaggggcaa ggaggtagcg tgggataat    9600 gagagatctt ggggcacctt atggaacttg ggtcctgacc ttcccttccc ttatagcatt    9660
gtggcctcta ggatgtgaga agggaaatgg gatgtaggga ttaggggt gagttgaggg     9720 agagagagaa ggtaagcaaa tttgggtcca ggggtattag gggatagctt ataatgaggt    9780
tttttttccc acccctctcc cctacatgaa taattggggg tgcagggaag gatgtgacac    9840
agggaaggag atttaagatc tcaaatttat cttcactgac atgtggcccc agagacttaa    9900
ggaattgggt tagggtgaaa tagagtacac aaggtgagaa tttggtgatc ttaccaaata    9960
tcaaccttgg ggtgatccaa ggatttatat tcatttttag aacatcacta tacacctaga   10020
aataggtgtg tgtctgggat aggtgtgtga ggggacagaa gtgaggttga aggtagggtg   10080
cttgaagaga agagagcaca aggattatca ggagcttggc aagagaactt aaaatccttt   10140
ttgactgtta ctttctcgtg gttctcagcc ttcagtgtac ataagaatca ccagaggagt   10200
ttgttaaaaa tacagattct agctccttgt tcagggatga atcccaagta tttatctgta   10260
tttttactaa tagacatccc tatcttggtg gattcctgag ctgtaagcta accccagaat   10320
gcctatggga agagcagcag ggtacaggaa ataattagg tattagggta cgggaggcag    10380
```

```
gaagagaagt agaggatcag atctggtaga gggtcagact tgggacagtc agagagatca   10440
ttggttttgg ggagtggagt gtgaagaaaa tgacagggag agatgggtgc aggctttatg   10500
atagggggatc acaggagata ggggaggcct ggctgtgagc tcaaactcat ccaccatgac  10560
aggtgattcc ctggaggtgg cggggagcag acgtgggacc tgggagaagg gaactggaga   10620
acatcagagg catcaagcgg ggtgggatgg gaaggcagaa gaaccagaat gtgtcaattg   10680
gaatgagtcg gtttcctgcc tgcaaatcca gatccttgca agagcaaaga gagggaggag   10740
aactaaggaa atctattggg gagggggaga gaatcacgtg gtggagagaa tctgcagtga   10800
tgaatagtgt gtggaagagg gaaacggttg caagaaaagg tagataagaa atcaggaaac   10860
aaaatggggg gcatgcctgg ccctgttgat aggtatctta tatgttcttg aatgtcctca   10920
ttgttcnnat taaccccctgt ctttagaaa gtggagggc actgagggc tgtgggagaa    10980
gctgggagca ggatctggag taatagatgt ggggagagtg caggaaggtg ggtcctgaga   11040
atggtaaaga tttacaaagt tgccctagtg ggaggcataa agaaaaacc ttccaatgtt    11100
gttgagcact gcccttggcc agagtgaggg tagggtgggc aacagagaat tctcagtgac   11160
tgctggttct tcagattcca acagcttccc ctggctcccc cttctccaac ttcccaccgt   11220
gtcccaaatg tcaggcctca gtgggaggta agcaggctcc agagtgcttt ctttatttcc   11280
tttctactta tcctccccctc ctggcaacat ttcaccctcc ttagtcccct gagccccctg   11340
tctgtgtccc ctctgccctg gctccccact ggctgccatt tcgtcttcac atgcattggg   11400
gttccagcag cttctgaaat gtcatatatc agtgggaggg gaacaggcag tgggagaccc   11460
aaggctggct cttcctcccc catttcccct cctcccaagc ttcctttctt ctccagcttt   11520
ctgcttgttt actttcccta gctccaagcc tctctttaag gcacctctca aattgtctgg   11580
tttcttgaga gttccattct attcattctc tctgttcttt cctcatccta cattcttccc   11640
tacttccacc ccccagtgtc ttttttttcta atggacctgt caaatgtcag cgcccagcag   11700
gagggatgga tcactgagcg ggacccccta ctggtcttgt tcctgttctc tcttwactta   11760
tcactagctc tgaaaagaga agaggggagga aacaaatgga aggtggggag aagggggttg   11820
cagaggtgag gaaggaattt tcataatatg gcttttgagca agctatctgg ggatgtggaa   11880
agagtttacc gtattcctac tgacttcttc cacccactgg tgtttgaagc atagaaacat   11940
ggggtaaagg gcttggtgac agagggaagg gggatgtctg agggtgagct gaaaggaggt   12000
aagtggtat gttcattaat accaaaggag gggtgtgcag gagaggtgat gggtaaggct     12060
ccagatggaa gacagagaag gaagtttaat gaaagargag aaaaaaggca cttgacagga   12120
agagatgcca gaaaggagaa gaaaacggta attaatgatg aaagtgagta attgagaaag   12180
gaactaatttt gttcgagaaa gataagagca ggaattgcag acagggagg ggccccagga    12240
gagcttgccc tcatctcctc ttgtctttca gtgtgatcca ggccaagcca ccaagtacct   12300
atatgagctg ctctacaacg accctatcaa gatcatcctt atgcctggct gcagctctgt   12360
ctccacgctg gtggctgagg ctgctaggat gtggaacctc attgtggtaa gcagggctat   12420
gggggtcaga agatggggtc attccctttt gagctctact gaagggacga tggcgattgt   12480
gggtttgtat tgaaaaggag tgtggaggac ctgctactaa gattcagagt cctctgcaga   12540
cctgagctag gcagcytcct agcaacagtg scctgacagt gctgcagctg acctccttct   12600
tcagaaggaa ttgaaattag atcagtgaaa gagcatcccg gttgtgaggg gtgtgtgggc   12660
ctttgagaat ctcttttcct taggcagacc agaggtgggg aggtttggag agagtaagga   12720
agagaaaccc aaaggcagga agagggttaa aggaactctt ggccactctt ggtgtcctca   12780
```

```
gtgaacagac cctgttgcac tcactctccc tgccccacag ctttcctatg gctccagctc   12840
accagccctg tcaaaccggc agcgtttccc cactttcttc cgaacgcacc catcagccac   12900
actccacaac cctacccgcg tgaaactctt tgaaaagtgg ggctggaaga agattgctac   12960
catccagcag accactgagg tcttcacttc ggtgaggagg ggttgggcaa ggggtaaagg   13020
gacataagct caaattccag caccaggaga tgtgacgtga gagtcacttt taggggcaag   13080
aacttgattc ttcattgaaa gagaacgcat tccatgtgga ttaagtgcag ttctttctgt   13140
agccagggga aagaatgagt tgagtttttg ggatcctctc tgtctttatg attttatgat   13200
ttttttcccc tgtttgatgc cctgttcccc agacatatag acccagaatg actcagttct   13260
gttaaagtag gttcaatcca aagtgggggc aagagatggg agcgaagatg ataggaat    13320 ccaggaaggc agcagattcc agaagctttc aaggggggtg gtgggtgggt gttaatggga   13380
acagaaggga tggagccagt ggattacmga rgagagaggg rgagraagag agagagagag   13440
aggaatgagg gagaggagag agaggggcag aaaggcagct gcatggatct ggtagttggt   13500
actaagagag agaagccgac agacaaggag aggttgaggg ggaagaggga gatttgggga   13560
ggtagagagg aaatacaggc tctacatctg aagaaggcag tctgctccct ccctttt att  13620 ctattctttg ggtcttctat ccactgtgtt cagtggccct ttaatcctcc cccactttca   13680
ctctgattca gaccattctt ctctgatcct ttgtctgtct gcccatttgc ctcttgaggt   13740
agacatcatg ctgtctgtcc cagtccttgc cttgtctttt cctggttcct ttatgtttct   13800
ttaccccatc tttgccttca gtggtaggag tgggtgaatg gagtggcttc ccccacacag   13860
agcctcagca ggggctcacc attcaccttc ccacttggaa tccacatcct aagaccagat   13920
gccttcccga actcctcact tcaggacag aagctgttga aggaaggttc agaatggctg   13980
cttctttgct ctatctgagt attgctctga aatccccagt taacctctct ggtctttatt   14040 cccctcatgca ccccgtgttt ttccaacttg ttttttattc ccacccaaga ctctggacga   14100
cctggaggaa cgagtgaagg aggctggaat tgagattact ttccgccaga gtttcttctc   14160
akatccagct gtgcccgtca aaacctgaa ggtcagatgg ctgggagtgg tgggctctgt   14220
ttacggaggg accaagctgg gggacagtga ctggttggas aggaaagcca ggcgggggca   14280
ggttttgatt ctctgaggca atancatctc ctggggaagt ttagctccat cttccagttg   14340
acgtttattc actatacgtt gagcgttacc ctgcactaag cactttggga tgggaaatca   14400
aagctgtgaa gacatctggc ttagcccctc aggcattccc gggcatccct caggagctgt   14460
ttctttctct gttgtagcgc caggatgccc gaatcatcgt gggacttttc tatgagactg   14520
aagcccggaa agttttttgt gaggtggart tggatctgaa gagggagggg cactgggtgg   14580
gagtttccct tggttttctt gtggggcctc ctcttggcat ctgtgcctga gttgatagca   14640
tatgatctga ggtgacgatt cataggatgt ctctgtctgt tggctctgac tgcatccctt   14700
gtctgcacac acatgatact ttcttcagat ctcattttc tactgctttg tgtttccyga   14760
gaagcccatg aattccatct gtcctgactg gctggaaaag gccactcaga aatacagggg   14820
ctggggagaa acttagaagg aagaattgtc agcctttcct actatcccca agacttgtag   14880
atttctcttt ttagttctac tgctcttccc tgattcccaa gaggctaaat agtatcaagt   14940
gagataagac aaaaacaaac aaatgagcaa acaaaaactc agccattctc ctctgtattc   15000
aggtgtacaa ggagcgtctc tttgggaaga agtacgtctg gttcctcatt gggtggtatg   15060
ctgacaattg gttcaagatc tacgacccctt ctatcaactg cacagtggat gagatgactg   15120
```

-continued

```
aggcggtgga gggccacatc acaactgaga ttgtcatgct gaatcctgcc aatacccgca    15180
gcatttccaa catggtgaga gtgtggggac ttgcagtctg gcacctggga gggtggagag    15240
gactgagggg sccttgcagg ggaaagggtg gcagggagag ggtgcggaat ttggatataa    15300
aggagaagag ggggctgtgc ccaccctgaa cttgtctgca ttatgtttcc tgtggatcct    15360
acctttgctc tgacttcctt gggtwgagag agaaaaaaaa aaaaacgatg gagttgtatg    15420
ttcagtaggt tcctgatgag tggaagggct gttaccatgg agacraggag cagttggtga    15480
gaagtcagga ggaaccggca ttaatgataa tatggatgct tgtwtactca agcacacctt    15540
tacaggagca ctgtgtctgg gcagaattgc atttcatttt cttggtgatt tatgttagtg    15600
ttttagagtt gcttaatatt cactcatgat tgatatgcma ttagcttgga tc            15652
```

<210> SEQ ID NO 61
<211> LENGTH: 13187
<212> TYPE: DNA
<213> ORGANISM: Homo sapiens
<220> FEATURE:
<221> NAME/KEY: misc_feature
<222> LOCATION: (1)...(13187)
<223> OTHER INFORMATION: n = A, T, G, or C
<220> FEATURE:
<221> NAME/KEY: misc_feature
<222> LOCATION: (1)...(15652)
<223> OTHER INFORMATION: r = G or A; y = T/U or C; m = A or C;
     k = G or T/U; s = G or C; w = A or T/U;
     b = G, C, or T/U; d = A, G, or T/U;
     h = A, C, or T/U; v = A, G, or C
<220> FEATURE:
<221> NAME/KEY: intron
<222> LOCATION: (1)...(1924)
<220> FEATURE:
<221> NAME/KEY: exon
<222> LOCATION: (1925)...(2167)
<220> FEATURE:
<221> NAME/KEY: intron
<222> LOCATION: (2168)...(2795)
<220> FEATURE:
<221> NAME/KEY: exon
<222> LOCATION: (2796)...(2859)
<220> FEATURE:
<221> NAME/KEY: intron
<222> LOCATION: (2860)...(4408)
<220> FEATURE:
<221> NAME/KEY: exon
<222> LOCATION: (4409)...(4486)
<220> FEATURE:
<221> NAME/KEY: intron
<222> LOCATION: (4487)...(6030)
<220> FEATURE:
<221> NAME/KEY: exon
<222> LOCATION: (6031)...(6181)
<220> FEATURE:
<221> NAME/KEY: intron
<222> LOCATION: (6182)...(6678)
<220> FEATURE:
<221> NAME/KEY: exon
<222> LOCATION: (6679)...(6811)
<220> FEATURE:
<221> NAME/KEY: intron
<222> LOCATION: (6812)...(8194)
<220> FEATURE:
<221> NAME/KEY: exon
<222> LOCATION: (8195)...(8311)
<220> FEATURE:
<221> NAME/KEY: intron
<222> LOCATION: (8312)...(8408)
<220> FEATURE:
<221> NAME/KEY: exon
<222> LOCATION: (8409)...(8516)
<220> FEATURE:
<221> NAME/KEY: intron
<222> LOCATION: (8517)...(8928)

```
<220> FEATURE:
<221> NAME/KEY: exon
<222> LOCATION: (8929)...(9022)
<220> FEATURE:
<221> NAME/KEY: intron
<222> LOCATION: (9023)...(9716)
<220> FEATURE:
<221> NAME/KEY: exon
<222> LOCATION: (9717)...(9844)
<220> FEATURE:
<221> NAME/KEY: intron
<222> LOCATION: (9845)...(10424)
<220> FEATURE:
<221> NAME/KEY: exon
<222> LOCATION: (10425)...(10553)
<220> FEATURE:
<221> NAME/KEY: intron
<222> LOCATION: (10554)...(10775)
<220> FEATURE:
<221> NAME/KEY: exon
<222> LOCATION: (10776)...(10919)
<220> FEATURE:
<221> NAME/KEY: intron
<222> LOCATION: (10920)...(11700)
<220> FEATURE:
<221> NAME/KEY: exon
<222> LOCATION: (11701)...(13187)

<400> SEQUENCE: 61
gaattcctga cctcaggtga tccaccctcc ttggcctccc aaagagctgg gattacaagt      60
gtgagccact gtgcccagcc tgacttgttt tttataatgc ctttttttt ttttttttgag    120
acggagtctt gctctgtcgc ccaggctgga gtgtagtggc gtcatctcag ctcactgtaa    180
cctccacctc ctgggttgaa gtgattttct cacctcagcc ctcagcctcc tgagtagttg    240
ggactgcaag tgcacaccac catgcccagc taattttttg tatttttagta gagatggggt   300
ttcaccatgt tgcccagctg gtctttaact cctgagctca ggcagtctgc ttaccttggc    360
ctcccaaagt gctaggatta aaggtgtgag ccactgtgcc tggccttttt tttttttttt    420
ttttttttga gcagttttag tttcccagca gaattgagat gaaggtacag aaacttccca    480
tatgcttccc acatgcatag ccttctacat tatcgacatc ctccgccaga gtggtacatt    540
tgttacaact gatgaaccta cattgataca tcataatcac ccaaagtcca tagtttacat    600
tagagttcac ccttggtgtt atatattcta tgggtttgga caaatgtata atgagacgta    660
tctactatta aatactttac agagtatttt cactggccta atccaatgga catttattgt    720
tacttcatta tggttgggca cagtgctaga tgctgatgat taagagaggg catgggattt    780
ggtcttgtcc tcaagggtag aacctaggcc cattgcatct tcaaagccca ggctccttca    840
aagcccagtg tagtagcaac tgctgtacct tgcctgtgcc cttttgcgtat ctcactcctc    900
tatctctcta gaaagttgga gagaaaagtg agcaaggcat gaggaacaaa gttatttatt    960
tattcttcat tcatctattt attctttcat taccgtttgt gttaaaacat tccaaaccca   1020
aacaattatt tgtatggtcc cctgtgtatt acttgtggtt tcccaagaag tagttgctaa   1080
gcttttcctt gtatggtttc tgtgaggtaa ggaaggaatg atgtgatttt ctccagtatg   1140
tagaatgcag ttccaagagg ttaagtaatt tacttacagt tatttagcca aacaaggtta   1200
ctgcaaggta tatgaagtca ggtctcttga cccagttcat gagagagtta aggaactat    1260
cattcttttt agctttcatg gaaaaagaag gttgagtgtt gggaggggtg tgggtaggat   1320
tgataatgga cttcaaaaat gtgaagggta tttctgtagt tttcattctt ctgaaagcct   1380
tctaagaggc agtgaaccaa agcacacaa gaatggcaag aagttagcat gctgaagaaa    1440
tatcctcctg gctggcaagc agagtgagaa gactgctatc accttttcta gaatctttg    1500
```

```
gaattgtagg agctgttaga tcctgggtta actctatgaa gaaagtcaga aggatcagag    1560
aacatcagtg tcacagctct tcattggaat atccatgtct cctcctttac tctgctctac    1620
cttccatcct ttgccactaa ttatccgag tgtttgtcaa aattctctgt ttgcagttct     1680
gagctagcaa ctgtacacac taacaccatc agacacagct aatacctact ctagtctagt    1740
agcttccgat ctaaggcaga cacatgggta tagttaaaga ttttgaatgt acatgtgtcc    1800
aatctgacaa cagtaacaca aaccatccat tcaagtagaa gtgattgagt cagaattgga    1860
ttgcacccct tcccccacac ccacacacat ttcagttctt tcctcatgat ttttcctcc     1920 caagacatcc caggaatttg tggagaaact aaccaagcga ctgaaaagac ccctgagga     1980 gacaggaggc ttccaggagg caccgctggc ctatgatgcc atctgggcct tggcactggc    2040
cctgaacaag acatctggag gaggcggccg ttctggtgtg cgcctggagg acttcaacta    2100
caacaaccag accattaccg accaaatcta ccgggcaatg aactcttcgt cctttgaggg    2160
tgtctctgtg agttaaaact tccttcatac tccctgtct tcccaatctt gagagagact     2220
cccaagaggc accttctaca aacatgcatt ctctgttttt ctcagttact tctttgcaga    2280
atcagtctcc gaccagagaa gtagggacct tcaaattaga agaacccatc aaagactaga    2340
ggaaaaaaaa tgatgtattc cattttttta aaccctccc ctcatttctt ttcaaactag     2400
accaagtatt catgagtcag atgagaacta taggattttg aaagacaaaa cagtctgaaa    2460
ggtcatcttc ttattccttt taaaatgaaa agattagttt ccagagagat ttgctgactt    2520
gcttaggcca cacaaccaga agcctgctgg tgttctgtct ggggatttt tcccattcaa     2580 atctcataag tgaagctcct tctccaaaga ataatgtttc taaaatctag ggtatgggca    2640
tctggggtat gtcctatatg caggcaaatg ccataaatag cattcattca gaggctcaat    2700
tacatcaaaa acagaaggat ttaaagagtc cctgatgttc tctttcactc ttgcttttgt    2760 ctccttttgcc ttgctccaca tgttccttcc ctcaggcca tgtggtgttt gatgccagcg    2820
gctctcggat ggcatggacg cttatcgagc agcttcaggg ttagtacagg ggcaggaggg    2880
gaccggacat ggggggctagg ctgggggctgg gctgggatgc cccctgggga agaatgccag    2940
agacatcaca agattgccct ggcacctccc aacttctgcc cttctctttt aactctgttc    3000
atcaagcttg taaataataa taataataag cttaactaca agaagattga tgtctttgag    3060
ttgcactggt tttgctcttg aaaagaggtg tgcaggctgg gtgtggtggc tcaccctgt    3120 aatcccagca cttttgggag gccaaggcag gcagatcatg atcatggtca ggagtttgag    3180
accagccaga ccaacatggt gaaacctgtc tctaccaaaa atacaaaaaa aaaaaaaaa     3240 attagctggg tgtggtggca ggtgcctgta gtcccagcta cttgggaggc tgaggcagga    3300
gaatcacttg aacccaggag gcagaggttg cagtgagctg agatcacgcc actgcactcc    3360
agcctgggtg atagagtaag actcgtctctc aaagaaaaaa gaaagaaaaa gagacatgca    3420
aattaaaaac agctactctc tttcccagtg gcttccatta atttcaggaa tttccccttg    3480
agtggcttgg gttgagaggt tgatgacctg tcagttagac tcaagaaagc tgaatctagg    3540
agaaccgcta ttttttttttt aagggaatct gccaaatttc cttgctgtgt aaagcttcaa    3600
tgtgtatagc ttggcttttg tagattgtat tttcttgaaa cttagcacac aggtatttgc    3660
agaacttcta ggagttaatt tttctgctcc actcggctct cagtctttta cggcatggcc    3720
aagagagcta tttcttggcc tcctgtgaaa agttcttc ttcctttctc cccacctcca      3780
catcctttca gctcctcttt gtatccagga caagaggaaa tggacttcag ccatggtgaa    3840
```

```
aggagtgtga gttggctttt gaaggaaaag ttatggtaac ggaaacagtt ctagaacaga    3900
aatcttagaa atgaccaaat tttactcaat ggcgctttaa gaggcagata taacttatcc    3960
aaggaattaa aacccaagcc aacagaagag aatgttctaa aattaaaatg aaagccactg    4020
ggaaaataga gcctgcccat catgagagga agaataagca gaaatatgtg taaagcttta    4080
gaagccaaam tcaaagtgag agacatctcg ccgagagagg tgtgaggaat ggaataggtg    4140
gcagacatgt tgtggagcct cctcactgaa gactttttaaa catagatatt cttatttatt    4200
tgagttgtct tgggaaccac cyyayattgc ttttaagtca tgttgctgat tcaagagtct    4260
cgtaggtcct tccaagcatc cttagggcct caggtgaaaa taaaatcaga tacaaccatg    4320
caaagctcta gggaagtggg aagttgaaaa tgcctaggat cagctctttg gctacctgtg    4380
gtcactcctt tyattgtcgt ctgcccaggt ggcagctaca agaagattgg ctactatgac    4440
agcaccaagg atgatctttc ctggtccaaa acagataaat ggattggtga gtggatcttg    4500
tttgtatttt ccttcagccc ctctcgacag tcaaggggaa aaagtcatgc ctttgagtga    4560
ggatggaatg gtagagactg ttaggttgga atgtggctgg cagctgggcc aggagaaagg    4620
gttaagtgag agtgaataca acccctaagg cgtgggtagg ggagactggt gtatttggag    4680
agggaatagg cggtggttag tactattttt aatggtgcat tgctggggta actggggatt    4740
agaggcaggg ggtgggcaga gggcgggaaa tggaaactcc atttgggttt cccagatgtc    4800
ctggtgtctt gatatatttg aaccagctac ttcaagccca gagctgtctc tttgtctgtc    4860
tctgtcagga aaacggttgc ttaaactatg gaggaggagg gaaaacctca tgtaattgtc    4920
atctgccaaa atgtgctttt tattttata tgtattttta aaaattttcc tattttatg    4980 taatttagag gtagacgtgc agttgtgtta catgaatata ttgcatagtg gtgaagtccg    5040
ggcgtttagt gtgcctgtca cccgaacagt gcaccttgta cctaataggt agtattacat    5100
ccctcaaaat atacttttta aagagagaaa gcaagcagtt attctttgtg tacttggtct    5160
aaatgatagg acataggaga gaaactgaag gtggacaaaa ggaaggacct actgataaaa    5220
gaaagcctcc ttgagaatga aggggaggct caaccattga agatggctgc cgtctgccct    5280
gcccagcaga tatccagtca ttcccagcac tgctggagtt ttgcccttttt ttttttttt    5340 ttacaattcg aatttaggac aatgttctgg attgctataa atgctgcatg gcctaaatta    5400
ttctttaaaa aaaactaag caaattgaaa ttagttttttt ttggtgaact ctgacaaatt    5460
gaacttcccc ctaataataa ctggaaaaca tatttgggaa tattaccctg ccaggattaa    5520
natttcagat kagctttcct tctttgtttg kttggtctta agaataggtg tccacactag    5580
atacttcaag gccttyttag ctttatgatt ccataattgt catttaaaam tttgatttgg    5640
gttataagaa accttataac attttttaak gatccccttc tttctcctcc cattttcctt    5700
tgctgtaaga aagacagaaa aacttaaaga acaaacaaaa acaaagacta caactttggg    5760
gacatgcctc agcattccc aacctatgga tagaccattc actccatctt ctcatctcat    5820
ttctggttgc ttcctaacgg ccccagtggc actgagcatt ctgcctgcag taacctctgt    5880
ccagtgcagt tagggcctca tgtccccagc caatgactga atgtccatca gcaatctagt    5940
tcttgtccct tttctcctat cccgtcttca ttcctttgtc ctccttccct tctctttcc    6000 cttcccctct tcctcccctg tgccatgcag gagggtcccc cccagctgac cagaccctgg    6060
tcatcaagac attccgcttc ctgtcacaga aactctttat ctccgtctca gttctctcca    6120
gcctgggcat tgtcctagct gttgtctgtc tgtcctttaa catctacaac tcacatgtcc    6180
ggtnagtttc tcttctgacg ttttccttgt ctgcctctct gagatactga tcwtgtttcc    6240
```

```
tggacaggat gagaataaaa cctgkgtway tcccatggcc natgtatcat ggagtttttc   6300
attctgactt gttgagaatg aaaacaggga aaccagatat aaccccccayt cctactccaa   6360 agtagctrrc gggaggaaaa aagaaaagaa gagaaaaaaa cmwcctttgg ggccaggtct   6420
cacagtcttg gactctacat aaatagcctg tattctagtg ggggcctgtg cttgggaagc   6480
cytctgcaac tccatcttca gccccatgac tgcattgctc tgcctctcra ggctccactg   6540
tcttctccaa tcctgtcttc ctttagcccc tggccctgaa attagggtca tgccattgcg   6600
tggtatttgg agagctcagc ctccctggag aagaggggta attctctctc cctctcaccc   6660
tctccacctc tgccctagtt atatccagaa ctcacagccc aacctgaaca acctgactgc   6720
tgtgggctgc tcactggctt tagctgctgt cttscccctg gggctcgatg gttaccacat   6780
tgggaggaac cagtttcctt tcgtctgcca ggtgaggagg tggtgggcaa attccttaca   6840
ggatgtgact ctcccacccg tctcaggagc accttccatg atttatgatt ctctgccctt   6900
cctcctcagc tttccctgac tcttgtccct gttctttcct tctagcatca ccctctgtt    6960 ctctgtttgg ctctgtccct tctttctgtg tctgcaggcc attttcattc tgtagtttac   7020
ttgtcagttc caaggttgcc atggcagscc tygcagagaa gaggagggag ccattgaagg   7080
caaaggaagg ggatctgctc aaaggtctcc tgaacaatgg tggcttgtct gtggtatggg   7140
ggctgagaat cagaactgtg gacttttttt gggagccttt gttgggtttg aaggataga   7200 agcagagatg gaaacacagc agagagttgg ggggaaggga ccactgccac acagggagg    7260 aggggctctg ggactgttgg tacatggaag gttctagtgc tgtggggaga ggccagcttc   7320
aacagtgata gttgagtggt tctcttttcc actggtggaa acacccactc tttctcctga   7380
tctgcctgcc tgtccttgct ctctcttttt cctctgctct gtgctgtcct gatcatacat   7440
ctgtgcacat ggcatttcca tgcacatgca catgcagttc atcaggaatc ctctgttccc   7500
agtgaggcca gagtgcagct ggagaagcag acaattagct gtagtgcaat aggagaggtt   7560
ccagagtagg gatctgcaca aagtgctttg ggggcaaaga agggaacaca gttcactgct   7620
ggcgtgattg ggtggacctc actgaagagg tggcatttga atactgaagg acaaatagga   7680
ttttatcagc tagagaaata gaggaaggct acttcagggg catagggagc atcgtgtggc   7740
tagaaaatac atgaaagaga gtagatgaag agaaagtgag tagttcagca tggctggagc   7800
gtggggtagg tgtggggctg ggagatgagc ctagctggac aggtggatgg gagcatgttg   7860
tgaagggtct gtgtcatatc cagaagtgtt caggctataa cttatagata ttggggagtg   7920
gttggaggtt tttggccact aaagccagga ggttttagca agatcaccct ggtggtgtgg   7980
aagtagaggg tggatgggag gaattgttca aggtggggag actgctctcc tcctgccgct   8040
ccccgtcctg ctcacatttt cgcatcctcc ctgtgccacc atgagctccc tgcccgtgct   8100
ccctgcccac tctcccttag ggttctgccc atccttactg cagtcccggc tactactcta   8160
ccctgttctg cctgtgccct ctcttccttt ctaggcccgc ctctggctcc tgggcctggg   8220
ctttagtctg ggctacggtt ccatgttcac caagatttgg tgggtccaca cggtcttcac   8280
aaagaaggaa gaaaagaagg agtggaggaa ggtgagctgc tgcccaatcc tcagccccca   8340
aatccttggc tcctggggca cagagcattt tcccctgacg tgcctgttct ccccacatat   8400
ttatccagac tctggaaccc tggaagctgt atgccacagt gggcctgctg gtgggcatgg   8460
atgtcctcac tctcgccatc tggcagatcg tggaccctct gcaccggacc attgaggtac   8520
cactggagag gaggtgctat ggtcaggaga atgagcaggg ctcagtggcc atcagggccc   8580
```

```
tggggctgtg tgtgtcttga gggatgaagc tacttggaga gagtgccttc ctcgtattgg    8640
aagctcttcc tttccttcct agaaggagcc cctcataggc ctccagattc agctgaaraa    8700
aggaagggt  gggaatctgg gaagggtgtg tagaacttcc aggcatcagg gaaagtgggg    8760
aacaagcacc tccaagggtt caggaaaaca ttcttaggcc tagaatgaga tttggcatca    8820
gcattgaggg tctcatagga aaacagttgg aagccagaga ctgagaagcg ttgaggagag    8880
gaggggaggc tggcaaccat ctttcttgtg acctygtttc tgccctagac atttgccaag    8940
gaggaaccta aggaagatat tgacgtctct attctgcccc agctggagca ttgcagctcc    9000
aggaagatga atacatggct tggtgtgtgg gatgtgggca aggagggca  gggatgcaca    9060
aaggcaggag ggaaggcagg ggtagagggc ttggagggag argggtcttt ggaagaggag    9120
gtagagagct tgtcaaccca gtttgaacac cctactcttt gttatkgcac tawtcttttc    9180
tgagaatagg ggagagttgy tcttttgcta tgaggagctt agggcccaaa gcacagaaag    9240
cacagatgaa gaacttgtgt tcagcagagg aacaagtggg ggtaacccca cctccagact    9300
tgacattaty ttttagatcc cccttggcct tattagcatt gttcgattca tggtcacaaa    9360
ttgcaaacct accytctgcc tggaaagcca ccttcccacc tgtagggtaa gggtgaggca    9420
tgtgtggccc agactggcct atttctagat attcaacaag cccttgcctg actgacagca    9480
gcttgccacc attgctttcc tgtgtgaatc caggaaaaa  gtgatgtggt ctgggcaagt    9540
tgggtggaca taagggatag gggacacagg gtgaggtttg ctaggtcaga ggggttggat    9600
tggagaggag ggcccccttt ccatttcaga gtaggtgaag ggcagagagg ggatggggat    9660
tgagtgagga gcattgtggt ccttgttgct caagtgactc tctcctgcca tcctaggcat    9720
tttctatggt tacaagggc  tgctgctgct gctgggaatc ttccttgctt atgagaccaa    9780
gagtgtgtcc actgagaaga tcaatgatca ccgggctgtg ggcatggcta tctacaatgt    9840
ggcagtgagc actgaccccca tggcattgac cctgtaggct gaccacagca gcccagatat    9900
agaggactag gaagaatcaa tgctagatct gggatcggtt gcttagaagt cttaaaaagt    9960
ttgttaattc ttcaggtcta taaagcactt tacagtttac aaagctcact acagacattg    10020
tatcattaat cttgcaacta cccagtgaag tagatattag tatccccact ttataggtga    10080
ggaaacagaa acacagagac gttaaattgc ttgtctgtgg ttaatgggct ggactctatt    10140
gacatttcct gccagggacc gactctggag gacccggaat ctgtgcatag agatcctggg    10200
agttcctgcc ttgaggggag gggttaacca agagtgaaaa ctggtttggg acagtttgag    10260
attttttctcm atctatattt gargatgatc ctgaatttgg atccttttca aagggaaagt    10320
tcaccaggaa actgtctgca tagactccct cccatgggaa gtaaactctg gatcttgtct    10380
gagcctgcag acctgagact ccctcaatgt gtctttccct ctaggtcctg tgcctcatca    10440
ctgctcctgt caccatgatt ctgtccagcc agcaggatgc agcctttgcc tttgcctctc    10500
ttgccatagt tttctcctcc tatatcactc ttgttgtgct ctttgtgccc aaggtaagga    10560
tctggctttt ctcccaccct ctttgttccc atgttccctc catccctcct tcctatatta    10620
ctgagttcct ctgcccttcc gttcaccctc ctctcactcc tccccttgtt ttgggcccaa    10680
ctcttatcag cattccttcc acctccaacc ttccatcagc cagtcactag tacagtcctt    10740
gctgggccac cccacgccca aacatttgcc cccagatgcg caggctgatc acccgagggg    10800
aatggcagtc ggaggcgcag gacaccatga agacagggtc atcgaccaac aacaacgagg    10860
aggagaagtc ccggctgttg gagaaggaga accgtgaact ggaaaagatc attgctgagg    10920
tgcgggggtg ggtgtcaggg tagggtgttg gartggtcca rgnaggcttg cgtcttarct    10980
```

```
tngggttgtc tgaagcccaa gcctgagata cagggtcaga tgttcttggc tcatggaggg    11040
agggtcctag gagacaacct gtaaggagtg aatggagcag catagggag gggaaagggc     11100 tgagcaagat tctatctcag gcaaaatcca gtgttggcct ggcaggtgga agggctctgg    11160
agtgggagct atgtggttga ctcagcctcc ttaaggcaag aggatggctg ttggctgtag    11220
gtgacaactg gagagaggca gctgtgagcc tctagtagtc aacactcaca gcagctgggt    11280
gtagcatgca sccccagcat aaaaggacct gggcaggcgt tcactgtgcc ccaggctgtc    11340
attaggggct ggtgcaatgc caaagagagg gatgttccaa ctgggttgac acatctctct    11400
gatttattgg aagctctgtg cactgacttt tctctccttc cccactttt cctttgttt     11460 ttaaattctc tcttatttcc ctgatcgcat ttttctatc ggtatcctta tgttctctgg     11520
cttttcttgt tctgttttga tttctccttt taatttattc tgtccactta ccctacgtcc    11580 tcccctaca ttyttctgtg cccttcctct ctttccctgt gcccttcctc tctttccctc     11640
ctccccactc cttcatcacc tcctcttctc ctactatccc aattgtgctt cttcctccag    11700
aaagaggagc gtgtctctga actgcgccat caactccagt ctcggcagca gctccgctcc    11760
cggcgccacc caccgacacc cccagaaccc tctgggggcc tgcccagggg accccctgag    11820 cccccgacc ggcttagctg tgatgggagt cgagtgcatt tgctttataa gtgagggtag     11880
ggtgagggag gacaggccag taggggagg gaaagggaga ggggaagggc aggggactca     11940
ggaagcaggg ggtccccatc cccagctggg aagaacatgc tatccaatct catctcttgt    12000
aaatacatgt ccccctgtga gttctgggct gatttgggtc tctcataccct ctgggaaaca   12060 gaccttttc tctcttactg cttcatgtaa ttttgtatca cctcttcaca atttagttcg     12120
tacctggctt gaagctgctc actgctcaca cgctgcctcc tcagcagcct cactgcatct    12180
ttctcttccc atgcaacacc ctcttctagt taccacggca acccctgcag ctcctctgcc   12240
tttgtgctct gttcctgtcc agcagggtc tcccaacaag tgctcttcc accccaaagg     12300 ggcctctcct tttctccact gtcataatct cttccatct tacttgcct tctatacttt     12360 ctcacatgtg gctcccctg aattttgctt cctttgggag tcattctttt cgccaaggc     12420 tcacatgctc cttgcctctg ctctgtgcac tcacgctcag cacacatgca tcctcccctc    12480
tcctgcgtgt gcccactgaa catgctcatg tgtacacacg cttttcccgt atgctttctt    12540
catgttcagt cacatgtgct ctcgggtgcc ctgcattcac agctacgtgt gcccctctca    12600
tggtcatggg tctgcccttg agcgtgtttg ggtaggcatg tgcaatttgt ctagcatgct    12660
gagtcatgtc tttcctattt gcacacgtcc atgtttatcc atgtactttc cctgtgtacc    12720
ctccatgtac cttgtgtact tcttcccctt aaatcatggt attcttctga cagagccata   12780
tgtaccctac cctgcacatt gttatgcact tttccccaat tcatgtttgg tggggccatc    12840
cacaccctct ccttgtcaca gaatctccat ttctgctcag attcccccca tctccattgc    12900
attcatgtac tacccctcagt ctacactcac aatcatcttc tcccaagact gctcccttt    12960 gttttgtgtt tttttgaggg gaattaagga aaaataagtg ggggcaggtt tggagagctg    13020
cttccagtgg atagttgatg agaatcctga ccaaaggaag gcacccttga ctgttgggat    13080
agacagatgg acctatgggg tgggaggtgg tgtccctttc acactgtggt gtctcttggg    13140
gaaggatctc cccgaatctc aataaaccag tgaacagtgt gactcgg                 13187
```

<210> SEQ ID NO 62
<211> LENGTH: 50
<212> TYPE: DNA

<213> ORGANISM: Rattus norvegicus

<400> SEQUENCE: 62
atgcgcgccg gcagccaaca tgctgctgct gctgctggtg cctctcttcc        50

<210> SEQ ID NO 63
<211> LENGTH: 25
<212> TYPE: DNA
<213> ORGANISM: Rattus norvegicus

<400> SEQUENCE: 63
ggtcatccag cgttgaggtg aagac        25

<210> SEQ ID NO 64
<211> LENGTH: 25
<212> TYPE: DNA
<213> ORGANISM: Rattus norvegicus

<400> SEQUENCE: 64
gaaggttgcc agattataca tccgc        25

<210> SEQ ID NO 65
<211> LENGTH: 25
<212> TYPE: DNA
<213> ORGANISM: Rattus norvegicus

<400> SEQUENCE: 65
ccacgatgat tcgagcatct tgacg        25

<210> SEQ ID NO 66
<211> LENGTH: 18
<212> TYPE: DNA
<213> ORGANISM: Homo sapiens

<400> SEQUENCE: 66
ctggttcctc ccaatgtg        18

<210> SEQ ID NO 67
<211> LENGTH: 21
<212> TYPE: DNA
<213> ORGANISM: Homo sapiens

<400> SEQUENCE: 67
ccagtggact atgagattga g        21

<210> SEQ ID NO 68
<211> LENGTH: 18
<212> TYPE: DNA
<213> ORGANISM: Homo sapiens

<400> SEQUENCE: 68
ctggttcctc ccaatgtg        18

<210> SEQ ID NO 69
<211> LENGTH: 21
<212> TYPE: DNA
<213> ORGANISM: Homo sapiens

<400> SEQUENCE: 69
ccagtggact atgagattga g        21

<210> SEQ ID NO 70
<211> LENGTH: 2700

```
<212> TYPE: DNA
<213> ORGANISM: Homo sapiens
<220> FEATURE:
<221> NAME/KEY: CDS
<222> LOCATION: (1)...(2697)

<400> SEQUENCE: 70
```

| | | | | | | | | | | | | | | | | |
|---|---|---|---|---|---|---|---|---|---|---|---|---|---|---|---|---|
| atg | ttg | ctg | ctg | ctg | cta | ctg | gcg | cca | ctc | ttc | ctc | cgc | ccc | ccg | ggc | 48 |
| Met | Leu | Leu | Leu | Leu | Leu | Leu | Ala | Pro | Leu | Phe | Leu | Arg | Pro | Pro | Gly | |
| 1 | | | | 5 | | | | | 10 | | | | | 15 | | |
| gcg | ggc | ggg | gcg | cag | acc | ccc | aac | gcc | acc | tca | gaa | ggt | tgc | cag | atc | 96 |
| Ala | Gly | Gly | Ala | Gln | Thr | Pro | Asn | Ala | Thr | Ser | Glu | Gly | Cys | Gln | Ile | |
| | | | 20 | | | | | 25 | | | | | 30 | | | |
| ata | cac | ccg | ccc | tgg | gaa | ggg | ggc | atc | agg | tac | cgg | ggc | ctg | act | cgg | 144 |
| Ile | His | Pro | Pro | Trp | Glu | Gly | Gly | Ile | Arg | Tyr | Arg | Gly | Leu | Thr | Arg | |
| | | 35 | | | | | 40 | | | | | 45 | | | | |
| gac | cag | gtg | aag | gct | atc | aac | ttc | ctg | cca | gtg | gac | tat | gag | att | gag | 192 |
| Asp | Gln | Val | Lys | Ala | Ile | Asn | Phe | Leu | Pro | Val | Asp | Tyr | Glu | Ile | Glu | |
| | 50 | | | | | 55 | | | | | 60 | | | | | |
| tat | gtg | tgc | cgg | ggg | gag | cgc | gag | gtg | gtg | ggg | ccc | aag | gtc | cgc | aag | 240 |
| Tyr | Val | Cys | Arg | Gly | Glu | Arg | Glu | Val | Val | Gly | Pro | Lys | Val | Arg | Lys | |
| 65 | | | | | 70 | | | | | 75 | | | | | 80 | |
| tgc | ctg | gcc | aac | ggc | tcc | tgg | aca | gat | atg | gac | aca | ccc | agc | cgc | tgt | 288 |
| Cys | Leu | Ala | Asn | Gly | Ser | Trp | Thr | Asp | Met | Asp | Thr | Pro | Ser | Arg | Cys | |
| | | | | 85 | | | | | 90 | | | | | 95 | | |
| gtg | aat | cga | acg | cca | cac | tca | gaa | cgg | cgc | gca | gtg | tac | atc | ggg | gca | 336 |
| Val | Asn | Arg | Thr | Pro | His | Ser | Glu | Arg | Arg | Ala | Val | Tyr | Ile | Gly | Ala | |
| | | | 100 | | | | | 105 | | | | | 110 | | | |
| ctg | ttt | ccc | atg | agc | ggg | ggc | tgg | cca | ggg | ggc | cag | gcc | tgc | cag | ccc | 384 |
| Leu | Phe | Pro | Met | Ser | Gly | Gly | Trp | Pro | Gly | Gly | Gln | Ala | Cys | Gln | Pro | |
| | | 115 | | | | | 120 | | | | | 125 | | | | |
| gcg | gtg | gag | atg | gcg | ctg | gag | gac | gtg | aat | agc | cgc | agg | gac | atc | ctg | 432 |
| Ala | Val | Glu | Met | Ala | Leu | Glu | Asp | Val | Asn | Ser | Arg | Arg | Asp | Ile | Leu | |
| | 130 | | | | | 135 | | | | | 140 | | | | | |
| ccg | gac | tat | gag | ctc | aag | ctc | atc | cac | cac | gac | agc | aag | tgt | gat | cca | 480 |
| Pro | Asp | Tyr | Glu | Leu | Lys | Leu | Ile | His | His | Asp | Ser | Lys | Cys | Asp | Pro | |
| 145 | | | | | 150 | | | | | 155 | | | | | 160 | |
| ggc | caa | gcc | acc | aag | tac | cta | tat | gag | ctg | ctc | tac | aac | gac | cct | atc | 528 |
| Gly | Gln | Ala | Thr | Lys | Tyr | Leu | Tyr | Glu | Leu | Leu | Tyr | Asn | Asp | Pro | Ile | |
| | | | | 165 | | | | | 170 | | | | | 175 | | |
| aag | atc | atc | ctt | atg | cct | ggc | tgc | agc | tct | gtc | tcc | acg | ctg | gtg | gct | 576 |
| Lys | Ile | Ile | Leu | Met | Pro | Gly | Cys | Ser | Ser | Val | Ser | Thr | Leu | Val | Ala | |
| | | | 180 | | | | | 185 | | | | | 190 | | | |
| gag | gct | gct | agg | atg | tgg | aac | ctc | att | gtg | ctt | tcc | tat | ggc | tcc | agc | 624 |
| Glu | Ala | Ala | Arg | Met | Trp | Asn | Leu | Ile | Val | Leu | Ser | Tyr | Gly | Ser | Ser | |
| | | 195 | | | | | 200 | | | | | 205 | | | | |
| tca | cca | gcc | ctg | tca | aac | cgg | cag | cgt | ttc | ccc | act | ttc | ttc | cga | acg | 672 |
| Ser | Pro | Ala | Leu | Ser | Asn | Arg | Gln | Arg | Phe | Pro | Thr | Phe | Phe | Arg | Thr | |
| | 210 | | | | | 215 | | | | | 220 | | | | | |
| cac | cca | tca | gcc | aca | ctc | cac | aac | cct | acc | cgc | gtg | aaa | ctc | ttt | gaa | 720 |
| His | Pro | Ser | Ala | Thr | Leu | His | Asn | Pro | Thr | Arg | Val | Lys | Leu | Phe | Glu | |
| 225 | | | | | 230 | | | | | 235 | | | | | 240 | |
| aag | tgg | ggc | tgg | aag | aag | att | gct | acc | atc | cag | cag | acc | act | gag | gtc | 768 |
| Lys | Trp | Gly | Trp | Lys | Lys | Ile | Ala | Thr | Ile | Gln | Gln | Thr | Thr | Glu | Val | |
| | | | | 245 | | | | | 250 | | | | | 255 | | |
| ttc | act | tcg | act | ctg | gac | gac | ctg | gag | gaa | cga | gtg | aag | gag | gct | gga | 816 |
| Phe | Thr | Ser | Thr | Leu | Asp | Asp | Leu | Glu | Glu | Arg | Val | Lys | Glu | Ala | Gly | |
| | | | 260 | | | | | 265 | | | | | 270 | | | |
| att | gag | att | act | ttc | cgc | cag | agt | ttc | ttc | tca | gat | cca | gct | gtg | ccc | 864 |
| Ile | Glu | Ile | Thr | Phe | Arg | Gln | Ser | Phe | Phe | Ser | Asp | Pro | Ala | Val | Pro | |
| | | 275 | | | | | 280 | | | | | 285 | | | | |

```
gtc aaa aac ctg aag cgc cag gat gcc cga atc atc gtg gga ctt ttc    912
Val Lys Asn Leu Lys Arg Gln Asp Ala Arg Ile Ile Val Gly Leu Phe
290                 295                 300 tat gag act gaa gcc cgg aaa gtt ttt tgt gag gtg tac aag gag cgt    960
Tyr Glu Thr Glu Ala Arg Lys Val Phe Cys Glu Val Tyr Lys Glu Arg
305                 310                 315                 320 ctc ttt ggg aag aag tac gtc tgg ttc ctc att ggg tgg tat gct gac   1008
Leu Phe Gly Lys Lys Tyr Val Trp Phe Leu Ile Gly Trp Tyr Ala Asp
                325                 330                 335 aat tgg ttc aag atc tac gac cct tct atc aac tgc aca gtg gat gag   1056
Asn Trp Phe Lys Ile Tyr Asp Pro Ser Ile Asn Cys Thr Val Asp Glu
        340                 345                 350 atg act gag gcg gtg gag ggc cac atc aca act gag att gtc atg ctg   1104
Met Thr Glu Ala Val Glu Gly His Ile Thr Thr Glu Ile Val Met Leu
355                 360                 365 aat cct gcc aat acc cgc agc att tcc aac atg aca tcc cag gaa ttt   1152
Asn Pro Ala Asn Thr Arg Ser Ile Ser Asn Met Thr Ser Gln Glu Phe
370                 375                 380 gtg gag aaa cta acc aag cga ctg aaa aga cac cct gag gag aca gga   1200
Val Glu Lys Leu Thr Lys Arg Leu Lys Arg His Pro Glu Glu Thr Gly
385                 390                 395                 400 ggc ttc cag gag gca ccg ctg gcc tat gat gcc atc tgg gcc ttg gca   1248
Gly Phe Gln Glu Ala Pro Leu Ala Tyr Asp Ala Ile Trp Ala Leu Ala
                405                 410                 415 ctg gcc ctg aac aag aca tct gga gga ggc ggc cgt tct ggt gtg cgc   1296
Leu Ala Leu Asn Lys Thr Ser Gly Gly Gly Gly Arg Ser Gly Val Arg
        420                 425                 430 ctg gag gac ttc aac tac aac aac cag acc att acc gac caa atc tac   1344
Leu Glu Asp Phe Asn Tyr Asn Asn Gln Thr Ile Thr Asp Gln Ile Tyr
                435                 440                 445 cgg gca atg aac tct tcg tcc ttt gag ggt gtc tct ggc cat gtg gtg   1392
Arg Ala Met Asn Ser Ser Ser Phe Glu Gly Val Ser Gly His Val Val
450                 455                 460 ttt gat gcc agc ggc tct cgg atg gca tgg acg ctt atc gag cag ctt   1440
Phe Asp Ala Ser Gly Ser Arg Met Ala Trp Thr Leu Ile Glu Gln Leu
465                 470                 475                 480 cag ggt ggc agc tac aag aag att ggc tac tat gac agc acc aag gat   1488
Gln Gly Gly Ser Tyr Lys Lys Ile Gly Tyr Tyr Asp Ser Thr Lys Asp
                485                 490                 495 gat ctt tcc tgg tcc aaa aca gat aaa tgg att gga ggg tcc ccc cca   1536
Asp Leu Ser Trp Ser Lys Thr Asp Lys Trp Ile Gly Gly Ser Pro Pro
        500                 505                 510 gct gac cag acc ctg gtc atc aag aca ttc cgc ttc ctg tca cag aaa   1584
Ala Asp Gln Thr Leu Val Ile Lys Thr Phe Arg Phe Leu Ser Gln Lys
            515                 520                 525 ctc ttt atc tcc gtc tca gtt ctc tcc agc ctg ggc att gtc cta gct   1632
Leu Phe Ile Ser Val Ser Val Leu Ser Ser Leu Gly Ile Val Leu Ala
530                 535                 540 gtt gtc tgt ctg tcc ttt aac atc tac aac tca cat gtc cgt tat atc   1680
Val Val Cys Leu Ser Phe Asn Ile Tyr Asn Ser His Val Arg Tyr Ile
545                 550                 555                 560 cag aac tca cag ccc aac ctg aac aac ctg act gct gtg ggc tgc tca   1728
Gln Asn Ser Gln Pro Asn Leu Asn Asn Leu Thr Ala Val Gly Cys Ser
                565                 570                 575 ctg gct tta gct gct gtc ttc ccc ctg ggg ctc gat ggt tac cac att   1776
Leu Ala Leu Ala Ala Val Phe Pro Leu Gly Leu Asp Gly Tyr His Ile
            580                 585                 590 ggg agg aac cag ttt cct ttc gtc tgc cag gcc cgc ctc tgg ctc ctg   1824
Gly Arg Asn Gln Phe Pro Phe Val Cys Gln Ala Arg Leu Trp Leu Leu
```

-continued

|  |  |  | 595 |  |  |  | 600 |  |  |  | 605 |  |  |  |  |
|---|---|---|---|---|---|---|---|---|---|---|---|---|---|---|---|
| ggc | ctg | ggc | ttt | agt | ctg | ggc | tac | ggt | tcc | atg | ttc | acc | aag | att | tgg | 1872 |
| Gly | Leu | Gly | Phe | Ser | Leu | Gly | Tyr | Gly | Ser | Met | Phe | Thr | Lys | Ile | Trp |
|  | 610 |  |  |  | 615 |  |  |  | 620 |  |  |  |

```
ggc ctg ggc ttt agt ctg ggc tac ggt tcc atg ttc acc aag att tgg      1872
Gly Leu Gly Phe Ser Leu Gly Tyr Gly Ser Met Phe Thr Lys Ile Trp
    610                 615                 620 tgg gtc cac acg gtc ttc aca aag aag gaa gaa aag aag gag tgg agg      1920
Trp Val His Thr Val Phe Thr Lys Lys Glu Glu Lys Lys Glu Trp Arg
625                 630                 635                 640 aag act ctg gaa ccc tgg aag ctg tat gcc aca gtg ggc ctg ctg gtg      1968
Lys Thr Leu Glu Pro Trp Lys Leu Tyr Ala Thr Val Gly Leu Leu Val
                645                 650                 655 ggc atg gat gtc ctc act ctc gcc atc tgg cag atc gtg gac cct ctg      2016
Gly Met Asp Val Leu Thr Leu Ala Ile Trp Gln Ile Val Asp Pro Leu
            660                 665                 670 cac cgg acc att gag aca ttt gcc aag gag gaa cct aag gaa gat att      2064
His Arg Thr Ile Glu Thr Phe Ala Lys Glu Glu Pro Lys Glu Asp Ile
        675                 680                 685 gac gtc tct att ctg ccc cag ctg gag cat tgc agc tcc agg aag atg      2112
Asp Val Ser Ile Leu Pro Gln Leu Glu His Cys Ser Ser Arg Lys Met
    690                 695                 700 aat aca tgg ctt ggc att ttc tat ggt tac aag ggg ctg ctg ctg ctg      2160
Asn Thr Trp Leu Gly Ile Phe Tyr Gly Tyr Lys Gly Leu Leu Leu Leu
705                 710                 715                 720 ctg gga atc ttc ctt gct tat gag acc aag agt gtg tcc act gag aag      2208
Leu Gly Ile Phe Leu Ala Tyr Glu Thr Lys Ser Val Ser Thr Glu Lys
                725                 730                 735 atc aat gat cac cgg gct gtg ggc atg gct atc tac aat gtg gca gtc      2256
Ile Asn Asp His Arg Ala Val Gly Met Ala Ile Tyr Asn Val Ala Val
            740                 745                 750 ctg tgc ctc atc act gct cct gtc acc atg att ctg tcc agc cag cag      2304
Leu Cys Leu Ile Thr Ala Pro Val Thr Met Ile Leu Ser Ser Gln Gln
        755                 760                 765 gat gca gcc ttt gcc ttt gcc tct ctt gcc ata gtt ttc tcc tcc tat      2352
Asp Ala Ala Phe Ala Phe Ala Ser Leu Ala Ile Val Phe Ser Ser Tyr
    770                 775                 780 atc act ctt gtt gtg ctc ttt gtg ccc aag atg cgc agg ctg atc acc      2400
Ile Thr Leu Val Val Leu Phe Val Pro Lys Met Arg Arg Leu Ile Thr
785                 790                 795                 800 cga ggg gaa tgg cag tcg gag gcg cag gac acc atg aag aca ggg tca      2448
Arg Gly Glu Trp Gln Ser Glu Ala Gln Asp Thr Met Lys Thr Gly Ser
                805                 810                 815 tcg acc aac aac aac gag gag gag aag tcc cgg ctg ttg gag aag gag      2496
Ser Thr Asn Asn Asn Glu Glu Glu Lys Ser Arg Leu Leu Glu Lys Glu
            820                 825                 830 aac cgt gaa ctg gaa aag atc att gct gag aaa gag gag cgt gtc tct      2544
Asn Arg Glu Leu Glu Lys Ile Ile Ala Glu Lys Glu Glu Arg Val Ser
        835                 840                 845 gaa ctg cgc cat caa ctc cag tct cgg cag cag ctc cgc tcc cgg cgc      2592
Glu Leu Arg His Gln Leu Gln Ser Arg Gln Gln Leu Arg Ser Arg Arg
    850                 855                 860 cac cca ccg aca ccc cca gaa ccc tct ggg ggc ctg ccc agg gga ccc      2640
His Pro Pro Thr Pro Pro Glu Pro Ser Gly Gly Leu Pro Arg Gly Pro
865                 870                 875                 880 cct gag ccc ccc gac cgg ctt agc tgt gat ggg agt cga gtg cat ttg      2688
Pro Glu Pro Pro Asp Arg Leu Ser Cys Asp Gly Ser Arg Val His Leu
                885                 890                 895 ctt tat aag tga                                                      2700
Leu Tyr Lys
```

<210> SEQ ID NO 71

<211> LENGTH: 899
<212> TYPE: PRT
<213> ORGANISM: Homo sapiens

<400> SEQUENCE: 71

```
Met Leu Leu Leu Leu Leu Ala Pro Leu Phe Leu Arg Pro Pro Gly
 1               5                  10                  15

Ala Gly Gly Ala Gln Thr Pro Asn Ala Thr Ser Glu Gly Cys Gln Ile
             20                  25                  30

Ile His Pro Pro Trp Glu Gly Gly Ile Arg Tyr Arg Gly Leu Thr Arg
             35                  40                  45

Asp Gln Val Lys Ala Ile Asn Phe Leu Pro Val Asp Tyr Glu Ile Glu
         50                  55                  60

Tyr Val Cys Arg Gly Glu Arg Glu Val Val Gly Pro Lys Val Arg Lys
 65                  70                  75                  80

Cys Leu Ala Asn Gly Ser Trp Thr Asp Met Asp Thr Pro Ser Arg Cys
                 85                  90                  95

Val Asn Arg Thr Pro His Ser Glu Arg Arg Ala Val Tyr Ile Gly Ala
            100                 105                 110

Leu Phe Pro Met Ser Gly Gly Trp Pro Gly Gly Gln Ala Cys Gln Pro
            115                 120                 125

Ala Val Glu Met Ala Leu Glu Asp Val Asn Ser Arg Arg Asp Ile Leu
        130                 135                 140

Pro Asp Tyr Glu Leu Lys Leu Ile His His Asp Ser Lys Cys Asp Pro
145                 150                 155                 160

Gly Gln Ala Thr Lys Tyr Leu Tyr Glu Leu Leu Tyr Asn Asp Pro Ile
                165                 170                 175

Lys Ile Ile Leu Met Pro Gly Cys Ser Ser Val Ser Thr Leu Val Ala
            180                 185                 190

Glu Ala Ala Arg Met Trp Asn Leu Ile Val Leu Ser Tyr Gly Ser Ser
        195                 200                 205

Ser Pro Ala Leu Ser Asn Arg Gln Arg Phe Pro Thr Phe Phe Arg Thr
    210                 215                 220

His Pro Ser Ala Thr Leu His Asn Pro Thr Arg Val Lys Leu Phe Glu
225                 230                 235                 240

Lys Trp Gly Trp Lys Lys Ile Ala Thr Ile Gln Gln Thr Thr Glu Val
                245                 250                 255

Phe Thr Ser Thr Leu Asp Asp Leu Glu Glu Arg Val Lys Glu Ala Gly
            260                 265                 270

Ile Glu Ile Thr Phe Arg Gln Ser Phe Phe Ser Asp Pro Ala Val Pro
        275                 280                 285

Val Lys Asn Leu Lys Arg Gln Asp Ala Arg Ile Ile Val Gly Leu Phe
    290                 295                 300

Tyr Glu Thr Glu Ala Arg Lys Val Phe Cys Glu Val Tyr Lys Glu Arg
305                 310                 315                 320

Leu Phe Gly Lys Lys Tyr Val Trp Phe Leu Ile Gly Trp Tyr Ala Asp
                325                 330                 335

Asn Trp Phe Lys Ile Tyr Asp Pro Ser Ile Asn Cys Thr Val Asp Glu
            340                 345                 350

Met Thr Glu Ala Val Glu Gly His Ile Thr Thr Glu Ile Val Met Leu
        355                 360                 365

Asn Pro Ala Asn Thr Arg Ser Ile Ser Asn Met Thr Ser Gln Glu Phe
    370                 375                 380

Val Glu Lys Leu Thr Lys Arg Leu Lys Arg His Pro Glu Glu Thr Gly
```

```
385                 390                 395                 400
Gly Phe Gln Glu Ala Pro Leu Ala Tyr Asp Ile Trp Ala Leu Ala
                405                 410                 415
Leu Ala Leu Asn Lys Thr Ser Gly Gly Gly Arg Ser Gly Val Arg
                420                 425                 430
Leu Glu Asp Phe Asn Tyr Asn Gln Thr Ile Thr Asp Gln Ile Tyr
                435                 440                 445
Arg Ala Met Asn Ser Ser Phe Glu Gly Val Ser Gly His Val Val
        450                 455                 460
Phe Asp Ala Ser Gly Ser Arg Met Ala Trp Thr Leu Ile Glu Gln Leu
465                 470                 475                 480
Gln Gly Gly Ser Tyr Lys Lys Ile Gly Tyr Tyr Asp Ser Thr Lys Asp
                485                 490                 495
Asp Leu Ser Trp Ser Lys Thr Asp Lys Trp Ile Gly Gly Ser Pro Pro
                500                 505                 510
Ala Asp Gln Thr Leu Val Ile Lys Thr Phe Arg Phe Leu Ser Gln Lys
                515                 520                 525
Leu Phe Ile Ser Val Ser Val Leu Ser Ser Leu Gly Ile Val Leu Ala
        530                 535                 540
Val Val Cys Leu Ser Phe Asn Ile Tyr Asn Ser His Val Arg Tyr Ile
545                 550                 555                 560
Gln Asn Ser Gln Pro Asn Leu Asn Asn Leu Thr Ala Val Gly Cys Ser
                565                 570                 575
Leu Ala Leu Ala Ala Val Phe Pro Leu Gly Leu Asp Gly Tyr His Ile
                580                 585                 590
Gly Arg Asn Gln Phe Pro Phe Val Cys Gln Ala Arg Leu Trp Leu Leu
                595                 600                 605
Gly Leu Gly Phe Ser Leu Gly Tyr Gly Ser Met Phe Thr Lys Ile Trp
        610                 615                 620
Trp Val His Thr Val Phe Thr Lys Lys Glu Lys Lys Glu Trp Arg
625                 630                 635                 640
Lys Thr Leu Glu Pro Trp Lys Leu Tyr Ala Thr Val Gly Leu Leu Val
                645                 650                 655
Gly Met Asp Val Leu Thr Leu Ala Ile Trp Gln Ile Val Asp Pro Leu
                660                 665                 670
His Arg Thr Ile Glu Thr Phe Ala Lys Glu Glu Pro Lys Glu Asp Ile
        675                 680                 685
Asp Val Ser Ile Leu Pro Gln Leu Glu His Cys Ser Ser Arg Lys Met
        690                 695                 700
Asn Thr Trp Leu Gly Ile Phe Tyr Gly Tyr Lys Gly Leu Leu Leu Leu
705                 710                 715                 720
Leu Gly Ile Phe Leu Ala Tyr Glu Thr Lys Ser Val Ser Thr Glu Lys
                725                 730                 735
Ile Asn Asp His Arg Ala Val Gly Met Ala Ile Tyr Asn Val Ala Val
                740                 745                 750
Leu Cys Leu Ile Thr Ala Pro Val Thr Met Ile Leu Ser Ser Gln Gln
                755                 760                 765
Asp Ala Ala Phe Ala Phe Ala Ser Leu Ala Ile Val Phe Ser Ser Tyr
        770                 775                 780
Ile Thr Leu Val Val Leu Phe Val Pro Lys Met Arg Arg Leu Ile Thr
785                 790                 795                 800
Arg Gly Glu Trp Gln Ser Glu Ala Gln Asp Thr Met Lys Thr Gly Ser
                805                 810                 815
```

Ser Thr Asn Asn Asn Glu Glu Glu Lys Ser Arg Leu Leu Glu Lys Glu
         820                 825                 830

Asn Arg Glu Leu Glu Lys Ile Ile Ala Glu Lys Glu Glu Arg Val Ser
         835                 840                 845

Glu Leu Arg His Gln Leu Gln Ser Arg Gln Gln Leu Arg Ser Arg Arg
         850                 855                 860

His Pro Pro Thr Pro Pro Glu Pro Ser Gly Gly Leu Pro Arg Gly Pro
865                 870                 875                 880

Pro Glu Pro Pro Asp Arg Leu Ser Cys Asp Gly Ser Arg Val His Leu
             885                 890                 895

Leu Tyr Lys

<210> SEQ ID NO 72
<211> LENGTH: 2518
<212> TYPE: DNA
<213> ORGANISM: Homo sapiens
<220> FEATURE:
<221> NAME/KEY: CDS
<222> LOCATION: (1)...(291)

<400> SEQUENCE: 72

| | | |
|---|---|---|
| atg ttg ctg ctg ctg cta ctg gcg cca ctc ttc ctc cgc ccc ccg ggc<br>Met Leu Leu Leu Leu Leu Leu Ala Pro Leu Phe Leu Arg Pro Pro Gly<br>1               5                   10                  15 | | 48 |
| gcg ggc ggg gcg cag acc ccc aac gcc acc tca gaa ggt tgc cag atc<br>Ala Gly Gly Ala Gln Thr Pro Asn Ala Thr Ser Glu Gly Cys Gln Ile<br>            20                  25                  30 | | 96 |
| ata cac ccg ccc tgg gaa ggg ggc atc agg tac cgg ggc ctg act cgg<br>Ile His Pro Pro Trp Glu Gly Gly Ile Arg Tyr Arg Gly Leu Thr Arg<br>        35                  40                  45 | | 144 |
| gac cag gtg aag gct atc aac ttc ctg cca gtg gac tat gag att gag<br>Asp Gln Val Lys Ala Ile Asn Phe Leu Pro Val Asp Tyr Glu Ile Glu<br>    50                  55                  60 | | 192 |
| tat gtg tgc cgg ggg gag cgc gag gtg gtg ggg ccc aag gtc cgc aag<br>Tyr Val Cys Arg Gly Glu Arg Glu Val Val Gly Pro Lys Val Arg Lys<br>65                  70                  75                  80 | | 240 |
| tgc ctg gcc aac ggc tcc tgg aca gat atg gac aca ccc agc cgc tgt<br>Cys Leu Ala Asn Gly Ser Trp Thr Asp Met Asp Thr Pro Ser Arg Cys<br>                85                  90                  95 | | 288 |
| gtg tgatccaggc caagccacca agtacctata tgagctgctc tacaacgacc<br>Val | | 341 |
| ctatcaagat catccttatg cctggctgca gctctgtctc cacgctggtg gctgaggctg | | 401 |
| ctaggatgtg gaacctcatt gtgctttcct atggctccag ctcaccagcc ctgtcaaacc | | 461 |
| ggcagcgttt ccccactttc ttccgaacgc acccatcagc cacactccac aaccctaccc | | 521 |
| gcgtgaaact ctttgaaaag tggggctgga agaagattgc taccatccag cagaccactg | | 581 |
| aggtcttcac ttcgactctg gacgacctgg aggaacgagt gaaggaggct ggaattgaga | | 641 |
| ttacttttcg ccagagtttc ttctcagatc cagctgtgcc cgtcaaaaac ctgaagcgcc | | 701 |
| aggatgcccg aatcatcgtg ggactttttct atgagactga agcccggaaa gttttttgtg | | 761 |
| aggtgtacaa ggagcgtctc tttgggaaga gtacgtctg gttcctcatt ggtggtatg | | 821 |
| ctgacaattg gttcaagatc tacgaccctt ctatcaactg cacagtggat gagatgactg | | 881 |
| aggcggtgga gggccacatc acaactgaga ttgtcatgct gaatcctgcc aatacccgca | | 941 |
| gcatttccaa catgacatcc caggaatttg tggagaaact aaccaagcga ctgaaaagac | | 1001 |
| accctgagga gacaggaggc ttccaggagg caccgctggc ctatgatgcc atctgggcct | | 1061 |

```
tggcactggc cctgaacaag acatctggag gaggcggccg ttctggtgtg cgcctggagg   1121
acttcaacta caacaaccag accattaccg accaaatcta ccgggcaatg aactcttcgt   1181
cctttgaggg tgtctctggc catgtggtgt ttgatgccag cggctctcgg atggcatgga   1241
cgcttatcga gcagcttcag ggtggcagct acaagaagat tggctactat gacagcacca   1301
aggatgatct ttcctggtcc aaaacagata aatggattgg agggtccccc ccagctgacc   1361
agaccctggt catcaagaca ttccgcttcc tgtcacagaa actctttatc tccgtctcag   1421
ttctctccag cctgggcatt gtcctagctg ttgtctgtct gtcctttaac atctacaact   1481
cacatgtccg ttatatccag aactcacagc ccaacctgaa caacctgact gctgtgggct   1541
gctcactggc tttagctgct gtcttccccc tggggctcga tggttaccac attgggagga   1601
accagtttcc tttcgtctgc caggcccgcc tctggctcct gggcctgggc tttagtctgg   1661
gctacggttc catgttcacc aagatttggt gggtccacac ggtcttcaca agaaggaag   1721 aaaagaagga gtggaggaag actctggaac cctggaagct gtatgccaca gtgggcctgc   1781
tggtgggcat ggatgtcctc actctcgcca tctggcagat cgtggaccct ctgcaccgga   1841
ccattgagac atttgccaag gaggaaccta aggaagatat tgacgtctct attctgcccc   1901
agctggagca ttgcagctcc aggaagatga atacatggct tggcatttc tatggttaca   1961 aggggctgct gctgctgctg ggaatcttcc ttgcttatga gaccaagagt gtgtccactg   2021
agaagatcaa tgatcaccgg gctgtgggca tggctatcta caatgtggca gtcctgtgcc   2081
tcatcactgc tcctgtcacc atgattctgt ccagccagca ggatgcagcc tttgcctttg   2141
cctctcttgc catagttttc tcctcctata tcactcttgt tgtgctcttt gtgcccaaga   2201
tgcgcaggct gatcacccga ggggaatggc agtcggaggc gcaggacacc atgaagacag   2261
ggtcatcgac caacaacaac gaggaggaga gtcccggct gttggagaag gagaaccgtg   2321
aactggaaaa gatcattgct gagaagagg agcgtgtctc tgaactgcgc catcaactcc   2381
agtctcggca gcagctccgc tcccggcgcc acccaccgac accccagaa ccctctgggg   2441 gcctgcccag ggaccccct gagccccccg accggcttag ctgtgatggg agtcgagtgc   2501
atttgcttta taagtga                                                  2518
```

<210> SEQ ID NO 73
<211> LENGTH: 97
<212> TYPE: PRT
<213> ORGANISM: Homo sapiens

<400> SEQUENCE: 73

```
Met Leu Leu Leu Leu Leu Ala Pro Leu Phe Leu Arg Pro Pro Gly
 1               5                  10                  15

Ala Gly Gly Ala Gln Thr Pro Asn Ala Thr Ser Glu Gly Cys Gln Ile
            20                  25                  30

Ile His Pro Pro Trp Glu Gly Ile Arg Tyr Arg Gly Leu Thr Arg
            35                  40                  45

Asp Gln Val Lys Ala Ile Asn Phe Leu Pro Val Asp Tyr Glu Ile Glu
     50                  55                  60

Tyr Val Cys Arg Gly Glu Arg Glu Val Val Gly Pro Lys Val Arg Lys
 65                  70                  75                  80

Cys Leu Ala Asn Gly Ser Trp Thr Asp Met Asp Thr Pro Ser Arg Cys
                 85                  90                  95

Val
```

<210> SEQ ID NO 74
<211> LENGTH: 2679
<212> TYPE: DNA
<213> ORGANISM: Homo sapiens
<220> FEATURE:
<221> NAME/KEY: CDS
<222> LOCATION: (1)...(2676)

<400> SEQUENCE: 74

| | | | | | | | | | | | | | | | | |
|---|---|---|---|---|---|---|---|---|---|---|---|---|---|---|---|---|
| atg | ttg | ctg | ctg | ctg | cta | ctg | gcg | cca | ctc | ttc | ctc | cgc | ccc | ccg | ggc | 48 |
| Met | Leu | Leu | Leu | Leu | Leu | Leu | Ala | Pro | Leu | Phe | Leu | Arg | Pro | Pro | Gly | |
| 1 | | | | 5 | | | | | 10 | | | | | 15 | | |
| gcg | ggc | ggg | gcg | cag | acc | ccc | aac | gcc | acc | tca | gaa | ggt | tgc | cag | atc | 96 |
| Ala | Gly | Gly | Ala | Gln | Thr | Pro | Asn | Ala | Thr | Ser | Glu | Gly | Cys | Gln | Ile | |
| | | | 20 | | | | | 25 | | | | | 30 | | | |
| ata | cac | ccg | ccc | tgg | gaa | ggg | ggc | atc | agg | tac | cgg | ggc | ctg | act | cgg | 144 |
| Ile | His | Pro | Pro | Trp | Glu | Gly | Gly | Ile | Arg | Tyr | Arg | Gly | Leu | Thr | Arg | |
| | 35 | | | | | 40 | | | | | 45 | | | | | |
| gac | cag | gtg | aag | gct | atc | aac | ttc | ctg | cca | gtg | gac | tat | gag | att | gag | 192 |
| Asp | Gln | Val | Lys | Ala | Ile | Asn | Phe | Leu | Pro | Val | Asp | Tyr | Glu | Ile | Glu | |
| 50 | | | | | 55 | | | | | 60 | | | | | | |
| tat | gtg | tgc | cgg | ggg | gag | cgc | gag | gtg | gtg | ggg | ccc | aag | gtc | cgc | aag | 240 |
| Tyr | Val | Cys | Arg | Gly | Glu | Arg | Glu | Val | Val | Gly | Pro | Lys | Val | Arg | Lys | |
| 65 | | | | | 70 | | | | | 75 | | | | | 80 | |
| tgc | ctg | gcc | aac | ggc | tcc | tgg | aca | gat | atg | gac | aca | ccc | agc | cgc | tgt | 288 |
| Cys | Leu | Ala | Asn | Gly | Ser | Trp | Thr | Asp | Met | Asp | Thr | Pro | Ser | Arg | Cys | |
| | | | | 85 | | | | | 90 | | | | | 95 | | |
| gaa | cgg | cgc | gca | gtg | tac | atc | ggg | gca | ctg | ttt | ccc | atg | agc | ggg | ggc | 336 |
| Glu | Arg | Arg | Ala | Val | Tyr | Ile | Gly | Ala | Leu | Phe | Pro | Met | Ser | Gly | Gly | |
| | | | 100 | | | | | 105 | | | | | 110 | | | |
| tgg | cca | ggg | ggc | cag | gcc | tgc | cag | ccc | gcg | gtg | gag | atg | gcg | ctg | gag | 384 |
| Trp | Pro | Gly | Gly | Gln | Ala | Cys | Gln | Pro | Ala | Val | Glu | Met | Ala | Leu | Glu | |
| | | | | 115 | | | | | 120 | | | | | 125 | | |
| gac | gtg | aat | agc | cgc | agg | gac | atc | ctg | ccg | gac | tat | gag | ctc | aag | ctc | 432 |
| Asp | Val | Asn | Ser | Arg | Arg | Asp | Ile | Leu | Pro | Asp | Tyr | Glu | Leu | Lys | Leu | |
| | 130 | | | | | 135 | | | | | 140 | | | | | |
| atc | cac | cac | gac | agc | aag | tgt | gat | cca | ggc | caa | gcc | acc | aag | tac | cta | 480 |
| Ile | His | His | Asp | Ser | Lys | Cys | Asp | Pro | Gly | Gln | Ala | Thr | Lys | Tyr | Leu | |
| 145 | | | | | 150 | | | | | 155 | | | | | 160 | |
| tat | gag | ctg | ctc | tac | aac | gac | cct | atc | aag | atc | atc | ctt | atg | cct | ggc | 528 |
| Tyr | Glu | Leu | Leu | Tyr | Asn | Asp | Pro | Ile | Lys | Ile | Ile | Leu | Met | Pro | Gly | |
| | | | | | 165 | | | | | 170 | | | | | 175 | |
| tgc | agc | tct | gtc | tcc | acg | ctg | gtg | gct | gag | gct | gct | agg | atg | tgg | aac | 576 |
| Cys | Ser | Ser | Val | Ser | Thr | Leu | Val | Ala | Glu | Ala | Ala | Arg | Met | Trp | Asn | |
| | | | 180 | | | | | 185 | | | | | 190 | | | |
| ctc | att | gtg | ctt | tcc | tat | ggc | tcc | agc | tca | cca | gcc | ctg | tca | aac | cgg | 624 |
| Leu | Ile | Val | Leu | Ser | Tyr | Gly | Ser | Ser | Ser | Pro | Ala | Leu | Ser | Asn | Arg | |
| | | | | 195 | | | | | 200 | | | | | 205 | | |
| cag | cgt | ttc | ccc | act | ttc | ttc | cga | acg | cac | cca | tca | gcc | aca | ctc | cac | 672 |
| Gln | Arg | Phe | Pro | Thr | Phe | Phe | Arg | Thr | His | Pro | Ser | Ala | Thr | Leu | His | |
| | 210 | | | | | 215 | | | | | 220 | | | | | |
| aac | cct | acc | cgc | gtg | aaa | ctc | ttt | gaa | aag | tgg | ggc | tgg | aag | aag | att | 720 |
| Asn | Pro | Thr | Arg | Val | Lys | Leu | Phe | Glu | Lys | Trp | Gly | Trp | Lys | Lys | Ile | |
| 225 | | | | | 230 | | | | | 235 | | | | | 240 | |
| gct | acc | atc | cag | cag | acc | act | gag | gtc | ttc | act | tcg | act | ctg | gac | gac | 768 |
| Ala | Thr | Ile | Gln | Gln | Thr | Thr | Glu | Val | Phe | Thr | Ser | Thr | Leu | Asp | Asp | |
| | | | | | 245 | | | | | 250 | | | | | 255 | |
| ctg | gag | gaa | cga | gtg | aag | gag | gct | gga | att | gag | att | act | ttc | cgc | cag | 816 |
| Leu | Glu | Glu | Arg | Val | Lys | Glu | Ala | Gly | Ile | Glu | Ile | Thr | Phe | Arg | Gln | |
| | | | 260 | | | | | 265 | | | | | 270 | | | |

| | | |
|---|---|---|
| agt ttc ttc tca gat cca gct gtg ccc gtc aaa aac ctg aag cgc cag<br>Ser Phe Phe Ser Asp Pro Ala Val Pro Val Lys Asn Leu Lys Arg Gln<br>275 280 285 | 864 | |
| gat gcc cga atc atc gtg gga ctt ttc tat gag act gaa gcc cgg aaa<br>Asp Ala Arg Ile Ile Val Gly Leu Phe Tyr Glu Thr Glu Ala Arg Lys<br>290 295 300 | 912 | |
| gtt ttt tgt gag gtg tac aag gag cgt ctc ttt ggg aag aag tac gtc<br>Val Phe Cys Glu Val Tyr Lys Glu Arg Leu Phe Gly Lys Lys Tyr Val<br>305 310 315 320 | 960 | |
| tgg ttc ctc att ggg tgg tat gct gac aat tgg ttc aag atc tac gac<br>Trp Phe Leu Ile Gly Trp Tyr Ala Asp Asn Trp Phe Lys Ile Tyr Asp<br>325 330 335 | 1008 | |
| cct tct atc aac tgc aca gtg gat gag atg act gag gcg gtg gag ggc<br>Pro Ser Ile Asn Cys Thr Val Asp Glu Met Thr Glu Ala Val Glu Gly<br>340 345 350 | 1056 | |
| cac atc aca act gag att gtc atg ctg aat cct gcc aat acc cgc agc<br>His Ile Thr Thr Glu Ile Val Met Leu Asn Pro Ala Asn Thr Arg Ser<br>355 360 365 | 1104 | |
| att tcc aac atg aca tcc cag gaa ttt gtg gag aaa cta acc aag cga<br>Ile Ser Asn Met Thr Ser Gln Glu Phe Val Glu Lys Leu Thr Lys Arg<br>370 375 380 | 1152 | |
| ctg aaa aga cac cct gag gag aca gga ggc ttc cag gag gca ccg ctg<br>Leu Lys Arg His Pro Glu Glu Thr Gly Gly Phe Gln Glu Ala Pro Leu<br>385 390 395 400 | 1200 | |
| gcc tat gat gcc atc tgg gcc ttg gca ctg gcc ctg aac aag aca tct<br>Ala Tyr Asp Ala Ile Trp Ala Leu Ala Leu Ala Leu Asn Lys Thr Ser<br>405 410 415 | 1248 | |
| gga gga ggc ggc cgt tct ggt gtg cgc ctg gag gac ttc aac tac aac<br>Gly Gly Gly Gly Arg Ser Gly Val Arg Leu Glu Asp Phe Asn Tyr Asn<br>420 425 430 | 1296 | |
| aac cag acc att acc gac caa atc tac cgg gca atg aac tct tcg tcc<br>Asn Gln Thr Ile Thr Asp Gln Ile Tyr Arg Ala Met Asn Ser Ser Ser<br>435 440 445 | 1344 | |
| ttt gag ggt gtc tct ggc cat gtg gtg ttt gat gcc agc ggc tct cgg<br>Phe Glu Gly Val Ser Gly His Val Val Phe Asp Ala Ser Gly Ser Arg<br>450 455 460 | 1392 | |
| atg gca tgg acg ctt atc gag cag ctt cag ggt ggc agc tac aag aag<br>Met Ala Trp Thr Leu Ile Glu Gln Leu Gln Gly Gly Ser Tyr Lys Lys<br>465 470 475 480 | 1440 | |
| att ggc tac tat gac agc acc aag gat gat ctt tcc tgg tcc aaa aca<br>Ile Gly Tyr Tyr Asp Ser Thr Lys Asp Asp Leu Ser Trp Ser Lys Thr<br>485 490 495 | 1488 | |
| gat aaa tgg att gga ggg tcc ccc cca gct gac cag acc ctg gtc atc<br>Asp Lys Trp Ile Gly Gly Ser Pro Pro Ala Asp Gln Thr Leu Val Ile<br>500 505 510 | 1536 | |
| aag aca ttc cgc ttc ctg tca cag aaa ctc ttt atc tcc gtc tca gtt<br>Lys Thr Phe Arg Phe Leu Ser Gln Lys Leu Phe Ile Ser Val Ser Val<br>515 520 525 | 1584 | |
| ctc tcc agc ctg ggc att gtc cta gct gtt gtc tgt ctg tcc ttt aac<br>Leu Ser Ser Leu Gly Ile Val Leu Ala Val Val Cys Leu Ser Phe Asn<br>530 535 540 | 1632 | |
| atc tac aac tca cat gtc cgt tat atc cag aac tca cag ccc aac ctg<br>Ile Tyr Asn Ser His Val Arg Tyr Ile Gln Asn Ser Gln Pro Asn Leu<br>545 550 555 560 | 1680 | |
| aac aac ctg act gct gtg ggc tgc tca ctg gct tta gct gct gtc ttc<br>Asn Asn Leu Thr Ala Val Gly Cys Ser Leu Ala Leu Ala Ala Val Phe<br>565 570 575 | 1728 | |
| ccc ctg ggg ctc gat ggt tac cac att ggg agg aac cag ttt cct ttc<br>Pro Leu Gly Leu Asp Gly Tyr His Ile Gly Arg Asn Gln Phe Pro Phe<br>580 585 590 | 1776 | |

```
gtc tgc cag gcc cgc ctc tgg ctc ctg ggc ctg ggc ttt agt ctg ggc      1824
Val Cys Gln Ala Arg Leu Trp Leu Leu Gly Leu Gly Phe Ser Leu Gly
    595                 600                 605 tac ggt tcc atg ttc acc aag att tgg tgg gtc cac acg gtc ttc aca      1872
Tyr Gly Ser Met Phe Thr Lys Ile Trp Trp Val His Thr Val Phe Thr
610                 615                 620 aag aag gaa gaa aag aag gag tgg agg aag act ctg gaa ccc tgg aag      1920
Lys Lys Glu Glu Lys Lys Glu Trp Arg Lys Thr Leu Glu Pro Trp Lys
625                 630                 635                 640 ctg tat gcc aca gtg ggc ctg ctg gtg ggc atg gat gtc ctc act ctc      1968
Leu Tyr Ala Thr Val Gly Leu Leu Val Gly Met Asp Val Leu Thr Leu
                645                 650                 655 gcc atc tgg cag atc gtg gac cct ctg cac cgg acc att gag aca ttt      2016
Ala Ile Trp Gln Ile Val Asp Pro Leu His Arg Thr Ile Glu Thr Phe
            660                 665                 670 gcc aag gag gaa cct aag gaa gat att gac gtc tct att ctg ccc cag      2064
Ala Lys Glu Glu Pro Lys Glu Asp Ile Asp Val Ser Ile Leu Pro Gln
        675                 680                 685 ctg gag cat tgc agc tcc agg aag atg aat aca tgg ctt ggc att ttc      2112
Leu Glu His Cys Ser Ser Arg Lys Met Asn Thr Trp Leu Gly Ile Phe
    690                 695                 700 tat ggt tac aag ggg ctg ctg ctg ctg gga atc ttc ctt gct tat           2160
Tyr Gly Tyr Lys Gly Leu Leu Leu Leu Gly Ile Phe Leu Ala Tyr
705                 710                 715                 720 gag acc aag agt gtg tcc act gag aag atc aat gat cac cgg gct gtg      2208
Glu Thr Lys Ser Val Ser Thr Glu Lys Ile Asn Asp His Arg Ala Val
                725                 730                 735 ggc atg gct atc tac aat gtg gca gtc ctg tgc ctc atc act gct cct      2256
Gly Met Ala Ile Tyr Asn Val Ala Val Leu Cys Leu Ile Thr Ala Pro
            740                 745                 750 gtc acc atg att ctg tcc agc cag cag gat gca gcc ttt gcc ttt gcc      2304
Val Thr Met Ile Leu Ser Ser Gln Gln Asp Ala Ala Phe Ala Phe Ala
        755                 760                 765 tct ctt gcc ata gtt ttc tcc tcc tat atc act ctt gtt gtg ctc ttt      2352
Ser Leu Ala Ile Val Phe Ser Ser Tyr Ile Thr Leu Val Val Leu Phe
    770                 775                 780 gtg ccc aag atg cgc agg ctg atc acc cga ggg gaa tgg cag tcg gag      2400
Val Pro Lys Met Arg Arg Leu Ile Thr Arg Gly Glu Trp Gln Ser Glu
785                 790                 795                 800 gcg cag gac acc atg aag aca ggg tca tcg acc aac aac aac gag gag      2448
Ala Gln Asp Thr Met Lys Thr Gly Ser Ser Thr Asn Asn Asn Glu Glu
                805                 810                 815 gag aag tcc cgg ctg ttg gag aag gag aac cgt gaa ctg gaa aag atc      2496
Glu Lys Ser Arg Leu Leu Glu Lys Glu Asn Arg Glu Leu Glu Lys Ile
            820                 825                 830 att gct gag aaa gag gag cgt gtc tct gaa ctg cgc cat caa ctc cag      2544
Ile Ala Glu Lys Glu Glu Arg Val Ser Glu Leu Arg His Gln Leu Gln
        835                 840                 845 tct cgg cag cag ctc cgc tcc cgg cgc cac cca ccg aca ccc cca gaa      2592
Ser Arg Gln Gln Leu Arg Ser Arg Arg His Pro Pro Thr Pro Pro Glu
    850                 855                 860 ccc tct ggg ggc ctg ccc agg gga ccc cct gag ccc ccc gac cgg ctt      2640
Pro Ser Gly Gly Leu Pro Arg Gly Pro Pro Glu Pro Pro Asp Arg Leu
865                 870                 875                 880 agc tgt gat ggg agt cga gtg cat ttg ctt tat aag tga                   2679
Ser Cys Asp Gly Ser Arg Val His Leu Leu Tyr Lys
                885                 890
```

<210> SEQ ID NO 75

```
<211> LENGTH: 892
<212> TYPE: PRT
<213> ORGANISM: Homo sapiens

<400> SEQUENCE: 75
```

| | | | | | | | | | | | | | | | |
|---|---|---|---|---|---|---|---|---|---|---|---|---|---|---|---|
| Met | Leu | Leu | Leu | Leu | Leu | Ala | Pro | Leu | Phe | Leu | Arg | Pro | Pro | Gly | |
| 1 | | | | 5 | | | | | 10 | | | | | 15 | |
| Ala | Gly | Gly | Ala | Gln | Thr | Pro | Asn | Ala | Thr | Ser | Glu | Gly | Cys | Gln | Ile |
| | | | 20 | | | | | 25 | | | | | 30 | | |
| Ile | His | Pro | Pro | Trp | Glu | Gly | Gly | Ile | Arg | Tyr | Arg | Gly | Leu | Thr | Arg |
| | | | 35 | | | | | 40 | | | | | 45 | | |
| Asp | Gln | Val | Lys | Ala | Ile | Asn | Phe | Leu | Pro | Val | Asp | Tyr | Glu | Ile | Glu |
| | 50 | | | | | 55 | | | | | 60 | | | | |
| Tyr | Val | Cys | Arg | Gly | Glu | Arg | Glu | Val | Val | Gly | Pro | Lys | Val | Arg | Lys |
| 65 | | | | | 70 | | | | | 75 | | | | | 80 |
| Cys | Leu | Ala | Asn | Gly | Ser | Trp | Thr | Asp | Met | Asp | Thr | Pro | Ser | Arg | Cys |
| | | | | 85 | | | | | 90 | | | | | 95 | |
| Glu | Arg | Arg | Ala | Val | Tyr | Ile | Gly | Ala | Leu | Phe | Pro | Met | Ser | Gly | Gly |
| | | | 100 | | | | | 105 | | | | | 110 | | |
| Trp | Pro | Gly | Gly | Gln | Ala | Cys | Gln | Pro | Ala | Val | Glu | Met | Ala | Leu | Glu |
| | | | 115 | | | | | 120 | | | | | 125 | | |
| Asp | Val | Asn | Ser | Arg | Arg | Asp | Ile | Leu | Pro | Asp | Tyr | Glu | Leu | Lys | Leu |
| | 130 | | | | | 135 | | | | | 140 | | | | |
| Ile | His | His | Asp | Ser | Lys | Cys | Asp | Pro | Gly | Gln | Ala | Thr | Lys | Tyr | Leu |
| 145 | | | | | 150 | | | | | 155 | | | | | 160 |
| Tyr | Glu | Leu | Leu | Tyr | Asn | Asp | Pro | Ile | Lys | Ile | Ile | Leu | Met | Pro | Gly |
| | | | | 165 | | | | | 170 | | | | | 175 | |
| Cys | Ser | Ser | Val | Ser | Thr | Leu | Val | Ala | Glu | Ala | Ala | Arg | Met | Trp | Asn |
| | | | 180 | | | | | 185 | | | | | 190 | | |
| Leu | Ile | Val | Leu | Ser | Tyr | Gly | Ser | Ser | Ser | Pro | Ala | Leu | Ser | Asn | Arg |
| | | | | 195 | | | | | 200 | | | | | 205 | |
| Gln | Arg | Phe | Pro | Thr | Phe | Phe | Arg | Thr | His | Pro | Ser | Ala | Thr | Leu | His |
| | 210 | | | | | 215 | | | | | 220 | | | | |
| Asn | Pro | Thr | Arg | Val | Lys | Leu | Phe | Glu | Lys | Trp | Gly | Trp | Lys | Lys | Ile |
| 225 | | | | | 230 | | | | | 235 | | | | | 240 |
| Ala | Thr | Ile | Gln | Gln | Thr | Thr | Glu | Val | Phe | Thr | Ser | Thr | Leu | Asp | Asp |
| | | | | 245 | | | | | 250 | | | | | 255 | |
| Leu | Glu | Glu | Arg | Val | Lys | Glu | Ala | Gly | Ile | Glu | Ile | Thr | Phe | Arg | Gln |
| | | | 260 | | | | | 265 | | | | | 270 | | |
| Ser | Phe | Phe | Ser | Asp | Pro | Ala | Val | Pro | Val | Lys | Asn | Leu | Lys | Arg | Gln |
| | | | | 275 | | | | | 280 | | | | | 285 | |
| Asp | Ala | Arg | Ile | Ile | Val | Gly | Leu | Phe | Tyr | Glu | Thr | Glu | Ala | Arg | Lys |
| | 290 | | | | | 295 | | | | | 300 | | | | |
| Val | Phe | Cys | Glu | Val | Tyr | Lys | Glu | Arg | Leu | Phe | Gly | Lys | Lys | Tyr | Val |
| 305 | | | | | 310 | | | | | 315 | | | | | 320 |
| Trp | Phe | Leu | Ile | Gly | Trp | Tyr | Ala | Asp | Asn | Trp | Phe | Lys | Ile | Tyr | Asp |
| | | | | 325 | | | | | 330 | | | | | 335 | |
| Pro | Ser | Ile | Asn | Cys | Thr | Val | Asp | Glu | Met | Thr | Glu | Ala | Val | Glu | Gly |
| | | | 340 | | | | | 345 | | | | | 350 | | |
| His | Ile | Thr | Thr | Glu | Ile | Val | Met | Leu | Asn | Pro | Ala | Asn | Thr | Arg | Ser |
| | | | | 355 | | | | | 360 | | | | | 365 | |
| Ile | Ser | Asn | Met | Thr | Ser | Gln | Glu | Phe | Val | Glu | Lys | Leu | Thr | Lys | Arg |
| | 370 | | | | | 375 | | | | | 380 | | | | |
| Leu | Lys | Arg | His | Pro | Glu | Glu | Thr | Gly | Gly | Phe | Gln | Glu | Ala | Pro | Leu |

```
                385                 390                 395                 400
Ala Tyr Asp Ala Ile Trp Ala Leu Ala Leu Ala Leu Asn Lys Thr Ser
                    405                 410                 415
Gly Gly Gly Gly Arg Ser Gly Val Arg Leu Glu Asp Phe Asn Tyr Asn
                    420                 425                 430
Asn Gln Thr Ile Thr Asp Gln Ile Tyr Arg Ala Met Asn Ser Ser Ser
                    435                 440                 445
Phe Glu Gly Val Ser Gly His Val Val Phe Asp Ala Ser Gly Ser Arg
                    450                 455                 460
Met Ala Trp Thr Leu Ile Glu Gln Leu Gln Gly Gly Ser Tyr Lys Lys
465                 470                 475                 480
Ile Gly Tyr Tyr Asp Ser Thr Lys Asp Asp Leu Ser Trp Ser Lys Thr
                    485                 490                 495
Asp Lys Trp Ile Gly Gly Ser Pro Pro Ala Asp Gln Thr Leu Val Ile
                    500                 505                 510
Lys Thr Phe Arg Phe Leu Ser Gln Lys Leu Phe Ile Ser Val Ser Val
                    515                 520                 525
Leu Ser Ser Leu Gly Ile Val Leu Ala Val Val Cys Leu Ser Phe Asn
                    530                 535                 540
Ile Tyr Asn Ser His Val Arg Tyr Ile Gln Asn Ser Gln Pro Asn Leu
545                 550                 555                 560
Asn Asn Leu Thr Ala Val Gly Cys Ser Leu Ala Leu Ala Ala Val Phe
                    565                 570                 575
Pro Leu Gly Leu Asp Gly Tyr His Ile Gly Arg Asn Gln Phe Pro Phe
                    580                 585                 590
Val Cys Gln Ala Arg Leu Trp Leu Leu Gly Leu Gly Phe Ser Leu Gly
                    595                 600                 605
Tyr Gly Ser Met Phe Thr Lys Ile Trp Trp Val His Thr Val Phe Thr
                    610                 615                 620
Lys Lys Glu Glu Lys Lys Glu Trp Arg Lys Thr Leu Glu Pro Trp Lys
625                 630                 635                 640
Leu Tyr Ala Thr Val Gly Leu Leu Val Gly Met Asp Val Leu Thr Leu
                    645                 650                 655
Ala Ile Trp Gln Ile Val Asp Pro Leu His Arg Thr Ile Glu Thr Phe
                    660                 665                 670
Ala Lys Glu Glu Pro Lys Glu Asp Ile Asp Val Ser Ile Leu Pro Gln
                    675                 680                 685
Leu Glu His Cys Ser Ser Arg Lys Met Asn Thr Trp Leu Gly Ile Phe
                    690                 695                 700
Tyr Gly Tyr Lys Gly Leu Leu Leu Leu Gly Ile Phe Leu Ala Tyr
705                 710                 715                 720
Glu Thr Lys Ser Val Ser Thr Glu Lys Ile Asn Asp His Arg Ala Val
                    725                 730                 735
Gly Met Ala Ile Tyr Asn Val Ala Val Leu Cys Leu Ile Thr Ala Pro
                    740                 745                 750
Val Thr Met Ile Leu Ser Ser Gln Gln Asp Ala Ala Phe Ala Phe Ala
                    755                 760                 765
Ser Leu Ala Ile Val Phe Ser Ser Tyr Ile Thr Leu Val Val Leu Phe
                    770                 775                 780
Val Pro Lys Met Arg Arg Leu Ile Thr Arg Gly Glu Trp Gln Ser Glu
785                 790                 795                 800
Ala Gln Asp Thr Met Lys Thr Gly Ser Ser Thr Asn Asn Asn Glu Glu
                    805                 810                 815
```

```
Glu Lys Ser Arg Leu Leu Glu Lys Glu Asn Arg Glu Leu Glu Lys Ile
            820                 825                 830

Ile Ala Glu Lys Glu Glu Arg Val Ser Glu Leu Arg His Gln Leu Gln
            835                 840                 845

Ser Arg Gln Gln Leu Arg Ser Arg Arg His Pro Thr Pro Pro Glu
            850                 855                 860

Pro Ser Gly Gly Leu Pro Arg Gly Pro Pro Glu Pro Pro Asp Arg Leu
865                 870                 875                 880

Ser Cys Asp Gly Ser Arg Val His Leu Leu Tyr Lys
                    885                 890

<210> SEQ ID NO 76
<211> LENGTH: 2661
<212> TYPE: DNA
<213> ORGANISM: Homo sapiens
<220> FEATURE:
<221> NAME/KEY: CDS
<222> LOCATION: (1)...(2658)

<400> SEQUENCE: 76 atg ttg ctg ctg ctg cta ctg gcg cca ctc ttc ctc cgc ccc ccg ggc     48
Met Leu Leu Leu Leu Leu Leu Ala Pro Leu Phe Leu Arg Pro Pro Gly
 1               5                  10                  15 gcg ggc ggg gcg cag acc ccc aac gcc acc tca gaa ggt tgc cag atc     96
Ala Gly Gly Ala Gln Thr Pro Asn Ala Thr Ser Glu Gly Cys Gln Ile
                20                  25                  30 ata cac ccg ccc tgg gaa ggg ggc atc agg tac cgg ggc ctg act cgg    144
Ile His Pro Pro Trp Glu Gly Gly Ile Arg Tyr Arg Gly Leu Thr Arg
            35                  40                  45 gac cag gtg aag gct atc aac ttc ctg cca gtg gac tat gag att gag    192
Asp Gln Val Lys Ala Ile Asn Phe Leu Pro Val Asp Tyr Glu Ile Glu
        50                  55                  60 tat gtg tgc cgg ggg gag cgc gag gtg gtg ggg ccc aag gtc cgc aag    240
Tyr Val Cys Arg Gly Glu Arg Glu Val Val Gly Pro Lys Val Arg Lys
 65                  70                  75                  80 tgc ctg gcc aac ggc tcc tgg aca gat atg gac aca ccc agc cgc tgt    288
Cys Leu Ala Asn Gly Ser Trp Thr Asp Met Asp Thr Pro Ser Arg Cys
                85                  90                  95 gtg aat cga acg cca cac tca gaa cgg cgc gca gtg tac atc ggg gca    336
Val Asn Arg Thr Pro His Ser Glu Arg Arg Ala Val Tyr Ile Gly Ala
                100                 105                 110 ctg ttt ccc gcg gtg gag atg gcg ctg gag gac gtg aat agc cgc agg    384
Leu Phe Pro Ala Val Glu Met Ala Leu Glu Asp Val Asn Ser Arg Arg
            115                 120                 125 gac atc ctg ccg gac tat gag ctc aag ctc atc cac cac gac agc aag    432
Asp Ile Leu Pro Asp Tyr Glu Leu Lys Leu Ile His His Asp Ser Lys
        130                 135                 140 tgt gat cca ggc caa gcc acc aag tac cta tat gag ctg ctc tac aac    480
Cys Asp Pro Gly Gln Ala Thr Lys Tyr Leu Tyr Glu Leu Leu Tyr Asn
145                 150                 155                 160 gac cct atc aag atc atc ctt atg cct ggc tgc agc tct gtc tcc acg    528
Asp Pro Ile Lys Ile Ile Leu Met Pro Gly Cys Ser Ser Val Ser Thr
                165                 170                 175 ctg gtg gct gag gct gct agg atg tgg aac ctc att gtg ctt tcc tat    576
Leu Val Ala Glu Ala Ala Arg Met Trp Asn Leu Ile Val Leu Ser Tyr
            180                 185                 190 ggc tcc agc tca cca gcc ctg tca aac cgg cag cgt ttc ccc act ttc    624
Gly Ser Ser Ser Pro Ala Leu Ser Asn Arg Gln Arg Phe Pro Thr Phe
        195                 200                 205
```

-continued

```
ttc cga acg cac cca tca gcc aca ctc cac aac cct acc cgc gtg aaa     672
Phe Arg Thr His Pro Ser Ala Thr Leu His Asn Pro Thr Arg Val Lys
    210             215                 220 ctc ttt gaa aag tgg ggc tgg aag aag att gct acc atc cag cag acc     720
Leu Phe Glu Lys Trp Gly Trp Lys Lys Ile Ala Thr Ile Gln Gln Thr
225             230                 235                 240 act gag gtc ttc act tcg act ctg gac gac ctg gag gaa cga gtg aag     768
Thr Glu Val Phe Thr Ser Thr Leu Asp Asp Leu Glu Glu Arg Val Lys
                245                 250                 255 gag gct gga att gag att act ttc cgc cag agt ttc ttc tca gat cca     816
Glu Ala Gly Ile Glu Ile Thr Phe Arg Gln Ser Phe Phe Ser Asp Pro
            260                 265                 270 gct gtg ccc gtc aaa aac ctg aag cgc cag gat gcc cga atc atc gtg     864
Ala Val Pro Val Lys Asn Leu Lys Arg Gln Asp Ala Arg Ile Ile Val
        275                 280                 285 gga ctt ttc tat gag act gaa gcc cgg aaa gtt ttt tgt gag gtg tac     912
Gly Leu Phe Tyr Glu Thr Glu Ala Arg Lys Val Phe Cys Glu Val Tyr
    290                 295                 300 aag gag cgt ctc ttt ggg aag aag tac gtc tgg ttc ctc att ggg tgg     960
Lys Glu Arg Leu Phe Gly Lys Lys Tyr Val Trp Phe Leu Ile Gly Trp
305             310                 315                 320 tat gct gac aat tgg ttc aag atc tac gac cct tct atc aac tgc aca    1008
Tyr Ala Asp Asn Trp Phe Lys Ile Tyr Asp Pro Ser Ile Asn Cys Thr
                325                 330                 335 gtg gat gag atg act gag gcg gtg gag ggc cac atc aca act gag att    1056
Val Asp Glu Met Thr Glu Ala Val Glu Gly His Ile Thr Thr Glu Ile
                340                 345                 350 gtc atg ctg aat cct gcc aat acc cgc agc att tcc aac atg aca tcc    1104
Val Met Leu Asn Pro Ala Asn Thr Arg Ser Ile Ser Asn Met Thr Ser
            355                 360                 365 cag gaa ttt gtg gag aaa cta acc aag cga ctg aaa aga cac cct gag    1152
Gln Glu Phe Val Glu Lys Leu Thr Lys Arg Leu Lys Arg His Pro Glu
        370                 375                 380 gag aca gga ggc ttc cag gag gca ccg ctg gcc tat gat gcc atc tgg    1200
Glu Thr Gly Gly Phe Gln Glu Ala Pro Leu Ala Tyr Asp Ala Ile Trp
385             390                 395                 400 gcc ttg gca ctg gcc ctg aac aag aca tct gga gga ggc ggc cgt tct    1248
Ala Leu Ala Leu Ala Leu Asn Lys Thr Ser Gly Gly Gly Gly Arg Ser
                405                 410                 415 ggt gtg cgc ctg gag gac ttc aac tac aac aac cag acc att acc gac    1296
Gly Val Arg Leu Glu Asp Phe Asn Tyr Asn Asn Gln Thr Ile Thr Asp
                420                 425                 430 caa atc tac cgg gca atg aac tct tcg tcc ttt gag ggt gtc tct ggc    1344
Gln Ile Tyr Arg Ala Met Asn Ser Ser Ser Phe Glu Gly Val Ser Gly
            435                 440                 445 cat gtg gtg ttt gat gcc agc ggc tct cgg atg gca tgg acg ctt atc    1392
His Val Val Phe Asp Ala Ser Gly Ser Arg Met Ala Trp Thr Leu Ile
        450                 455                 460 gag cag ctt cag ggt ggc agc tac aag aag att ggc tac tat gac agc    1440
Glu Gln Leu Gln Gly Gly Ser Tyr Lys Lys Ile Gly Tyr Tyr Asp Ser
465             470                 475                 480 acc aag gat gat ctt tcc tgg tcc aaa aca gat aaa tgg att gga ggg    1488
Thr Lys Asp Asp Leu Ser Trp Ser Lys Thr Asp Lys Trp Ile Gly Gly
                485                 490                 495 tcc ccc cca gct gac cag acc ctg gtc atc aag aca ttc cgc ttc ctg    1536
Ser Pro Pro Ala Asp Gln Thr Leu Val Ile Lys Thr Phe Arg Phe Leu
                500                 505                 510 tca cag aaa ctc ttt atc tcc gtc tca gtt ctc tcc agc ctg ggc att    1584
Ser Gln Lys Leu Phe Ile Ser Val Ser Val Leu Ser Ser Leu Gly Ile
            515                 520                 525
```

-continued

| | | |
|---|---|---|
| gtc cta gct gtt gtc tgt ctg tcc ttt aac atc tac aac tca cat gtc<br>Val Leu Ala Val Val Cys Leu Ser Phe Asn Ile Tyr Asn Ser His Val<br>530                             535                        540 | 1632 |
| cgt tat atc cag aac tca cag ccc aac ctg aac aac ctg act gct gtg<br>Arg Tyr Ile Gln Asn Ser Gln Pro Asn Leu Asn Asn Leu Thr Ala Val<br>545                             550                        555                        560 | 1680 |
| ggc tgc tca ctg gct tta gct gct gtc ttc ccc ctg ggg ctc gat ggt<br>Gly Cys Ser Leu Ala Leu Ala Ala Val Phe Pro Leu Gly Leu Asp Gly<br>                    565                        570                        575 | 1728 |
| tac cac att ggg agg aac cag ttt cct ttc gtc tgc cag gcc cgc ctc<br>Tyr His Ile Gly Arg Asn Gln Phe Pro Phe Val Cys Gln Ala Arg Leu<br>             580                        585                        590 | 1776 |
| tgg ctc ctg ggc ctg ggc ttt agt ctg ggc tac ggt tcc atg ttc acc<br>Trp Leu Leu Gly Leu Gly Phe Ser Leu Gly Tyr Gly Ser Met Phe Thr<br>595                             600                        605 | 1824 |
| aag att tgg tgg gtc cac acg gtc ttc aca aag aag gaa gaa aag aag<br>Lys Ile Trp Trp Val His Thr Val Phe Thr Lys Lys Glu Glu Lys Lys<br>        610                        615                        620 | 1872 |
| gag tgg agg aag act ctg gaa ccc tgg aag ctg tat gcc aca gtg ggc<br>Glu Trp Arg Lys Thr Leu Glu Pro Trp Lys Leu Tyr Ala Thr Val Gly<br>625                             630                        635                        640 | 1920 |
| ctg ctg gtg ggc atg gat gtc ctc act ctc gcc atc tgg cag atc gtg<br>Leu Leu Val Gly Met Asp Val Leu Thr Leu Ala Ile Trp Gln Ile Val<br>                    645                        650                        655 | 1968 |
| gac cct ctg cac cgg acc att gag aca ttt gcc aag gag gaa cct aag<br>Asp Pro Leu His Arg Thr Ile Glu Thr Phe Ala Lys Glu Glu Pro Lys<br>             660                        665                        670 | 2016 |
| gaa gat att gac gtc tct att ctg ccc cag ctg gag cat tgc agc tcc<br>Glu Asp Ile Asp Val Ser Ile Leu Pro Gln Leu Glu His Cys Ser Ser<br>675                             680                        685 | 2064 |
| agg aag atg aat aca tgg ctt ggc att ttc tat ggt tac aag ggg ctg<br>Arg Lys Met Asn Thr Trp Leu Gly Ile Phe Tyr Gly Tyr Lys Gly Leu<br>        690                        695                        700 | 2112 |
| ctg ctg ctg ctg gga atc ttc ctt gct tat gag acc aag agt gtg tcc<br>Leu Leu Leu Leu Gly Ile Phe Leu Ala Tyr Glu Thr Lys Ser Val Ser<br>705                             710                        715                        720 | 2160 |
| act gag aag atc aat gat cac cgg gct gtg ggc atg gct atc tac aat<br>Thr Glu Lys Ile Asn Asp His Arg Ala Val Gly Met Ala Ile Tyr Asn<br>                        725                        730                        735 | 2208 |
| gtg gca gtc ctg tgc ctc atc act gct cct gtc acc atg att ctg tcc<br>Val Ala Val Leu Cys Leu Ile Thr Ala Pro Val Thr Met Ile Leu Ser<br>                    740                        745                        750 | 2256 |
| agc cag cag gat gca gcc ttt gcc ttt gcc tct ctt gcc ata gtt ttc<br>Ser Gln Gln Asp Ala Ala Phe Ala Phe Ala Ser Leu Ala Ile Val Phe<br>        755                        760                        765 | 2304 |
| tcc tcc tat atc act ctt gtt gtg ctc ttt gtg ccc aag atg cgc agg<br>Ser Ser Tyr Ile Thr Leu Val Val Leu Phe Val Pro Lys Met Arg Arg<br>770                             775                        780 | 2352 |
| ctg atc acc cga ggg gaa tgg cag tcg gag gcg cag gac acc atg aag<br>Leu Ile Thr Arg Gly Glu Trp Gln Ser Glu Ala Gln Asp Thr Met Lys<br>785                             790                        795                        800 | 2400 |
| aca ggg tca tcg acc aac aac aac gag gag gag aag tcc cgg ctg ttg<br>Thr Gly Ser Ser Thr Asn Asn Asn Glu Glu Glu Lys Ser Arg Leu Leu<br>                    805                        810                        815 | 2448 |
| gag aag gag aac cgt gaa ctg gaa aag atc att gct gag aaa gag gag<br>Glu Lys Glu Asn Arg Glu Leu Glu Lys Ile Ile Ala Glu Lys Glu Glu<br>820                             825                        830 | 2496 |
| cgt gtc tct gaa ctg cgc cat caa ctc cag tct cgg cag cag ctc cgc<br>Arg Val Ser Glu Leu Arg His Gln Leu Gln Ser Arg Gln Gln Leu Arg | 2544 |

-continued

```
              835                 840                 845
tcc cgg cgc cac cca ccg aca ccc cca gaa ccc tct ggg ggc ctg ccc    2592
Ser Arg Arg His Pro Pro Thr Pro Pro Glu Pro Ser Gly Gly Leu Pro
    850                 855                 860 agg gga ccc cct gag ccc ccc gac cgg ctt agc tgt gat ggg agt cga    2640
Arg Gly Pro Pro Glu Pro Pro Asp Arg Leu Ser Cys Asp Gly Ser Arg
865                 870                 875                 880 gtg cat ttg ctt tat aag tga                                        2661
Val His Leu Leu Tyr Lys
                885

<210> SEQ ID NO 77
<211> LENGTH: 886
<212> TYPE: PRT
<213> ORGANISM: Homo sapiens

<400> SEQUENCE: 77

Met Leu Leu Leu Leu Leu Ala Pro Leu Phe Leu Arg Pro Pro Gly
 1               5                  10                  15

Ala Gly Gly Ala Gln Thr Pro Asn Ala Thr Ser Glu Gly Cys Gln Ile
                20                  25                  30

Ile His Pro Pro Trp Glu Gly Gly Ile Arg Tyr Arg Gly Leu Thr Arg
            35                  40                  45

Asp Gln Val Lys Ala Ile Asn Phe Leu Pro Val Asp Tyr Glu Ile Glu
    50                  55                  60

Tyr Val Cys Arg Gly Glu Arg Glu Val Val Gly Pro Lys Val Arg Lys
65                  70                  75                  80

Cys Leu Ala Asn Gly Ser Trp Thr Asp Met Asp Thr Pro Ser Arg Cys
                85                  90                  95

Val Asn Arg Thr Pro His Ser Glu Arg Arg Ala Val Tyr Ile Gly Ala
            100                 105                 110

Leu Phe Pro Ala Val Glu Met Ala Leu Glu Asp Val Asn Ser Arg Arg
        115                 120                 125

Asp Ile Leu Pro Asp Tyr Glu Leu Lys Leu Ile His His Asp Ser Lys
    130                 135                 140

Cys Asp Pro Gly Gln Ala Thr Lys Tyr Leu Tyr Glu Leu Leu Tyr Asn
145                 150                 155                 160

Asp Pro Ile Lys Ile Ile Leu Met Pro Gly Cys Ser Ser Val Ser Thr
                165                 170                 175

Leu Val Ala Glu Ala Ala Arg Met Trp Asn Leu Ile Val Leu Ser Tyr
            180                 185                 190

Gly Ser Ser Ser Pro Ala Leu Ser Asn Arg Gln Arg Phe Pro Thr Phe
        195                 200                 205

Phe Arg Thr His Pro Ser Ala Thr Leu His Asn Pro Thr Arg Val Lys
    210                 215                 220

Leu Phe Glu Lys Trp Gly Trp Lys Lys Ile Ala Thr Ile Gln Gln Thr
225                 230                 235                 240

Thr Glu Val Phe Thr Ser Thr Leu Asp Asp Leu Glu Glu Arg Val Lys
                245                 250                 255

Glu Ala Gly Ile Glu Ile Thr Phe Arg Gln Ser Phe Phe Ser Asp Pro
            260                 265                 270

Ala Val Pro Val Lys Asn Leu Lys Arg Gln Asp Ala Arg Ile Ile Val
        275                 280                 285

Gly Leu Phe Tyr Glu Thr Glu Ala Arg Lys Val Phe Cys Glu Val Tyr
    290                 295                 300
```

```
Lys Glu Arg Leu Phe Gly Lys Lys Tyr Val Trp Phe Leu Ile Gly Trp
305                 310                 315                 320

Tyr Ala Asp Asn Trp Phe Lys Ile Tyr Asp Pro Ser Ile Asn Cys Thr
                325                 330                 335

Val Asp Glu Met Thr Glu Ala Val Glu Gly His Ile Thr Thr Glu Ile
                340                 345                 350

Val Met Leu Asn Pro Ala Asn Thr Arg Ser Ile Ser Asn Met Thr Ser
                355                 360                 365

Gln Glu Phe Val Glu Lys Leu Thr Lys Arg Leu Lys Arg His Pro Glu
                370                 375                 380

Glu Thr Gly Gly Phe Gln Glu Ala Pro Leu Ala Tyr Asp Ala Ile Trp
385                 390                 395                 400

Ala Leu Ala Leu Ala Leu Asn Lys Thr Ser Gly Gly Gly Gly Arg Ser
                405                 410                 415

Gly Val Arg Leu Glu Asp Phe Asn Tyr Asn Asn Gln Thr Ile Thr Asp
                420                 425                 430

Gln Ile Tyr Arg Ala Met Asn Ser Ser Ser Phe Glu Gly Val Ser Gly
                435                 440                 445

His Val Val Phe Asp Ala Ser Gly Ser Arg Met Ala Trp Thr Leu Ile
                450                 455                 460

Glu Gln Leu Gln Gly Gly Ser Tyr Lys Lys Ile Gly Tyr Tyr Asp Ser
465                 470                 475                 480

Thr Lys Asp Asp Leu Ser Trp Ser Lys Thr Asp Lys Trp Ile Gly Gly
                485                 490                 495

Ser Pro Pro Ala Asp Gln Thr Leu Val Ile Lys Thr Phe Arg Phe Leu
                500                 505                 510

Ser Gln Lys Leu Phe Ile Ser Val Ser Val Leu Ser Ser Leu Gly Ile
                515                 520                 525

Val Leu Ala Val Val Cys Leu Ser Phe Asn Ile Tyr Asn Ser His Val
                530                 535                 540

Arg Tyr Ile Gln Asn Ser Gln Pro Asn Leu Asn Asn Leu Thr Ala Val
545                 550                 555                 560

Gly Cys Ser Leu Ala Leu Ala Ala Val Phe Pro Leu Gly Leu Asp Gly
                565                 570                 575

Tyr His Ile Gly Arg Asn Gln Phe Pro Phe Val Cys Gln Ala Arg Leu
                580                 585                 590

Trp Leu Leu Gly Leu Gly Phe Ser Leu Gly Tyr Gly Ser Met Phe Thr
                595                 600                 605

Lys Ile Trp Trp Val His Thr Val Phe Thr Lys Lys Glu Glu Lys Lys
                610                 615                 620

Glu Trp Arg Lys Thr Leu Glu Pro Trp Lys Leu Tyr Ala Thr Val Gly
625                 630                 635                 640

Leu Leu Val Gly Met Asp Val Leu Thr Leu Ala Ile Trp Gln Ile Val
                645                 650                 655

Asp Pro Leu His Arg Thr Ile Glu Thr Phe Ala Lys Glu Glu Pro Lys
                660                 665                 670

Glu Asp Ile Asp Val Ser Ile Leu Pro Gln Leu Glu His Cys Ser Ser
                675                 680                 685

Arg Lys Met Asn Thr Trp Leu Gly Ile Phe Tyr Gly Tyr Lys Gly Leu
                690                 695                 700

Leu Leu Leu Leu Gly Ile Phe Leu Ala Tyr Glu Thr Lys Ser Val Ser
705                 710                 715                 720

Thr Glu Lys Ile Asn Asp His Arg Ala Val Gly Met Ala Ile Tyr Asn
```

```
                    725                 730                 735
Val Ala Val Leu Cys Leu Ile Thr Ala Pro Val Thr Met Ile Leu Ser
                740                 745                 750

Ser Gln Gln Asp Ala Ala Phe Ala Phe Ala Ser Leu Ala Ile Val Phe
            755                 760                 765

Ser Ser Tyr Ile Thr Leu Val Val Leu Phe Val Pro Lys Met Arg Arg
        770                 775                 780

Leu Ile Thr Arg Gly Glu Trp Gln Ser Glu Ala Gln Asp Thr Met Lys
785                 790                 795                 800

Thr Gly Ser Ser Thr Asn Asn Glu Glu Lys Ser Arg Leu Leu
                805                 810                 815

Glu Lys Glu Asn Arg Glu Leu Glu Lys Ile Ile Ala Glu Lys Glu Glu
                820                 825                 830

Arg Val Ser Glu Leu Arg His Gln Leu Gln Ser Arg Gln Leu Arg
            835                 840                 845

Ser Arg Arg His Pro Pro Thr Pro Pro Glu Pro Ser Gly Gly Leu Pro
            850                 855                 860

Arg Gly Pro Pro Glu Pro Pro Asp Arg Leu Ser Cys Asp Gly Ser Arg
865                 870                 875                 880

Val His Leu Leu Tyr Lys
                885

<210> SEQ ID NO 78
<211> LENGTH: 1692
<212> TYPE: DNA
<213> ORGANISM: Homo sapiens
<220> FEATURE:
<221> NAME/KEY: CDS
<222> LOCATION: (1)...(1689)

<400> SEQUENCE: 78 atg ttg ctg ctg ctg cta ctg gcg cca ctc ttc ctc cgc ccc ccg ggc      48
Met Leu Leu Leu Leu Leu Leu Ala Pro Leu Phe Leu Arg Pro Pro Gly
  1               5                  10                  15 gcg ggc ggg gcg cag acc ccc aac gcc acc tca gaa ggt tgc cag atc      96
Ala Gly Gly Ala Gln Thr Pro Asn Ala Thr Ser Glu Gly Cys Gln Ile
                 20                  25                  30 ata cac ccg ccc tgg gaa ggg ggc atc agg tac cgg ggc ctg act cgg     144
Ile His Pro Pro Trp Glu Gly Gly Ile Arg Tyr Arg Gly Leu Thr Arg
             35                  40                  45 gac cag gtg aag gct atc aac ttc ctg cca gtg gac tat gag att gag     192
Asp Gln Val Lys Ala Ile Asn Phe Leu Pro Val Asp Tyr Glu Ile Glu
         50                  55                  60 tat gtg tgc cgg ggg gag cgc gag gtg gtg ggg ccc aag gtc cgc aag     240
Tyr Val Cys Arg Gly Glu Arg Glu Val Val Gly Pro Lys Val Arg Lys
 65                  70                  75                  80 tgc ctg gcc aac ggc tcc tgg aca gat atg gac aca ccc agc cgc tgt     288
Cys Leu Ala Asn Gly Ser Trp Thr Asp Met Asp Thr Pro Ser Arg Cys
                 85                  90                  95 gtc cga atc tgc tcc aag tct tat ttg acc att acc gac caa atc tac     336
Val Arg Ile Cys Ser Lys Ser Tyr Leu Thr Ile Thr Asp Gln Ile Tyr
            100                 105                 110 cgg gca atg aac tct tcg tcc ttt gag ggt gtc tct ggc cat gtg gtg     384
Arg Ala Met Asn Ser Ser Ser Phe Glu Gly Val Ser Gly His Val Val
        115                 120                 125 ttt gat gcc agc ggc tct cgg atg gca tgg acg ctt atc gag cag ctt     432
Phe Asp Ala Ser Gly Ser Arg Met Ala Trp Thr Leu Ile Glu Gln Leu
    130                 135                 140
```

```
cag ggt ggc agc tac aag aag att ggc tac tat gac agc acc aag gat         480
Gln Gly Gly Ser Tyr Lys Lys Ile Gly Tyr Tyr Asp Ser Thr Lys Asp
145                 150                 155                 160 gat ctt tcc tgg tcc aaa aca gat aaa tgg att gga ggg tcc ccc cca         528
Asp Leu Ser Trp Ser Lys Thr Asp Lys Trp Ile Gly Gly Ser Pro Pro
                165                 170                 175 gct gac cag acc ctg gtc atc aag aca ttc cgc ttc ctg tca cag aaa         576
Ala Asp Gln Thr Leu Val Ile Lys Thr Phe Arg Phe Leu Ser Gln Lys
            180                 185                 190 ctc ttt atc tcc gtc tca gtt ctc tcc agc ctg ggc att gtc cta gct         624
Leu Phe Ile Ser Val Ser Val Leu Ser Ser Leu Gly Ile Val Leu Ala
        195                 200                 205 gtt gtc tgt ctg tcc ttt aac atc tac aac tca cat gtc cgt tat atc         672
Val Val Cys Leu Ser Phe Asn Ile Tyr Asn Ser His Val Arg Tyr Ile
    210                 215                 220 cag aac tca cag ccc aac ctg aac aac ctg act gct gtg ggc tgc tca         720
Gln Asn Ser Gln Pro Asn Leu Asn Asn Leu Thr Ala Val Gly Cys Ser
225                 230                 235                 240 ctg gct tta gct gct gtc ttc ccc ctg ggg ctc gat ggt tac cac att         768
Leu Ala Leu Ala Ala Val Phe Pro Leu Gly Leu Asp Gly Tyr His Ile
                245                 250                 255 ggg agg aac cag ttt cct ttc gtc tgc cag gcc cgc ctc tgg ctc ctg         816
Gly Arg Asn Gln Phe Pro Phe Val Cys Gln Ala Arg Leu Trp Leu Leu
            260                 265                 270 ggc ctg ggc ttt agt ctg ggc tac ggt tcc atg ttc acc aag att tgg         864
Gly Leu Gly Phe Ser Leu Gly Tyr Gly Ser Met Phe Thr Lys Ile Trp
        275                 280                 285 tgg gtc cac acg gtc ttc aca aag aag gaa gaa aag aag gag tgg agg         912
Trp Val His Thr Val Phe Thr Lys Lys Glu Glu Lys Lys Glu Trp Arg
    290                 295                 300 aag act ctg gaa ccc tgg aag ctg tat gcc aca gtg ggc ctg ctg gtg         960
Lys Thr Leu Glu Pro Trp Lys Leu Tyr Ala Thr Val Gly Leu Leu Val
305                 310                 315                 320 ggc atg gat gtc ctc act ctc gcc atc tgg cag atc gtg gac cct ctg        1008
Gly Met Asp Val Leu Thr Leu Ala Ile Trp Gln Ile Val Asp Pro Leu
                325                 330                 335 cac cgg acc att gag aca ttt gcc aag gag gaa cct aag gaa gat att        1056
His Arg Thr Ile Glu Thr Phe Ala Lys Glu Glu Pro Lys Glu Asp Ile
            340                 345                 350 gac gtc tct att ctg ccc cag ctg gag cat tgc agc tcc agg aag atg        1104
Asp Val Ser Ile Leu Pro Gln Leu Glu His Cys Ser Ser Arg Lys Met
        355                 360                 365 aat aca tgg ctt ggc att ttc tat ggt tac aag ggg ctg ctg ctg ctg        1152
Asn Thr Trp Leu Gly Ile Phe Tyr Gly Tyr Lys Gly Leu Leu Leu Leu
    370                 375                 380 ctg gga atc ttc ctt gct tat gag acc aag agt gtg tcc act gag aag        1200
Leu Gly Ile Phe Leu Ala Tyr Glu Thr Lys Ser Val Ser Thr Glu Lys
385                 390                 395                 400 atc aat gat cac cgg gct gtg ggc atg gct atc tac aat gtg gca gtc        1248
Ile Asn Asp His Arg Ala Val Gly Met Ala Ile Tyr Asn Val Ala Val
                405                 410                 415 ctg tgc ctc atc act gct cct gtc acc atg att ctg tcc agc cag cag        1296
Leu Cys Leu Ile Thr Ala Pro Val Thr Met Ile Leu Ser Ser Gln Gln
            420                 425                 430 gat gca gcc ttt gcc ttt gcc tct ctt gcc ata gtt ttc tcc tcc tat        1344
Asp Ala Ala Phe Ala Phe Ala Ser Leu Ala Ile Val Phe Ser Ser Tyr
        435                 440                 445 atc act ctt gtt gtg ctc ttt gtg ccc aag atg cgc agg ctg atc acc        1392
Ile Thr Leu Val Val Leu Phe Val Pro Lys Met Arg Arg Leu Ile Thr
    450                 455                 460
```

```
cga ggg gaa tgg cag tcg gag gcg cag gac acc atg aag aca ggg tca    1440
Arg Gly Glu Trp Gln Ser Glu Ala Gln Asp Thr Met Lys Thr Gly Ser
465                 470                 475                 480 tcg acc aac aac aac gag gag gag aag tcc cgg ctg ttg gag aag gag    1488
Ser Thr Asn Asn Asn Glu Glu Glu Lys Ser Arg Leu Leu Glu Lys Glu
                485                 490                 495 aac cgt gaa ctg gaa aag atc att gct gag aaa gag gag cgt gtc tct    1536
Asn Arg Glu Leu Glu Lys Ile Ile Ala Glu Lys Glu Glu Arg Val Ser
            500                 505                 510 gaa ctg cgc cat caa ctc cag tct cgg cag cag ctc cgc tcc cgg cgc    1584
Glu Leu Arg His Gln Leu Gln Ser Arg Gln Gln Leu Arg Ser Arg Arg
        515                 520                 525 cac cca ccg aca ccc cca gaa ccc tct ggg ggc ctg ccc agg gga ccc    1632
His Pro Pro Thr Pro Pro Glu Pro Ser Gly Gly Leu Pro Arg Gly Pro
    530                 535                 540 cct gag ccc ccc gac cgg ctt agc tgt gat ggg agt cga gtg cat ttg    1680
Pro Glu Pro Pro Asp Arg Leu Ser Cys Asp Gly Ser Arg Val His Leu
545                 550                 555                 560 ctt tat aag tga                                                    1692
Leu Tyr Lys <210> SEQ ID NO 79
<211> LENGTH: 563
<212> TYPE: PRT
<213> ORGANISM: Homo sapiens

<400> SEQUENCE: 79

Met Leu Leu Leu Leu Leu Leu Ala Pro Leu Phe Leu Arg Pro Pro Gly
 1               5                  10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
        35                  40                  45

Asp Gln Val Lys Ala Ile Asn Phe Leu Pro Val Asp Tyr Glu Ile Glu
    50                  55                  60

Tyr Val Cys Arg Gly Glu Arg Glu Val Val Gly Pro Lys Val Arg Lys
65                  70                  75                  80

Cys Leu Ala Asn Gly Ser Trp Thr Asp Met Asp Thr Pro Ser Arg Cys
                85                  90                  95

Val Arg Ile Cys Ser Lys Ser Tyr Leu Thr Ile Thr Asp Gln Ile Tyr
            100                 105                 110

Arg Ala Met Asn Ser Ser Ser Phe Glu Gly Val Ser Gly His Val Val
        115                 120                 125

Phe Asp Ala Ser Gly Ser Arg Met Ala Trp Thr Leu Ile Glu Gln Leu
    130                 135                 140

Gln Gly Gly Ser Tyr Lys Lys Ile Gly Tyr Tyr Asp Ser Thr Lys Asp
145                 150                 155                 160

Asp Leu Ser Trp Ser Lys Thr Asp Lys Trp Ile Gly Gly Ser Pro Pro
                165                 170                 175

Ala Asp Gln Thr Leu Val Ile Lys Thr Phe Arg Phe Leu Ser Gln Lys
            180                 185                 190

Leu Phe Ile Ser Val Ser Val Leu Ser Ser Leu Gly Ile Val Leu Ala
        195                 200                 205

Val Val Cys Leu Ser Phe Asn Ile Tyr Asn Ser His Val Arg Tyr Ile
    210                 215                 220

Gln Asn Ser Gln Pro Asn Leu Asn Asn Leu Thr Ala Val Gly Cys Ser
```

```
                225                 230                 235                 240
Leu Ala Leu Ala Ala Val Phe Pro Leu Gly Leu Asp Gly Tyr His Ile
                    245                 250                 255
Gly Arg Asn Gln Phe Pro Phe Val Cys Gln Ala Arg Leu Trp Leu Leu
                260                 265                 270
Gly Leu Gly Phe Ser Leu Gly Tyr Gly Ser Met Phe Thr Lys Ile Trp
            275                 280                 285
Trp Val His Thr Val Phe Thr Lys Lys Glu Lys Lys Glu Trp Arg
    290                 295                 300
Lys Thr Leu Glu Pro Trp Lys Leu Tyr Ala Thr Val Gly Leu Leu Val
305                 310                 315                 320
Gly Met Asp Val Leu Thr Leu Ala Ile Trp Gln Ile Val Asp Pro Leu
                325                 330                 335
His Arg Thr Ile Glu Thr Phe Ala Lys Glu Pro Lys Glu Asp Ile
                340                 345                 350
Asp Val Ser Ile Leu Pro Gln Leu Glu His Cys Ser Ser Arg Lys Met
                355                 360                 365
Asn Thr Trp Leu Gly Ile Phe Tyr Gly Tyr Lys Gly Leu Leu Leu Leu
            370                 375                 380
Leu Gly Ile Phe Leu Ala Tyr Glu Thr Lys Ser Val Ser Thr Glu Lys
385                 390                 395                 400
Ile Asn Asp His Arg Ala Val Gly Met Ala Ile Tyr Asn Val Ala Val
                405                 410                 415
Leu Cys Leu Ile Thr Ala Pro Val Thr Met Ile Leu Ser Ser Gln Gln
                420                 425                 430
Asp Ala Ala Phe Ala Phe Ala Ser Leu Ala Ile Val Phe Ser Ser Tyr
                435                 440                 445
Ile Thr Leu Val Val Leu Phe Val Pro Lys Met Arg Arg Leu Ile Thr
            450                 455                 460
Arg Gly Glu Trp Gln Ser Glu Ala Gln Asp Thr Met Lys Thr Gly Ser
465                 470                 475                 480
Ser Thr Asn Asn Asn Glu Glu Lys Ser Arg Leu Leu Glu Lys Glu
                485                 490                 495
Asn Arg Glu Leu Glu Lys Ile Ile Ala Glu Lys Glu Glu Arg Val Ser
            500                 505                 510
Glu Leu Arg His Gln Leu Gln Ser Arg Gln Gln Leu Arg Ser Arg Arg
        515                 520                 525
His Pro Pro Thr Pro Pro Glu Pro Ser Gly Gly Leu Pro Arg Gly Pro
        530                 535                 540
Pro Glu Pro Pro Asp Arg Leu Ser Cys Asp Gly Ser Arg Val His Leu
545                 550                 555                 560
Leu Tyr Lys

<210> SEQ ID NO 80
<211> LENGTH: 2602
<212> TYPE: DNA
<213> ORGANISM: Homo sapiens
<220> FEATURE:
<221> NAME/KEY: CDS
<222> LOCATION: (1)...(315)

<400> SEQUENCE: 80 atg ttg ctg ctg ctg cta ctg gcg cca ctc ttc ctc cgc ccc ccg ggc         48
Met Leu Leu Leu Leu Leu Ala Pro Leu Phe Leu Arg Pro Pro Gly
  1               5                  10                  15
```

-continued

| | |
|---|---|
| gcg ggc ggg gcg cag acc ccc aac gcc acc tca gaa ggt tgc cag atc<br>Ala Gly Gly Ala Gln Thr Pro Asn Ala Thr Ser Glu Gly Cys Gln Ile<br>             20                      25                      30 | 96 |
| ata cac ccg ccc tgg gaa ggg ggc atc agg tac cgg ggc ctg act cgg<br>Ile His Pro Pro Trp Glu Gly Gly Ile Arg Tyr Arg Gly Leu Thr Arg<br>     35                      40                      45 | 144 |
| gac cag gtg aag gct atc aac ttc ctg cca gtg gac tat gag att gat<br>Asp Gln Val Lys Ala Ile Asn Phe Leu Pro Val Asp Tyr Glu Ile Asp<br>50                     55                      60 | 192 |
| gaa tcg aac gcc aca ctc aga acg gcg cgc agt gta cat cgg ggc act<br>Glu Ser Asn Ala Thr Leu Arg Thr Ala Arg Ser Val His Arg Gly Thr<br>65                      70                      75                      80 | 240 |
| gtt tcc cat gag cgg ggg ctg gcc agg ggg cca ggc tg cca gcc cgc<br>Val Ser His Glu Arg Gly Leu Ala Arg Gly Pro Gly Leu Pro Ala Arg<br>             85                      90                      95 | 288 |
| ggt gga gat ggc gct gga gga cgt gaa tagccgcagg gacatcctgc<br>Gly Gly Asp Gly Ala Gly Gly Arg Glu<br>            100                     105 | 335 |
| cggactatga gctcaagctc atccaccacg acagcaagtg tgatccaggc caagccacca | 395 |
| agtacctata tgagctgctc tacaacgacc ctatcaagat catccttatg cctggctgca | 455 |
| gctctgtctc cacgctggtg gctgaggctg ctaggatgtg aacctcatt gtgctttcct | 515 |
| atggctccag ctcaccagcc ctgtcaaacc ggcagcgttt ccccactttc ttccgaacgc | 575 |
| acccatcagc cacactccac aaccctaccc gcgtgaaact ctttgaaaag tggggctgga | 635 |
| agaagattgc taccatccag cagaccactg aggtcttcac ttcgactctg gacgacctgg | 695 |
| aggaacgagt gaaggaggct ggaattgaga ttactttccg ccagagtttc ttctcagatc | 755 |
| cagctgtgcc cgtcaaaaac ctgaagcgcc aggatgcccg aatcatcgtg gactttttct | 815 |
| atgagactga agcccggaaa gttttttgtg aggtgtacaa ggagcgtctc tttgggaaga | 875 |
| agtacgtctg gttcctcatt gggtggtatg ctgacaattg gttcaagatc tacgacccttt | 935 |
| ctatcaactg cacagtggat gagatgactg aggcggtgga gggccacatc acaactgaga | 995 |
| ttgtcatgct gaatcctgcc aatacccgca gcatttccaa catgcatcc caggaatttg | 1055 |
| tggagaaact aaccaagcga ctgaaaagac ccctgaggaa acaggaggc ttccaggagg | 1115 |
| caccgctggc ctatgatgcc atctgggcct tggcactggc cctgaacaag acatctggag | 1175 |
| gaggcggccg ttctggtgtg cgcctggagg acttcaacta caacaaccag accattaccg | 1235 |
| accaaatcta ccgggcaatg aactcttcgt cctttgaggg tgtctctggc catgtggtgt | 1295 |
| tgatgccag cggctctcgg atggcatgga cgcttatcga gcagcttcag ggtggcagct | 1355 |
| acaagaagat tggctactat gacagcacca aggatgatct ttcctggtcc aaaacagata | 1415 |
| aatggattgg agggtccccc ccagctgacc agacctggt catcaagaca ttccgcttcc | 1475 |
| tgtcacagaa actctttatc tccgtctcag ttctctccag cctgggcatt gtcctagctg | 1535 |
| ttgtctgtct gtccttaac atctacaact cacatgtccg ttatatccag aactcacagc | 1595 |
| ccaacctgaa caacctgact gctgtgggct gctcactggc tttagctgct gtcttccccc | 1655 |
| tggggctcga tggttaccac attgggagga accagtttcc tttcgtctgc caggcccgcc | 1715 |
| tctggctcct gggcctgggc tttagtctgg ctacggttc catgttcacc aagatttggt | 1775 |
| gggtccacac ggtcttcaca aagaaggaag aaaagaagga gtggaggaag actctggaac | 1835 |
| cctggaagct gtatgccaca gtgggcctgc tggtgggcat ggatgtcctc actctcgcca | 1895 |
| tctggcagat cgtggaccct ctgaccggac ccattgagac atttgccaag gaggaaccta | 1955 |
| aggaagatat tgacgtctct attctgcccc agctggagca ttgcagctcc aggaagatga | 2015 |

-continued

```
atacatggct tggcattttc tatggttaca aggggctgct gctgctgctg ggaatcttcc      2075
ttgcttatga gaccaagagt gtgtccactg agaagatcaa tgatcaccgg gctgtgggca      2135
tggctatcta caatgtggca gtcctgtgcc tcatcactgc tcctgtcacc atgattctgt      2195
ccagccagca ggatgcagcc tttgcctttg cctctcttgc catagttttc tcctcctata      2255
tcactcttgt tgtgctcttt gtgcccaaga tgcgcaggct gatcacccga ggggaatggc      2315
agtcggaggc gcaggacacc atgaagacag gtcatcgac caacaacaac gaggaggaga       2375
agtcccggct gttggagaag gagaaccgtg aactggaaaa gatcattgct gagaaagagg      2435
agcgtgtctc tgaactgcgc atcaactcc agtctcggca gcagctccgc tcccggcgcc       2495
acccaccgac acccccagaa ccctctgggg gcctgcccag gggacccct gagccccccg       2555 accggcttag ctgtgatggg agtcgagtgc atttgcttta taagtga                   2602
```

<210> SEQ ID NO 81
<211> LENGTH: 105
<212> TYPE: PRT
<213> ORGANISM: Homo sapiens

<400> SEQUENCE: 81

```
Met Leu Leu Leu Leu Leu Leu Ala Pro Leu Phe Leu Arg Pro Pro Gly
1               5                   10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
        35                  40                  45

Asp Gln Val Lys Ala Ile Asn Phe Leu Pro Val Asp Tyr Glu Ile Asp
    50                  55                  60

Glu Ser Asn Ala Thr Leu Arg Thr Ala Arg Ser Val His Arg Gly Thr
65                  70                  75                  80

Val Ser His Glu Arg Gly Leu Ala Arg Gly Pro Gly Leu Pro Ala Arg
                85                  90                  95

Gly Gly Asp Gly Ala Gly Gly Arg Glu
            100                 105
```

<210> SEQ ID NO 82
<211> LENGTH: 2367
<212> TYPE: DNA
<213> ORGANISM: Homo sapiens
<220> FEATURE:
<221> NAME/KEY: CDS
<222> LOCATION: (1)...(291)

<400> SEQUENCE: 82

```
atg ttg ctg ctg ctg cta ctg gcg cca ctc ttc ctc cgc ccc ccg ggc       48
Met Leu Leu Leu Leu Leu Leu Ala Pro Leu Phe Leu Arg Pro Pro Gly
1               5                   10                  15 gcg ggc ggg gcg cag acc ccc aac gcc acc tca gaa ggt tgc cag atc       96
Ala Gly Gly Ala Gln Thr Pro Asn Ala Thr Ser Glu Gly Cys Gln Ile
            20                  25                  30 ata cac ccg ccc tgg gaa ggg ggc atc agg tac cgg ggc ctg act cgg      144
Ile His Pro Pro Trp Glu Gly Gly Ile Arg Tyr Arg Gly Leu Thr Arg
        35                  40                  45 gac cag gtg aag gct atc aac ttc ctg cca gtg gac tat gag att gag      192
Asp Gln Val Lys Ala Ile Asn Phe Leu Pro Val Asp Tyr Glu Ile Glu
    50                  55                  60 tat gtg tgc cgg ggg gag cgc gag gtg gtg ggg ccc aag gtc cgc aag      240
Tyr Val Cys Arg Gly Glu Arg Glu Val Val Gly Pro Lys Val Arg Lys
```

```
                  65                  70                  75                  80
tgc ctg gcc aac ggc tcc tgg aca gat atg gac aca ccc agc cgc tgt      288
Cys Leu Ala Asn Gly Ser Trp Thr Asp Met Asp Thr Pro Ser Arg Cys
                    85                  90                  95 gtg tgatccaggc caagccacca agtacctata tgagctgctc tacaacgacc           341
Val ctatcaagat catccttatg cctggctgca gctctgtctc cacgctggtg gctgaggctg    401
ctaggatgtg gaacctcatt gtgctttcct atggctccag ctcaccagcc ctgtcaaacc    461
ggcagcgttt ccccactttc ttccgaacgc acccatcagc cacactccac aaccctaccc    521
gcgtgaaact ctttgaaaag tggggctgga agaagattgc taccatccag cagaccactg    581
aggtcttcac ttcgactctg gacgacctgg aggaacgagt gaaggaggct ggaattgaga    641
ttactttccg ccagagtttc ttctcagatc cagctgtgcc cgtcaaaaac ctgaagcgcc    701
aggatgcccg aatcatcgtg ggactttcct atgagactga agcccggaaa gttttttgtg    761
aggtgtacaa ggagcgtctc tttgggaaga agtacgtctg gttcctcatt gggtggtatg    821
ctgacaattg gttcaagatc tacgacccct ctatcaactg cacagtggat gagatgactg    881
aggcggtgga gggccacatc acaactgaga ttgtcatgct gaatcctgcc aatacccgca    941
gcatttccaa catgacatcc caggaatttg tggagaaact aaccaagcga ctgaaaagac    1001
accctgagga gacaggaggc ttccaggagg caccgctggc ctatgatgcc atctgggcct    1061
tggcactggc cctgaacaag acatctggag gaggcggccg ttctggtgtg cgcctggagg    1121
acttcaacta caacaaccag accattaccg accaaatcta ccgggcaatg aactcttcgt    1181
cctttgaggg tgtctctggc catgtggtgt tgatgccag cggctctcgg atggcatgga    1241
cgcttatcga gcagcttcag ggtggcagct acaagaagat tggctactat gacagcacca    1301
aggatgatct ttcctggtcc aaaacagata atggattgt tatatccaga actcacagcc    1361
caacctgaac aacctgactg ctgtgggctg ctcactggct ttagctgctg tcttccccct    1421
ggggctcgat ggttaccaca ttgggaggaa ccagtttcct ttcgtctgcc aggcccgcct    1481
ctggctcctg ggcctgggct ttagtctggg ctacggttcc atgttcacca agatttggtg    1541
ggtccacacg gtcttcacaa agaaggaaga aaagaaggag tggaggaaga ctctggaacc    1601
ctggaagctg tatgccacag tgggcctgct ggtgggcatg gatgtcctca ctctcgccat    1661
ctggcagatc gtggaccctc tgcaccggac cattgagaca tttgccaagg aggaacctaa    1721
ggaagatatt gacgtctcta ttctgcccca gctggagcat gcagctccca ggaagatgaa    1781
tacatggctt ggcattttct atggttacaa ggggctgctg ctgctgctgg aatcttcct    1841
tgcttatgag accaagagtg tgtccactga aagatcaat gatcaccggg ctgtgggcat    1901
ggctatctac aatgtggcag tcctgtgcct catcactgct cctgtcacca tgattctgtc    1961
cagccagcag gatgcagcct ttgccttgc ctctcttgcc atagttttct cctcctatat    2021
cactcttgtt gtgctctttg tgcccaagat gcgcaggctg atcacccgag gggaatggca    2081
gtcggaggcg caggacacca tgaagacagg gtcatcgacc aacaacaacg aggaggagaa    2141
gtcccggctg ttggagaagg agaaccgtga actggaaaag atcattgctg agaaagagga    2201
gcgtgtctct gaactgcgcc atcaactcca gtctcggcag cagctccgct cccggcgcca    2261
cccaccgaca ccccagaac cctctggggg cctgccagg gaccccctg agcccccga     2321
ccggcttagc tgtgatggga gtcgagtgca tttgctttat aagtga                 2367
```

<210> SEQ ID NO 83

<211> LENGTH: 97
<212> TYPE: PRT
<213> ORGANISM: Homo sapiens

<400> SEQUENCE: 83

```
Met Leu Leu Leu Leu Leu Ala Pro Leu Phe Leu Arg Pro Pro Gly
 1               5                  10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
         35                  40                  45

Asp Gln Val Lys Ala Ile Asn Phe Leu Pro Val Asp Tyr Glu Ile Glu
     50                  55                  60

Tyr Val Cys Arg Gly Glu Arg Glu Val Val Gly Pro Lys Val Arg Lys
 65                  70                  75                  80

Cys Leu Ala Asn Gly Ser Trp Thr Asp Met Asp Thr Pro Ser Arg Cys
                 85                  90                  95

Val
```

<210> SEQ ID NO 84
<211> LENGTH: 2489
<212> TYPE: DNA
<213> ORGANISM: Homo sapiens
<220> FEATURE:
<221> NAME/KEY: CDS
<222> LOCATION: (1)...(1488)

<400> SEQUENCE: 84

```
atg ttg ctg ctg ctg cta ctg gcg cca ctc ttc ctc cgc ccc ccg ggc        48
Met Leu Leu Leu Leu Leu Ala Pro Leu Phe Leu Arg Pro Pro Gly
 1               5                  10                  15 gcg ggc ggg gcg cag acc ccc aac gcc acc tca gaa ggt tgc cag atc        96
Ala Gly Gly Ala Gln Thr Pro Asn Ala Thr Ser Glu Gly Cys Gln Ile
            20                  25                  30 ata cac ccg ccc tgg gaa ggg ggc atc agg tac cgg ggc ctg act cgg       144
Ile His Pro Pro Trp Glu Gly Gly Ile Arg Tyr Arg Gly Leu Thr Arg
         35                  40                  45 gac cag gtg aag gct atc aac ttc ctg cca gtg gac tat gag att gag       192
Asp Gln Val Lys Ala Ile Asn Phe Leu Pro Val Asp Tyr Glu Ile Glu
     50                  55                  60 tat gtg tgc cgg ggg gag cgc gag gtg gtg ggg ccc aag gtc cgc aag       240
Tyr Val Cys Arg Gly Glu Arg Glu Val Val Gly Pro Lys Val Arg Lys
 65                  70                  75                  80 tgc ctg gcc aac ggc tcc tgg aca gat atg gac aca ccc agc cgc tgt       288
Cys Leu Ala Asn Gly Ser Trp Thr Asp Met Asp Thr Pro Ser Arg Cys
                 85                  90                  95 gtc cga atc tgc tcc aag tct tat ttg acc ctg gaa aat ggg aag gtt       336
Val Arg Ile Cys Ser Lys Ser Tyr Leu Thr Leu Glu Asn Gly Lys Val
                100                 105                 110 ttc ctg acg ggt ggg gac ctc cca gct ctg gac gga gcc cgg gtg gat       384
Phe Leu Thr Gly Gly Asp Leu Pro Ala Leu Asp Gly Ala Arg Val Asp
            115                 120                 125 ttc cgg tgt gac ccc gac ttc cat ctg tgt gat cca ggc caa gcc acc       432
Phe Arg Cys Asp Pro Asp Phe His Leu Cys Asp Pro Gly Gln Ala Thr
        130                 135                 140 aag tac cta tat gag ctg ctc tac aac gac cct atc aag atc atc ctt       480
Lys Tyr Leu Tyr Glu Leu Leu Tyr Asn Asp Pro Ile Lys Ile Ile Leu
145                 150                 155                 160 atg cct ggc tgc agc tct gtc tcc acg ctg gtg gct gag gct gct agg       528
Met Pro Gly Cys Ser Ser Val Ser Thr Leu Val Ala Glu Ala Ala Arg
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 165 |     |     |     |     | 170 |     |     |     |     | 175 |     |     |      |
| atg | tgg | aac | ctc | att | gtg | ctt | tcc | tat | ggc | tcc | agc | tca | cca | gcc | ctg | 576  |
| Met | Trp | Asn | Leu | Ile | Val | Leu | Ser | Tyr | Gly | Ser | Ser | Ser | Pro | Ala | Leu |      |
|     |     |     | 180 |     |     |     |     | 185 |     |     |     |     | 190 |     |     |      |
| tca | aac | cgg | cag | cgt | ttc | ccc | act | ttc | ttc | cga | acg | cac | cca | tca | gcc | 624  |
| Ser | Asn | Arg | Gln | Arg | Phe | Pro | Thr | Phe | Phe | Arg | Thr | His | Pro | Ser | Ala |      |
|     |     | 195 |     |     |     |     | 200 |     |     |     |     | 205 |     |     |     |      |
| aca | ctc | cac | aac | cct | acc | cgc | gtg | aaa | ctc | ttt | gaa | aag | tgg | ggc | tgg | 672  |
| Thr | Leu | His | Asn | Pro | Thr | Arg | Val | Lys | Leu | Phe | Glu | Lys | Trp | Gly | Trp |      |
|     | 210 |     |     |     |     | 215 |     |     |     |     | 220 |     |     |     |     |      |
| aag | aag | att | gct | acc | atc | cag | cag | acc | act | gag | gtc | ttc | act | tcg | act | 720  |
| Lys | Lys | Ile | Ala | Thr | Ile | Gln | Gln | Thr | Thr | Glu | Val | Phe | Thr | Ser | Thr |      |
| 225 |     |     |     |     | 230 |     |     |     |     | 235 |     |     |     |     | 240 |      |
| ctg | gac | gac | ctg | gag | gaa | cga | gtg | aag | gag | gct | gga | att | gag | att | act | 768  |
| Leu | Asp | Asp | Leu | Glu | Glu | Arg | Val | Lys | Glu | Ala | Gly | Ile | Glu | Ile | Thr |      |
|     |     |     |     | 245 |     |     |     |     | 250 |     |     |     |     | 255 |     |      |
| ttc | cgc | cag | agt | ttc | ttc | tca | gat | cca | gct | gtg | ccc | gtc | aaa | aac | ctg | 816  |
| Phe | Arg | Gln | Ser | Phe | Phe | Ser | Asp | Pro | Ala | Val | Pro | Val | Lys | Asn | Leu |      |
|     |     |     | 260 |     |     |     |     | 265 |     |     |     |     | 270 |     |     |      |
| aag | cgc | cag | gat | gcc | cga | atc | atc | gtg | gga | ctt | ttc | tat | gag | act | gaa | 864  |
| Lys | Arg | Gln | Asp | Ala | Arg | Ile | Ile | Val | Gly | Leu | Phe | Tyr | Glu | Thr | Glu |      |
|     |     | 275 |     |     |     |     | 280 |     |     |     |     | 285 |     |     |     |      |
| gcc | cgg | aaa | gtt | ttt | tgt | gag | gtg | tac | aag | gag | cgt | ctc | ttt | ggg | aag | 912  |
| Ala | Arg | Lys | Val | Phe | Cys | Glu | Val | Tyr | Lys | Glu | Arg | Leu | Phe | Gly | Lys |      |
|     | 290 |     |     |     |     | 295 |     |     |     |     | 300 |     |     |     |     |      |
| aag | tac | gtc | tgg | ttc | ctc | att | ggg | tgg | tat | gct | gac | aat | tgg | ttc | aag | 960  |
| Lys | Tyr | Val | Trp | Phe | Leu | Ile | Gly | Trp | Tyr | Ala | Asp | Asn | Trp | Phe | Lys |      |
| 305 |     |     |     |     | 310 |     |     |     |     | 315 |     |     |     |     | 320 |      |
| atc | tac | gac | cct | tct | atc | aac | tgc | aca | gtg | gat | gag | atg | act | gag | gcg | 1008 |
| Ile | Tyr | Asp | Pro | Ser | Ile | Asn | Cys | Thr | Val | Asp | Glu | Met | Thr | Glu | Ala |      |
|     |     |     |     | 325 |     |     |     |     | 330 |     |     |     |     | 335 |     |      |
| gtg | gag | ggc | cac | atc | aca | act | gag | att | gtc | atg | ctg | aat | cct | gcc | aat | 1056 |
| Val | Glu | Gly | His | Ile | Thr | Thr | Glu | Ile | Val | Met | Leu | Asn | Pro | Ala | Asn |      |
|     |     |     | 340 |     |     |     |     | 345 |     |     |     |     | 350 |     |     |      |
| acc | cgc | agc | att | tcc | aac | atg | aca | tcc | cag | gaa | ttt | gtg | gag | aaa | cta | 1104 |
| Thr | Arg | Ser | Ile | Ser | Asn | Met | Thr | Ser | Gln | Glu | Phe | Val | Glu | Lys | Leu |      |
|     |     | 355 |     |     |     |     | 360 |     |     |     |     | 365 |     |     |     |      |
| acc | aag | cga | ctg | aaa | aga | cac | cct | gag | gag | aca | gga | ggc | ttc | cag | gag | 1152 |
| Thr | Lys | Arg | Leu | Lys | Arg | His | Pro | Glu | Glu | Thr | Gly | Gly | Phe | Gln | Glu |      |
|     | 370 |     |     |     |     | 375 |     |     |     |     | 380 |     |     |     |     |      |
| gca | ccg | ctg | gcc | tat | gat | gcc | atc | tgg | gcc | ttg | gca | ctg | gcc | ctg | aac | 1200 |
| Ala | Pro | Leu | Ala | Tyr | Asp | Ala | Ile | Trp | Ala | Leu | Ala | Leu | Ala | Leu | Asn |      |
| 385 |     |     |     |     | 390 |     |     |     |     | 395 |     |     |     |     | 400 |      |
| aag | aca | tct | gga | gga | ggc | ggc | cgt | tct | ggt | gtg | cgc | ctg | gag | gac | ttc | 1248 |
| Lys | Thr | Ser | Gly | Gly | Gly | Gly | Arg | Ser | Gly | Val | Arg | Leu | Glu | Asp | Phe |      |
|     |     |     |     | 405 |     |     |     |     | 410 |     |     |     |     | 415 |     |      |
| aac | tac | aac | aac | cag | acc | att | acc | gac | caa | atc | tac | cgg | gca | atg | aac | 1296 |
| Asn | Tyr | Asn | Asn | Gln | Thr | Ile | Thr | Asp | Gln | Ile | Tyr | Arg | Ala | Met | Asn |      |
|     |     |     | 420 |     |     |     |     | 425 |     |     |     |     | 430 |     |     |      |
| tct | tcg | tcc | ttt | gag | ggt | gtc | tct | ggc | cat | gtg | gtg | ttt | gat | gcc | agc | 1344 |
| Ser | Ser | Ser | Phe | Glu | Gly | Val | Ser | Gly | His | Val | Val | Phe | Asp | Ala | Ser |      |
|     |     | 435 |     |     |     |     | 440 |     |     |     |     | 445 |     |     |     |      |
| ggc | tct | cgg | atg | gca | tgg | acg | ctt | atc | gag | cag | ctt | cag | ggt | ggc | agc | 1392 |
| Gly | Ser | Arg | Met | Ala | Trp | Thr | Leu | Ile | Glu | Gln | Leu | Gln | Gly | Gly | Ser |      |
|     | 450 |     |     |     |     | 455 |     |     |     |     | 460 |     |     |     |     |      |
| tac | aag | aag | att | ggc | tac | tat | gac | agc | acc | aag | gat | gat | ctt | tcc | tgg | 1440 |
| Tyr | Lys | Lys | Ile | Gly | Tyr | Tyr | Asp | Ser | Thr | Lys | Asp | Asp | Leu | Ser | Trp |      |
| 465 |     |     |     |     | 470 |     |     |     |     | 475 |     |     |     |     | 480 |      |
| tcc | aaa | aca | gat | aaa | tgg | att | gtt | ata | tcc | aga | act | cac | agc | cca | acc | 1488 |

-continued

```
Ser Lys Thr Asp Lys Trp Ile Val Ile Ser Arg Thr His Ser Pro Thr
            485                 490                 495
```

| | |
|---|---:|
| tgaacaacct gactgctgtg ggctgctcac tggctttagc tgctgtcttc ccctggggc | 1548 |
| tcgatggtta ccacattggg aggaaccagt ttcctttcgt ctgccaggcc cgcctctggc | 1608 |
| tcctgggcct gggctttagt ctgggctacg gttccatgtt caccaagatt tggtgggtcc | 1668 |
| acacggtctt cacaaagaag gaagaaaaga aggagtggag gaagactctg gaaccctgga | 1728 |
| agctgtatgc cacagtgggc ctgctggtgg gcatggatgt cctcactctc gccatctggc | 1788 |
| agatcgtgga ccctctgcac cggaccattg agacatttgc caaggaggaa cctaaggaag | 1848 |
| atattgacgt ctctattctg ccccagctgg agcattgcag ctccaggaag atgaatacat | 1908 |
| ggcttggcat tttctatggt tacaaggggc tgctgctgct gctgggaatc ttccttgctt | 1968 |
| atgagaccaa gagtgtgtcc actgagaaga tcaatgatca ccgggctgtg ggcatggcta | 2028 |
| tctacaatgt ggcagtcctg tgcctcatca ctgctcctgt caccatgatt ctgtccagcc | 2088 |
| agcaggatgc agcctttgcc tttgcctctc ttgccatagt tttctcctcc tatatcactc | 2148 |
| ttgttgtgct ctttgtgccc aagatgcgca ggctgatcac ccgagggaa tggcagtcgg | 2208 |
| aggcgcagga caccatgaag acagggtcat cgaccaacaa caacgaggag gagaagtccc | 2268 |
| ggctgttgga gaaggagaac cgtgaactgg aaaagatcat tgctgagaaa gaggagcgtg | 2328 |
| tctctgaact gcgccatcaa ctccagtctc ggcagcagct ccgctcccgg cgccacccac | 2388 |
| cgacaccccc agaaccctct gggggcctgc cagggggacc ccctgagccc ccgaccggc | 2448 |
| ttagctgtga tgggagtcga gtgcatttgc tttataagtg a | 2489 |

<210> SEQ ID NO 85
<211> LENGTH: 496
<212> TYPE: PRT
<213> ORGANISM: Homo sapiens

<400> SEQUENCE: 85

```
Met Leu Leu Leu Leu Leu Ala Pro Leu Phe Leu Arg Pro Pro Gly
  1               5                  10                  15

Ala Gly Gly Ala Gln Thr Pro Asn Ala Thr Ser Glu Gly Cys Gln Ile
             20                  25                  30

Ile His Pro Pro Trp Glu Gly Gly Ile Arg Tyr Arg Gly Leu Thr Arg
         35                  40                  45

Asp Gln Val Lys Ala Ile Asn Phe Leu Pro Val Asp Tyr Glu Ile Glu
     50                  55                  60

Tyr Val Cys Arg Gly Glu Arg Glu Val Val Gly Pro Lys Val Arg Lys
 65                  70                  75                  80

Cys Leu Ala Asn Gly Ser Trp Thr Asp Met Asp Thr Pro Ser Arg Cys
                 85                  90                  95

Val Arg Ile Cys Ser Lys Ser Tyr Leu Thr Leu Glu Asn Gly Lys Val
            100                 105                 110

Phe Leu Thr Gly Gly Asp Leu Pro Ala Leu Asp Gly Ala Arg Val Asp
        115                 120                 125

Phe Arg Cys Asp Pro Asp Phe His Leu Cys Asp Pro Gly Gln Ala Thr
    130                 135                 140

Lys Tyr Leu Tyr Glu Leu Leu Tyr Asn Asp Pro Ile Lys Ile Ile Leu
145                 150                 155                 160

Met Pro Gly Cys Ser Ser Val Ser Thr Leu Val Ala Glu Ala Ala Arg
                165                 170                 175

Met Trp Asn Leu Ile Val Leu Ser Tyr Gly Ser Ser Ser Pro Ala Leu
```

-continued

```
                    180                 185                 190
Ser Asn Arg Gln Arg Phe Pro Thr Phe Phe Arg Thr His Pro Ser Ala
        195                 200                 205

Thr Leu His Asn Pro Thr Arg Val Lys Leu Phe Glu Lys Trp Gly Trp
    210                 215                 220

Lys Lys Ile Ala Thr Ile Gln Gln Thr Thr Glu Val Phe Thr Ser Thr
225                 230                 235                 240

Leu Asp Asp Leu Glu Glu Arg Val Lys Glu Ala Gly Ile Glu Ile Thr
                245                 250                 255

Phe Arg Gln Ser Phe Ser Asp Pro Ala Val Pro Val Lys Asn Leu
        260                 265                 270

Lys Arg Gln Asp Ala Arg Ile Ile Val Gly Leu Phe Tyr Glu Thr Glu
        275                 280                 285

Ala Arg Lys Val Phe Cys Glu Val Tyr Lys Glu Arg Leu Phe Gly Lys
        290                 295                 300

Lys Tyr Val Trp Phe Leu Ile Gly Trp Tyr Ala Asp Asn Trp Phe Lys
305                 310                 315                 320

Ile Tyr Asp Pro Ser Ile Asn Cys Thr Val Asp Glu Met Thr Glu Ala
                325                 330                 335

Val Glu Gly His Ile Thr Thr Glu Ile Val Met Leu Asn Pro Ala Asn
                340                 345                 350

Thr Arg Ser Ile Ser Asn Met Thr Ser Gln Glu Phe Val Glu Lys Leu
        355                 360                 365

Thr Lys Arg Leu Lys Arg His Pro Glu Glu Thr Gly Gly Phe Gln Glu
        370                 375                 380

Ala Pro Leu Ala Tyr Asp Ala Ile Trp Ala Leu Ala Leu Ala Leu Asn
385                 390                 395                 400

Lys Thr Ser Gly Gly Gly Arg Ser Gly Val Arg Leu Glu Asp Phe
                405                 410                 415

Asn Tyr Asn Asn Gln Thr Ile Thr Asp Gln Ile Tyr Arg Ala Met Asn
                420                 425                 430

Ser Ser Ser Phe Glu Gly Val Ser Gly His Val Val Phe Asp Ala Ser
        435                 440                 445

Gly Ser Arg Met Ala Trp Thr Leu Ile Glu Gln Leu Gln Gly Gly Ser
    450                 455                 460

Tyr Lys Lys Ile Gly Tyr Tyr Asp Ser Thr Lys Asp Asp Leu Ser Trp
465                 470                 475                 480

Ser Lys Thr Asp Lys Trp Ile Val Ile Ser Arg Thr His Ser Pro Thr
                485                 490                 495
```